US010900094B2

(12) United States Patent
Muchero et al.

(10) Patent No.: US 10,900,094 B2
(45) Date of Patent: Jan. 26, 2021

(54) METHODS OF IDENTIFYING AND MODULATING PATHOGEN RESISTANCE IN PLANTS

(71) Applicants: UT-Battelle, LLC, Oak Ridge, TN (US); Oregon State University, Corvallis, OR (US)

(72) Inventors: Wellington Muchero, Oak Ridge, TN (US); Jay Chen, Oak Ridge, TN (US); Gerald A. Tuskan, Oak Ridge, TN (US); Jared Leboldus, Corvallis, OR (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 16/148,319

(22) Filed: Oct. 1, 2018

(65) Prior Publication Data

US 2019/0194763 A1  Jun. 27, 2019

Related U.S. Application Data

(60) Provisional application No. 62/585,105, filed on Nov. 13, 2017.

(51) Int. Cl.
  *C12Q 1/68* (2018.01)
  *C12N 15/82* (2006.01)
  *C12Q 1/6895* (2018.01)

(52) U.S. Cl.
  CPC ........ *C12Q 1/6895* (2013.01); *C12N 15/8213* (2013.01); *C12N 15/8218* (2013.01); *C12N 15/8282* (2013.01); *C12Q 2600/13* (2013.01); *C12Q 2600/156* (2013.01); *C12Q 2600/158* (2013.01)

(58) Field of Classification Search
  None
  See application file for complete search history.

(56) References Cited

PUBLICATIONS

Vaid et al (2013 Molecular Plant 6:1405-1418 (Year: 2013).*
Leboldus, J.M., et al., "A method to induce stem cankers by inoculating nonwounded Populus clones with Septoria musiva spore suspensions", Plant Dis., (2010), 94, 1238-1242.
Belhaj, et al., "Plant genome editing made easy: targeted mutagenesis in model and crop plants using the CRISPR/Cas system." Plant methods, (2013), 9.1: 39.
Carroll, D. "Genome engineering with zinc-finger nucleases." Genetics, (2011), 188.4: 773-782.
Liang, H., et al. "Comparative expression analysis of resistant and susceptible Populus clones inoculated with Septoria musiva." Plant Science, (2014), 223: 69-78.
Newcombe, G., et al., "Recessive resistance to Septoria stem canker of hybrid poplar." Phytopathology, (2001), 91.11:1081-1084.
Zhang Y. et al "Transcription activator-like effector nucleases enable efficient plant genome engineering." Plant physiology, (2013), 161. 1: 20-27.
Cobb, R.C., et al., "Ecosystem transformation by emerging infectious disease: loss of large tanoak from California forests", J. Ecol., (2012), 100, 712-722.
Anagnostakis, S.L., "Chestnut blight: the classical problem of an introduced pathogen", Mycologia, (1987), 79, 23-37.
Kinloch, Jr, B.B., "White pine blister rust in North America: past and prognosis", Phytopathol., (2003), 93, 1044-1047.
Slavov, G.T., et al., "Genome resequencing reveals multiscale geographic structure and extensive linkage disequilibnum in the forest tree *Populus trichocarpa*", New Phytol., (2012), 196, 713-725.
Herath, P. et al., "Anthopogenic signature in the incidence and distribution of an emerging pathogen of poplars", Biol. Invasions, (2016), doi: 10.1007/s10530-015-1051-8.
Harvell, C.D. et al. "Climate Warming and Disease Risks for Terrestrial and Marine Biota", Science, (2002), 296, 2158-2162.
Jones, J.D. et al., "The plant immune system", Nature, (2006), 444, 323-329.
Shiu, S.H. et al., "Expansion of the receptor-like kinase/Pelle gene family and receptor-like proteins in *Arabidopsis*", Plant Physiol., (2003), 132, 530-543.
Liebrand, T.W. et al., "Receptor-like kinase SOBIR1/EVR interacts with receptor-like proteins in plant immunity against fungal infection", Proc. Natl. Acad. Sci. USA, (2013), 110, 10010-10015.
Duplessis, S. et al., "Melampsora larici-populina transcript profiling during germination and time-course infection of poplar leaves reveals dynamic expression patterns associated with virulence and biotrophy", Mol. Plant Microbe Interact., (2011), 24, 808-818.
Chen, W. et al., "A B-lectin receptor-kinase gene conferring rice blast resistance", Plant J., (2006), 46, 794-804.
Navarro-Gochicoa, M.T. et al., "Characterization of four lectin-like receptor kinases expressed in roots of Medicago truncatula: structure, location, regulation of expression, and potential role in the symbiosis with Sinorhizobium meliloti", Plant Physiol., (2003), 133, 1893-1910.
Ohm, R.A. et al., "Diverse lifestyles and strategies of plant pathogenesis encoded in the genomes of eighteen Dothideomycete fungi", PLoS Pathog., (2012), 8, e1003037.
Lorang, J. et al., "Tricking the guard: Exploiting plant defense for disease susceptibility", Science, (2012), 338, 659-662.
Cingolani P, et al., "A program for annotating and predicting the effects of single nucleotide polymorphisms, SnpEff: SNPs in the genome of *Drosophila melanogaster* strain w1118; iso-2; iso-3", Fly (Austin), (2012), 6: 80-92.

(Continued)

*Primary Examiner* — Brent T Page
(74) *Attorney, Agent, or Firm* — Scully, Scott, Murphy & Presser, P.C.

(57) ABSTRACT

Pathogenic fungi from the genus *Sphaerulina* cause damage to a diverse array of economically important plant species. The present disclosure provides methods of determining whether a plant is susceptible to pathogenic fungi infections. The disclosure further provides methods of engineering pathogenic fungi-resistant plants from susceptible plants using targeted genome editing techniques.

22 Claims, 10 Drawing Sheets
(9 of 10 Drawing Sheet(s) Filed in Color)
Specification includes a Sequence Listing.

(56) References Cited

PUBLICATIONS

Joshi, N.A. et al., "Sickle: A sliding-window, adaptive, quality-based trimming tool for FastQ files" (V1.33). https://github.com/najoshi/sickle (2011).

Chinchilla, D., et al., "One for all: the receptor-associated kinase BAK1", Trends Plant Sci., (2009), 14, 535-541.

Xu, X., et al. "Physical and functional interactions between pathogen-induced *Arabidopsis* WRKY18, WRKY40, and WRKY60 transcription factors", Plant Cell, (2006), 18, 1310-1326.

Zhang, Y., et al., "A gain-of-function mutation in a plant disease resistance gene leads to constitutive activation of downstream signal transduction pathways in suppressor of npr1-1, constitutive 1", Plant Cell, (2003), 15, 2636-2646.

Zhang, Y. et al., "*Arabidopsis* snc2-1D activates receptor-like protein-mediated immunity transduced through WRKY70", Plant Cell, (2010), 22, 3153-316.

Burdon, J.J. et al., "Co-evolution of plants and their pathogens in natural habitats", Science, (2009), 324, 755-756.

Boller, T. et al., "Innate immunity in plants: an arms race between pattern recognition receptors in plants and effectors in microbial pathogens", Science, (2009), 324, 742-743.

Brasier, C.M. "*Ophiostoma novo-ulmi* sp. nov., causative agent of current Dutch elm disease pandemics", Mycopathologia, (1991), 115, 151-161.

Tomlinson, I. "The discovery of ash dieback in the UK: the making of a focusing event", Environ. Polit., (2015), 25, 1-23.

Tobias, P.A. et al., "Tree immunity: Growing old without antibodies", Trends Plant Sci., (2014), 19, 367-370.

Feau, N., et al., "Recent advances related to poplar leaf spot and canker caused by Septoria musiva", Can. J. Plant Pathol., (2010), 32, 122-134.

Kang, H. M. et al., "Variance component model to account for sample structure in genome-wide association studies", Nat. Genet., (2010), 42, 348-354.

Trapnell, C. et al., "Differential gene and transcript expression analysis of RNAseq experiments with TopHat and Cufflinks", Nat Protoc., (2012), 7, 562-578.

Langmead, B. et al., "Fast gapped-read alignment with Bowtie 2", Nat. Methods, (2012), 9, 357-359.

* cited by examiner

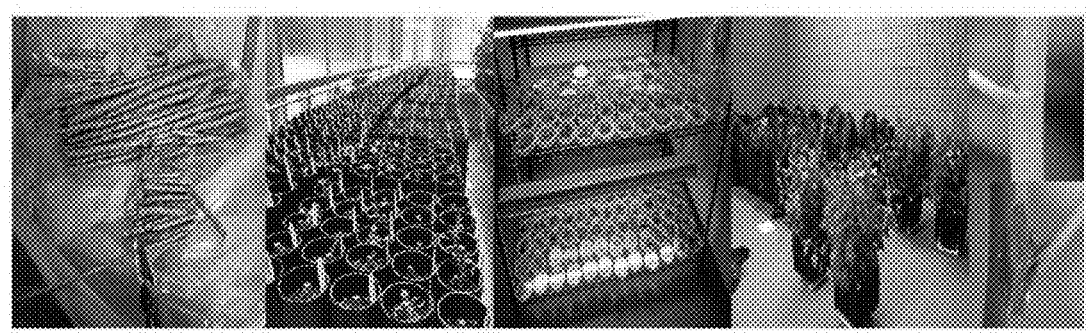
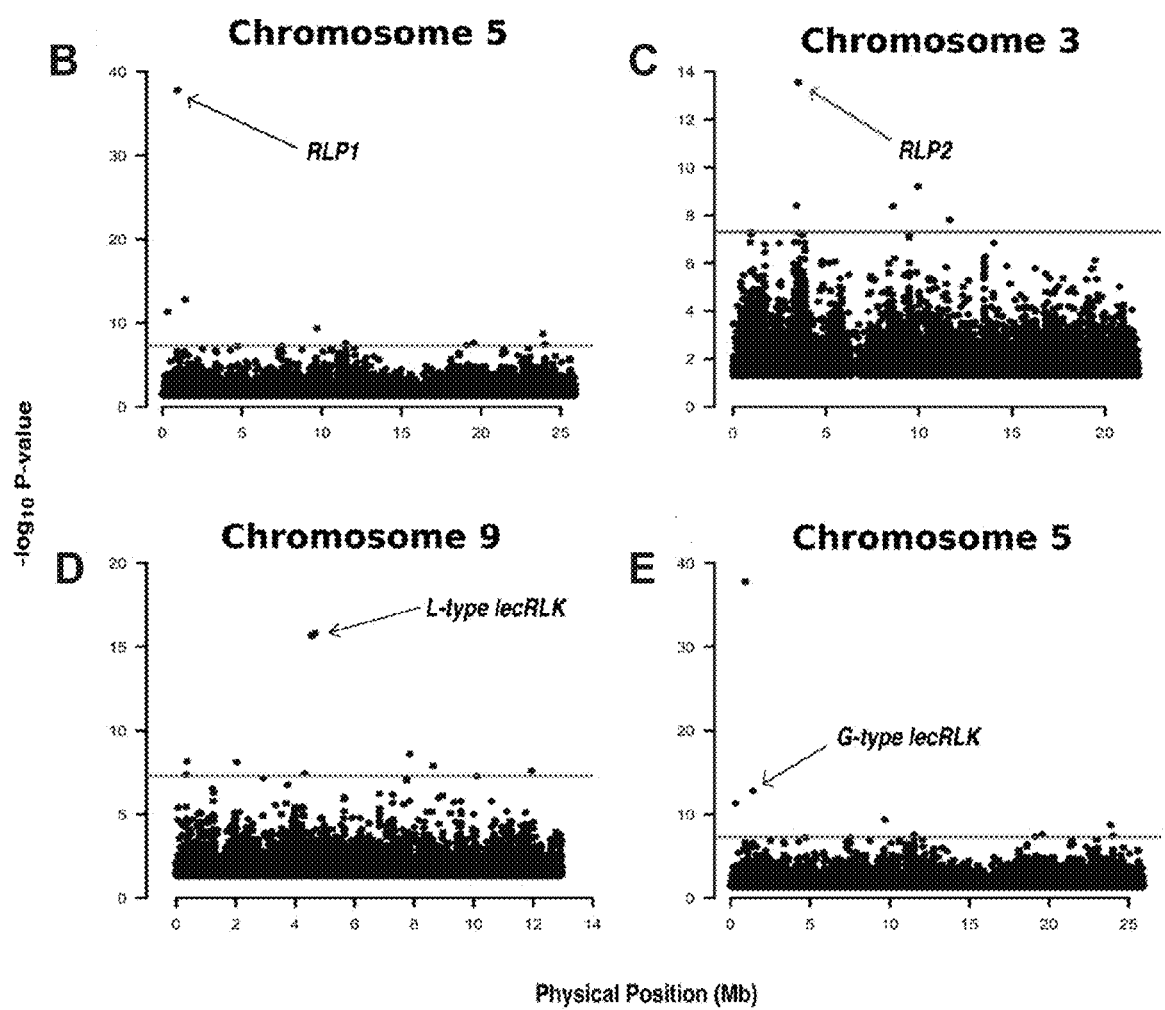
Fig. 1A – 1E

|  | Domain prediction | Amino acid position |
|---|---|---|
| Potri.005G012100 | signal peptide | 1-27 |
|  | plant specific LRR | 31-69 |
|  | LRR | 103-910 |
|  | transmembrane | 983-1005 |
| Potri.003G028200 | signal peptide | 1-27 |
|  | plant specific LRR | 31-68 |
|  | LRR | 102-961 |
|  | transmembrane | 1033-1055 |
| Potri.009G036300 | singal peptide | 1-25 |
|  | Legume lectin | 28-286 |
|  | transmembrane | 297-318 |
|  | protein kinase | 332-631 |
| Potri.005G018000 | singal peptide | 1-24 |
|  | Bulb lectin | 29-189 |
|  | S-locus glycoprotein | 204-304 |
|  | PAN | 322-406 |
|  | protein kinase | 408-700 |

Fig. 6

SEQUENCE LISTING

<160> NUMBER OF SEQ ID NOS: 48

<210> SEQ ID NO 1
<211> LENGTH: 6001
<212> TYPE: DNA
<213> ORGANISM: Populus trichocarpa

<400> SEQUENCE: 1

| | | | | | |
|---|---|---|---|---|---|
| gtagtataaa | taggacctct | atggttgccc | gaatgcacat | atgacataac | aaacaacaat | 60 |
| attctacgta | gtacttcata | gaattatcca | agatgatgat | gaaaaaaatg | ggggcttgga | 120 |
| tgttgctagc | attattgact | ttggttggcg | attggtgtgg | tcgttgttat | gggtgtttgg | 180 |
| aggaagagag | aattggtctc | ttggagatca | aagctttgat | ccacccagat | tacctttcct | 240 |
| tgagggattg | ggtggagtac | agtagtaatt | gttgtgagtg | gtctgggatc | gagtgtgata | 300 |
| acactacaag | gcgagtgatc | caactctctc | ttcagtatgc | aagggatcag | agtttggggg | 360 |
| attgggttct | caacgcatct | ttgtttctgc | cttttaaaga | actgcaaagt | cttgatttga | 420 |
| gttataatgg | actggttggt | tgctctgaga | atcaaggtcg | gttcaatgct | tctgttcttg | 480 |
| taatcataaa | ataaattcat | atcattgtgt | gaatcttata | ctgagattac | gctgatgaag | 540 |
| tggctagctg | gtgtttaatg | tcaattatct | tgctttgatg | tgtttctctt | ccaggcttcg | 600 |
| aagtcctatc | atcaaaactg | aggaaactgg | aggtacttta | cctaagtggc | aaccgattta | 660 |
| atgatgataa | aagcatttca | tcatgcttca | atgggctttc | atctctcaag | tctttggatc | 720 |
| tgtcattcaa | tggggtgaca | ggatcaggta | gcttctatgg | tgaccgttta | atttttttagc | 780 |
| tttgaaacat | tttctttttct | ccttctcata | tgatttagct | tctatgcgtt | tatttccttc | 840 |
| caatatgctt | aattttgaga | aacatcatgc | aggtctcaaa | gtcttgtcat | caaggttgaa | 900 |
| aaagctggag | atcctttacc | tgcgtgacaa | tcaatgcaac | gatagcatct | tttcatctat | 960 |
| aactgggttt | tcatctctca | agtctttgga | tctgtcaggc | aatcagctga | caggatcagg | 1020 |
| tagcttctat | ggtgaccgtt | taattattta | gctttgaaac | attttctttt | ctccttgtca | 1080 |
| tatgatttag | cttctatgcg | tttatttcct | tccaatatgc | ttaattttga | gaaacatcat | 1140 |
| gcaggtctca | aagtcttgtc | atcaaggttg | aaaaagctgg | agaaccttca | cctgagtggg | 1200 |
| aatcaatgca | acgatagcat | cttttcatct | ctaactgggt | tttcatctct | caagtctttg | 1260 |
| gatctgttag | gcaatcaggt | gacaggatca | tctactggta | tcaatagtaa | gttgcattct | 1320 |
| cttaagaaaa | ttgaggactt | tatatctact | tagtaattaa | tgatagcatt | aattaatttc | 1380 |
| gtcatgtttg | actgagcttt | catctctaaa | gatttatatt | tatatataaa | ttgttttttct | 1440 |
| aataagaccg | gaagagatca | aaattaggat | gattaaaaat | tacttttttga | caattaggat | 1500 |
| gattaaaggt | atatattgtt | acagctgtta | ttatggtcac | tgttagtgca | gattaattag | 1560 |
| ggtagcttgc | agatgcatgg | acacgtgtta | gaagttgtta | agagtcggtt | agagttagtt | 1620 |
| aacaatataa | taaatcgtgt | aatgcatgtg | gggaagtata | tatgcacgtt | ttggattacg | 1680 |
| cacgcaagaa | ataacagaat | cattccgctc | tgcttcattc | tgttagttaa | caatacacaa | 1740 |
| aatggatact | tccactctat | ccttcttgac | caaaaaacgc | aatcttaatt | aaggcataaa | 1800 |
| atcaatacct | agcttctgac | aatcttcttt | caggttttca | agtgctagct | tcaggattga | 1860 |
| agaatttgga | ggaacttgat | ctgactcaca | ataaattgaa | cgacatcatt | ttatcagctc | 1920 |
| tcggtggttt | ttcaactctc | aaatctctat | atctatcggg | caacatgttc | acaggatcaa | 1980 |
| ctggtctcaa | tggtaaagtt | gtaaatcatt | cctacctcgg | atggcattcc | ctcgtgaggt | 2040 |
| ttaataatta | catgtgtatt | aacccttaac | taattgtttg | gatgaagcct | taaaaaggct | 2100 |

```
ttatataatt aattctttaa ggtaagtgaa ataatttgaa acttacgtac atatacacgc    2160
tattaacttt tgttcaattt cttaatttat ttttaaataa atgaaggggt atatttaatt    2220
aataaaattt taatatgata ttaaaattat tttaatttta aaacttaagc tatgtcttgt    2280
atattaactc tagcattata aattatttaa ttattgtaaa taatcattat tgattgttct    2340
ctctatcaca ggtttaagga atttagaaac cttgtatctg tattggactg acttcaagga    2400
aagcattttg atagagtcat gggagcgtt gccatccctc aagaccttag atgcaagttt    2460
tagtaaattt aaacactttg ggaaaggtca gtgacagttt tggtgcctaa aacaatatga    2520
tatttataat atattgatgg atttatctga tctgttccac agggttgtgg aattcgtcta    2580
cccttgaaga agtgttcctc gatgattctt ctctcccagc aagctttctt aggaacattg    2640
gacacttgtc tactcttaaa atcctatcct tgaacagagt tgacttcaat agcaccctac    2700
ctgctgaagg taattctaca aaagaacaat tataagagta ttgaaatcca ataacagtt    2760 gttcattaga tatttgtgtt atatctatgt tttatccaac taatgttacg tatagaaaag    2820
gataaaatct agagtttctc aatctctaaa atttctcaga cttaaattta gggtagctgg    2880
cagatgcatg gacacgtgtt agaagttgtt aagagatggt tagagttagt taacaataga    2940
ataaaccgtg taatgcatgt ggggaagtat atatatataa tggtaggagg attacgcacg    3000
caagaaataa cagagttatt ctcctctcat ttatttctct gttttccttc tgcttaacag    3060
atgattatat tacaatacac aaaatggata cttccaatct atccttctta acaaaaacgc    3120
aatcttaatt aataatattg aaaggaatgg ttactctgta ccaccactat tttcatcgta    3180 cctttcttc tttaacttaa ttaaggcata caaccatccc tctgtaccaa tttaagtcaa    3240
tattgaaagg aatggctact ctgtaccacc actattttca tcgtataggc ataaaaaattt    3300 ctaggcctaa ttagagaaca aaacctagct atagaacatt gttaaaatat cagtttgata    3360
taaccgatcg gataaaagat tataaccata acaagaagtt ttctacgaaa taatggacaa    3420
ctgcctgctc acagaatttt gtctctggaa agctagtata tatgctaaat ggcaccctgc    3480
ctcaccaaag taaattaaat cactaataaa cttgtattgt tgaatagatc tctcaataaa    3540
tagtacatca ttgatatatt cctattccct taacatgaac attttgatat attctgcagg    3600
ctggtgtgaa ctgaagaatc ttgaacaact atctctctca ggaaacaatc taaagggcgt    3660
actccctcct tgtttgggaa atctatcatt tctacaattc ttggatttat ctcgcaatca    3720
attggaggga atattgcct ctagtcacct ttcccatctt acgcggctcc aatacctctc    3780
agtttcaaat aaccactttc aagttccaat atcatttggt tcatttatga acctctccaa    3840
cctcaagttc tttgcatgcg ataacaatga gctaatagct gcacccagtt ttcagccttc    3900
agctcccaag ttccagcttc gttttttag tgcttcaaac tgtacttcaa aaccacacga    3960
ggctggattt ccaaacttcc tccagagcca atatgatctt gtggttgttg atctatccca    4020
caacaaattc gttggagaac ctttcccatc ttggctgttt gagaataata caaagttaaa    4080
tcgactatat ttgagagaca cctcatttat aggtcctttg cagctgccac aacatccaac    4140
acccaacctt cagacagtag atatgtctgg caacaacata catggtcaag ttgcaagcaa    4200
catatgttcg attttccac gtttgaagaa cttcatgatg gctaacaaca gcctcacagg    4260
ttgtattcct ccttgttttg ggaatatgag ctctctggaa tacttggatc tttccaacaa    4320
tcacatgtct tgtgaactgc ttgagcataa ttttccaaca gtaggctcct cgttgtggta    4380
cttaaagttg tccaataaca atttcaaagg gcgattacca ctctctgtgt tcaacatgac    4440
```

-continued

| | |
|---|---|
| tgacctacgt tacctctttc tcgatggaaa caaatttgct ggacaagtat ctggtacctt | 4500 |
| ttctcttgca ttatcatttt tgtggtttga tatcagtaac aatattctgt caggcatgct | 4560 |
| tccaagggga tagggaact cttcactaaa cagcttgcag ggaattgact tgtccagaaa | 4620 |
| tcattttgaa ggtaccattc aatagaata tttcaattct tctgggcttg aattttaga | 4680 |
| tctttctgaa acaatctgt ctgggtcatt accgttgggc ttcaatgcat tagatttacg | 4740 |
| ctatgtccac ctatacggaa atagattgag cggtccactg ccatatgatt tttataatct | 4800 |
| ctcttcgttg gcgacattag atctcggcga taacaactta actgggccca ttccaattgg | 4860 |
| attgatagcc tttcggaatt gagcattttt gttctcaaat ctaatcaatt caatgggaaa | 4920 |
| cttcctcatc agttatgctc gttaaggaaa ttaagcatat tggatctttc agaaaataat | 4980 |
| ttttctggtc tgttaccctc atgtttgaga aatttaaatt ttacggcatc ggatgaaaaa | 5040 |
| actttagatg cccctcgtac gggatcggat tatgaagcg gggaagaaat atttgcatcc | 5100 |
| ataggggga gaggattttc tcttgatgac aatattttgt gggcagagat cagtgtaaaa | 5160 |
| atatctgtag agcttacagc aaagaaaaat ttctacactt acgaaggcga tatccttcgt | 5220 |
| tacatgtctg ttatggatct ttcttgtaac agattcaatg gagaaattcc gacagaatgg | 5280 |
| ggaaacttaa gtgggatata ttctctaaat ctgtcacaaa ataatctcac tggattgatc | 5340 |
| ccttcatcct tcttcaatct gaagcagata gagagcttgg atctttctca caacaatttg | 5400 |
| aatgggagaa ttcctgcaca actcgttgaa ctgacctttc tagaagtttt caacgtgtcg | 5460 |
| tacaataatt tgtcaggaag aacaccggag atgaaaaatc aatttgctac ctttgatgag | 5520 |
| agcagttata aagggaatcc tcttctttgt ggacctccat tgcaaaacag ttgcgacaaa | 5580 |
| acagaatcac catcagcgag agtgcctaac gatttcaatg gagatggtgg cttcatagac | 5640 |
| atggacagtt tctatgccag cttggtgtg tgttacataa ttgtggtgtt gacaattgca | 5700 |
| gcagtactgt gcataaatcc gcattggcga cgcaggtggt tttacttcat tgaagaatgc | 5760 |
| attgacactt actgctgctt tctggctatt aactttccca agttgtccag attcagaagg | 5820 |
| tgattggatc ttatcaggag cgtgtgggcg gctttctgaa tttgttgtaa tcctctgtgg | 5880 |
| agaagcagtc gcattccaaa tcaatggttg ctcactgcat gtttagcaat ttgcctgtga | 5940 |
| gaagtgttct gtggaagtgt tcttgtgctt agcctttcta ttttgatgtg acttgtgttt | 6000 |
| g | 6001 |

<210> SEQ ID NO 2
<211> LENGTH: 1039
<212> TYPE: PRT
<213> ORGANISM: Populus trichocarpa

<400> SEQUENCE: 2

Met Met Met Lys Lys Met Gly Ala Trp Met Leu Leu Ala Leu Leu Thr
1               5                   10                  15

Leu Val Gly Asp Trp Cys Gly Arg Cys Tyr Gly Cys Leu Glu Glu Glu
            20                  25                  30

Arg Ile Gly Leu Leu Glu Ile Lys Ala Leu Ile His Pro Asp Tyr Leu
        35                  40                  45

Ser Leu Arg Asp Trp Val Glu Tyr Ser Ser Asn Cys Cys Glu Trp Ser
    50                  55                  60

Gly Ile Glu Cys Asp Asn Thr Thr Arg Arg Val Ile Gln Leu Ser Leu
65                  70                  75                  80

Gln Tyr Ala Arg Asp Gln Ser Leu Gly Asp Trp Val Leu Asn Ala Ser
                85                  90                  95

-continued

```
Leu Phe Leu Pro Phe Lys Glu Leu Gln Ser Leu Asp Leu Ser Tyr Asn
            100                 105                 110
Gly Leu Val Gly Cys Ser Glu Asn Gln Gly Phe Glu Val Leu Ser Ser
            115                 120                 125
Lys Leu Arg Lys Leu Glu Val Leu Tyr Leu Ser Gly Asn Arg Phe Asn
            130                 135                 140
Asp Asp Lys Ser Ile Ser Ser Cys Phe Asn Gly Leu Ser Ser Leu Lys
145                 150                 155                 160
Ser Leu Asp Leu Ser Phe Asn Gly Val Thr Gly Ser Gly Phe Gln Val
                165                 170                 175
Leu Ala Ser Gly Leu Lys Asn Leu Glu Glu Leu Asp Leu Thr His Asn
            180                 185                 190
Lys Leu Asn Asp Ile Ile Leu Ser Ala Leu Gly Gly Phe Ser Thr Leu
            195                 200                 205
Lys Ser Leu Tyr Leu Ser Gly Asn Met Phe Thr Gly Ser Thr Gly Leu
            210                 215                 220
Asn Gly Leu Arg Asn Leu Glu Thr Leu Tyr Leu Tyr Trp Thr Asp Phe
225                 230                 235                 240
Lys Glu Ser Ile Leu Ile Glu Ser Leu Gly Ala Leu Pro Ser Leu Lys
                245                 250                 255
Thr Leu Asp Ala Ser Phe Ser Lys Phe Lys His Phe Gly Lys Gly Leu
            260                 265                 270
Trp Asn Ser Ser Thr Leu Glu Glu Val Phe Leu Asp Asp Ser Ser Leu
            275                 280                 285
Pro Ala Ser Phe Leu Arg Asn Ile Gly His Leu Ser Thr Leu Lys Ile
            290                 295                 300
Leu Ser Leu Asn Arg Val Asp Phe Asn Ser Thr Leu Pro Ala Glu Gly
305                 310                 315                 320
Trp Cys Glu Leu Lys Asn Leu Glu Gln Leu Ser Leu Ser Gly Asn Asn
                325                 330                 335
Leu Lys Gly Val Leu Pro Pro Cys Leu Gly Asn Leu Ser Phe Leu Gln
            340                 345                 350
Phe Leu Asp Leu Ser Arg Asn Gln Leu Glu Gly Asn Ile Ala Ser Ser
            355                 360                 365
His Leu Ser His Leu Thr Arg Leu Gln Tyr Leu Ser Val Ser Asn Asn
            370                 375                 380
His Phe Gln Val Pro Ile Ser Phe Gly Ser Phe Met Asn Leu Ser Asn
385                 390                 395                 400
Leu Lys Phe Phe Ala Cys Asp Asn Asn Glu Leu Ile Ala Ala Pro Ser
                405                 410                 415
Phe Gln Pro Ser Ala Pro Lys Phe Gln Leu Arg Phe Phe Ser Ala Ser
            420                 425                 430
Asn Cys Thr Ser Lys Pro His Glu Ala Gly Phe Pro Asn Phe Leu Gln
            435                 440                 445
Ser Gln Tyr Asp Leu Val Val Val Asp Leu Ser His Asn Lys Phe Val
            450                 455                 460
Gly Glu Pro Phe Pro Ser Trp Leu Phe Glu Asn Asn Thr Lys Leu Asn
465                 470                 475                 480
Arg Leu Tyr Leu Arg Asp Thr Ser Phe Ile Gly Pro Leu Gln Leu Pro
                485                 490                 495
Gln His Pro Thr Pro Asn Leu Gln Thr Val Asp Met Ser Gly Asn Asn
            500                 505                 510
```

-continued

```
Ile His Gly Gln Val Ala Ser Asn Ile Cys Ser Ile Phe Pro Arg Leu
515                 520                 525

Lys Asn Phe Met Met Ala Asn Asn Ser Leu Thr Gly Cys Ile Pro Pro
530                 535                 540

Cys Phe Gly Asn Met Ser Ser Leu Glu Tyr Leu Asp Leu Ser Asn Asn
545                 550                 555                 560

His Met Ser Cys Glu Leu Leu Glu His Asn Phe Pro Thr Val Gly Ser
                565                 570                 575

Ser Leu Trp Tyr Leu Lys Leu Ser Asn Asn Phe Lys Gly Arg Leu
                580                 585                 590

Pro Leu Ser Val Phe Asn Met Thr Asp Leu Arg Tyr Leu Phe Leu Asp
                595                 600                 605

Gly Asn Lys Phe Ala Gly Gln Val Ser Gly Thr Phe Ser Leu Ala Leu
610                 615                 620

Ser Phe Leu Trp Phe Asp Ile Ser Asn Asn Ile Leu Ser Gly Met Leu
625                 630                 635                 640

Pro Arg Gly Ile Gly Asn Ser Ser Leu Asn Ser Leu Gln Gly Ile Asp
                645                 650                 655

Leu Ser Arg Asn His Phe Glu Gly Thr Ile Pro Ile Glu Tyr Phe Asn
                660                 665                 670

Ser Ser Gly Leu Glu Phe Leu Asp Leu Ser Glu Asn Asn Leu Ser Gly
            675                 680                 685

Ser Leu Pro Leu Gly Phe Asn Ala Leu Asp Leu Arg Tyr Val His Leu
                690                 695                 700

Tyr Gly Asn Arg Leu Ser Gly Pro Leu Pro Tyr Asp Phe Tyr Asn Leu
705                 710                 715                 720

Ser Ser Leu Ser Glu Leu Ser Ile Phe Val Leu Lys Ser Asn Gln Phe
                725                 730                 735

Asn Gly Lys Leu Pro His Gln Leu Cys Ser Leu Arg Lys Leu Ser Ile
                740                 745                 750

Leu Asp Leu Ser Glu Asn Asn Phe Ser Gly Leu Leu Pro Ser Cys Leu
                755                 760                 765

Arg Asn Leu Asn Phe Thr Ala Ser Asp Glu Lys Thr Leu Asp Ala Pro
770                 775                 780

Arg Thr Gly Ser Asp Tyr Gly Ser Gly Glu Glu Ile Phe Ala Ser Ile
785                 790                 795                 800

Gly Gly Arg Gly Phe Ser Leu Asp Asp Asn Ile Leu Trp Ala Glu Ile
                805                 810                 815

Ser Val Lys Ile Ser Val Glu Leu Thr Ala Lys Lys Asn Phe Tyr Thr
                820                 825                 830

Tyr Glu Gly Asp Ile Leu Arg Tyr Met Ser Val Met Asp Leu Ser Cys
                835                 840                 845

Asn Arg Phe Asn Gly Glu Ile Pro Thr Glu Trp Gly Asn Leu Ser Gly
850                 855                 860

Ile Tyr Ser Leu Asn Leu Ser Gln Asn Asn Leu Thr Gly Leu Ile Pro
865                 870                 875                 880

Ser Ser Phe Phe Asn Leu Lys Gln Ile Glu Ser Leu Asp Leu Ser His
                885                 890                 895

Asn Asn Leu Asn Gly Arg Ile Pro Ala Gln Leu Val Glu Leu Thr Phe
                900                 905                 910

Leu Glu Val Phe Asn Val Ser Tyr Asn Leu Ser Gly Arg Thr Pro
                915                 920                 925

Glu Met Lys Asn Gln Phe Ala Thr Phe Asp Glu Ser Ser Tyr Lys Gly
```

```
                930              935             940
Asn Pro Leu Leu Cys Gly Pro Pro Leu Gln Asn Ser Cys Asp Lys Thr
945                 950             955                 960

Glu Ser Pro Ser Ala Arg Val Pro Asn Asp Phe Asn Gly Asp Gly Gly
                965             970             975

Phe Ile Asp Met Asp Ser Phe Tyr Ala Ser Phe Gly Val Cys Tyr Ile
            980             985             990

Ile Val Val Leu Thr Ile Ala Ala  Val Leu Cys Ile Asn  Pro His Trp
        995             1000            1005

Arg Arg  Arg Trp Phe Tyr Phe  Ile Glu Glu Cys Ile  Asp Thr Tyr
    1010            1015            1020

Cys Cys  Phe Leu Ala Ile Asn  Phe Pro Lys Leu Ser  Arg Phe Arg
    1025            1030            1035

Arg

<210> SEQ ID NO 3
<211> LENGTH: 5674
<212> TYPE: DNA
<213> ORGANISM: Populus trichocarpa

<400> SEQUENCE: 3
acataacaaa caacaatatt ctacgtagat gatgatgaaa agaatgggga gttggatgtt      60
gctagcatta ttgactttgg ttggcgaatg gtatggtcgt tgttatgggt gtttggagga    120
agagaggatt ggtctcttgg agatccaatc ttcgatcgac ccagatggcg tttccttgag    180
agattgggtg gacggtagta attgttgtga gtggcatagg atcgagtgtg ataacactac    240
aaggcgagtg atccaactct ctcttagagg atcaagggac gagagcttgg gcgattgggt    300
tctcaacgca tctttgtttc agccttttaa agaattgcaa agtcttgaat tggaaggtaa    360
tggattggtt ggttgcttgg agaatgaagg ttagttcaat gttgtgcac ttaaatataa    420 tcataaaata aatgaaggtt ggttggtgtt taatgtcaat tatcttgctc tttccaggct    480
tcgaagtcct atcatcaaaa ctgaggaaac ttgacctaag ttataacgga tttaataatg    540
ataaaagcat tttgtcatgt ttcaatggta acctttccac tctcaagtct ttggatctat    600
cagagaatgg gttgacagct ggatcaggag gtagcttcta tggtaacctt ttaattattt    660
agcttcgaaa ccttttcttt tctccttctc atatcatttt tttctacgca tttaaatgat    720
caggaggtag ctgctatttta ggtctcaaag tcttgtcctc aaggttgaaa aagctggaga    780
accttcttct aagttggaat cattgcaacg atagcatttt tccatctctt actggatttt    840
catccctcaa gtctttggat ctgtcgtaca atgagttgac aggatcaggt ataatacaca    900
gtttctacct aaatgcttca catgacattc tcttaattat attgtttctt tatcaacaaa    960
aatgagaact ttatatctac gtaaagaggc atatatttta ttcttatttt ggcccttta   1020 tgccaaaagt gttgtaatat ttagattaaa ttagcaatca gaagttcact tcaaaactct    1080
cctataaata tatattttat atttatcttt ttaaataaat atattttat atatgttttt    1140 tctgtcttga gatccttagt cgaacacaac tctaagtatt tttttttatg aatttgagtt    1200
tgaatgggtt ttgaataaca taataagaag ctctctccta taatattata tataattaag   1260
aaaattgtaa ttattaaaac ttggatctta acatcaattc aaaaaaaaac tatccaatac    1320
aaatcactag acagccaacg agagaggcat ttagcatctt acagaggcag ttagtttttg    1380
aaactatcat aactaattaa ttagtttttc aaaattaggc aatatttgaa cttacatgga    1440
tcgattatta ttcttgtttt aattaccgat gagatcttaa ttataagttt ctttatttg    1500
```

```
ttttgtaagt ctatcataac ttagcttcca tctttagcga ctttataacc gtaaattgtt    1560
tttttttttc caatgatcaa aattagaatg atatttaaaa attgtatctt aatcttagaa    1620
gcgtgcacaa cctatttat  aattaaatat gcgttcatgt atcatttcta tgcttttgag    1680
gaacatcatg caggtctcaa agtccttgtca tcaaggttga aaaagcttga gaaccttcat   1740
ctaagacgga atcaatacaa cgatagcatt tttccatctc taactgggtt ttcatctctc    1800
aagtctttgg atctgtcaaa caatcagctg acaggatcta tcaatagtaa gttgcattct    1860
gtttatcaag aaaattgagg actttatata tatttaaaaa tcaacgatag catttcatca    1920
tgtttgattg cgcttaatt  tcatctatga agattaatat ctatggagct ttgatcttat    1980
ccataaatta tttcttaatc tattatataa ttaaatatgc gttcatatat cattctttt    2040 atgtataatt tgagaatcat atatcaattg aacaacatct catcaattct aattatcttt    2100
agtttctata tattatgcat atcgtgagct cataattatg acttactctt agaaacaact    2160
ccttgcaggt tttgagatca tatcatcaca tttggggaaa ctcgagaacc tggacctgag    2220
ctataatata ttcaacgaca gcattttatc acatccgagt ggactttcat ccctcaagtc    2280
tttaaattta tcaggcaata tgttgctagg atcgacggct gtcaatggta aagttgtgaa    2340
tatctcttgg catcttctat tatttgggca atttgttgtt tctatcaaaa aatcatctca    2400
ctacaaaagt accagttctt tatcatagct ttaagaactc gatcaagata acacttaatt    2460
tcactactta cttgattgcc tgttttcaat tctacacatc ataggttcaa ggaagctgga    2520
cttcctacag tcattgtgtt cattgccatc cctgaagacc ctttctctca aggatactaa    2580
tttaagtcaa ggttaatagt ttagtttctt aaaatcttaa ttaataatat tgaatggaat    2640
ggctatatat tctgtaccac cactatttc  atcatatctc ttcttctttc tttttcatag    2700
ggactttgtt caattcgagc acccttgaag aattgcatct agataatact tctctcccaa    2760
taaactttct ccagaacatt ggagcattgc ctgctcttaa agttttgtct gttggtgaat    2820
gtgacctcca tggcacccta cctgctcaag gtaaattaac aactctccat ccgcctataa    2880
ttacatcatc aacaaagat  tcttccaaca ctattttgac tatttcaaga taaattgtac    2940
aggttggtgt gaattgaaga atctgaagca gttacatctc tctagaaata atttaggagg    3000
ttcactccca gattgtttgg ggaacatgtc atctttacaa ctattagatg tttctgaaaa    3060
ccagtttact ggaaatattg ctttcggtcc tcttaccaac ctcatatccc ttgaattcct    3120
ctcactatca ataacctct  ttgaagttcc catttcaata aagcctttta tgaaccactc    3180
aagcctcaag ttcttctcca gtgagaacaa caagctagta acagaacctg ctgcctttga    3240
taatttgatt ccaaagttcc aactagtctt tttccgcttg tcaagtagtc caacatcgga    3300
agcactcaat gtaattcccg acttcctcta ttaccaatta gacttaagag cccttgatct    3360
ctcccacaac aacatcactg gaatgtttcc atcgtggttg cttaagaaca atacacgatt    3420
ggaacaacta tatctgagcg acaactcctt tattggtgct ttgcagttgc aagatcacct    3480
ccatccgaat atgaccaatt tagatatatc caacaacaac atgaacggtc aaattccaaa    3540
agatatttgt ttgatctttc caaatctaca caccttaagg atggctaaga atggattcac    3600
aggttgtatt ccttcctgtt taggaaatat tagctctctt tcattttag  atttatccaa    3660 caatcaattg tctacagtaa aactagaaca actaacaaca atatgggttc tcaagctgtc    3720
aaacaacaat ttgggtggga aaataccgac ctcggtgttc aattcttctc gcctgaattt    3780
tctttaccta aatggtaaca acttttgggg tcagatatca gattttccat tatataggtg    3840
```

```
gaatgtatgg aatgtattag atttgagtaa caatcaattt tcgggcatgc ttccaaggag    3900
cttcgttaat ttttcgatcc ttggagtaat tgatttgtcc ggaaaccatt ttaagggtcc    3960
gatcccaaga gattttgta agtttgacca gcttgaatat ttggaccttt ctgagaacaa     4020
cttgtctgga tataccat cttgttttag tccaccacaa ataacccatg tgcatctatc      4080
gaaaaataga ctgagcggtc cattaacata tgcattttt  aacagctctt acctggttac    4140
gatggatctt cgagaaaaca gcttcaccgg ctccattcca aattggattg caatctttc     4200
atcattgagt gttcttcttc tgagggctaa tcactttgat ggtgagctcc ctattcagtt    4260
atgcttgtta gaacaattaa gcattttgga tgtttcacac aaccagctct ctggtccact    4320
accctcctgt ttaggcaatc ttactttcaa gaaaagtgac aagaaagcga tattggaagt    4380
cgcatatggt tttatatcag agtccataga aaaagcttat tatgaaataa tgggcccacc    4440
actagtggat agtgtggaca acttgagaaa tttttttttg tttaacttta cagaagaagt    4500
gacagaattt acaactaaaa atatgtatta tgggtacaag gggaaagttc tcaactacat    4560
gtttggtatt gatctctcca ataacaactt catcggagca atcccaccag aatttggaaa    4620
cttaagtaag atactgtcag taaacttatc acacaacaat ctcactggat ctatccctgc    4680
aacattctca aacctaatgc atattgagag tttggatctt tcttacaaca acttgaatgg    4740
tgccatccct ccacaattta ctgaagttac cacactggaa gttttagtg tggcgcacaa     4800
taacttgtca ggcaagacac ccgagagaat atatcagttt gggaccttcg atgaaagctg    4860
ttacgaagga aatcctttct tgtgtggacc tccattgcca aacaattgta gtgagaaggc    4920
agtggtgtca cagccagtgc ctaatgatga acaaggagat gatggtttca tagatatgga    4980
gttttctac atcagtttcg gtgtatgtta cacagttgtg gtgatgacga ttgcagcagt    5040
tctctacatc aatccatatt ggcgacgcag gtggttgtac ttcatcgaag actgcataga    5100
tacttgctac tattttgtgg tggctagttt tcgcaagttc tctaacttca gaaggtgaat    5160
ttgttattgg ggagacggtc gttcctagtt tgtgatgatt gtttatctag ttattggcaa    5220
tatgtagtgt actatctcta agctcagcct ttctatttga ttagttattt gggttaaata    5280
tataagctgg acttctcatt cctgaatcat taggaaggaa actgatttgg attggtcatt    5340
gactcgggtg tgattactct ttcaactctc aagacttgtc cgaaaataaa ttgccacaac    5400
cactactaaa gtataaacaa aatgttctat gtctttgttt caagggcgac cccacctcag    5460
ttattcaatc aaagcattga aatcggagca agaagatcca ccttcttcaa cagccttcct    5520
ggccgtttct ttgctctgct actcatttcc tctgcttctt cacccatcat aatttgagtg    5580
attgccttct ctacagcttc acttttaaca tgatctccat gcactctaag ccattcctta    5640
actccaattt taaaacatc agtcgccaac tttt                                 5674
```

<210> SEQ ID NO 4
<211> LENGTH: 1090
<212> TYPE: PRT
<213> ORGANISM: Populus trichocarpa

<400> SEQUENCE: 4

Met Met Met Lys Arg Met Gly Ser Trp Met Leu Leu Ala Leu Leu Thr
1               5                   10                  15

Leu Val Gly Glu Trp Tyr Gly Arg Cys Tyr Gly Cys Leu Glu Glu Glu
                20                  25                  30

Arg Ile Gly Leu Leu Glu Ile Gln Ser Ser Ile Asp Pro Asp Gly Val
            35                  40                  45

-continued

```
Ser Leu Arg Asp Trp Val Asp Gly Ser Asn Cys Cys Glu Trp His Arg
 50                  55                  60

Ile Glu Cys Asp Asn Thr Thr Arg Arg Val Ile Gln Leu Ser Leu Arg
65                  70                  75                  80

Gly Ser Arg Asp Glu Ser Leu Gly Asp Trp Val Leu Asn Ala Ser Leu
                85                  90                  95

Phe Gln Pro Phe Lys Glu Leu Gln Ser Leu Glu Leu Glu Gly Asn Gly
               100                 105                 110

Leu Val Gly Cys Leu Glu Asn Glu Gly Phe Glu Val Leu Ser Ser Lys
               115                 120                 125

Leu Arg Lys Leu Asp Leu Ser Tyr Asn Gly Phe Asn Asn Asp Lys Ser
130                 135                 140

Ile Leu Ser Cys Phe Asn Gly Asn Leu Ser Thr Leu Lys Ser Leu Asp
145                 150                 155                 160

Leu Ser Glu Asn Gly Leu Thr Ala Gly Ser Gly Leu Lys Val Leu
                165                 170                 175

Ser Ser Arg Leu Lys Lys Leu Glu Asn Leu Leu Leu Ser Trp Asn His
               180                 185                 190

Cys Asn Asp Ser Ile Phe Pro Ser Leu Thr Gly Phe Ser Ser Leu Lys
               195                 200                 205

Ser Leu Asp Leu Ser Tyr Asn Glu Leu Thr Gly Ser Gly Phe Glu Ile
               210                 215                 220

Ile Ser Ser His Leu Gly Lys Leu Glu Asn Leu Asp Leu Ser Tyr Asn
225                 230                 235                 240

Ile Phe Asn Asp Ser Ile Leu Ser His Pro Ser Gly Leu Ser Ser Leu
               245                 250                 255

Lys Ser Leu Asn Leu Ser Gly Asn Met Leu Leu Gly Ser Thr Ala Val
               260                 265                 270

Asn Gly Ser Arg Lys Leu Asp Phe Leu Gln Ser Leu Cys Ser Leu Pro
               275                 280                 285

Ser Leu Lys Thr Leu Ser Leu Lys Asp Thr Asn Leu Ser Gln Gly Thr
               290                 295                 300

Leu Phe Asn Ser Ser Thr Leu Glu Glu Leu His Leu Asp Asn Thr Ser
305                 310                 315                 320

Leu Pro Ile Asn Phe Leu Gln Asn Ile Gly Ala Leu Pro Ala Leu Lys
               325                 330                 335

Val Leu Ser Val Gly Glu Cys Asp Leu His Gly Thr Leu Pro Ala Gln
               340                 345                 350

Gly Trp Cys Glu Leu Lys Asn Leu Lys Gln Leu His Leu Ser Arg Asn
               355                 360                 365

Asn Leu Gly Gly Ser Leu Pro Asp Cys Leu Gly Asn Met Ser Ser Leu
               370                 375                 380

Gln Leu Leu Asp Val Ser Glu Asn Gln Phe Thr Gly Asn Ile Ala Phe
385                 390                 395                 400

Gly Pro Leu Thr Asn Leu Ile Ser Leu Glu Phe Leu Ser Leu Ser Asn
               405                 410                 415

Asn Leu Phe Glu Val Pro Ile Ser Ile Lys Pro Phe Met Asn His Ser
               420                 425                 430

Ser Leu Lys Phe Phe Ser Ser Glu Asn Asn Lys Leu Val Thr Glu Pro
               435                 440                 445

Ala Ala Phe Asp Asn Leu Ile Pro Lys Phe Gln Leu Val Phe Phe Arg
450                 455                 460

Leu Ser Ser Ser Pro Thr Ser Glu Ala Leu Asn Val Ile Pro Asp Phe
```

-continued

```
            465                 470                 475                 480
        Leu Tyr Tyr Gln Leu Asp Leu Arg Ala Leu Asp Leu Ser His Asn Asn
                        485                 490                 495

Ile Thr Gly Met Phe Pro Ser Trp Leu Leu Lys Asn Asn Thr Arg Leu
                        500                 505                 510

Glu Gln Leu Tyr Leu Ser Asp Asn Ser Phe Ile Gly Ala Leu Gln Leu
                        515                 520                 525

Gln Asp His Leu His Pro Asn Met Thr Asn Leu Asp Ile Ser Asn Asn
                        530                 535                 540

Asn Met Asn Gly Gln Ile Pro Lys Asp Ile Cys Leu Ile Phe Pro Asn
        545                 550                 555                 560

Leu His Thr Leu Arg Met Ala Lys Asn Gly Phe Thr Gly Cys Ile Pro
                        565                 570                 575

Ser Cys Leu Gly Asn Ile Ser Ser Leu Ser Phe Leu Asp Leu Ser Asn
                        580                 585                 590

Asn Gln Leu Ser Thr Val Lys Leu Glu Gln Leu Thr Thr Ile Trp Val
                        595                 600                 605

Leu Lys Leu Ser Asn Asn Asn Leu Gly Gly Lys Ile Pro Thr Ser Val
                        610                 615                 620

Phe Asn Ser Ser Arg Leu Asn Phe Leu Tyr Leu Asn Gly Asn Asn Phe
        625                 630                 635                 640

Trp Gly Gln Ile Ser Asp Phe Pro Leu Tyr Arg Trp Asn Val Trp Asn
                        645                 650                 655

Val Leu Asp Leu Ser Asn Asn Gln Phe Ser Gly Met Leu Pro Arg Ser
                        660                 665                 670

Phe Val Asn Phe Ser Ile Leu Gly Val Ile Asp Leu Ser Gly Asn His
                        675                 680                 685

Phe Lys Gly Pro Ile Pro Arg Asp Phe Cys Lys Phe Asp Gln Leu Glu
                        690                 695                 700

Tyr Leu Asp Leu Ser Glu Asn Asn Leu Ser Gly Tyr Ile Pro Ser Cys
        705                 710                 715                 720

Phe Ser Pro Pro Gln Ile Thr His Val His Leu Ser Lys Asn Arg Leu
                        725                 730                 735

Ser Gly Pro Leu Thr Tyr Ala Phe Phe Asn Ser Ser Tyr Leu Val Thr
                        740                 745                 750

Met Asp Leu Arg Glu Asn Ser Phe Thr Gly Ser Ile Pro Asn Trp Ile
                        755                 760                 765

Gly Asn Leu Ser Ser Leu Ser Val Leu Leu Leu Arg Ala Asn His Phe
                        770                 775                 780

Asp Gly Glu Leu Pro Ile Gln Leu Cys Leu Leu Glu Gln Leu Ser Ile
        785                 790                 795                 800

Leu Asp Val Ser His Asn Gln Leu Ser Gly Pro Leu Pro Ser Cys Leu
                        805                 810                 815

Gly Asn Leu Thr Phe Lys Lys Ser Asp Lys Lys Ala Ile Leu Glu Val
                        820                 825                 830

Ala Tyr Gly Phe Ile Ser Glu Ser Ile Glu Lys Ala Tyr Tyr Glu Ile
                        835                 840                 845

Met Gly Pro Pro Leu Val Asp Ser Val Asp Asn Leu Arg Asn Phe Phe
                        850                 855                 860

Leu Phe Asn Phe Thr Glu Glu Val Thr Glu Phe Thr Thr Lys Asn Met
        865                 870                 875                 880

Tyr Tyr Gly Tyr Lys Gly Lys Val Leu Asn Tyr Met Phe Gly Ile Asp
                        885                 890                 895
```

Leu Ser Asn Asn Asn Phe Ile Gly Ala Ile Pro Glu Phe Gly Asn
              900                 905                 910

Leu Ser Lys Ile Leu Ser Val Asn Leu Ser His Asn Asn Leu Thr Gly
          915                 920                 925

Ser Ile Pro Ala Thr Phe Ser Asn Leu Met His Ile Glu Ser Leu Asp
      930                 935                 940

Leu Ser Tyr Asn Asn Leu Asn Gly Ala Ile Pro Pro Gln Phe Thr Glu
945                 950                 955                 960

Val Thr Thr Leu Glu Val Phe Ser Val Ala His Asn Asn Leu Ser Gly
              965                 970                 975

Lys Thr Pro Glu Arg Ile Tyr Gln Phe Gly Thr Phe Asp Glu Ser Cys
          980                 985                 990

Tyr Glu Gly Asn Pro Phe Leu Cys Gly Pro Pro Leu Pro Asn Asn Cys
      995                 1000                1005

Ser Glu Lys Ala Val Val Ser Gln Pro Val Pro Asn Asp Glu Gln
    1010                1015                1020

Gly Asp Asp Gly Phe Ile Asp Met Glu Phe Tyr Ile Ser Phe
    1025                1030                1035

Gly Val Cys Tyr Thr Val Val Val Met Thr Ile Ala Ala Val Leu
    1040                1045                1050

Tyr Ile Asn Pro Tyr Trp Arg Arg Arg Trp Leu Tyr Phe Ile Glu
    1055                1060                1065

Asp Cys Ile Asp Thr Cys Tyr Tyr Phe Val Val Ala Ser Phe Arg
    1070                1075                1080

Lys Phe Ser Asn Phe Arg Arg
    1085                1090

<210> SEQ ID NO 5
<211> LENGTH: 3455
<212> TYPE: DNA
<213> ORGANISM: Populus trichocarpa

<400> SEQUENCE: 5
gcccaagtca tagcaatgtg acgagacttg tttataattc agtctttaga ctgaggattt    60
gaaactgtaa ctgaagaagc aaataaggag aaactcgaag cgaaaaaagt ttgttttctt   120
ttaccaatgt gtaactgaag aagcaaaaac aatcttctgc acgttcttat gatgattgca   180
tcgttcaaat cattgcactt tctactcggc ctgtttgttt ccttgaagct cttggcctta   240
gctcaagagg aaaaccactt catctatcat ggcttcactg gcgccaacct gctcctcagc   300
gagattgcaa aaatccatcc aaatggtctc ttagagctga caaacacttc aacacagcaa   360
attggccgtg ctttcttccc attcccttttt cagttcaaca catctttatt caacaattct   420
cggtctctct ccttctctac ccagtttgcg ttttccatgg tcccggagct gcctacccct   480
ggtggccatg gcatggcctt cacgatctct ccatctgtga acttcacagg ggcttgggca   540
actcagtact tgggaatcct caattctaca agcaatggcc tgtcttcaaa ccatctattg   600
gcagttgagc tggatgcaat tcgaagcctg gattttaaag acatcaatga caaccacgtt   660
ggaattgatg taaacgactt gacatccatt gaatctgctc cggtgaccta ctttttcaggt   720 gaggaaaacg agaataagag cttggctctc ataagtggtc ttgtgatgca cgtgtggata   780
gattacgatg aagtagagaa gctactcaat gttacggttg ctcctatcac aagaacaaaa   840
ccaaccttgc ctctcttgtc aacaccgctc gatcttctt ctgttatgtt ggattctatg   900
tacgttggtt tttcttcatc tactggagca gtggctagca gccactatat tctggggtgg   960

-continued

```
agcttcaaca gaggcggaca agctcaaagt cttgatgtgt caaagttgcc ttcacttccc      1020
catcaaagaa aatcaaggaa gaaatcacat ttaagaattc tggtcccagc aataacagca      1080
gtcattttgc tggtagcaat ctctggtgct gcttatataa taaggagtaa gaaatatgaa      1140
gaactgcgcg aagattggga acaggagtat ggtcctcaaa gattctccta caaggattta      1200
tacaaagcaa ctacaggttt cacggacagg aagttggtgg gaagtggagg ttttggaaag      1260
gtttacagag gagtattgcc ttcttccaaa atgcaagtcg cgatcaagaa agtatcccat      1320
gattccatac aaggaactaa gcagtttgtt gctgagattg ttagcatggg aaggctgagg      1380
cacaggaact tggtccagct cctaggctat tgccggagaa agggagagct cctcttggtc      1440
tatgattaca tgcccaatgg aagccttgat aaactcctat ttcgcaatga cacacccagc      1500
cttaattggg ttcagcgata tcaggtcctc agaggagttg cgtctgccct tatttacctc      1560
catgaagagt gggaacaggt tgttctgcat agagatgtga aagctagcaa tatactgtta      1620
gatgatgatt tcaatggtcg actaggagat tttgggcttg ctaaattcta tgatcgtggg      1680
gctaatcctc aaacaacctg tgtggttgga acagttggat atatcgcgcc agaggttact      1740
agaacaggaa gggccactac cagcagtgat gttttttgctt ttggcacttt tatgcttgaa      1800
atggcttgtg gaaggaaacc tgtagagcca gaacaatcag cagaaaagat gattttggtt      1860
gactgggttc ttgattcctg gaaaatagga gacattcttc gaacaggtga tccaagattg      1920
gaaggtaatt acgtggtgga ggaaatggaa ttggttttaa ggctaggtct gctttgttct      1980
ttctctacac cacaagctag gccaagcatg aggcaaattt cgcaatatct ggatgggaat      2040
gctagcctgc cagagatgcc tcttgatggt gctagcatag gtttgatgcc agttagtcat      2100
gaagagcctg gggatttcac cttgtctttc catagatcta atgattactc tgctcattcc      2160
ttctctagta ccgactcaat cctcagctgt ggtcgttgaa tcatggctta acgaggtaaa      2220
aattctttaa cctaaagact aacagctggc atgtggcaag cctggtatta gtggtgaaga      2280
ggaaggtaga ttggaatact tagagggtta ccttgtttgt gcataccata gtaatcctca      2340
aaacacaaca aagactgctc catgaggggt taattaatta gcatacaaac ataggtataa      2400
tttatgattt aagcaaaaca catggttgaa atagtacaat gtttgatgaa acaatgctgg      2460
tcaatgatgg ccgtttagct tcttccattc tcctcagtgc tctaaccccca ccccacaatt      2520 caactcaact atgcctcatt cccaaactag ttagaatcag tttcacagat cttccttctc      2580
cattcattta gtccttgttc cttttttgat aaaactctcc acttacttct gttatggact      2640
caaaagatta atcacttatg cctacctcgt ttttacatgg aaggttaatt acatattgaa      2700
ctattctgac ttctgatata gtgatctgca gaaagcatag gcttcagtca acttttaaa      2760 atacagaaaa tccaacaccc agtatcatcg attatcctaa ctagagtgca gttcagtgtg      2820
atatggctgc tggccgggtg gtttattcac agactagtag tggaataaaa aaaaatggtg      2880
ataatgtatc ttgatgctga tgttatacac acatataact gttttaatct ttctacaaac      2940
agtcaagatt gcaaaaacca cgttcaagga agaaagaaga tatagacagc agctttgtag      3000
gctgaaaagg gtttaaaaca ccagccaaga aaaagtaaaa gaaacattgc aacaaaattt      3060
gcaataagaa ggcagcaata ttaataatcc tgctttcaga aagagtgtag atatccaatt      3120
acctaatgaa aaggctagag atgtctgatc aataagcttc catcatttct cctggttatt      3180
gggtcacagc ttgttgcgga tgaggcagcg caacctcttg ggacagggta cgttcacttg      3240
ttgtgcagcc tttcctgcat ccaagtaccc taagtgatta aacagactct aatttattaa      3300
```

-continued

```
gcactggaga ttagttgtaa tgatcaactt taattctaat ttgggtccct caaagaactt    3360
acacagagca agttaaacat gaagtgactt gattccatct taggaaaaac aagctcgtac    3420
tggaaagatt taacagacat tagcctcccc gaaaa                               3455
```

<210> SEQ ID NO 6
<211> LENGTH: 676
<212> TYPE: PRT
<213> ORGANISM: Populus trichocarpa

<400> SEQUENCE: 6

```
Met Met Ile Ala Ser Phe Lys Ser Leu His Phe Leu Gly Leu Phe
1               5                   10                  15

Val Ser Leu Lys Leu Leu Ala Leu Ala Gln Glu Glu Asn His Phe Ile
            20                  25                  30

Tyr His Gly Phe Thr Gly Ala Asn Leu Leu Leu Ser Glu Ile Ala Lys
        35                  40                  45

Ile His Pro Asn Gly Leu Leu Glu Leu Thr Asn Thr Ser Thr Gln Gln
50                  55                  60

Ile Gly Arg Ala Phe Phe Pro Phe Pro Phe Gln Phe Asn Thr Ser Leu
65                  70                  75                  80

Phe Asn Asn Ser Arg Ser Leu Ser Phe Ser Thr Gln Phe Ala Phe Ser
                85                  90                  95

Met Val Pro Glu Leu Pro Thr Leu Gly Gly His Gly Met Ala Phe Thr
            100                 105                 110

Ile Ser Pro Ser Val Asn Phe Thr Gly Ala Trp Ala Thr Gln Tyr Leu
        115                 120                 125

Gly Ile Leu Asn Ser Thr Ser Asn Gly Leu Ser Ser Asn His Leu Leu
130                 135                 140

Ala Val Glu Leu Asp Ala Ile Arg Ser Leu Asp Phe Lys Asp Ile Asn
145                 150                 155                 160

Asp Asn His Val Gly Ile Asp Val Asn Asp Leu Thr Ser Ile Glu Ser
                165                 170                 175

Ala Pro Val Thr Tyr Phe Ser Gly Glu Glu Asn Glu Asn Lys Ser Leu
            180                 185                 190

Ala Leu Ile Ser Gly Leu Val Met His Val Trp Ile Asp Tyr Asp Glu
        195                 200                 205

Val Glu Lys Leu Leu Asn Val Thr Val Ala Pro Ile Thr Arg Thr Lys
210                 215                 220

Pro Thr Leu Pro Leu Leu Ser Thr Pro Leu Asp Leu Ser Ser Val Met
225                 230                 235                 240

Leu Asp Ser Met Tyr Val Gly Phe Ser Ser Thr Gly Ala Val Ala
                245                 250                 255

Ser Ser His Tyr Ile Leu Gly Trp Ser Phe Asn Arg Gly Gly Gln Ala
            260                 265                 270

Gln Ser Leu Asp Val Ser Lys Leu Pro Ser Leu Pro His Gln Arg Lys
        275                 280                 285

Ser Arg Lys Lys Ser His Leu Arg Ile Leu Val Pro Ala Ile Thr Ala
290                 295                 300

Val Ile Leu Leu Val Ala Ile Ser Gly Ala Ala Tyr Ile Ile Arg Ser
305                 310                 315                 320

Lys Lys Tyr Glu Glu Leu Arg Glu Asp Trp Glu Gln Glu Tyr Gly Pro
                325                 330                 335

Gln Arg Phe Ser Tyr Lys Asp Leu Tyr Lys Ala Thr Thr Gly Phe Thr
            340                 345                 350
```

Asp Arg Lys Leu Val Gly Ser Gly Gly Phe Gly Lys Val Tyr Arg Gly
            355                 360                 365

Val Leu Pro Ser Ser Lys Met Gln Val Ala Ile Lys Lys Val Ser His
    370                 375                 380

Asp Ser Ile Gln Gly Thr Lys Gln Phe Val Ala Glu Ile Val Ser Met
385                 390                 395                 400

Gly Arg Leu Arg His Arg Asn Leu Val Gln Leu Leu Gly Tyr Cys Arg
                405                 410                 415

Arg Lys Gly Glu Leu Leu Leu Val Tyr Asp Tyr Met Pro Asn Gly Ser
            420                 425                 430

Leu Asp Lys Leu Leu Phe Arg Asn Asp Thr Pro Ser Leu Asn Trp Val
        435                 440                 445

Gln Arg Tyr Gln Val Leu Arg Gly Val Ala Ser Ala Leu Ile Tyr Leu
    450                 455                 460

His Glu Glu Trp Glu Gln Val Val Leu His Arg Asp Val Lys Ala Ser
465                 470                 475                 480

Asn Ile Leu Leu Asp Asp Phe Asn Gly Arg Leu Gly Asp Phe Gly
                485                 490                 495

Leu Ala Lys Phe Tyr Asp Arg Gly Ala Asn Pro Gln Thr Thr Cys Val
            500                 505                 510

Val Gly Thr Val Gly Tyr Ile Ala Pro Glu Val Thr Arg Thr Gly Arg
        515                 520                 525

Ala Thr Thr Ser Ser Asp Val Phe Ala Phe Gly Thr Phe Met Leu Glu
    530                 535                 540

Met Ala Cys Gly Arg Lys Pro Val Glu Pro Glu Gln Ser Ala Glu Lys
545                 550                 555                 560

Met Ile Leu Val Asp Trp Val Leu Asp Ser Trp Lys Ile Gly Asp Ile
                565                 570                 575

Leu Arg Thr Gly Asp Pro Arg Leu Glu Gly Asn Tyr Val Val Glu Glu
            580                 585                 590

Met Glu Leu Val Leu Arg Leu Gly Leu Leu Cys Ser Phe Ser Thr Pro
        595                 600                 605

Gln Ala Arg Pro Ser Met Arg Gln Ile Ser Gln Tyr Leu Asp Gly Asn
    610                 615                 620

Ala Ser Leu Pro Glu Met Pro Leu Asp Gly Ala Ser Ile Gly Leu Met
625                 630                 635                 640

Pro Val Ser His Glu Glu Pro Gly Asp Phe Thr Leu Ser Phe His Arg
                645                 650                 655

Ser Asn Asp Tyr Ser Ala His Ser Phe Ser Ser Thr Asp Ser Ile Leu
            660                 665                 670

Ser Cys Gly Arg
        675

<210> SEQ ID NO 7
<211> LENGTH: 4023
<212> TYPE: DNA
<213> ORGANISM: Populus trichocarpa

<400> SEQUENCE: 7
atgtgtgtta ttacaaagcc aagtttctgg ttctttgtgc tgttgttgct attcgtttcc      60
cactggaatt gcttctccat tgaaggtgat acccttttga ttggccagtc tctctctgca     120
agccagacac tgtatatctca aaatggcatt tttgaactcg gtttcttcaa gccaggcgct     180
tctttaaaca tttaccttgg aatttggtat aagaactccg cagataagat gattgtttgg     240

```
gtggcaaaca gggagagccc tttaaacaac cctgcttcat cgaagcttga attatcaccg    300
gatggcattc ttgtcctact gacaaatttc accaaaacag tttggtcaac agctcttgca    360
tcttcagtgc cgaataacag tacagcacaa gcagcacttc ttgataatgg aaactttgtc    420
attaaagatg gctcaaaccc atccgctatt tactggcaga gttttgacaa tccaactgat    480
acattgctac ctggtggaaa gcttggaatc aacaagcaca ctgggaaagt gcagaagctt    540
atttcctgga aaaacccaga agatcctgca ccaggtatgt tctcgattac gatggacccc    600
aatggcagta gtcagatttt tatagagtgg aacaaggtca cacatgtatt ggagcagtgg    660
ggtttggaat ggacaaagat tttccatggt tcctgagatg aatttgaact attatttcaa    720
ttatagttat atatcgaatg aaaatgaaag ctatttcacc ttttctgtgt acaatgctga    780
aatgctctca agatacgtga ttgatgtttc aggacaaatc aaacaattaa attggttagc    840
aggtgttagg aattggtcag aattctgggc ccagcccagt gaccaagctg tgtttatgg     900 tttatgcggg gttttggag tcttcatgg aaactcatcg agctcttgtg aatgcttgaa      960
aggttttgaa ccattagtac aaaatgattg gtcaagcggt tgtgttagga aatctccttt    1020
gcagtgtcaa aataagaaaa gtactgggaa aaagatggg ttcctgaaga tgtcgattct     1080
gacattacca gaaaattcaa agcatatca aaagtgagt gttgcaagat gtagattgta      1140
ttgcatgaaa aattgttatt gcgtggctta tgcctataat agcagtgggt gttttttatg    1200
ggaaggagat cttataaact aaaacagtc agagattgct gctgggaggg ctggagcaga     1260
aatttacatc agacttgctg cttctgagct tgaacctcag attggtagtg gcagtatccg    1320
aacaggtaag gtagaaaggt tttatatata tagttataaa tgatccaata gatgttgagc    1380
aatgatttct tacaaaataa cagcatagtc tttccagata aaatggtgga tgaaatgttt    1440
cctgtagaga agtgtggaag acataaccta acttcccata tctttctatc aaaataaaaa    1500
catcttaatt cgttaaaagt aaatttcttg gtttatgatt tggttaatgt ttgatctatg    1560
cttacaagta ggcaaatatc aaatggaaaa tacggacaac cttggctgtg gctgttccag    1620
taactctgat tacccttaggc ctcttcatat acttcagctg tctgcgcaag ggaaagctca    1680
tacacaaagg tacatcctgt tcttgcttta atttctgctg tctcctggta ggctttaatt    1740
aaccctcaag ttactggtga ctagaaaaaa ccctcctttg taattgatta tgtcttaggt    1800
atgcagatgg taaggttcat tttgatggag atagagggac agaaatgttt tgttttgcat    1860
aaaatatttt accgaaataa gttttatttt tttatttatt tatatatgtt tgtttcttgt    1920
aaaatatctg acaagaagag tgatcaatat aaattatttt atagttaacc ttcatattag    1980
ttcatttatt aaaaatattt ctcatctctt aaaatttat aaaatatttt atgaaaaata     2040
aaacaatcac aatatcttac aacaaattta tccatataaa atgttaggaa ggtaaaatat    2100
tttatgtcaa acaaacacca aagtttctta tttatgaaaa aaactgacat ttagaatacc    2160
ttttaacgtc cgaattgtgg ttatgctaac ctgaagttgt tacctttttt gcttgatatt    2220
atcagaatag ctggatattg ttcaacaaag tgaatgtgtt caatcatttt tattttttata    2280 tttttcttga aacagcgaag gaacgtgcaa gtcacaattt attgcgtttt aatttcgatg    2340
ccgatcctaa ctcaactacc aatgaatcta gctctgttga caatcggaag aaaagatgga    2400
gtaaaaatat agaatttcca ttattcagtt atgagagcgt atcagtggca actggacagt    2460
tctcagataa gctggagag ggaggattcg gacctgttta aaggtaaat ttacgttcaa      2520 atgagaaatg ctgattttcc taagaaaaat gttaaaatag ttcgaatgaa ctttcagaat    2580
```

-continued

```
gactttggt  tcatttaaca  gggcaaatta  cccacgggac  tggaaatagc  agtgaagagg   2640
ctttcagaaa  gatctgggca  ggggcttgag  gagttcagaa  atgagacaac  tctaatcgcc   2700
aaactccagc  accggaatct  tgtcaggcta  ctgggttcct  gtattgaatg  ggatgagaaa   2760
atgctaatct  atgagtacat  gccaaataaa  agcttggatt  tctttctcta  tggtcagcat   2820
ttagttcttt  tctaatttca  ttaactttc   aaatgcttca  agaaatttat  aacagatttg   2880
tgtataaaat  ataacagat   gcaaacagag  gacaaatctt  agattggggt  gcacggattc   2940
ggataatcga  aggaattgct  caaggccttc  tgtatctaca  tagatactcg  cggttacgaa   3000
tcattcacag  ggatttaaag  cctagcaaca  ttctattaga  cagtgagatg  aatccaaaaa   3060
tatccgattt  cgggatggct  cgaattttcg  gaggcaacga  aactcaagca  cacaccaaca   3120
ggatcgttgg  aacatagtaa  gtttcttaaa  ttctgttttc  caggacatgc  tacttaacat   3180
gatctgcgct  gaccttttca  aatgttagtg  gctatatgtc  ccctgaatat  gctatggagg   3240
gtctcttctc  aataaaatct  gatgtgttta  gcttcggggt  gctggtactt  gagattgtca   3300
gcggcaagaa  gaacactagt  ttctaccaca  gcgacaccct  ccatcttctt  ggacatgtgg   3360
ggagctttca  tacaccctct  tttctttta   ttcctccttg  aattgtattt  gaatactttc   3420
ctagtctcca  cactaatggt  gcagcatttg  cgttgttata  caatagacat  ggaagttatg   3480
gaattctaat  aaagctttgg  acttgatgga  tccaatcctg  ggagatcctc  cttcaactgc   3540
tacgctgttg  agatacataa  acatagggct  tctttgtgtc  caggaaagtc  ctgctgatcg   3600
gcctacaatg  tctgatgtta  tatccatgat  tgcaaacgaa  cacgtagctc  tcccagaacc   3660
aaagcaacct  gcttttgttg  catgcagaaa  catggcagaa  caaggaccat  tgatgagctc   3720
ttctggggta  ccttccgcga  ataatgtgac  aataacagcg  atagatggga  gatagttttt   3780
tcatcaagag  gtctaaagga  catgaagcta  cttcaatatc  agagcgagga  agctatgagt   3840
atggagctta  gatcaagctt  atttgtataa  gttctccgat  ttgaatcgta  caatagtttg   3900
tttcagtttt  tcctattatt  ctcgttgtat  tgaaacatga  acaaaatcaa  atcaagtatt   3960
cataaaacac  atttaattca  gatcttaaat  atattaaaaa  ctcatttcc  ttttagtaca   4020 aat                                                                    4023
```

<210> SEQ ID NO 8
<211> LENGTH: 724
<212> TYPE: PRT
<213> ORGANISM: Populus trichocarpa

<400> SEQUENCE: 8

```
Met Cys Val Ile Thr Lys Pro Ser Phe Trp Phe Val Leu Leu Leu
1               5                   10                  15

Leu Phe Val Ser His Trp Asn Cys Phe Ser Ile Glu Gly Asp Thr Leu
                20                  25                  30

Leu Ile Gly Gln Ser Leu Ser Ala Ser Gln Thr Leu Ile Ser Gln Asn
            35                  40                  45

Gly Ile Phe Glu Leu Gly Phe Phe Lys Pro Gly Ala Ser Leu Asn Ile
        50                  55                  60

Tyr Leu Gly Ile Trp Tyr Lys Asn Ser Ala Asp Lys Met Ile Val Trp
65                  70                  75                  80

Val Ala Asn Arg Glu Ser Pro Leu Asn Asn Pro Ala Ser Ser Lys Leu
                85                  90                  95

Glu Leu Ser Pro Asp Gly Ile Leu Val Leu Leu Thr Asn Phe Thr Lys
            100                 105                 110
```

```
Thr Val Trp Ser Thr Ala Leu Ala Ser Ser Val Pro Asn Ser Thr
            115                 120                 125

Ala Gln Ala Ala Leu Leu Asp Asn Gly Asn Phe Val Ile Lys Asp Gly
130                 135                 140

Ser Asn Pro Ser Ala Ile Tyr Trp Gln Ser Phe Asp Asn Pro Thr Asp
145                 150                 155                 160

Thr Leu Leu Pro Gly Gly Lys Leu Gly Ile Asn Lys His Thr Gly Lys
                165                 170                 175

Val Gln Lys Leu Ile Ser Trp Lys Asn Pro Glu Asp Pro Ala Pro Gly
            180                 185                 190

Met Phe Ser Ile Thr Met Asp Pro Asn Gly Ser Ser Gln Ile Phe Ile
            195                 200                 205

Glu Trp Asn Lys Met Asn Leu Asn Tyr Tyr Phe Asn Tyr Ser Tyr Ile
            210                 215                 220

Ser Asn Glu Asn Glu Ser Tyr Phe Thr Phe Ser Val Tyr Asn Ala Glu
225                 230                 235                 240

Met Leu Ser Arg Tyr Val Ile Asp Val Ser Gly Gln Ile Lys Gln Leu
                245                 250                 255

Asn Trp Leu Ala Gly Val Arg Asn Trp Ser Glu Phe Trp Ala Gln Pro
            260                 265                 270

Ser Asp Gln Ala Gly Val Tyr Gly Leu Cys Gly Val Phe Gly Val Phe
            275                 280                 285

His Gly Asn Ser Ser Ser Cys Glu Cys Leu Lys Gly Phe Glu Pro
            290                 295                 300

Leu Val Gln Asn Asp Trp Ser Ser Gly Cys Val Arg Lys Ser Pro Leu
305                 310                 315                 320

Gln Cys Gln Asn Lys Lys Ser Thr Gly Lys Lys Asp Gly Phe Leu Lys
                325                 330                 335

Met Ser Ile Leu Thr Leu Pro Glu Asn Ser Lys Ala Tyr Gln Lys Val
            340                 345                 350

Ser Val Ala Arg Cys Arg Leu Tyr Cys Met Lys Asn Cys Tyr Cys Val
            355                 360                 365

Ala Tyr Ala Tyr Asn Ser Ser Gly Cys Phe Leu Trp Glu Gly Asp Leu
370                 375                 380

Ile Asn Leu Lys Gln Ser Glu Ile Ala Ala Gly Arg Ala Gly Ala Glu
385                 390                 395                 400

Ile Tyr Ile Arg Leu Ala Ala Ser Glu Leu Glu Pro Gln Ile Gly Ser
                405                 410                 415

Gly Ser Ile Arg Thr Gly Lys Gly Lys Leu Pro Thr Gly Leu Glu Ile
            420                 425                 430

Ala Val Lys Arg Leu Ser Glu Arg Ser Gly Gln Gly Leu Glu Glu Phe
            435                 440                 445

Arg Asn Glu Thr Thr Leu Ile Ala Lys Leu Gln His Arg Asn Leu Val
450                 455                 460

Arg Leu Leu Gly Ser Cys Ile Glu Trp Asp Glu Lys Met Leu Ile Tyr
465                 470                 475                 480

Glu Tyr Met Pro Asn Lys Ser Leu Asp Phe Phe Leu Tyr Asp Ala Asn
                485                 490                 495

Arg Gly Gln Ile Leu Asp Trp Gly Ala Arg Ile Arg Ile Ile Glu Gly
            500                 505                 510

Ile Ala Gln Gly Leu Leu Tyr Leu His Arg Tyr Ser Arg Leu Arg Ile
            515                 520                 525

Ile His Arg Asp Leu Lys Pro Ser Asn Ile Leu Leu Asp Ser Glu Met
```

```
              530                 535                 540
Asn Pro Lys Ile Ser Asp Phe Gly Met Ala Arg Ile Phe Gly Gly Asn
545                 550                 555                 560

Glu Thr Gln Ala His Thr Asn Arg Ile Val Gly Thr Tyr Gly Tyr Met
                565                 570                 575

Ser Pro Glu Tyr Ala Met Glu Gly Leu Phe Ser Ile Lys Ser Asp Val
                580                 585                 590

Phe Ser Phe Gly Val Leu Val Leu Glu Ile Val Ser Gly Lys Lys Asn
                595                 600                 605

Thr Ser Phe Tyr His Ser Asp Thr Leu His Leu Leu Gly His Thr Trp
                610                 615                 620

Lys Leu Trp Asn Ser Asn Lys Ala Leu Asp Leu Met Asp Pro Ile Leu
625                 630                 635                 640

Gly Asp Pro Pro Ser Thr Ala Thr Leu Leu Arg Tyr Ile Asn Ile Gly
                645                 650                 655

Leu Leu Cys Val Gln Glu Ser Pro Ala Asp Arg Pro Thr Met Ser Asp
                660                 665                 670

Val Ile Ser Met Ile Ala Asn Glu His Val Ala Leu Pro Glu Pro Lys
                675                 680                 685

Gln Pro Ala Phe Val Ala Cys Arg Asn Met Ala Glu Gln Gly Pro Leu
                690                 695                 700

Met Ser Ser Ser Gly Val Pro Ser Ala Asn Asn Val Thr Ile Thr Ala
705                 710                 715                 720

Ile Asp Gly Arg

<210> SEQ ID NO 9
<211> LENGTH: 2395
<212> TYPE: DNA
<213> ORGANISM: Populus trichocarpa

<400> SEQUENCE: 9
tcgatggaat aaataaattc tcatgcaagg acgcgtgtac tacagtactg taaaggactc    60
gcccatctaa ggactacatg agttttctga aaggccaaaa ctatatcagc acatgcagat   120
aaaatcttaa gaggagtgtg gagatgatga actattcatc agaaatggtt acctgtttgt   180 tctactttt cattgtcttc cttgcaggcc atggagcaag cttgaataac acaggatcat   240
gtggaaaccg tggccctgac atccgatttc ctttccgaaa catggacaaa caaccagacc   300
actgtggttg tcctgggttt gatctatcct gctcagatga acacagcaca gtgcttaagc   360
tgccaactgg attgagtttc ctcatcgaaa gaattgacta tagacatcaa cttatttatg   420
caagggatcc tcaaggttgc tttccagggc aacgtttaaa cttcagttta ggggcttctc   480
acttccaaat taagaacgat tggctgtatg attggacctt gttcaattgt tcactttcta   540
gtgagaaaag gtctgggttc atgtataaaa tcccatgtct gagtactttt aaccatgaag   600
tttatgcctt tgactcaagt accaccatca gtgactctga tttgttatct gtaccaaga   660 tgtacaacat ttatggaatt tcatatagta tgataccgga agaaaatgat gttcttacta   720
tgtcttggtc caatccaact tgtgaatctt ctgaaactga atgctacctt cagcacacta   780
aaggtatgct tttctatctt ccttttcttt tttcaaatta aactcttttc ttctttgttg   840
ctttcatgat tttaccaatt gccttaaagg gagaagctaa taagtattcg atcccttaca   900
gatgtgcggc caaagctact gattactggt tagtagtctg ctcaaatctc cacctcaatt   960
ttacacttgg ttcaatacat tacttcccaa aaaaaaaaaa aagagtttcc tgactcagaa  1020
```

-continued

```
tgttgatatg caggtgtgat tttaggattc ttccttttg caatagtgat tattgcactc    1080
taccgcgcct atagcaacga taaaacacaa agagaatatc aagccagggt tgaaatgttt    1140
ttggatgatt acagatcact gaatcccact aggtactcct acgctgatct caagaggatc    1200
acaaatcaat tcggtgatga attgggccaa ggagcttatg gaaccgtgtt caaaggaaag    1260
ctaaccactg aaattgctgt agctgtgaag ctcctcaata attccatagg aaaggggag     1320 gaattcatca atgaagtggg aacaatggca aggatccacc atgtcaatgt tgttcgcttg    1380
atcggtttct gtgctgatgg atttagacga gctctagttt atgagtactt gccaaatgac    1440
tcgttacaga agttcatatc ctcagcagac tcaaggaacc atttccttgg ctgggaaagg    1500
ttgaatcgtg ttgctctagg catagccaag gggattgaat atcttcacca ggggtgtgat    1560
caaagaatcc tccattttga tatcaaacca cagaatatcc tgcttgacaa cgaattcaat    1620
cccaaaatcg ccgattttgg gatggctaag ttgtgttcca aggataaaag tgctatttcc    1680
atgacgactg ctaggggac tgttggctac attgccccag aagtgttctc gaggaacttc     1740
gggaatgttt cctataaatc agatgtttac agctttggaa tgttagtgtt ggaaatggtt    1800
ggaggaagga agaacgtcga tgatacagca gaaaatggcg accagatata cttcccggaa    1860
tggatttata atctcttaga aaggaagaa gacctgcggt ttcatatcga tggagaagaa     1920
gatgctaaaa ttgcaaagaa actagcaatt gtggggctgt ggtgcattca gtggaaccca    1980
gcagagcgtc cttccatgaa aactgttgtc caaatgcttg aagggaagg tgaaaactta     2040 acaaagcctc ctgatccttt tagctcctct gtccctaaga gaacaagtgc aggccacatg    2100
ccagcgagac gccttcacca agagttggca gccatctcag aaatagagtg atcagaaatt    2160 tactctttc agtaataaca tattagtgag caataatgaa agaaattgtt gtgacctgtg     2220
agataggttc atggattatg tgtaaactta ttggtctagt actagcttct tcttttctgt    2280
caattcacct tctaagttct taattaccaa tgcagtgtca attcacagtt tgagatgtat    2340
caaatcaata aattaaactg tgtaaatatc tttgcaaatc caacccttta ttcat         2395
```

<210> SEQ ID NO 10
<211> LENGTH: 594
<212> TYPE: PRT
<213> ORGANISM: Populus trichocarpa

<400> SEQUENCE: 10

```
Met Met Asn Tyr Ser Ser Glu Met Val Thr Cys Leu Phe Tyr Phe Phe
1               5                   10                  15

Ile Val Phe Leu Ala Gly His Gly Ala Ser Leu Asn Asn Thr Gly Ser
            20                  25                  30

Cys Gly Asn Arg Gly Pro Asp Ile Arg Phe Pro Phe Arg Asn Met Asp
        35                  40                  45

Lys Gln Pro Asp His Cys Gly Cys Pro Gly Phe Asp Leu Ser Cys Ser
    50                  55                  60

Asp Asp Asn Ser Thr Val Leu Lys Leu Pro Thr Gly Leu Ser Phe Leu
65                  70                  75                  80

Ile Glu Arg Ile Asp Tyr Arg His Gln Leu Ile Tyr Ala Arg Asp Pro
                85                  90                  95

Gln Gly Cys Phe Pro Gly Gln Arg Leu Asn Phe Ser Leu Gly Ala Ser
            100                 105                 110

His Phe Gln Ile Lys Asn Asp Trp Leu Tyr Asp Trp Thr Leu Phe Asn
        115                 120                 125

Cys Ser Leu Ser Ser Glu Lys Arg Ser Gly Phe Met Tyr Lys Ile Pro
```

```
            130                 135                 140
Cys Leu Ser Thr Phe Asn His Glu Val Tyr Ala Phe Asp Ser Ser Thr
145                 150                 155                 160

Thr Ile Ser Asp Ser Asp Leu Leu Ser Cys Thr Lys Met Tyr Asn Ile
                165                 170                 175

Tyr Gly Ile Ser Tyr Ser Met Ile Pro Glu Asn Asp Val Leu Thr
            180                 185                 190

Met Ser Trp Ser Asn Pro Thr Cys Glu Ser Ser Glu Thr Glu Cys Tyr
                195                 200                 205

Leu Gln His Thr Lys Asp Val Arg Pro Lys Leu Leu Ile Thr Gly Val
            210                 215                 220

Ile Leu Gly Phe Phe Leu Phe Ala Ile Val Ile Ala Leu Tyr Arg
225                 230                 235                 240

Ala Tyr Ser Asn Asp Lys Thr Gln Arg Glu Tyr Gln Ala Arg Val Glu
                245                 250                 255

Met Phe Leu Asp Asp Tyr Arg Ser Leu Asn Pro Thr Arg Tyr Ser Tyr
                260                 265                 270

Ala Asp Leu Lys Arg Ile Thr Asn Gln Phe Gly Asp Glu Leu Gly Gln
            275                 280                 285

Gly Ala Tyr Gly Thr Val Phe Lys Gly Lys Leu Thr Thr Glu Ile Ala
290                 295                 300

Val Ala Val Lys Leu Leu Asn Asn Ser Ile Gly Lys Gly Glu Glu Phe
305                 310                 315                 320

Ile Asn Glu Val Gly Thr Met Ala Arg Ile His His Val Asn Val Val
                325                 330                 335

Arg Leu Ile Gly Phe Cys Ala Asp Gly Phe Arg Arg Ala Leu Val Tyr
            340                 345                 350

Glu Tyr Leu Pro Asn Asp Ser Leu Gln Lys Phe Ile Ser Ser Ala Asp
            355                 360                 365

Ser Arg Asn His Phe Leu Gly Trp Glu Arg Leu Asn Arg Val Ala Leu
            370                 375                 380

Gly Ile Ala Lys Gly Ile Glu Tyr Leu His Gln Gly Cys Asp Gln Arg
385                 390                 395                 400

Ile Leu His Phe Asp Ile Lys Pro Gln Asn Ile Leu Leu Asp Asn Glu
                405                 410                 415

Phe Asn Pro Lys Ile Ala Asp Phe Gly Met Ala Lys Leu Cys Ser Lys
                420                 425                 430

Asp Lys Ser Ala Ile Ser Met Thr Thr Ala Arg Gly Thr Val Gly Tyr
            435                 440                 445

Ile Ala Pro Glu Val Phe Ser Arg Asn Phe Gly Asn Val Ser Tyr Lys
            450                 455                 460

Ser Asp Val Tyr Ser Phe Gly Met Leu Val Leu Glu Met Val Gly Gly
465                 470                 475                 480

Arg Lys Asn Val Asp Asp Thr Ala Glu Asn Gly Asp Gln Ile Tyr Phe
                485                 490                 495

Pro Glu Trp Ile Tyr Asn Leu Leu Glu Lys Glu Glu Asp Leu Arg Phe
                500                 505                 510

His Ile Asp Gly Glu Glu Asp Ala Lys Ile Ala Lys Lys Leu Ala Ile
            515                 520                 525

Val Gly Leu Trp Cys Ile Gln Trp Asn Pro Ala Glu Arg Pro Ser Met
530                 535                 540

Lys Thr Val Val Gln Met Leu Glu Gly Glu Gly Glu Asn Leu Thr Lys
545                 550                 555                 560
```

Pro Pro Asp Pro Phe Ser Ser Val Pro Lys Arg Thr Ser Ala Gly
                565                 570                 575

His Met Pro Ala Arg Arg Leu His Gln Glu Leu Ala Ala Ile Ser Glu
        580                 585                 590

Ile Glu

<210> SEQ ID NO 11
<211> LENGTH: 2363
<212> TYPE: DNA
<213> ORGANISM: Populus trichocarpa

<400> SEQUENCE: 11

| | |
|---|---|
| gctgagaaaa atgcaatgca atccctccat tgttaaaagg atcccttcga ctccacttct | 60 |
| ggtcactact tagccctagg agacactaaa gagagcaccc gagggtctac atgctccaat | 120 |
| cttggcctct actcagctct agttgagaga ccagagagag cacacccaaa ccccagaaaa | 180 |
| tggattcttc ttggcatggg aatttaccag caaacagaaa gaaggcgata gatgagctcg | 240 |
| ttagaggtca agaaattgcg gcacaactta aacttgtaat gaacaagtct ataggggttg | 300 |
| atgagtctgt gtttgctgag gatcttgtca agaaaatcat gaattctttc aacagttctc | 360 |
| tttatatatt aaatgggggt gagtttgatg aggttgcctc tcaaattcca caagtgggtt | 420 |
| cgccttgttg ggatggccgg aagtcgtcga aggattccgg ggagagtggc aggggtactg | 480 |
| ccgagttgaa ggtgaaggac aggagaggat gttacaagag aaggtaatta attaattaca | 540 |
| aataattaat atatgctgct gatcattatt gataaaaacc gcattaataa tattattttt | 600 |
| catttacaat tccattagcc aagtagagct tgttgaaata cggtcaagga gtagggatcc | 660 |
| atagttaaac tataatctag ccctctcatc tgagtctaga gagtctccga tttggatttt | 720 |
| tcttttccga ctctattttt attttatttt attttttga aaaaaattta ggaatcaaac | 780 |
| taattaagga tgatctttat tattcttttt gttaaaaaga atttagatgc ctatatatta | 840 |
| tttttcatta atctcctttc ctaaaggtca tgatggatgt agatgggata aatttacccc | 900 |
| atatgtgttg cttgtaatta tattttcttt taggctcagg ccccattcct catgcttgaa | 960 |
| aaaaaaaaga aaaaaaaga agaaaccaac gaagaacttc caagttgcta gttaggacac | 1020 |
| caagaaacaa gaaggtatct ttgctttgag tggacaatgt ttttggtccc ctccttggca | 1080 |
| agctcgaaat taatttacta aatatcatgg ttggatattg ccgatttttc tatgtttatt | 1140 |
| cttcatataa aggtacttgt aatattattt ttacttgatg atgttataac ttgattataa | 1200 |
| gaataaataa tatcaaaact aaaattaatc tctaaattat aattaattaa tgcattttc | 1260 |
| tagcaattag tttttttta tttcatccca attacactaa aattgaattt tattacttgc | 1320 |
| agaaaaagtt cccactcaag aacagatgac tccactactc taaccgatga tggccatgca | 1380 |
| tggagaaaat atggacagaa agtgatcctc aatgctaaat atccaaggta tatatatata | 1440 |
| attaattttca agactgaatt tcgaacataa ttaaccaatc catattttaa ttcttatctc | 1500 |
| ttaatcatca aatttctagg aaaacctagt taatgatcga acaattaatg aaacgcaata | 1560 |
| ttgctgctgt gccctacagg aactacttca ggtgcactca caagtatgat caacaatgtc | 1620 |
| aagcaatcaa gcaagtgcaa agaattcaag aagaacctcc tctataccgt acaacatatt | 1680 |
| atgggcatca cacgtgcaag aatttgctaa aagcttctca atttgtcttg gatccaagtg | 1740 |
| atcaccacga tatagattcc tccatactga taagctttaa gagcaatggt gatcacgctt | 1800 |
| cgaacaagcc aagcaactcc ctcctcacat ccttccaaac agtaaaacaa gaatgttgcc | 1860 |

-continued

```
acaaggagga tgacatgaac ataccaatta gttatgatcc aaccacccag tataataatc    1920
aagcatcatc ctctgattat ctcttgtcac ctgatgatta tatgtctgca tttgatcacg    1980
gcgatgtgat ttctggggtc aactcatctt gcactacgag ctcacacagt ctggacatgg    2040
atggtatcat gatggaatct gctgatttcg atgatgatgg tgttttcgga ttttaacctt    2100
gatagataat tattttcacg acattagata ttgcagcttc tttgtaattt ccgcctagta    2160
atcaagaatg tcctggttat tttctttgac aagtgttaga agctgcctag ctaggtagct    2220
aggttagcac aatgtagaaa ctagaaaggt cgatgttttc tctttctttt tttgcttttg    2280
gactgtgtac ttaatttgct tgaaaattaa ggaaataatc gaggtgaagt actttccagt    2340
ctctatcagt tgcatttcca agt                                            2363
```

<210> SEQ ID NO 12
<211> LENGTH: 321
<212> TYPE: PRT
<213> ORGANISM: Populus trichocarpa

<400> SEQUENCE: 12

```
Met Asp Ser Ser Trp His Gly Asn Leu Pro Ala Asn Arg Lys Lys Ala
1               5                   10                  15

Ile Asp Glu Leu Val Arg Gly Gln Glu Ile Ala Ala Gln Leu Lys Leu
            20                  25                  30

Val Met Asn Lys Ser Ile Gly Val Asp Glu Ser Val Phe Ala Glu Asp
        35                  40                  45

Leu Val Lys Lys Ile Met Asn Ser Phe Asn Ser Ser Leu Tyr Ile Leu
    50                  55                  60

Asn Gly Gly Glu Phe Asp Glu Val Ala Ser Gln Ile Pro Gln Val Gly
65                  70                  75                  80

Ser Pro Cys Trp Asp Gly Arg Lys Ser Ser Lys Asp Ser Gly Glu Ser
                85                  90                  95

Gly Arg Gly Thr Ala Glu Leu Lys Val Lys Asp Arg Arg Gly Cys Tyr
            100                 105                 110

Lys Arg Arg Lys Ser Ser His Ser Arg Thr Asp Asp Ser Thr Thr Leu
        115                 120                 125

Thr Asp Asp Gly His Ala Trp Arg Lys Tyr Gly Gln Lys Val Ile Leu
    130                 135                 140

Asn Ala Lys Tyr Pro Arg Asn Tyr Phe Arg Cys Thr His Lys Tyr Asp
145                 150                 155                 160

Gln Gln Cys Gln Ala Ile Lys Gln Val Gln Arg Ile Gln Glu Glu Pro
                165                 170                 175

Pro Leu Tyr Arg Thr Thr Tyr Tyr Gly His His Thr Cys Lys Asn Leu
            180                 185                 190

Leu Lys Ala Ser Gln Phe Val Leu Asp Pro Ser Asp His His Asp Ile
        195                 200                 205

Asp Ser Ser Ile Leu Ile Ser Phe Lys Ser Asn Gly Asp His Ala Ser
    210                 215                 220

Asn Lys Pro Ser Asn Ser Leu Leu Thr Ser Phe Gln Thr Val Lys Gln
225                 230                 235                 240

Glu Cys Cys His Lys Glu Asp Asp Met Asn Ile Pro Ile Ser Tyr Asp
                245                 250                 255

Pro Thr Thr Gln Tyr Asn Asn Gln Ala Ser Ser Ser Asp Tyr Leu Leu
            260                 265                 270

Ser Pro Asp Asp Tyr Met Ser Ala Phe Asp His Gly Asp Val Ile Ser
        275                 280                 285
```

Gly Val Asn Ser Ser Cys Thr Thr Ser Ser His Ser Leu Asp Met Asp
            290                 295                 300

Gly Ile Met Met Glu Ser Ala Asp Phe Asp Asp Gly Val Phe Gly
305                 310                 315                 320

Phe

<210> SEQ ID NO 13
<211> LENGTH: 1678
<212> TYPE: DNA
<213> ORGANISM: Populus trichocarpa

<400> SEQUENCE: 13

```
aaacaagcag gaaagaaaca aaaactggaa ataatgggca cttgtttgag tgaaaaacta      60
tcatcaagca gggaaagggt gataaaagaa cttgttcaag ccatgaatt tgcagcccaa     120
cttcaaattc gcctccagaa accttgtgga aattttgatg ggcgttttc ttcagcgggt     180
gagcttgtag ggaagatctt aagatctttt tctgagactc tttctgtcat tacttctagt     240
gaatctgcag gtggtgagat tgtcaaaat ctagcaagtt cactaggaga ctctgcgtgt     300
tatgatgacc ggaggtctga agattccggc gagagcaaga gaggccggc taccaccaag     360
gataggagag gttgttacaa gagaaagtaa gtttaaccat atccatcgtt attatgtaaa     420
tgttagttat acatccaatt actgcacttc taacttaatt agtagttaac catcataatt     480
aaagatattc atgataatga cctgcacttc tgatacctt agagggggg attgtgagat     540
tttcttttc ttctggattg tgctgaatta atgtgagata attggtgata catttgcatg     600
atttatttat ttttaaatt ttaatgaaaa ctaatacaaa catctttgct tgctcccaga     660
aagatttccc aatcatggac tacagtctgt cctacgattg aagacagtca tgcatggaga     720
aaatatgggc agaaggggat cttgaatgct aaatacccaa ggtaagaac ctctcatttc     780
atttgatgct tcattattcc gatatataat tatggatcca ttaattttga gtctcgttgc     840
aatcttgaaa agtagtggag tcctcgacca ttaattttca taaagcaatc aaaagtgaag     900
atagaaaagg gagcactagt ggagaaggat tggcttttgc ggctatatat cactacatat     960
agtttaagaa attgcacatg tactgtgaag aaattattgt tgcgctaatc tcacttcgtt    1020
gattgattac aggagttact ttaggtgttc tcgcaagtat gaacaaggtt gcaaggcaac    1080
aaaacaagtc caaagaatgg aagacaaccc agcttgtac cataccacat acattggcag    1140
ccatacatgc agaaacatcc ctgaggctcc acaaatcatc acagattctg atccctggga    1200
atcttacaat cttacgagta gtgtgatcag ttctcattca aagattccta gatatgaaga    1260
acaagatcat catcccatta tggggtcacc ctgtgaagta gagcaagaat ctaaggaaga    1320
tcagacacca agtggtctag cagacaatgt ttcgtcttta gattcattca tgtggaagga    1380
tctcatacca tttgaagaac cagtggatga gccttccatg atattgaggt ctgattatga    1440
ggcagtggat tctatacact tgttctcatg tacagaggtc acctctcaaa gtttggacat    1500
ggattttgtc gtcaagtctt tgattttga ctgtgatttt cattttgatt agagcaagtt    1560
ttctaggcgg ctacaataat taattaaatc ctgtttaaaa ttagtattca tatatacacc    1620
cccacctcaa cagaatatat tctgcatgtg tatacatatt tatctattat aattaatt    1678
```

<210> SEQ ID NO 14
<211> LENGTH: 324
<212> TYPE: PRT
<213> ORGANISM: Populus trichocarpa

<400> SEQUENCE: 14

| | | | | | | | | | | | | | | |
|---|---|---|---|---|---|---|---|---|---|---|---|---|---|---|
| Met | Gly | Thr | Cys | Leu | Ser | Glu | Lys | Leu | Ser | Ser | Arg | Glu | Arg | Val |
| 1 | | | | 5 | | | | | 10 | | | | | 15 |
| Ile | Lys | Glu | Leu | Val | Gln | Gly | His | Glu | Phe | Ala | Ala | Gln | Leu | Gln | Ile |
| | | | 20 | | | | | 25 | | | | | 30 | | |
| Arg | Leu | Gln | Lys | Pro | Cys | Gly | Asn | Phe | Asp | Gly | Arg | Phe | Ser | Ser | Ala |
| | | 35 | | | | | 40 | | | | | 45 | | | |
| Gly | Glu | Leu | Val | Gly | Lys | Ile | Leu | Arg | Ser | Phe | Ser | Glu | Thr | Leu | Ser |
| 50 | | | | | 55 | | | | | 60 | | | | | |
| Val | Ile | Thr | Ser | Ser | Glu | Ser | Ala | Gly | Gly | Glu | Ile | Cys | Gln | Asn | Leu |
| 65 | | | | | 70 | | | | | 75 | | | | | 80 |
| Ala | Ser | Ser | Leu | Gly | Asp | Ser | Ala | Cys | Tyr | Asp | Asp | Arg | Arg | Ser | Glu |
| | | | | 85 | | | | | 90 | | | | | 95 | |
| Asp | Ser | Gly | Glu | Ser | Lys | Lys | Arg | Pro | Ala | Thr | Thr | Lys | Asp | Arg | Arg |
| | | | 100 | | | | | 105 | | | | | 110 | | |
| Gly | Cys | Tyr | Lys | Arg | Lys | Lys | Ile | Ser | Gln | Ser | Trp | Thr | Thr | Val | Cys |
| | | | 115 | | | | | 120 | | | | | 125 | | |
| Pro | Thr | Ile | Glu | Asp | Ser | His | Ala | Trp | Arg | Lys | Tyr | Gly | Gln | Lys | Gly |
| | | 130 | | | | | 135 | | | | | 140 | | | |
| Ile | Leu | Asn | Ala | Lys | Tyr | Pro | Arg | Ser | Tyr | Phe | Arg | Cys | Ser | Arg | Lys |
| 145 | | | | | 150 | | | | | 155 | | | | | 160 |
| Tyr | Glu | Gln | Gly | Cys | Lys | Ala | Thr | Lys | Gln | Val | Gln | Arg | Met | Glu | Asp |
| | | | | 165 | | | | | 170 | | | | | 175 | |
| Asn | Pro | Asp | Leu | Tyr | His | Thr | Thr | Tyr | Ile | Gly | Ser | His | Thr | Cys | Arg |
| | | | 180 | | | | | 185 | | | | | 190 | | |
| Asn | Ile | Pro | Glu | Ala | Pro | Gln | Ile | Ile | Thr | Asp | Ser | Asp | Pro | Trp | Glu |
| | | | 195 | | | | | 200 | | | | | 205 | | |
| Ser | Tyr | Asn | Leu | Thr | Ser | Ser | Val | Ile | Ser | Ser | His | Ser | Lys | Ile | Pro |
| | | 210 | | | | | 215 | | | | | 220 | | | |
| Arg | Tyr | Glu | Glu | Gln | Asp | His | His | Pro | Ile | Met | Gly | Ser | Pro | Cys | Glu |
| 225 | | | | | 230 | | | | | 235 | | | | | 240 |
| Val | Glu | Gln | Glu | Ser | Lys | Glu | Asp | Gln | Thr | Pro | Ser | Gly | Leu | Ala | Asp |
| | | | | 245 | | | | | 250 | | | | | 255 | |
| Asn | Val | Ser | Ser | Leu | Asp | Ser | Phe | Met | Trp | Lys | Asp | Leu | Ile | Pro | Phe |
| | | | 260 | | | | | 265 | | | | | 270 | | |
| Glu | Glu | Pro | Val | Asp | Glu | Pro | Ser | Met | Ile | Leu | Arg | Ser | Asp | Tyr | Glu |
| | | 275 | | | | | 280 | | | | | 285 | | | |
| Ala | Val | Asp | Ser | Ile | His | Leu | Phe | Ser | Cys | Thr | Glu | Val | Thr | Ser | Gln |
| | | 290 | | | | | 295 | | | | | 300 | | | |
| Ser | Leu | Asp | Met | Asp | Phe | Val | Val | Lys | Ser | Phe | Asp | Phe | Asp | Cys | Asp |
| 305 | | | | 310 | | | | | 315 | | | | | 320 | |
| Phe | His | Phe | Asp | | | | | | | | | | | | |

<210> SEQ ID NO 15
<211> LENGTH: 1646
<212> TYPE: DNA
<213> ORGANISM: Populus trichocarpa

<400> SEQUENCE: 15
gctgtgtgaa cgaaacgtcc tccaaaaaaa aattctaacc actatgcacg agagatcaat     60
attcacttat aaataagggc ttatacgtct cctatttgcc ttttctaata acactcctgg    120
caaaattttc atccatactg tatggtattg aagctatctt gatattctta agctcataaa    180
ccatggatgt ctttccctct tgcaaagaaa aggtatgttt tcttctagtt gtgtgtgtgt    240

-continued

```
gtgtgaattc tagtactact tggagaagag tatagagggt gggaagcaaa gaaaaacatt       300
gagcatataa tgaaataagg agcaggaaat agctaaaagt ttgtacatat taatttaggg       360
ttcatgcttg aaaaatgaag ttaatgtttc tcaagcagta gatgttatct tactcaggtg       420
gaagctcttc aattcgagtt ggaacacagg cagaaagaga atgaaagtct tagatttatg       480
cttggagtta tgaccagaag attcagcatt cttcaagccg agattcaaga aaccgaagaa       540
catcaacaaa agacagctag caacttagcg gatggagatc aagcttgtca tgaaatcctt       600
gactcgaaca agagagcaag atttgaagtt cccataacca aggcatcgag aatcttggtg       660
agaagtcact ccaatgacaa gagcctggta attaagttcc tctagtcagt ttgatatata       720
cataatttgc acatgaagtt tttgagttga agattcctag atcttacata tgataataaa       780
aagctctttc acaaatgtga atttagattg tgaaagatgg atatcaatgg agaaagtatg       840
gccagaaggt tactaaggat aacccatcac ctcgagctta cttcaggtgt tccatggctc       900
ctaattgccc cgtcaagaag aaggtatgct cgagttttct tttgaaaacc agtcaaaaca       960
tctgtaatta aatagcatcc tgaagtttat gtcgagaaag agctttcaaa gggcaacttc       1020
aaggttcatg tgtgcaatca aaaacagtac tgagcatgtg ataacaccag tcttctttga       1080
tttattcttg gttttcaggt ccaaagatgt gtagaagatg attcagtact tgttgcaagc       1140
tatgatggag aacacaacca tgaacccaat ggttcacatg gacaatattt atgttctcca       1200
catacctcat catcaaaaat ttccataact aatcatgtcc tcaagtgtcc aatcgaaatt       1260
cctcctcttc aaccatctat agctcttgat cttactcttt caagtcccag taatcaacag       1320
aaggaaaatc cttctaaaag atccatggaa gactgcggca agattaataa taactgcaac       1380
aagaactaca ttgaagaata tgtggcatct ttaactaaag atcctacctt ctctgtagct       1440
ttagctgcgg ctgttgcaag ttcaatgagt gacctgtctt cgtcaagaat gctgtgaaat       1500
aattattgtc ttatttatga atggtttatg ctctttctca caaggctacg ttgtatttgc       1560
ttgtgttctt acgctcccga tatatatata aaaaatgaat ataaaaaaaa aattgaagtt       1620
ataaaaaatt atttagtatt attatt                                           1646
```

<210> SEQ ID NO 16
<211> LENGTH: 271
<212> TYPE: PRT
<213> ORGANISM: Populus trichocarpa

<400> SEQUENCE: 16

```
Met Asp Val Phe Pro Ser Cys Lys Glu Lys Val Glu Ala Leu Gln Phe
1               5                   10                  15

Glu Leu Glu His Arg Gln Lys Glu Asn Glu Ser Leu Arg Phe Met Leu
            20                  25                  30

Gly Val Met Thr Arg Arg Phe Ser Ile Leu Gln Ala Glu Ile Gln Glu
        35                  40                  45

Thr Glu Glu His Gln Gln Lys Thr Ala Ser Asn Leu Ala Asp Gly Asp
    50                  55                  60

Gln Ala Cys His Glu Ile Leu Asp Ser Asn Lys Arg Ala Arg Phe Glu
65                  70                  75                  80

Val Pro Ile Thr Lys Ala Ser Arg Ile Leu Val Arg Ser His Ser Asn
                85                  90                  95

Asp Lys Ser Leu Ile Val Lys Asp Gly Tyr Gln Trp Arg Lys Tyr Gly
            100                 105                 110

Gln Lys Val Thr Lys Asp Asn Pro Ser Pro Arg Ala Tyr Phe Arg Cys
```

115                 120                 125
Ser Met Ala Pro Asn Cys Pro Val Lys Lys Val Gln Arg Cys Val
    130                 135                 140

Glu Asp Asp Ser Val Leu Val Ala Ser Tyr Asp Gly Glu His Asn His
145                 150                 155                 160

Glu Pro Asn Gly Ser His Gly Gln Tyr Leu Cys Ser Pro His Thr Ser
                165                 170                 175

Ser Ser Lys Ile Ser Ile Thr Asn His Val Leu Lys Cys Pro Ile Glu
            180                 185                 190

Ile Pro Pro Leu Gln Pro Ser Ile Ala Leu Asp Leu Thr Leu Ser Ser
        195                 200                 205

Pro Ser Asn Gln Gln Lys Glu Asn Pro Ser Lys Arg Ser Met Glu Asp
    210                 215                 220

Cys Gly Lys Ile Asn Asn Asn Cys Asn Lys Asn Tyr Ile Glu Glu Tyr
225                 230                 235                 240

Val Ala Ser Leu Thr Lys Asp Pro Thr Phe Ser Val Ala Leu Ala Ala
                245                 250                 255

Ala Val Ala Ser Ser Met Ser Asp Leu Ser Ser Ser Arg Met Leu
            260                 265                 270

<210> SEQ ID NO 17
<211> LENGTH: 2021
<212> TYPE: DNA
<213> ORGANISM: Populus trichocarpa

<400> SEQUENCE: 17
atggatttca acaacaaaac agaaggtttc atctgtagat ttatgggagt cgactgctgg      60
catcctgatg agaacagagt cttaaacatc agactctctg acctggggct caagggccag     120
ttccctcttg gattggataa gtgtacgagc gtaagtggtt tggacctttc acataatgag     180
cttcagggac cgattccagc tgacatctct aaaaggctac cattcatcac taaccttgac     240
ctatccttca caacttttc tggtgaaatc ccatcaagta ttgccaattt atctttctta     300
aacgatctaa aactcgacaa caacaagcta acaggtcaaa ttccaccaca aattggccag     360
ctcgatcgga tcaaggtctt tactgttact agcaatcgat tatcagggcc agtgccaaat     420
tttatacatg ctaatattcc accagacagc tttgcgaaca acgaaggact ctgtgggaag     480
cctttgaatg gctgctcaat tcatcaaatg aagtttgatt actcattcaa agtggttttt     540
gtgattggtt atagttttt caacttcagt tgcaattttt tttacatcct gctgtgtacc     600
atgggtgtat attggggaga agaaaaaaaa aatcacgata tcagaaatga tgatgttgat     660
ggtgaagagg aagcataaga taacagatga tgatcaagca ggcagctccc caacaagagg     720
tctcttggag gaaggaatta agaggtact  actctttaag attgatatct tttttgtttt     780
agttttgtta gttttttttt tttaattcct tattcaagtt ttgagcgaga gcagttcagt     840
ttttacttcc acttcaggga tgcttatcta cacaagaccc tgaattcttg aagctggttc     900
aattgcaatg tatatgtatg ttcttcagta ctaatatatt gagatttctg tccacagatt     960
tccatgttgg agaagagggt cacaagaatg agctacgcag atcttaatga tgccaccgat    1020
aatttcagcg agaacaatgt catcggacag ggaagaggat ggatgctgta caaggcatca    1080
ttgcctaatg ttatgtcct tgcagtgaag aagttgcatg actatcagtt ccttgaagaa    1140
caatttatat cagagttgaa gatacttggt tcattgagac atatcaacgt acttccactg    1200
ttggggtttt gcgttgagtc aaaccaaagg tttctggttt acaattatat gccaaatggt    1260

```
aacctttatg attggctaca tcccatggaa gaaggtcggg aaaaagctat ggaatggggt    1320
gtgagggtta aagtcgccgt cggattagca agaggcttgg catggcttca tcagaactgt    1380
cataccgtca aaataatcca tcttgacatt agctcaaaat gcatattact tgatcagaac    1440
ttccagccca agttatcaaa ttttggagag gcaatgctca tgagttcgac ctgcgcttcc    1500
tccgtaaata gtgagttttg ggagatggca tttgtgaagg aagatgtgca tggatttgga    1560
gttgtgcttc ttgagatgat tactggggtg gatcctagca acatgactgg ttcctcaaac    1620
aatgttctta atgaatggat tggtcatctt tcgagcagtt cggattttca tggcgcgata    1680
gataagtctc tgatcgggca aggatttgac gctgagatca ttcagctgct taaagttgca    1740
tgtacctgtg ttgatcccat tccagatcga agaccccgat aatggttcaa gtgtacgaag    1800
acataaaagc aataagggac agatgtgacc tagtagatga ttcatcgatg ctaatgcaac    1860
ctgaaatttg ccccgctact tcaaaaaaat ctgtggagat tgaaatggca gaattccaac    1920
gaaaacaaca ggacaaacaa aaagcaagtc tgcattttct agtttctatc gcatgctttg    1980
gtgtaatgaa ccaatattgt acacaatatg atagctttg a                        2021
```

<210> SEQ ID NO 18
<211> LENGTH: 527
<212> TYPE: PRT
<213> ORGANISM: Populus trichocarpa

<400> SEQUENCE: 18

```
Met Asp Phe Asn Asn Lys Thr Glu Gly Phe Ile Cys Arg Phe Met Gly
1               5                   10                  15

Val Asp Cys Trp His Pro Asp Glu Asn Arg Val Leu Asn Ile Arg Leu
            20                  25                  30

Ser Asp Leu Gly Leu Lys Gly Gln Phe Pro Leu Gly Leu Asp Lys Cys
        35                  40                  45

Thr Ser Val Ser Gly Leu Asp Leu Ser His Asn Glu Leu Gln Gly Pro
    50                  55                  60

Ile Pro Ala Asp Ile Ser Lys Arg Leu Pro Phe Ile Thr Asn Leu Asp
65                  70                  75                  80

Leu Ser Phe Asn Asn Phe Ser Gly Glu Ile Pro Ser Ser Ile Ala Asn
                85                  90                  95

Leu Ser Phe Leu Asn Asp Leu Lys Leu Asp Asn Asn Lys Leu Thr Gly
            100                 105                 110

Gln Ile Pro Pro Gln Ile Gly Gln Leu Asp Arg Ile Lys Val Phe Thr
        115                 120                 125

Val Thr Ser Asn Arg Leu Ser Gly Pro Val Pro Asn Phe Ile His Ala
    130                 135                 140

Asn Ile Pro Pro Asp Ser Phe Ala Asn Asn Glu Gly Leu Cys Gly Lys
145                 150                 155                 160

Pro Leu Asn Gly Cys Ser Ile His Gln Met Lys Phe Asp Tyr Ser Phe
                165                 170                 175

Lys Ser Gly Phe Val Ile Ala Gly Ser Ile Ala Met Tyr Met Tyr Ile
            180                 185                 190

Ser Met Leu Glu Lys Arg Val Thr Arg Met Ser Tyr Ala Asp Leu Asn
        195                 200                 205

Asp Ala Thr Asp Asn Phe Ser Glu Asn Asn Val Ile Gly Gln Gly Lys
    210                 215                 220

Met Gly Met Leu Tyr Lys Ala Ser Leu Pro Asn Gly Tyr Val Leu Ala
225                 230                 235                 240
```

```
Val Lys Lys Leu His Asp Tyr Gln Phe Leu Glu Gln Phe Ile Ser
            245                 250                 255

Glu Leu Lys Ile Leu Gly Ser Leu Arg His Ile Asn Val Leu Pro Leu
260                 265                 270

Leu Gly Phe Cys Val Glu Ser Asn Gln Arg Phe Leu Val Tyr Asn Tyr
            275                 280                 285

Met Pro Asn Gly Asn Leu Tyr Asp Trp Leu His Pro Met Glu Glu Gly
290                 295                 300

Arg Glu Lys Ala Met Glu Trp Gly Val Arg Val Lys Val Ala Val Gly
305                 310                 315                 320

Leu Ala Arg Gly Leu Ala Trp Leu His Gln Asn Cys His Thr Val Lys
                325                 330                 335

Ile Ile His Leu Asp Ile Ser Ser Lys Cys Ile Leu Leu Asp Gln Asn
            340                 345                 350

Phe Gln Pro Lys Leu Ser Asn Phe Gly Glu Ala Met Leu Met Ser Ser
        355                 360                 365

Thr Cys Ala Ser Ser Val Asn Ser Glu Phe Trp Glu Met Ala Phe Val
    370                 375                 380

Lys Glu Asp Val His Gly Phe Gly Val Val Leu Leu Glu Met Ile Thr
385                 390                 395                 400

Gly Val Asp Pro Ser Asn Met Thr Gly Ser Ser Asn Asn Val Leu Asn
                405                 410                 415

Glu Trp Ile Gly His Leu Ser Ser Ser Asp Phe His Gly Ala Ile
            420                 425                 430

Asp Lys Ser Leu Ile Gly Gln Gly Phe Asp Ala Glu Ile Ile Gln Leu
        435                 440                 445

Leu Lys Val Ala Leu Tyr Glu Asp Ile Lys Ala Ile Arg Asp Arg Cys
    450                 455                 460

Asp Leu Val Asp Ser Ser Met Leu Met Gln Pro Glu Ile Cys Pro
465                 470                 475                 480

Ala Thr Ser Lys Lys Ser Val Glu Ile Glu Met Ala Glu Phe Gln Arg
                485                 490                 495

Lys Gln Asp Lys Gln Lys Ala Ser Leu His Phe Leu Val Ser Ile
        500                 505                 510

Ala Cys Phe Gly Val Met Asn Gln Tyr Cys Thr Gln Tyr Asp Ser
    515                 520                 525

<210> SEQ ID NO 19
<211> LENGTH: 2021
<212> TYPE: DNA
<213> ORGANISM: Populus trichocarpa

<400> SEQUENCE: 19
atggatttca acaacaaaac agcaggtttc atctgtagat ttatgggcgt cgactgctgg      60
catcctgatg agaacagagt cttaaacatc agactctctg acctggggct caagggccag    120
ttccctcttg gattggataa gtgtacgagc gtaagtggtt ggacctttc acataatgag      180 cttcagggac cgattccagc tgacatctct aaaaggctac tattcatcac taaccttgac    240
ctatccttca caactttc tggtgaaatc ccatcaagta ttgccaattt atctttctta      300
aactatctaa aactcgacaa caacaagcta acaggtcaaa ttccaccaca aattggccag    360
ctcgatcgga tcaaggtctt tactgttact agcaatcgat tatcagggcc agtgccaaat    420
tttatacatg ctaatattcc agcagacagc tttgcgaaca cgaaggact ctgtgggaag      480 cctttgaatg gctgctcaat tcatcaaatg aagtttgatt actcattcaa aagtggtttt    540
```

```
gtgattggtt atatagttt  ttcaacttca  gttgcaattt ttttacatc ctgctgtgta    600
ccatgggtgt atattgggga gaagaaaaaa aaaatcacga tatcagaaat gatgatgttg    660
atggtgaaga ggaagcataa gataacagat gatgatcaag caggcagctc cccaacaaga    720
ggtctcttgg aggaaggaat taaagaggta ctactcttta agattgatat cttttttgtt    780
ttagttttgt tagttttat tttttaattc cttattcaag ttttgagaga gagcagttca    840
gttttactt ccacttacag gatgcttatc tacacaagac cctgaattct tgaagctggt    900
tcaattgcaa tgtatatgta tgttcttcag tactaatata ttgagatttg tgtccacaga    960
tttccatgtt ggagaagagg gttacaagaa tgagctacgc agatcttaat gatgccaccg   1020
ataattcag cgagaacaat gtcatcggac agggaaagat ggggatgctg tacaaggcat   1080
cattgcctaa tggttatgtc cttgcagtga agaagttgca tgactctcag ttccttgaag   1140
aacaatttat atcagagttg aagatacttg gttcattgag acatatcaac gtacttccac   1200
tgttggggtt ttgcgttgag tcaaaccaaa ggtttctggt ttacaattat atgccaaatg   1260
gtaacctta tgattggcta catcccatgg aagaaggtcg ggaaaaagct atggaatggg   1320
gtgtgagggt taaagtcgcc gtcggattag caagaggctt ggcatggctt catcagaact   1380
gtcataccgt caaaataatc catcttgaca ttagctcaaa atgcatatta cttgatcaga   1440
acttccagcc caagttatca aattttggag aggcaatgct catgagttcg acctgcgctt   1500
cctccgtaaa tagtgagttt tgggagatgg catttgtgaa ggaagatgtg catggatttg   1560
gagttgtgct tcttgaaatg attactgggg tggatcctag caacatgact ggttcctcaa   1620
acaatgttct taatgaatgg attggtcatc tttcgagcag ttcggatttt catggcgcga   1680
tagataagtc tctgatcggg caaggatttg acgctgagat cattcagctg cttaaagttg   1740
catgtacctg tgttgatccc attccagatc gaagaccgat aatggttcaa gtgtacgaag   1800
acataaaagc aataagggac agatgtgacc tagtagatga ttcatcgatg ctaatgcaac   1860
ctgaaatttg ccccgctact tcaaaaaaat ctgtggagat tgaaatggca gaattccaac   1920
gaaaacaaca ggacaaacaa aaagcaagtc tgcattttct agtttctatc gcatgctttg   1980
gtgtaatgaa ccaatattgt acacaatatg atagcttttg a                      2021
```

<210> SEQ ID NO 20
<211> LENGTH: 602
<212> TYPE: PRT
<213> ORGANISM: Populus trichocarpa
<400> SEQUENCE: 20

```
Met Asp Phe Asn Asn Lys Thr Ala Gly Phe Ile Cys Arg Phe Met Gly
1               5                   10                  15

Val Asp Cys Trp His Pro Asp Glu Asn Arg Val Leu Asn Ile Arg Leu
            20                  25                  30

Ser Asp Leu Gly Leu Lys Gly Gln Phe Pro Leu Gly Leu Asp Lys Cys
        35                  40                  45

Thr Ser Val Ser Gly Leu Asp Leu Ser His Asn Glu Leu Gln Gly Pro
    50                  55                  60

Ile Pro Ala Asp Ile Ser Lys Arg Leu Leu Phe Ile Thr Asn Leu Asp
65                  70                  75                  80

Leu Ser Phe Asn Asn Phe Ser Gly Glu Ile Pro Ser Ser Ile Ala Asn
                85                  90                  95

Leu Ser Phe Leu Asn Tyr Leu Lys Leu Asp Asn Asn Lys Leu Thr Gly
            100                 105                 110
```

```
Gln Ile Pro Pro Gln Ile Gly Gln Leu Asp Arg Ile Lys Val Phe Thr
        115                 120                 125
Val Thr Ser Asn Arg Leu Ser Gly Pro Val Pro Asn Phe Ile His Ala
    130                 135                 140
Asn Ile Pro Ala Asp Ser Phe Ala Asn Glu Gly Leu Cys Gly Lys
145                 150                 155                 160
Pro Leu Asn Gly Cys Ser Ile His Gln Met Lys Phe Asp Tyr Ser Phe
                165                 170                 175
Lys Ser Gly Phe Val Ile Gly Tyr Ile Val Phe Ser Thr Ser Val Ala
                180                 185                 190
Ile Phe Phe Thr Ser Cys Cys Val Pro Trp Val Tyr Ile Gly Glu Lys
        195                 200                 205
Lys Lys Lys Ile Thr Ile Ser Glu Met Met Met Leu Met Val Lys Arg
    210                 215                 220
Lys His Lys Ile Thr Asp Asp Asp Gln Ala Gly Ser Ser Pro Thr Arg
225                 230                 235                 240
Gly Leu Leu Glu Glu Gly Ile Lys Glu Ile Ser Met Leu Glu Lys Arg
                245                 250                 255
Val Thr Arg Met Ser Tyr Ala Asp Leu Asn Asp Ala Thr Asp Asn Phe
                260                 265                 270
Ser Glu Asn Asn Val Ile Gly Gln Gly Lys Met Gly Met Leu Tyr Lys
            275                 280                 285
Ala Ser Leu Pro Asn Gly Tyr Val Leu Ala Val Lys Lys Leu His Asp
        290                 295                 300
Ser Gln Phe Leu Glu Glu Gln Phe Ile Ser Glu Leu Lys Ile Leu Gly
305                 310                 315                 320
Ser Leu Arg His Ile Asn Val Leu Pro Leu Leu Gly Phe Cys Val Glu
                325                 330                 335
Ser Asn Gln Arg Phe Leu Val Tyr Asn Tyr Met Pro Asn Gly Asn Leu
                340                 345                 350
Tyr Asp Trp Leu His Pro Met Glu Glu Gly Arg Glu Lys Ala Met Glu
            355                 360                 365
Trp Gly Val Arg Val Lys Val Ala Val Gly Leu Ala Arg Gly Leu Ala
        370                 375                 380
Trp Leu His Gln Asn Cys His Thr Val Lys Ile Ile His Leu Asp Ile
385                 390                 395                 400
Ser Ser Lys Cys Ile Leu Leu Asp Gln Asn Phe Gln Pro Lys Leu Ser
                405                 410                 415
Asn Phe Gly Glu Ala Met Leu Met Ser Ser Thr Cys Ala Ser Ser Val
            420                 425                 430
Asn Ser Glu Phe Trp Glu Met Ala Phe Val Lys Glu Asp Val His Gly
        435                 440                 445
Phe Gly Val Val Leu Leu Glu Met Ile Thr Gly Val Asp Pro Ser Asn
    450                 455                 460
Met Thr Gly Ser Ser Asn Asn Val Leu Asn Glu Trp Ile Gly His Leu
465                 470                 475                 480
Ser Ser Ser Ser Asp Phe His Gly Ala Ile Asp Lys Ser Leu Ile Gly
                485                 490                 495
Gln Gly Phe Asp Ala Glu Ile Ile Gln Leu Leu Lys Val Ala Cys Thr
                500                 505                 510
Cys Val Asp Pro Ile Pro Asp Arg Arg Pro Ile Met Val Gln Val Tyr
            515                 520                 525
```

```
Glu Asp Ile Lys Ala Ile Arg Asp Arg Cys Asp Leu Val Asp Asp Ser
        530                 535                 540
Ser Met Leu Met Gln Pro Glu Ile Cys Pro Ala Thr Ser Lys Lys Ser
545                 550                 555                 560
Val Glu Ile Glu Met Ala Glu Phe Gln Arg Lys Gln Gln Asp Lys Gln
                565                 570                 575
Lys Ala Ser Leu His Phe Leu Val Ser Ile Ala Cys Phe Gly Val Met
            580                 585                 590
Asn Gln Tyr Cys Thr Gln Tyr Asp Ser Phe
        595                 600

<210> SEQ ID NO 21
<211> LENGTH: 36
<212> TYPE: DNA
<213> ORGANISM: Artificial Sequence
<220> FEATURE:
<223> OTHER INFORMATION: Oligonucleotide

<400> SEQUENCE: 21
aacttgtact ttcaaggcca gtctctctct gcaagc                              36

<210> SEQ ID NO 22
<211> LENGTH: 36
<212> TYPE: DNA
<213> ORGANISM: Artificial Sequence
<220> FEATURE:
<223> OTHER INFORMATION: Oligonucleotide

<400> SEQUENCE: 22
acaagaaagc tgggtcctaa cctggtgcag gatctt                              36

<210> SEQ ID NO 23
<211> LENGTH: 35
<212> TYPE: DNA
<213> ORGANISM: Artificial Sequence
<220> FEATURE:
<223> OTHER INFORMATION: Oligonucleotide

<400> SEQUENCE: 23
aacttgtact ttcaaggcca cttcatctat catgg                               35

<210> SEQ ID NO 24
<211> LENGTH: 37
<212> TYPE: DNA
<213> ORGANISM: Artificial Sequence
<220> FEATURE:
<223> OTHER INFORMATION: Oligonucleotide

<400> SEQUENCE: 24
acaagaaagc tgggtcctaa ggcaactttg acacatc                             37

<210> SEQ ID NO 25
<211> LENGTH: 33
<212> TYPE: DNA
<213> ORGANISM: Artificial Sequence
<220> FEATURE:
<223> OTHER INFORMATION: Oligonucleotide

<400> SEQUENCE: 25
aacttgtact ttcaaggcgt ggaattgccg ccg                                 33

<210> SEQ ID NO 26
<211> LENGTH: 36
<212> TYPE: DNA
```

<213> ORGANISM: Artificial Sequence
<220> FEATURE:
<223> OTHER INFORMATION: Oligonucleotide

<400> SEQUENCE: 26
acaagaaagc tgggtcctac gaacgggaaa tgatac                         36

<210> SEQ ID NO 27
<211> LENGTH: 52
<212> TYPE: DNA
<213> ORGANISM: Artificial Sequence
<220> FEATURE:
<223> OTHER INFORMATION: Oligonucleotide

<400> SEQUENCE: 27
ggggacaagt ttgtacaaaa aagcaggctc tgaaaacttg tactttcaag gc        52

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide

<400> SEQUENCE: 28
ggggaccact ttgtacaaga aagctgggtc                                30

<210> SEQ ID NO 29
<211> LENGTH: 22
<212> TYPE: DNA
<213> ORGANISM: Artificial Sequence
<220> FEATURE:
<223> OTHER INFORMATION: Oligonucleotide

<400> SEQUENCE: 29
gccttcgtgg tggttattaa gc                                        22

<210> SEQ ID NO 30
<211> LENGTH: 22
<212> TYPE: DNA
<213> ORGANISM: Artificial Sequence
<220> FEATURE:
<223> OTHER INFORMATION: Oligonucleotide

<400> SEQUENCE: 30
tccaacaatg gccagtaaac ac                                        22

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
tggcatcctg atgagaacag                                           20

<210> SEQ ID NO 32
<211> LENGTH: 21
<212> TYPE: DNA
<213> ORGANISM: Artificial Sequence
<220> FEATURE:
<223> OTHER INFORMATION: Oligonucleotide

<400> SEQUENCE: 32
aaaggtccaa accacttacg c                                         21

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide

<400> SEQUENCE: 33
ggagatggca tttgtgaagg                                              20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide

<400> SEQUENCE: 34
gctcgaaaga tgaccaatcc                                              20

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide

<400> SEQUENCE: 35
catggatgtc tttccctctt g                                            21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide

<400> SEQUENCE: 36
ttctctttct gcctgtgttc c                                            21

<210> SEQ ID NO 37
<211> LENGTH: 22
<212> TYPE: DNA
<213> ORGANISM: Artificial Sequence
<220> FEATURE:
<223> OTHER INFORMATION: Oligonucleotide

<400> SEQUENCE: 37
actatcatca agcagggaaa gg                                           22

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
ttctggaggc gaatttgaag                                              20

<210> SEQ ID NO 39
<211> LENGTH: 22
<212> TYPE: DNA
<213> ORGANISM: Artificial Sequence
<220> FEATURE:

<223> OTHER INFORMATION: Oligonucleotide

<400> SEQUENCE: 39
gaatctgctg atttcgatga tg                                    22

<210> SEQ ID NO 40
<211> LENGTH: 21
<212> TYPE: DNA
<213> ORGANISM: Artificial Sequence
<220> FEATURE:
<223> OTHER INFORMATION: Oligonucleotide

<400> SEQUENCE: 40
aggcggaaat tacaaagaag c                                     21

<210> SEQ ID NO 41
<211> LENGTH: 11
<212> TYPE: DNA
<213> ORGANISM: Populus trichocarpa

<400> SEQUENCE: 41
cttcagcagg t                                                11

<210> SEQ ID NO 42
<211> LENGTH: 13
<212> TYPE: DNA
<213> ORGANISM: Populus trichocarpa

<400> SEQUENCE: 42
tccattacct tcc                                              13

<210> SEQ ID NO 43
<211> LENGTH: 11
<212> TYPE: DNA
<213> ORGANISM: Populus trichocarpa

<400> SEQUENCE: 43
cagaagaaga a                                                11

<210> SEQ ID NO 44
<211> LENGTH: 15
<212> TYPE: DNA
<213> ORGANISM: Populus trichocarpa

<400> SEQUENCE: 44
ggtgaagaag cagag                                            15

<210> SEQ ID NO 45
<211> LENGTH: 15
<212> TYPE: DNA
<213> ORGANISM: Populus trichocarpa

<400> SEQUENCE: 45
aaacggccag gaagg                                            15

<210> SEQ ID NO 46
<211> LENGTH: 19
<212> TYPE: DNA
<213> ORGANISM: Populus trichocarpa

<400> SEQUENCE: 46
atgaggcaat ttattttca                                        19

```
<210> SEQ ID NO 47
<211> LENGTH: 16
<212> TYPE: DNA
<213> ORGANISM: Populus trichocarpa

<400> SEQUENCE: 47
ggtcgccctt gaaaca                                                   16

<210> SEQ ID NO 48
<211> LENGTH: 19
<212> TYPE: DNA
<213> ORGANISM: Populus trichocarpa

<400> SEQUENCE: 48
ttagataatt ctatgaact                                                19
```

METHODS OF IDENTIFYING AND MODULATING PATHOGEN RESISTANCE IN PLANTS

CROSS REFERENCE TO RELATED APPLICATIONS

This application claims the benefit of priority from U.S. Provisional Application No. 62/585,105, filed Nov. 13, 2017, the entire contents of which are incorporated herein by reference.

STATEMENT REGARDING FEDERALLY SPONSORED RESEARCH OR DEVELOPMENT

This invention was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in an ASCII text file, 33716_3685_1_SEQ_Feb. 14, 2019 ST25.txt of 99 KB, created on Feb. 14, 2019, and submitted to the United States Patent and Trademark Office via EFS-Web, is incorporated herein by reference.

BACKGROUND

Host-pathogen co-evolution has been described for many species interactions and is the major focus of research on innate immunity in plant and animal systems. In what is commonly referred to as a co-evolutionary "arms race", models predict adaptation and counter-adaption, whereby both host and pathogen genomes undergo complementary changes to thwart or facilitate infection, respectively (Boller, T. & He, S. Y., *Science*, 324, 742 (2009)). Because of the focus on co-evolved hosts and microbes, there exist few models that predict the mechanism by which exotic pathogens counter innate immune responses and infect non-coevolved host species (Anagnostakis, S. L., *Mycologia*, 79, 23-37 (1987)). Diseases that exemplify such interactions include Dutch elm disease, chestnut blight (Anagnostakis, S. L., *Mycologia,* 79, 23-37 (1987)), white pine blister rust (Kinloch, Jr. et al., *Phytopathol,* 93, 1044-1047 (2003)), sudden oak death (Tomlinson, I., *Environ. Polit.,* 25, 1-20 (2015)) and Chalara dieback of ash (Harvell, C. D. et al., *Science,* 296, 2158-2162 (2002)). These examples highlight the catastrophic consequences of exotic diseases. In each case, most genotypes of the host species are susceptible, as these genotypes disappear; ecosystem structure and function are perturbed, resulting in declines in forest health (Cobb, R. C. et al., *J. Ecol.,* 100, 712-722 (2012)). This is particularly problematic in an age where global trade and climate change are permanently altering species distributions, potentially resulting in new host-pathogen sympatries (Tobias, P. A. & Guest, D. I., *Trends Plant Sci.,* 19, 367-370 (2014)).

Plant innate immune systems that combat co-evolved pathogens consist of multiple layers, including constitutive and inducible defenses that collectively function to protect against pathogens (Jones, J. D. & Dangl, J. L, Nature 444, 323-329 (2006)). In the so-called PAMP-triggered immunity (PTI), pattern recognition receptors (PRR) recognize conserved pathogen-associated molecular patterns (PAMP) to trigger an immune response (Feau, N. et al., *Can. J. Plant Pathol.,* 32, 122-134 (2010)). Compatible pathogens deploy an arsenal of effector proteins; collectively dampening PTI and promoting susceptibility. In a second layer of immunity, genotypes of the host can encode resistance proteins that recognize the presence or action of a corresponding effector, leading to a rapid and robust immune response called effector triggered immunity (ETI). The evolutionary interplay continues as pathogen populations remold their repertoire of effectors and host populations gain new resistance specificities. It is unclear whether this model sufficiently describes the interactions between plants and exotic, non-adapted pathogens.

Poplar trees (*Populus*), as foundation species within many ecosystems, occur across most of North America in native populations hundreds- to thousands-of-years old. These species are ecologically and commercially important as a result of their broad geographic distribution and potential use as a bioenergy feedstock. The primary limitation to the use of *Populus* for fiber, biomass, and bioenergy in central and eastern North America are the fungal diseases.

*Populus* is cultivated worldwide for pulp and paper, veneer, packing material, engineered wood products (e.g., oriented strand board), lumber, and has recently emerged as the preeminent fast-growing woody crop for bioenergy research. *Populus* can be grown on economically marginal agricultural land thereby minimizing the competition between food and fuel production.

Fungi that infect a living host, but kill host cells in order to obtain their nutrients, are called necrotrophic fungi. The family of fungi in the *Sphaerulina* family are pathogenic, necrotrophic fungi for many commercially important plants. For example, *Sphaerulina rubi* is a fungal plant pathogen infecting caneberries, *Sphaerulina oryzina* is a fungal plant pathogen infecting rice, *Sphaerulina rehmiana* is a fungal plant pathogen infecting roses, and *Sphaerulina musiva* (aka. *Septoria musiva*) is a fungal plant pathogen infecting poplar trees.

Stem canker, caused by *Septoria musiva*, is the most serious disease limiting intensive hybrid poplar cultures in eastern North America. *Populus deltoides* Marshall, the Eastern cottonwood, is known to be resistant to stem canker. *S. musiva* does cause leaf spots on *P. deltoides*, but this disease is seldom associated with serious damage. However, hybrids of *P. deltoides* with species in *Populus* section *Tacamahaca* are typically susceptible to stem canker. In particular, *P. trichocatpa* Torr. & Gray×*P. deltoides* F1 hybrids have proven susceptible in many locations in eastern North America. The susceptibility of *P. trichocarpa* itself has also been demonstrated many times in various trials where stem canker occurs.

The cankers often develop on the primary shoots of 2- to 3-year-old trees, leading to restrictions in the movement of water and nutrients and weakening the wood within a few feet of ground level. The weakened trunks collapse easily, greatly reducing the production of biomass. Cankers caused by *S. musiva* can greatly hamper the production of hybrid poplars in the eastern United States and Canada and threaten poplars in western North America.

*Septoria musiva* (*S. musiva*), taxonomic name: *Sphaerulina musiva* (teleomorph: *Mycosphaerella populorum*), is an ascomycete fungus responsible of a leaf spot and canker disease on poplar trees. It is native on the eastern cottonwood poplar *Populus deltoides* (*P. deltoides*), causing only a leaf spot symptom. On susceptible hybrid poplars, *S. musiva* causes necrotic lesions on the leaves which lead to premature defoliation, and cankers on the stem and branches which can reduce growth, predispose the tree to colonization by secondary organisms, and cause stem breakage.

A major concern with *S. musiva* is with migration to new areas. The pathogen is endemic and appears to have originated on poplars in eastern North America, where it occurs commonly on leaves of the eastern cottonwood, *P. deltoides*. During the past 20 years *S. musiva* has appeared in South America and western Canada, where it is spreading rapidly on native and hybrid poplars causing economic damage as well as threatening native poplars in important riparian zones. It is not yet known in Europe or Asia but has the potential to cause extensive damage if introduced to those areas. Global warming and trade may facilitate the spread of the disease by making northern popular-growing areas more favorable to growth of the fungus.

In eastern North America the fungal pathogen *Sphaerulina musiva* is endemic in natural stands of *Populus* where it has co-evolved with its host *P. deltoides* and causes leaf-spot disease. However, *S. musiva* was recently introduced to western North America (Herath, P. et al. *Biol. Invasions*, doi: 10.1007/s10530-015-1051-8 (2016)) and when it interacts with a non-co-evolved host, *P. trichocarpa*, it causes severe stem and branch cankers that often girdle the vascular tissue of the tree, leading to premature crown death and an increased risk of stem breakage. It is predicted that as a non-co-evolved host, *P. trichocarpa* will either: 1) lack immunity to *S. musiva* due to niche separation; or 2) that there will be a trade-off in immunity in terms of the ability to recognize and respond to pathogenic vs. beneficial microbes.

SUMMARY OF THE DISCLOSURE

In one aspect, this disclosure provides a method of selecting for a plant resistant to a necrotrophic fungus comprising sequencing the RLP1, RLP2, and L-type lecRLK genes of the plant, and determining that said plant is resistant to the necrotrophic fungi if each of the RLP1, RLP2, and L-type lecRLK genes in said plant is substantially functional.

In some embodiments, the plant of this disclosure is selected from the group consisting of Populus, corn, soybean, rose, rice, caneberry, Salix (willow), alder, spruce, chestnut, oak, citrus, grape, eucalyptus, coffee, pine, rhododendron, birch, cucumber, tomato, betulia, clover, wheat, maize, sorghum, and blueberry. In some embodiments, the necrotropic fungus is from the *Sphaerulina* genus.

In some embodiments, the necrotropic fungus of this disclosure is selected from the group consisting of *Sphaerulina abeliceae, Sphaerulina aceris, Sphaerulina acetabulum, Sphaerulina acori, Sphaerulina aechmeae, Sphaerulina affinis, Sphaerulina albispiculata, Sphaerulina alni, Sphaerulina amelanchier, Sphaerulina amicta, Sphaerulina amphilomatis, Sphaerulina amygdali, Sphaerulina anemones, Sphaerulina annae, Sphaerulina antarctica, Sphaerulina arctica, Sphaerulina arthoniae, Sphaerulina assurgens, Sphaerulina aucubae, Sphaerulina azaleae, Sphaerulina baccarum, Sphaerulina bambusicola, Sphaerulina berberidis, Sphaerulina betulae, Sphaerulina blyttii, Sphaerulina bonariana, Sphaerulina boudieriana, Sphaerulina bryophila, Sphaerulina callista, Sphaerulina camelliae, Sphaerulina camelliae, Sphaerulina carestiae, Sphaerulina caricae, Sphaerulina caricis, Sphaerulina ceanothi, Sphaerulina centellae, Sphaerulina cercidis, Sphaerulina cetraricola, Sphaerulina cetrariicola, Sphaerulina chlorococca, Sphaerulina cibotii, Sphaerulina citri, Sphaerulina codiicola, Sphaerulina coffaeicola, Sphaerulina coffeicola, Sphaerulina concinna, Sphaerulina conflicta, Sphaerulina coriariae, Sphaerulina cornicola, Sphaerulina corniculata, Sphaerulina coronillae-junceae, Sphaerulina corynephora, Sphaerulina cucumeris, Sphaerulina cucurbitae, Sphaerulina datiscae, Sphaerulina diapensiae, Sphaerulina dioscoreae, Sphaerulina divergens, Sphaerulina dolichotera, Sphaerulina dryadis, Sphaerulina dryophila, Sphaerulina dubiella, Sphaerulina empetri, Sphaerulina endococcoidea, Sphaerulina epigaea, Sphaerulina eucalypti, Sphaerulina ferruginosa, Sphaerulina frondicola, Sphaerulina fuegiana, Sphaerulina gei, Sphaerulina gentianae, Sphaerulina gigantea, Sphaerulina giliae, Sphaerulina hainensis, Sphaerulina halophila, Sphaerulina hamadryadum, Sphaerulina hederae, Sphaerulina helicicola, Sphaerulina hyperici, Sphaerulina inaequalis, Sphaerulina inquinans, Sphaerulina intermedia, Sphaerulina intermixta, Sphaerulina Ipomoeae, Sphaerulina islandica, Sphaerulina iwatensis, Sphaerulina juglandis, Sphaerulina leightonii, Sphaerulina lepidiotae, Sphaerulina limnanthemi, Sphaerulina lini, Sphaerulina linicola, Sphaerulina ludwigiae, Sphaerulina mappiae, Sphaerulina marattiae, Sphaerulina marginata, Sphaerulina maroccana, Sphaerulina marsileae, Sphaerulina maydis, Sphaerulina menispermi, Sphaerulina microthyrioides, Sphaerulina mimosae-pigrae, Sphaerulina miyakei, Sphaerulina musae, Sphaerulina muscicola, Sphaerulina muscorum, Sphaerulina musicola, Sphaerulina musiva, Sphaerulina myriadea, Sphaerulina myriadea subsp. myriadea, Sphaerulina myrtillina, Sphaerulina naumovii, Sphaerulina nephromiaria, Sphaerulina oleifolia, Sphaerulina orae-maris, Sphaerulina oryzae, Sphaerulina oryzina, Sphaerulina oxalidis, Sphaerulina oxyacanthae, Sphaerulina pallens, Sphaerulina parvipuncta, Sphaerulina patriniae, Sphaerulina paulistana, Sphaerulina peckii, Sphaerulina pedicellata, Sphaerulina pelargonii, Sphaerulina phalaenopsidis, Sphaerulina phellogena, Sphaerulina phoenicis, Sphaerulina phyllostachydis, Sphaerulina pini, Sphaerulina plantaginea, Sphaerulina pleuropogonis, Sphaerulina polygonorum, Sphaerulina polypodii, Sphaerulina polypodii, Sphaerulina polyspora, Sphaerulina populi, Sphaerulina populicola, Sphaerulina porothelia, Sphaerulina potebniae, Sphaerulina potentillae, Sphaerulina poterii, Sphaerulina primulicola, Sphaerulina pruni, Sphaerulina pseudovirgaureae, Sphaerulina pterocarpi, Sphaerulina pulii, Sphaerulina quercicola, Sphaerulina quercifolia, Sphaerulina quitensis, Sphaerulina rehmiana, Sphaerulina rhabdoclinis, Sphaerulina rhodeae, Sphaerulina rhododendri, Sphaerulina rhododendricola, Sphaerulina rubi, Sphaerulina saccardiana, Sphaerulina saccardoana, Sphaerulina sacchari, Sphaerulina salicina, Sphaerulina sambucina, Sphaerulina sasae, Sphaerulina schaereri, Sphaerulina scirpi, Sphaerulina sepincola, Sphaerulina serograpta, Sphaerulina silacincola, Sphaerulina smilacincola, Sphaerulina socia, Sphaerulina spartii, Sphaerulina staphyleae, Sphaerulina staurochili, Sphaerulina steganostroma, Sphaerulina subgen. Pharcidiella, Sphaerulina subgen, Sphaerulina, Sphaerulina sub glacialis, Sphaerulina subtropica, Sphaerulina suchumica, Sphaerulina tabacinae, Sphaerulina tanaceti, Sphaerulina tarda, Sphaerulina taxi, Sphaerulina taxicola, Sphaerulina thujopsidis, Sphaerulina tiliaris, Sphaerulina tirolensis, Sphaerulina todeae, Sphaerulina trapae-bispinosae, Sphaerulina trifolii, Sphaerulina tritici, Sphaerulina umbilicata, Sphaerulina valerianae, Sphaerulina viciae, Sphaerulina vincae, Sphaerulina violae, Sphaerulina vismiae, Sphaerulina vulpina, Sphaerulina westendorpii, Sphaerulina worsdellii, Sphaerulina xerophylli, Sphaerulina yerbae, Sphaerulina ziziphi, Sphaerulina zizyphae*, and *Sphaerulina zizyphi*.

Another aspect of this disclosure provides a method of determining necrotropic fungi resistance in a plant comprising infecting the plant with a necrotropic fungus; and detecting the expression level of at least one gene selected from the group consisting of RLP1, RLP2, and L-type lecRLK genes before and after the infection, wherein a transient increase in the expression level of the at least one gene 24 hours after the infection indicates that the plant is resistant to the necrotropic fungus.

An additional aspect of this application provides a method of converting a necrotropic fungi-susceptible plant into a necrotropic fungi-resistant plant comprising sequencing the RLP1, RLP2, and L-type lecRLK genes in the plant; determining the presence of a deleterious mutation in at least one of the RLP1, RLP2, and L-type lecRLK genes; and restoring the function of the at least one of the RLP1, RLP2, and L-type lecRLK genes comprising the deleterious mutation.

In some embodiments, the restoring of the function of the at least one of the RLP1, RLP2, and L-type lecRLK genes is achieved by CRISPR-mediated genome editing. In some embodiments, CRISPR-mediated genome editing comprises introducing into the plant a first nucleic acid encoding a Cas9 nuclease, a second nucleic acid comprising a guide RNA (gRNA) and a third nucleic acid comprising a homologous repair template of the at least one of RLP1, RLP2, and L-type lecRLK genes comprising the deleterious mutation.

In some embodiments, the restoring of the function of said at least one of the RLP1, L-type lecRLK genes comprising the deleterious mutation is achieved by introducing into the plant at least one plasmid comprising a substantially functional RLP1, RLP2, or L-type lecRLK gene corresponding to the at least one mutated RLP1, RLP2, or L-type lecRLK gene. In other words, if the RLP1 gene comprises a deleterious mutation in a plant, its function is restored by introducing into the plant a plasmid comprising a substantially functional RLP1 gene. If the RLP2 gene comprises a deleterious mutation in a plant, its function is restored by introducing into the plant a plasmid comprising substantially functional RLP2 gene. If the L-type lecRLK gene comprises a deleterious mutation in a plant, its function is restored by introducing into the plant a plasmid comprising substantially functional L-type lecRLK gene.

In some embodiments, the deleterious mutation in the RLP1 gene is selected from the group consisting of the genomic mutations described Table 1.

In some embodiments, the deleterious mutation in the RLP2 gene is e group consisting of the genomic mutations described. Table 2.

In some embodiments, the deleterious mutation in the L-type lecRLK gene is selected from the group consisting of the genomic mutations described Table 3.

In some embodiments, the present method further comprises inactivating the G-type lecRLK gene in the plant.

An aspect of this disclosure provides a method of converting a necrotropic fungi-susceptible plant into a necrotropic fungi-resistant plant comprising inactivating a G-type lecRLK gene in the plant.

Another aspect of this disclosure provides a method of determining necrotropic fungi resistance in a plant comprising infecting the plant with a necrotropic fungus; and determining expression levels of one or more genes selected from the group consisting of RLP1, RLP2, L-type lecRLK, BAK1a, BAK1b, S-NPR1, WRKY40, WRKY70a and WRKY70b genes before and after the infection, wherein a transient increase in the expression level of the one or more genes around 24 hours after the infection indicates that the plant is resistant to the necrotropic fungus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-1E, Experimental timeline and genome-wide associations of resistance and susceptibility loci. A, Experimental timeline illustrating the five months required to grow, inoculate, phenotype, and map candidate resistance/susceptibility loci. B, Manhattan plot of *Populus trichocarpa* chromosome 5 depicting significant associations of receptor-like protein 1 (RLP1=Potri.005G012100, genomic nucleotide sequence defined by SEQ ID NO: 1, amino acid sequence defined by SEQ ID NO: 2; p-value=1.56E-38) with resistance to *Sphaerulina musiva*. C, Manhattan plot of *P. trichocarpa* chromosome 3 depicting significant association of receptor-like protein 2 (RLP2=Potri.003G02820, genomic nucleotide sequence defined by SEQ ID NO: 3, amino acid sequence defined by SEQ ID NO: 4; p-value=2.78E-14) with resistance to *S. musiva*. D, Manhattan plot of *P. trichocarpa* chromosome 9 depicting significant association of L-type lectin receptor-like kinase (L-type lecRLK=Potri.009G036300, genomic nucleotide sequence defined by SEQ ID NO: 5, amino acid sequence defined by SEQ ID NO: 6, p-value=2.15E-16) with resistance to *S. musiva*. E, Manhattan plot of *P. trichocarpa* chromosome 5 depicting significant association of G-type lectin receptor-like kinase (G-type lecRLK=Potri.005G018000, genomic nucleotide sequence defined by SEQ ID NO: 7, amino acid sequence defined by SEQ ID NO: 8, p-value=1.161E-13) with susceptibility to *S. musiva*. Each black dot on the Manhattan plots (B, C, D, E) corresponds to a marker, its level of significance, and its physical position on the chromosome. The red line (B, C, D, E) represents the Bonferroni-corrected significance threshold based on 8.2 million markers.

Figure 3:
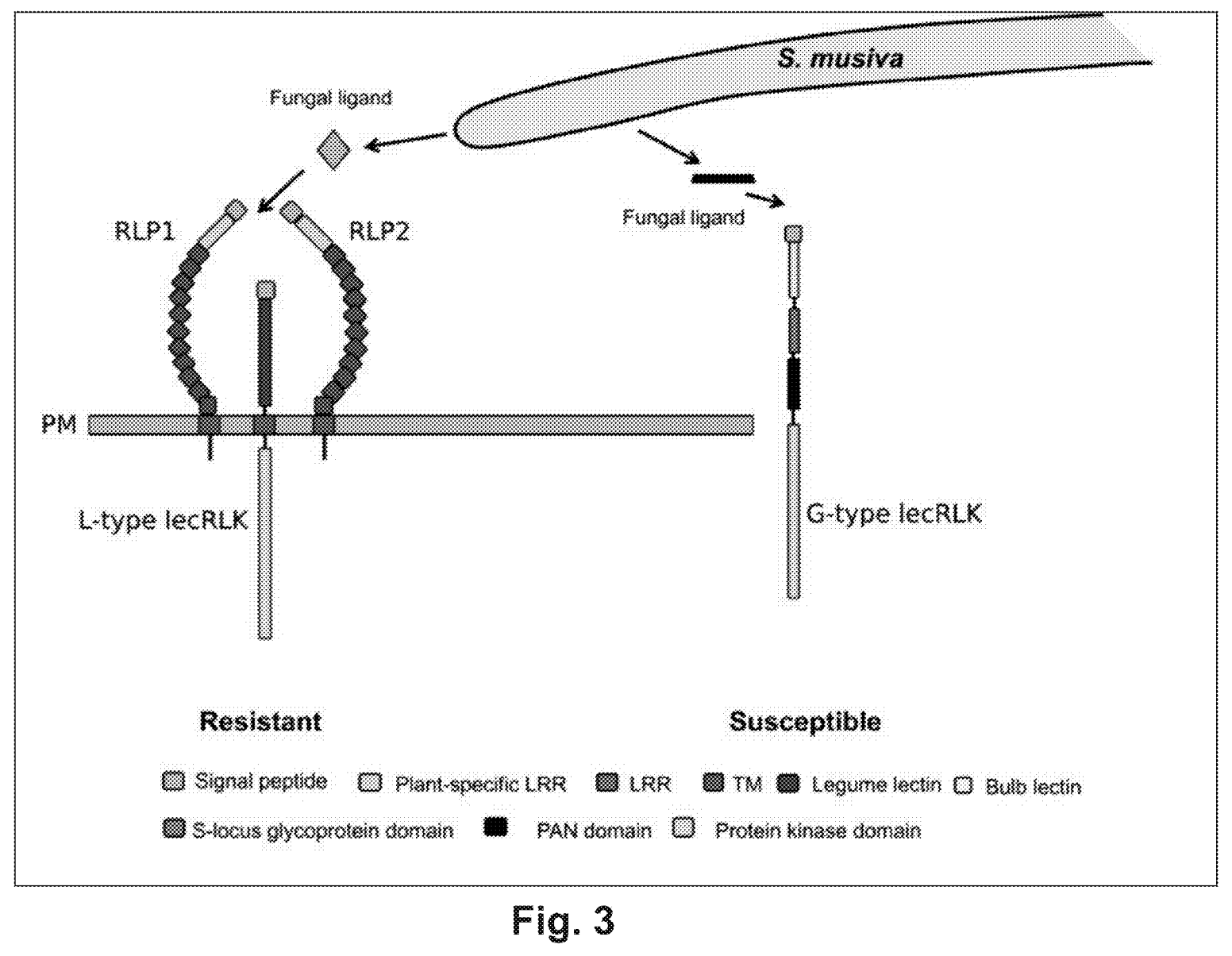

FIG. 3. A conceptual molecular model for the RLP-RLK-mediated resistance and RLK-mediated susceptibility responses controlling the *P. trichocarpa-S. musiva* interaction. A pathogen derived ligand interacts with the plasma membrane (PM) bound RLP1& 2/L-type lecRLK complex and signals a resistance response. A G-type lecRLK is shown as a target of an alternative fungal ligand either leading to suppression of the host defense response or triggering of susceptibility.

Figure 5A:
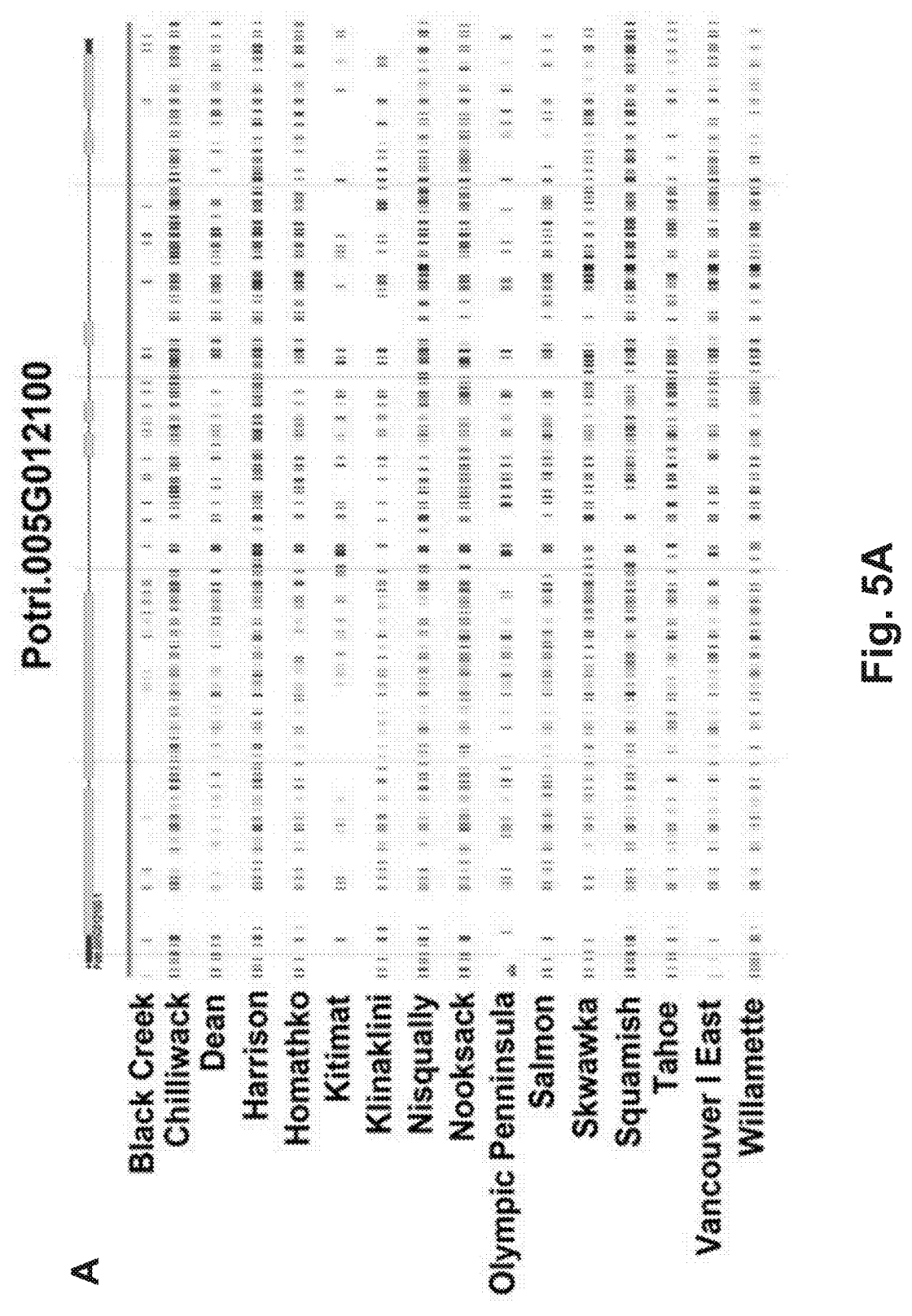
Figure 5B:
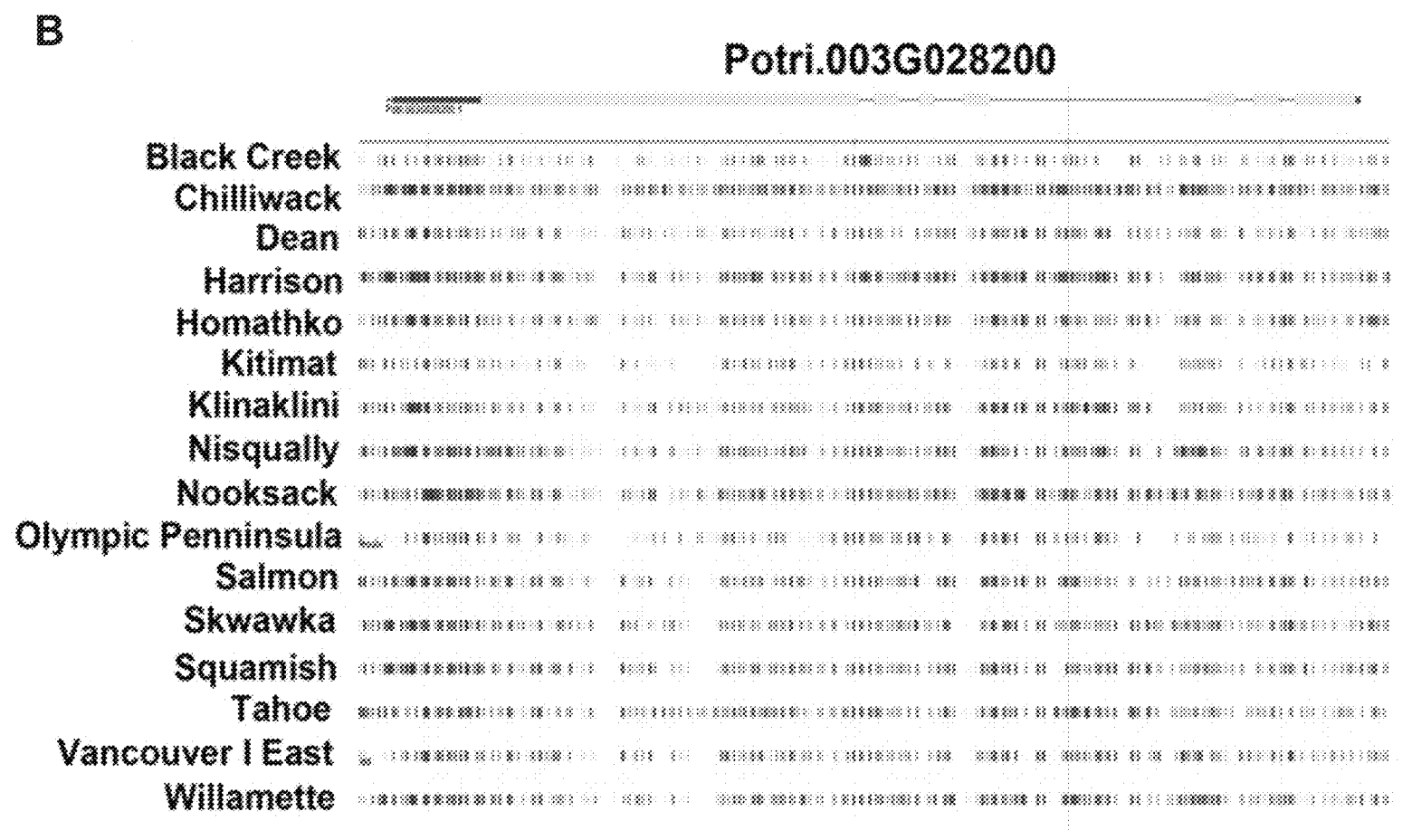
Figure 5C:
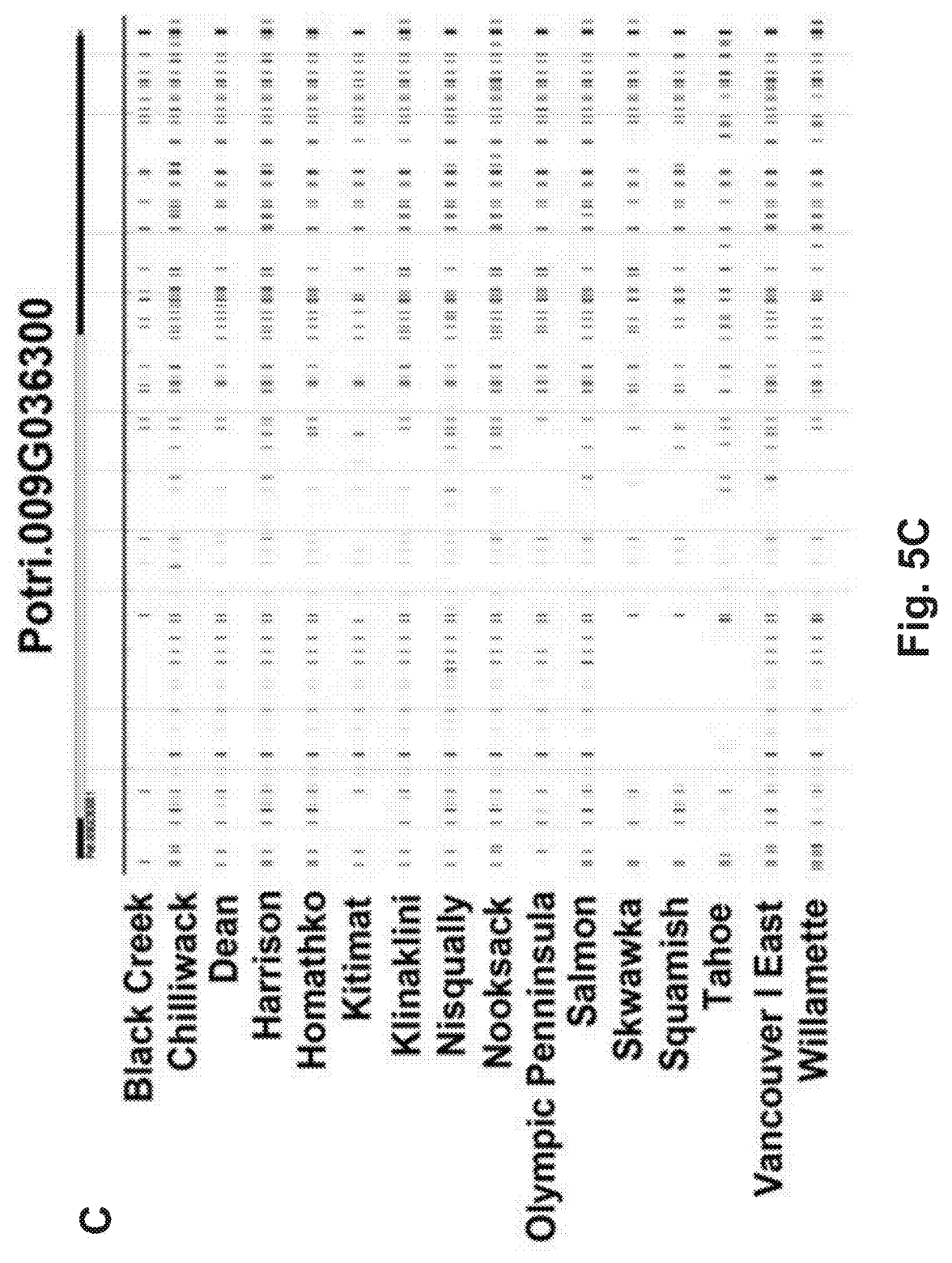

FIG. 5A-5D. Population-wide mutations in all four candidate genes grouped by the drainage where the *Populus trichocarpa* genotype was collected (A: RLP1=Potri.005G012100, B: RLP2=Potri.003G028200, C: L-type lecRLK=Potri.009G036300, and D: G-type lecRLK=Potri.005G018000.) Each drainage consists of multiple genotypes with all predicted mutations for all genotypes mapped to the physical position along each gene model. Blue lines are synonymous substitutions; green lines represent insertion/deletions (indels); yellow lines represent non-synonymous substitutions; and red lines represent high-impact mutations (stop gained, frame shift, splice site donor, and splice site acceptor). Gene models are depicted above each figure with yellow boxes representing exons and grey lines representing introns (from Phytozome, a webtool from the Plant Comparative Genomics portal of the Department of Energy's Joint Genome Institute).

FIG. 6. Protein domain prediction of RLP1 Potri.005G012100, RLP2=Potri.003G028200, L-type lecRLK=Potri.009G036300, and G-type lecRLK=Potri.005G018000 genes and the boundaries of the domains (by amino acid position)

DETAILED DESCRIPTION OF THE INVENTION

Figures 2A, 2B, 2C, 2D, 2E:
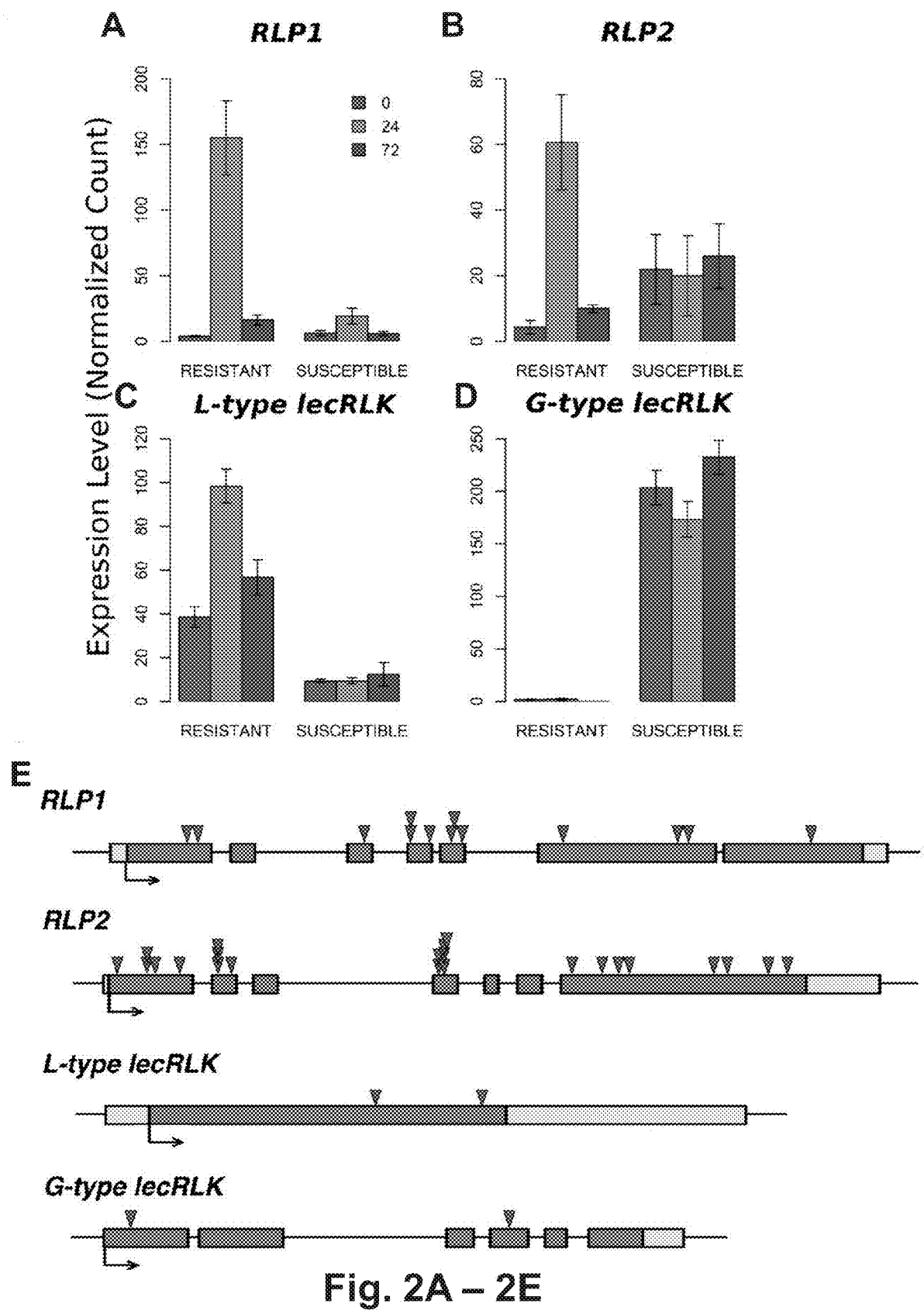
FIG. 2A-2E. A comparison of normalized gene counts and gene models of the four loci with the strongest associations to resistant and susceptible interactions between *P. trichocarpa* and *S. musiva*. Expression levels (normalized count) of four candidate loci in a resistant (BESC-22) and susceptible (BESC-801) genotypes of *P. trichocarpa* inoculated with *S. musiva* across three time points (first, second and third bars in each group represent 0-, 24- and 72 h post-inoculation (hpi) in that order). (A) Receptor-like protein 1 (RLP1=Potri.005G012100) with expression level peaking at 24-h post-inoculation in the resistant genotype. (B) Receptor-like protein 2 (RLP2=Potri.003G028200) with expression peaking at 24-h post-inoculation in the resistant genotype. (C) L-type lectin receptor-like kinase (L-type lecRLK=Potri.009G036300) with expression peaking at the 24-h post-inoculation. (D) G-type lectin receptor-like kinase (G-type lecRLK=Potri.005G018000) (bottom right graph) expressed at statistically similar levels across all three time-points in the susceptible genotype and low expression in the resistant genotype. Black bars represent the standard error of the mean for the three biological replicates. (E) Position of high-impact mutations including premature stop codons, frame shifts, and splice site mutations indicated by red arrows, in the three resistance loci (RLP1, RLP2 and L-type lecRLK) and one susceptibility locus (G-type lecRLK). The blue boxes represent the exons, the black lines represent introns, the grey boxes represent the 5' and 3' UTR (untranslated region) regions, and the black arrows represent the 5' start position of the coding region.
Figures 4A, 4B, 4C, 4D, 4E, 4F:
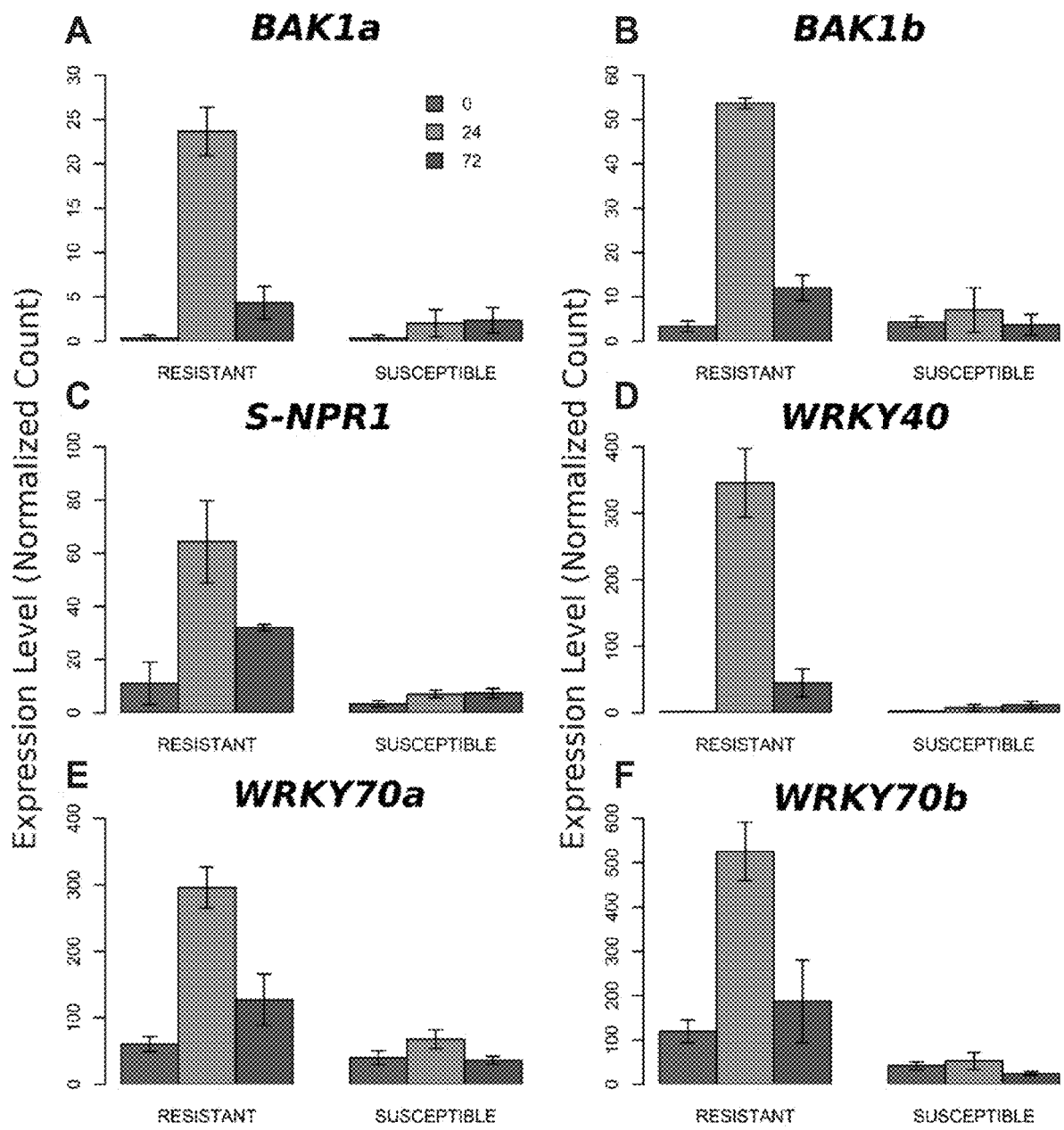
FIG. 4A-4F. A comparison of normalized counts of marker genes for plant immune responses across three time-points (0 h, 24 h and 72 h) post-inoculation for resistant (BESC-22) and susceptible (BESC-801) *Populus trichocarpa* genotypes inoculated with *Sphaerulina musiva*. (A) BRI1-ASSOCIATED RECEPTOR KINASE 1A (BAK1a=Potri.017G003 600, genomic nucleotide sequence defined by SEQ ID NO 17, amino acid sequence defined by SEQ ID NO: 18) expression peaks at 24-h post-inoculation in the resistant genotype. (B) a, BRI1-ASSOCIATED RECEPTOR KINASE 1B (BAK1b=Potri.T075000, genomic nucleotide sequence defined by SEQ ID NO 19, amino acid sequence defined by SEQ ID NO: 20) expression peaks at 24-h post-inoculation in the resistant genotype. (C) Suppressor of Nonexpresser of Pathogenesis-related genes 1\(S-NPR1=Potri.017G035500, genomic nucleotide sequence defined by SEQ ID NO 9, amino acid sequence defined by SEQ. ID NO: 10) expression peaks at 24-h post-inoculation in the resistant genotype. (B) The transcription factor WRKY40 (Potri.018G019700, genomic nucleotide sequence defined by SEQ ID NO 15, amino acid sequence defined by SEQ ID NO: 16) expression peaks at 24-h post-inoculation in the resistant genotype. (E) The transcription factor WRKY70a (Potri.013G090300, genomic nucleotide sequence defined by SEQ ID NO: 11, amino acid sequence defined by SEQ ID NO: 12) expression peaks at 24-h post-inoculation in the resistant genotype. (F) The transcription factor WRKY70b (Potri.016G137900, genomic nucleotide sequence defined by SEQ ID NO: 13, amino acid sequence defined by SEQ ID NO: 14) also peaked at 24-h post-inoculation in the resistant genotype. Black bars represent the standard error of the mean for the three biological replicates.
Figure 5D:
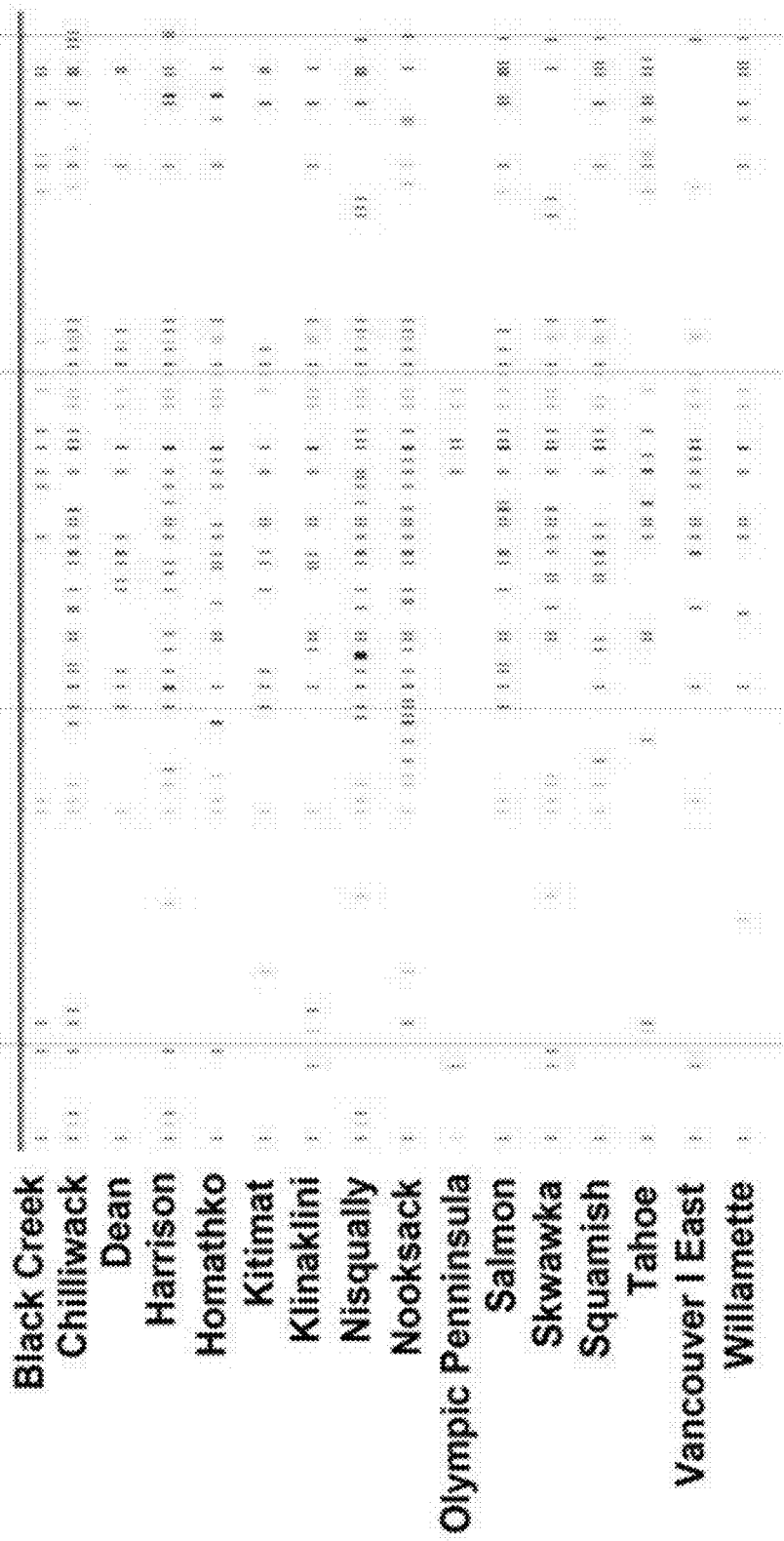
Figure 7:
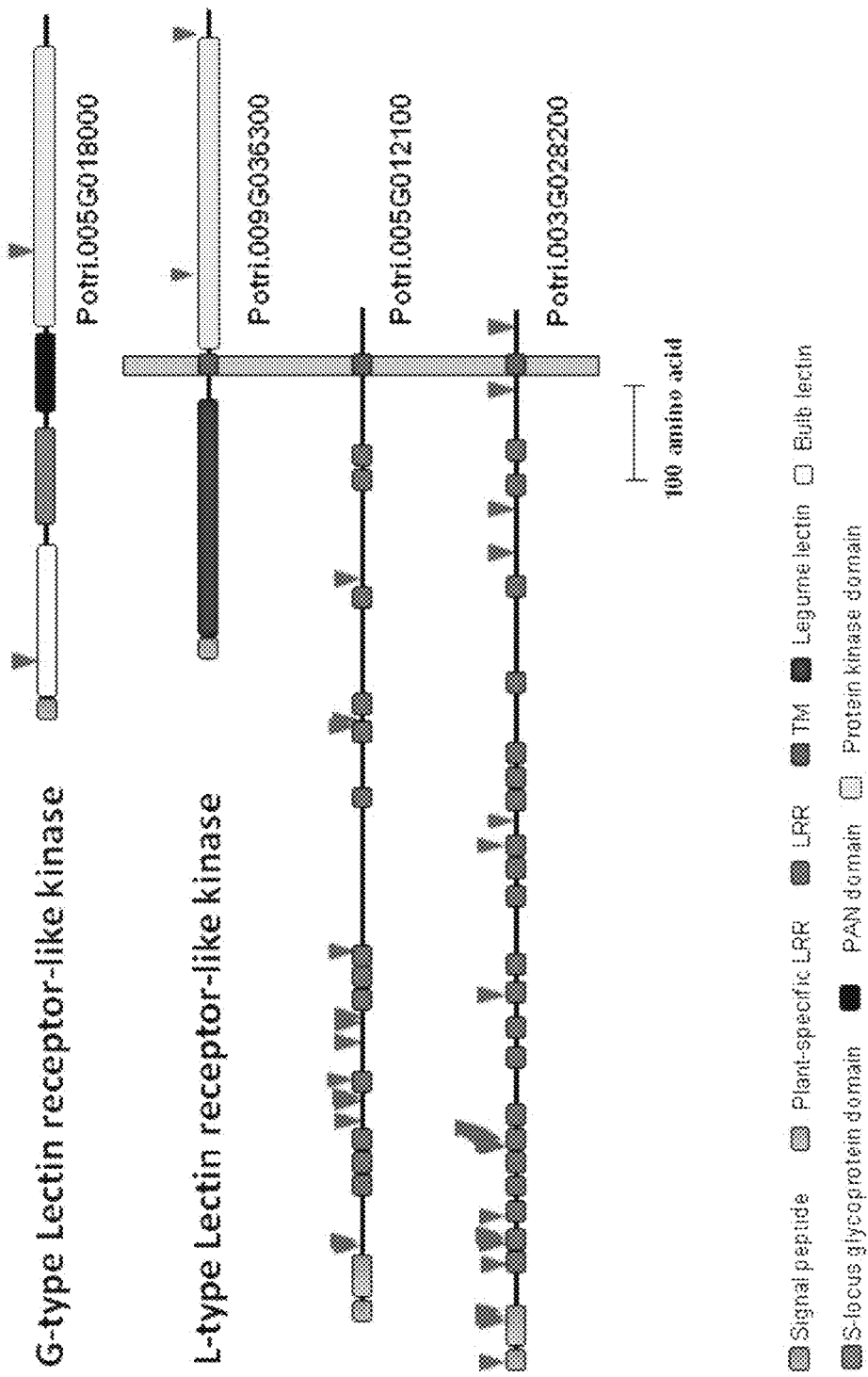
FIG. 7. Domain organization of the A) G-type lecRLK, B) L-type lecRLK, C) RLP1 and D) RLP2 genes. Arrows point to deleterious point mutations discovered in these genes. LRR: Leucine rich repeat domain, TM: Transmembrane domain

Pathogenic fungi, especially necrotrophic fungi, infections are deleterious to plant species used for biofuels, bioproducts, food and fiber production, therefore have a significant economic impact. In order to increase plant health and product yield, there is a great need for methods of identifying susceptible plants, and also for methods to confer disease resistance to necrotrophic fungi susceptible plants. Accordingly, the present application is directed to methods of selecting necrotrophic fungi-resistant plants for growing, and methods of genetically engineering susceptible plants to make them resistant to necrotrophic fungi infections.

Pathogenic Fungi

In some embodiments, the pathogenic fungus is a necrotrophic fungus. In some embodiments said necrotrophic fungus is from genus *Sphaerulina*. In other embodiments, said necrotropic fungus is selected from the group consisting of *Sphaerulina musiva*, *Sphaerulina oryzina*, *Sphaerulina rehmiana* and *Sphaerulina rubi*.

In yet another embodiment, the necrotropic fungus is selected from the group consisting of *Sphaerulina abeliceae*, *Sphaerulina aceris*, *Sphaerulina acetabulum*, *Sphaerulina acori*, *Sphaerulina aechmeae*, *Sphaerulina affinis*, *Sphaerulina albispiculata*, *Sphaerulina alni*, *Sphaerulina amelanchier*, *Sphaerulina amicta*, *Sphaerulina amphilomatis*, *Sphaerulina amygdali*, *Sphaerulina anemones*, *Sphaerulina annae*, *Sphaerulina antarctica*, *Sphaerulina arctica*, *Sphaerulina arthoniae*, *Sphaerulina assurgens*, *Sphaerulina aucubae*, *Sphaerulina azaleae*, *Sphaerulina baccarum*, *Sphaerulina bambusicola*, *Sphaerulina berberidis*, *Sphaerulina betulae*, *Sphaerulina blyttii*, *Sphaerulina bonariana*, *Sphaerulina boudieriana*, *Sphaerulina bryophila*, *Sphaerulina callista*, *Sphaerulina camelliae*, *Sphaerulina camelliae*, *Sphaerulina carestiae*, *Sphaerulina caricae*, *Sphaerulina caricis*, *Sphaerulina ceanothi*, *Sphaerulina centellae*, *Sphaerulina cercidis*, *Sphaerulina cetraricola*, *Sphaerulina cetrariicola*, *Sphaerulina chlorococca*, *Sphaerulina cibotii*, *Sphaerulina citri*, *Sphaerulina codiicola*, *Sphaerulina coffaeicola*, *Sphaerulina coffeicola*, *Sphaerulina concinna*, *Sphaerulina conflicta*, *Sphaerulina coriariae*, *Sphaerulina cornicola*, *Sphaerulina corniculata*, *Sphaerulina coronillaejunceae*, *Sphaerulina corynephora*, *Sphaerulina cucumeris*, *Sphaerulina cucurbitae*, *Sphaerulina datiscae*, *Sphaerulina diapensiae*, *Sphaerulina dioscoreae*, *Sphaerulina divergens*, *Sphaerulina dolichotera*, *Sphaerulina dryadis*, *Sphaerulina dryophila*, *Sphaerulina dubiella*, *Sphaerulina empetri*, *Sphaerulina endococcoidea*, *Sphaerulina epigaea*, *Sphaerulina eucalypti*, *Sphaerulina ferruginosa*, *Sphaerulina frondicola*, *Sphaerulina fuegiana*, *Sphaerulina gei*, *Sphaerulina gentianae*, *Sphaerulina gigantea*, *Sphaerulina giliae*, *Sphaerulina hainensis*, *Sphaerulina halophila*, *Sphaerulina hamadryadum*, *Sphaerulina hederae*, *Sphaerulina helicicola*, *Sphaerulina hyperici*, *Sphaerulina inaequalis*, *Sphaerulina inquinans*, *Sphaerulina intermedia*, *Sphaerulina intermixta*, *Sphaerulina Ipomoeae*, *Sphaerulina islandica*, *Sphaerulina iwatensis*, *Sphaerulina juglandis*, *Sphaerulina leightonii*, *Sphaerulina lepidiotae*, *Sphaerulina limnanthemi*, *Sphaerulina lini*, *Sphaerulina linicola*, *Sphaerulina ludwigiae*, *Sphaerulina mappiae*, *Sphaerulina marattiae*, *Sphaerulina marginata*, *Sphaerulina maroccana*, *Sphaer-*

*ulina marsileae, Sphaerulina maydis, Sphaerulina menispermi, Sphaerulina microthyrioides, Sphaerulina mimosaepigrae, Sphaerulina miyakei, Sphaerulina musae, Sphaerulina muscicola, Sphaerulina muscorum, Sphaerulina musicola, Sphaerulina musiva, Sphaerulina myriadea, Sphaerulina myriadea* subsp. *myriadea, Sphaerulina myrtillina, Sphaerulina naumovii, Sphaerulina nephromiaria, Sphaerulina oleifolia, Sphaerulina orae-maxis, Sphaerulina oryzae, Sphaerulina oryzina, Sphaerulina oxalidis, Sphaerulina oxyacanthae, Sphaerulina pallens, Sphaerulina parvipuncta, Sphaerulina patriniae, Sphaerulina paulistana, Sphaerulina peckii, Sphaerulina pedicellata, Sphaerulina pelargonii, Sphaerulina phalaenopsidis, Sphaerulina phellogena, Sphaerulina phoenicis, Sphaerulina phyllostachydis, Sphaerulina pini, Sphaerulina plantaginea, Sphaerulina pleuropogonis, Sphaerulina polygonorum, Sphaerulina polypodii, Sphaerulina polypodii, Sphaerulina polyspora, Sphaerulina populi, Sphaerulina populicola, Sphaerulina porothelia, Sphaerulina potebniae, Sphaerulina potentillae, Sphaerulina poterii, Sphaerulina primulicola, Sphaerulina pruni, Sphaerulina pseudovirgaureae, Sphaerulina pterocarpi, Sphaerulina pulii, Sphaerulina quercicola, Sphaerulina quercifolia, Sphaerulina quitensis, Sphaerulina rehmiana, Sphaerulina rhabdoclinis, Sphaerulina rhodeae, Sphaerulina rhododendri, Sphaerulina rhododendricola, Sphaerulina rubi, Sphaerulina saccardiana, Sphaerulina saccardoana, Sphaerulina sacchari, Sphaerulina salicina, Sphaerulina sambucina, Sphaerulina sasae, Sphaerulina schaereri, Sphaerulina scirpi, Sphaerulina sepincola, Sphaerulina serograpta, Sphaerulina silacincola, Sphaerulina smilacincola, Sphaerulina socia, Sphaerulina spartii, Sphaerulina staphyleae, Sphaerulina staurochili, Sphaerulina steganostroma, Sphaerulina subgen. Pharcidiella, Sphaerulina subgen, Sphaerulina, Sphaerulina sub glacialis, Sphaerulina subtropica, Sphaerulina suchumica, Sphaerulina tabacinae, Sphaerulina tanaceti, Sphaerulina tarda, Sphaerulina taxi, Sphaerulina taxicola, Sphaerulina thujopsidis, Sphaerulina tiliaris, Sphaerulina tirolensis, Sphaerulina todeae, Sphaerulina trapae-bispinosae, Sphaerulina trifolii, Sphaerulina tritici, Sphaerulina umbilicata, Sphaerulina valerianae, Sphaerulina viciae, Sphaerulina vincae, Sphaerulina violae, Sphaerulina vismiae, Sphaerulina vulpina, Sphaerulina westendorpii, Sphaerulina worsdellii, Sphaerulina xerophylli, Sphaerulina yerbae, Sphaerulina ziziphi, Sphaerulina zizyphae,* and *Sphaerulina zizyphi.*

Plant Species

In some embodiments, the plant species of this disclosure can be selected from any plant used for producing biofuels, bioproducts, food and fiber. In another embodiment the plant is selected from the group consisting of *Populus*, corn, soybean, rose, rice, caneberry, *Salix* (willow), alder, spruce, chestnut, oak, citrus, grape, eucalyptus, coffee, pine, rhododendron, birch, cucumber, tomato, betulia, clover, wheat, maize, sorghum, and blueberry.

"A resistant plant" refers to a plant that exhibits no symptoms or insignificant symptoms in response to a pathogenic fungal infection.

"A susceptible plant" refers to a plant that exhibits symptoms of infection in response to a pathogenic fungal infection. Symptoms of infection include, hut are not limited to, necrotic lesions on the leaves which lead to premature defoliation, and cankers on the stem and branches which can reduce growth, predispose the tree to colonization by secondary organisms, and cause stem breakage.

Resistance Genes

The present inventors investigated susceptible and resistant *Populus* plants to find genotypes that are associated with plant resistance to necrotrophic fungi infection. The inventors discovered that RLP1 (Potri.005G012100), RLP2 (Potri.003G028200), and L-type lecRLK (Potri.009G036300) genes were all substantially functional in nectrotrophic fungi-resistant *Populus* plants. The inventors also discovered that a deleterious mutation in any one of these three genes rendered a plant susceptible. The inventors also discovered that a substantially functional copy of G-type lecRLK (Potri.005G018000) is associated with disease susceptibility.

In some embodiments, a substantially functional RLP1 gene (Potri.005G012100) has the wild type genomic nucleotide sequence as defined by SEQ ID NO: 1, and encodes a protein with the wild type amino acid sequence as defined by SEQ ID NO: 2.

In some embodiments, a substantially functional RLP2 gene (Potri.003G028200) has the wild type genomic nucleotide sequence as defined by SEQ ID NO: 3, and encodes a protein with the wild type amino acid sequence as defined by SEQ ID NO: 4.

In some embodiments, a substantially functional L-type lecRLK (Potri.009G036300) gene has the wild type genomic nucleotide sequence as defined by SEQ ID NO: 5, and encodes a protein with the wild type amino acid sequence as defined by SEQ ID NO: 6.

In some embodiments, a substantially functional G-type lecRLK gene (Potri.005G018000) has the wild type genomic nucleotide sequence as defined by SEQ ID NO: 7, and encodes a protein with the wild type amino acid sequence as defined by SEQ ID NO: 8.

In some embodiments, a substantially functional RLP1 gene has a nucleotide sequence that is at least 80%, 85%, 90%, 95%, 98% or 99% identical to the wild type nucleotide sequence as defined by SEQ ID NO: 1, and encodes a protein that is at least 80%, 85%, 90%, 95%, 98% or 99% identical to the wild type amino acid sequence as defined by SEQ ID NO: 2.

In some embodiments, a substantially functional RLP2 gene has a nucleotide sequence that is at least 80%, 85%, 90%, 95%, 98% or 99% identical to the wild type nucleotide sequence as defined by SEQ ID NO: 3, and encodes a protein that is at least 80%, 85%, 90%, 95%, 98% or 99% identical to the wild type amino acid sequence as defined by SEQ ID NO: 4.

In some embodiments, a substantially functional L-type lecRLK gene has a nucleotide sequence that is at least 80%, 85%, 90%, 95%, 98% or 99% identical to the wild type nucleotide sequence as defined by SEQ ID NO: 5, and encodes a protein that is at least 80%, 85%, 90%, 95%, 98% or 99% identical to the wild type amino acid sequence as defined by SEQ ID NO: 6.

In some embodiments, a substantially functional G-type lecRLK gene has a nucleotide sequence that is at least 80%, 85%, 90%, 95%, 98% or 99% identical to the wild type nucleotide sequence as defined by SEQ ID NO: 7, and encodes a protein that is at least 80%, 85%, 90%, 95%, 98% or 99% identical to the wild type amino acid sequence as defined by SEQ ID NO: 8.

In some embodiments, a substantially functional gene lacks deleterious mutations including, but not limited to, early termination codons, frameshift mutations, inversions, deletions and non-conservative mutations which result in an amino acid change that has different properties than the wild type.

In some embodiments, a substantially functional gene retains all domains that are believed to be critical for functionality intact. For example, for the RLP1 and RLP2 genes, some of the critical domains are Leucine-rich Repeat (LRR) domains, plant specific Leucine-rich Repeat (LRR) domains and the signal peptide. On the other hand, for the L-type lectin receptor-like kinase (L-type lecRLK) gene, some of the critical domains are Protein Kinase domain, transmembrane domain, Legume lectin domain and the signal peptide. For the G-type lectin receptor-like kinase (G-type lecRLK) gene, some of the critical domains are Protein Kinase domain, PAN domain, S-locus glycoprotein domain, Bulb lectin domain and the signal peptide. The boundaries of the functional domains of RLP1 (Potri.005G012100), RLP2 (Potri.003G028200), L-type lecRLK (Potri.009G0363001) and G-type lecRLK (Potri.005G018000) genes are disclosed in FIG. 6.

In some embodiments, for the RLP1 and RLP2 genes, a mutation in the extracellular domain, which comprises the Leucine-rich Repeat (LRR) domains, plant specific Leucine-rich Repeat (LRR) domains and the signal peptide, is believed to be deleterious to functionality.

In some embodiments, for the L-type lectin receptor-like kinase (L-type lecRLK) gene, a mutation in the protein kinase domain is believed to be deleterious to functionality.

In some embodiments, for the G-type lectin receptor-like kinase (G-type lecRLK) gene, a mutation in the protein kinase domain or in the Bulb lectin domain is believed to be deleterious to functionality.

In some embodiments, for the RLP1 gene, a functionally deleterious mutation is selected from the mutations listed in Table 1.

In some embodiments, for the RLP2 gene, a functionally deleterious mutation is selected from the mutations listed in Table 2.

In some embodiments, for the L-type lecRLK gene, a functionally deleterious mutation is selected from the mutations listed in Table 3.

In some embodiments, for the G-type lecRLK gene, a functionally deleterious mutation is selected from the mutations listed in Table 4.

In one embodiment, in order to determine whether a plant is resistant to a necrotrophic fungus that can infect said plant, RLP1, RLP2, and L-type lecRLK genes of said plant are sequenced and it is determined that said plant is resistant to necrotrophic fungus infection if all of the RLP1, RLP2, L-type lecRLK genes are substantially functional.

Infection of Plants

In some embodiments, plants are infected with pathogenic fungi. Inoculation with pathogenic fungi is carried out as described in LeBoldus et al. (*Plant Dis.*, (2010), 94, 1238-1242 (2010)). Briefly, plants are grown until a minimum height of 30 cm (e.g., approximately 54 days after planting for *Populus*). Pathogenic fungi are grown on plates (petri dishes) containing KV-8 growth media amended with chloramphenicol at 300 mg/liter and streptomycin sulfate at 25 mg/liter. These dishes are then sealed with Parafilm and placed on a light bench under Gro-Lux wide-spectrum fluorescent bulbs (Sylvania; Osram GmbH, Munich) at room temperature, where they receive 24 hours of light. Pure colonies are obtained by making transfers to K-V8 medium and allowing the fungi to grow until sporulation occurs. Isolates are stored at −90° C. in vials containing 300 µl of 50% glycerol and 700 µl of potato dextrose broth (PDB; Difco laboratories)

On the day of infection, approximately 1 ml of deionized water is added to a plate of grown fungi. An inoculation loop is rubbed on the plate surface to dislodge the spores and the spore suspension is collected with a pipette. The spore suspension (infection solution) to be applied to plants comprise between $1\times10^4$ and $5\times10^6$ spores conidia)/liter. In a specific embodiment the spore suspension (infection solution) comprises $1\times10^6$ spores (conidia)/liter. Plants are sprayed with the spore suspension until the entire leaf and stem are wet, and placed into a black plastic bag for 48 hours, Following incubation plants are placed on the greenhouse bench for 3 weeks.

In a specific embodiment, in order to determine whether a plant is resistant to a neurotrophic fungus, said plant is infected with the necrotrophic fungus as described above; and gene expression levels of one or more of RLP1, RLP2, and L-type lecRLK genes are measured at least at 0, 24 and 72 hours after infection. In some embodiments, measurements can be made every 8, 12 or 24 hours. If expression levels of one or more of the RLP1, RLP2, and L-type lecRLK genes transiently increase and peak around the 24 hour time point after infection in said plant (similar to shown in FIGS. 2A-2C), this transient increase in expression levels of one or more of these genes indicates that said plant is resistant to necrotrophic fungus infection. In some embodiments, the transient increase is at least about 1.5 folds, about 2 folds, about 3 folds, about 4 folds, about 4 folds, about 6 folds, about 8 folds, about 10 folds or about 15 folds over the baseline (0 hour) levels. The increase in expression levels is transient if around 72 hours the expression levels of said genes return to baseline (0 hour) levels. On the other hand, if expression levels of one or more of the RLP1, RLP2, and L-type lecRLK genes do not change significantly between 0, 24 and 72 hours after infection, this indicates that said plant is susceptible to necrotrophic fungi infection. A "significant change in expression levels" is a change that is more than 1.5 folds over the baseline (0) hours.

In yet another embodiment, in order to determine whether a plant is resistant to a necrotrophic fungus, said plant is infected with the necrotrophic fungus and gene expression levels of one or more of BAK1a, BAK1b, S-NPR1, WRKY40, WRKY70a and WRKY70b genes are measured at 0, 24 and 72 hours after infection. In some embodiments, measurements can be made every 8, 12 or 24 hours. If expression levels of one or more of the BAK1a, BAK1b, S-NPR1, WRKY40, WRKY70a or WRKY70b genes transiently increase and peak at about the 24 hour time point after infection in said plant as shown in FIGS. 4A-4F, it indicates that said plant is resistant to necrotrophic fungus infection. The increase in expression levels is transient if around 72 hours the expression levels of said genes return to baseline (0 hour) levels. On the other hand, if expression levels of one or more of the BAK1a, BAK1b, S-NPR1, WRKY40, WRKY70a or WRKY70b genes do not change significantly between 0, 24 and 72 hours after infection, this indicates that said plant is susceptible to necrotrophic fungi infection.

Gene expression changes can be measured with methods including, but not limited to, Reverse Transcriptase Polymerase Chain Reaction (RT-PCR), Real-time RT-PCR, Western Blotting, Northern Blotting, in-situ hybridization and RNA sequencing (RNA-seq).

Methods of Using Resistant Plants

In some embodiments, plants that are resistant to necrotropic fungi are used in producing lignocellulosic products. The term "lignocellulosic" refers to a composition containing both lignin and cellulose. In a specific embodiment, the lignocellulosic products include, but are not limited to, paper and pulp.

In some embodiments, plants that are resistant to necrotropic fungi are used for producing food.

In some embodiments, plants that are resistant to necrotropic fungi are used for producing biofuels.

Converting a Necrotropic Fungi-Susceptible Plant into a Necrotropic Fungi-Resistant Plant In some embodiments, a necrotropic fungi-susceptible plant is converted into a necrotropic fungi-resistant plant. Briefly, the RLP1, RLP2, and L-type lecRLK genes are sequenced and if there is a deleterious mutation in one or more of these genes, then the plant can be converted into a necrotropic fungi-resistant plant by restoring the function of said one or more mutated genes in the plant.

Targeted genome engineering (also known as genome editing) has emerged as an alternative to classical plant breeding and transgenic (Genetically Modified Organism—GMO) methods to improve crop plants. Available methods for introducing site-specific double strand DNA breaks include zinc finger nucleases (ZFNs), TAL effector nucleases (TALENs) and CRISPR/Cas system. ZFNs are reviewed in Carroll, D. (*Genetics,* 188.4 (2011): 773-782), and TALENs are reviewed in Zhang et al, (*Plant Physiology,* 161.1 (2013): 20-27), which are incorporated herein in their entirety.

CRISPR/Cas system is a method based on the bacterial type II CRISPR (clustered regularly interspaced short palindromic repeats)/Cas (CRISPR-associated) immune system. The CRISPR/Cas system allows targeted cleavage of genomic DNA guided by a customizable small noncoding RNA, resulting in gene modifications by both non-homologous end joining (NHEJ) and homology-directed repair (HDR) mechanisms. Belhaj et al. (*Plant Methods,* 2013, 9:39) summarizes and discusses applications of the CRISPR-Cas technology in plants and is incorporated herein in its entirety.

In some embodiments, restoring function to a mutated gene is achieved by genome editing technologies. In a specific embodiment genome editing is achieved by CRISPR (Clustered regularly-interspaced short palindromic repeats)/Cas technology. CRISPR-Cas and similar gene targeting systems are well known in the art, with reagents and protocols readily available. Exemplary genome editing protocols are described in Jennifer Doudna, and Prashant Mali "*CRISPR-Cas: A Laboratory Manual*" (2016) (*CSHL Press*, ISBN: 978-1-621821-30-4) and Ran, F. Ann, et al. (*Nature Protocols* (2013), 8 (11): 2281-2308).

In a specific embodiment, CRISPR-mediated gene repair comprises introducing said plant a first nucleic acid encoding a wild type Cas9 nuclease, a second nucleic acid comprising a guide RNA (gRNA) specific for targeting the mutated genomic region and a third nucleic acid comprising a homologous repair template (aka. Homology Directed Repair—HDR template) of said RLP1, RLP2, L-type lecRLK genes with said deleterious mutation. In this embodiment, the specific guide RNA targets the Cas9 nuclease to the mutated genomic region and the Cas9 nuclease introduces a double strand break in the targeted DNA region. In the presence of the homology template which contains a substantially functional copy of the mutated genomic region (with the deleterious mutation corrected), DNA repair mechanism favors Homology Directed Repair (HDR) and the mutation in the targeted gene is corrected.

In another specific embodiment, CRISPR-mediated gene repair comprises introducing said plant a first nucleic acid encoding a mutated Cas9 nuclease, wherein said mutated Cas9 nuclease can only introduce single strand nicks to the genome, a second nucleic acid comprising a guide RNA (gRNA) specific for targeting the mutated genomic region, a third nucleic acid comprising a guide RNA (gRNA) specific for targeting the mutated genomic region in the reverse complement strand and a third nucleic acid comprising a homologous repair template (HDR template) of said RLP1, RLP2, L-type lecRLK genes with said deleterious mutation. In this embodiment, one of the specific guide RNAs targets the mutated Cas9 nuclease to one strand of the mutated genomic region and the mutated Cas9 nuclease introduces a single strand nick in the targeted. DNA region. The second specific guide RNA is designed to target the mutated Cas9 nuclease to the opposite strand of the mutated genomic region, and the mutated Cas9 nuclease introduces a single strand nick in the targeted DNA region in the opposite strand as well. The two single nicks on opposite strands effectively cause a double strand break in the targeted region. In the presence of the homology template which contains a substantially functional copy of the mutated genomic region (with the deleterious mutation corrected), DNA repair mechanism favors Homology Directed Repair (HDR) and the mutation in the targeted gene is corrected.

In some embodiments, restoration of mutated gene function in one or more of RLP1, RLP2, and L-type lecRLK genes is achieved by introduction of a substantially functional RLP1, RLP2, or L-type lecRLK gene corresponding to the mutated gene by plasmid delivery. Plasmid delivery methods comprise agrobacterium-mediated transformation, viral based transformation, particle bombardment/biolistics electro-transfection, delivery by silicon carbide fibers, polymer-based transfection (polyfection), liposome-mediated transfection (lipofection), micro injection, wave and beam mediated transformation and desiccation based transformation. Methods of plasmid (DNA) delivery to produce transgenic plants are described in Behrooz D. al. (*Biotechnology*, (2008), 7: 385-402).

In some embodiments, inactivation of the G-type lecRLK gene confers resistance to neurotrophic fungi in a susceptible plant. In specific embodiments, the inactivation of the G-type lecRLK gene includes a deletion of the whole or a part of the gene such that no functional protein product is expressed (also known as gene knock out). The inactivation of a gene may include a deletion of the promoter or the coding region, in whole or in part, such that no functional protein product is expressed. In other embodiments, the inactivation of G-type lecRLK includes introducing an inactivating mutation to the gene, such as an early STOP codon in the coding sequence of the gene, such that no functional protein product is expressed.

In some embodiments, gene inactivation is achieved using available gene targeting technologies in the art. Examples of gene targeting technologies include the Cre/Lox system (described in Kühn, R., & M. Torres, R., *Transgenesis Techniques: Principles and Protocols*, (2002), 175-204), homologous recombination (described in Capecchi, Mario R., *Science* (1989), 244: 1288-1292), and TALENs (described in Sommer et al., *Chromosome Research* (2015), 23: 43-55, and Cermak et al. *Nucleic Acids Research* (2011): gkr218).

In one embodiment, G-type lecRLK inactivation is achieved by a CRISPR/Cas system. CRISPR-Cas and similar gene targeting systems are well known in the art with reagents and protocols readily available. Exemplary genome editing protocols are described in Jennifer Doudna, and Prashant Mali, "*CRISPR-Cas: A Laboratory Manual*" (2016) (*CSHL Press*, ISBN: 978-1-621821-30-4) and Ran, F. Ann, et al. *Nature Protocols* (2013), 8 (11): 2281-2308.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present description is further illustrated by the following examples, which should not be construed as limiting in any way.

EXAMPLES

Materials and Methods:
Plant Material

Plant material from 1,081 Populus trichocarpa (Torr & Gray) genotypes, originally collected from wild populations in California, Oregon, Washington and British Columbia, were planted in a stool bed at the Oregon State University Research Farm in Corvallis, Oreg. (Slavov et al., New Phytol; 196(3):71.3-25 (2012)). During January 2014 dormant branch cuttings were collected and sent to the North Dakota State University's Agricultural experiment station research greenhouse complex in Fargo, N.Dak. For each genotype, branches were cut into 10 cuttings, measuring 10 cm in length, with at least one bud. Cuttings were soaked in distilled water for 48 h, planted in cone-tainers (Ray Leach SC10 Super Cone-tainers, Stuewe and Sons, Inc. Tangent, Ore., USA) measuring 3.8-cm in diameter and 21-cm deep filled with growing medium (SunGro Professional Mix #8; SunGro Horticulture Ltd., Agawam, Mass.) amended with 12 g of Nutricote slow release fertilizer (15-9-12) (N-P-K) (7.0% $NH_3N$, 8.0% $NO_3$—N, 9.0% $P_2O_5$, 12.0% $K_2O$, 1.0% Mg, 2.3% S, 0.02% B, 0.05% Cu, 0.45% Fe, 0.23% chelated Fe, 0.06% Mn, 0.02% Mo, 0.05% Zn; Scotts Osmocote Plus; Scotts Company Ltd., Marysville, Ohio). The cuttings were planted such that the upper most bud remained above the surface of the growing medium. Plants were grown in a greenhouse with a temperature regime of 20° C./16° C. (day/night) and an 18-h photoperiod supplemented with 600 W high-pressure sodium lamps. Slow release fertilizer was added weekly with 15-30-15 (N-P-K) Jack's fertilizer (JR PETERS INC; Allentown, Pa.) at 200 ppm for two months to promote root growth and subsequently fertilized with 20-20-20 (N-P-K) liquid fertilizer (Scotts Peters Professional; Scotts Company Ltd., Marysville, Ohio) once a week. Plants were watered as needed.

Pathogen Culture

Three isolates of Sphaerulina musiva (MN-12, MN-14, MN-20) collected in Minnesota, were chosen for inoculation and transferred from storage (−80° C.) onto K-V8 (180 ml of V8 juice [Campbell Soup Company, Camden, N.J.]; 2 g of calcium carbonate, 20 g of agar, and 820 ml of deionized water) growing media, sealed with Parafilm (Structure Probe Inc., West Chester, Pa.) and placed on a light bench under full-spectrum fluorescent bulbs (Sylvania; Osram Gmbh, Munich) at room temperature until sporulation was observed. Following sporulation, five 5-mm plugs were transferred onto another K-V8 plate for 14 days under continuous light. There were a total of total of 200 plates for each isolate.

Inoculation

Plants were inoculated when they reached a minimum height of 30 cm (~54 days after planting). Plates containing isolates were unsealed and 1 mL of deionized water was added to the plate. Rubbing the media surface with an inoculation loop dislodged the spores and the spore suspension was collected with a pipette. The spore suspensions were individually bulked from the three isolates at a concentration of $10^6$ spores $mL^{-1}$ for each isolate. Plants were taken out of the greenhouse and there heights were measured prior to inoculation, sprayed with a HVLP gravity fed air spray gun (Central Pneumatic, Harbor Freight Tools) at 20 psi until the entire leaf and stem was wet (15 ml), and placed into a black plastic bag for 48 hours. Following incubation plants were placed on the greenhouse bench for 3 weeks.

Phenotyping

At three weeks post-inoculation phenotypic responses were characterized by measuring the height and caliper of each tree. Subsequently, the number of cankers was counted and digital images were acquired. This information was analyzed providing a range of phenotypes: (i) number of cankers; (ii) number of cankers per cm; and (iii) disease severity based on digital imagery. In total 280 person hours were expended to collect the phenotypic data for the genome-wide association study.

GWAS Analysis

To assess genetic control, the emmax algorithm was used with kinship as the correction factor for genetic background effects (Lorang, J. et al. Tricking the guard: Exploiting plant defense for disease susceptibility. Science 338, 659-662 (2012)) to compute genotype to phenotype associations using 8.2 million SNP variants with minor allele frequencies >0.05 identified from whole-genome resequencing (Slavov, G. T. et al., New Phytol, 196, 713-725 (2012)). A number of loci highly associated with Sphaerulina response were identified (i.e. susceptibility/resistance loci) (Table 5).

RNAseq Experiment

The resistant genotype BESC-22 and the susceptible genotype BESC-801 were selected based on the results from the GWAS described above. The experimental design was a randomized complete block design with three blocks. Each plant by time point combination occurred once per block.

Inoculum was prepared in an identical manner to that described above. However, in order to ensure that only tissue exposed to the fungal pathogen was used for transcriptome sequencing, position-based inoculations at the lenticels rather than whole-tree inoculations were conducted. A total of three lenticels on each plant were inoculated with a 5 mm plug of sporulating mycelium wrapped in parafilm. At the time of sample collection tissue from all three lenticels was sampled, placed in a single extraction tube, and flash frozen.

Approximately 100 mg of symptomatic tissue from each inoculation point was harvested, placed in a MP Biomedicals® Lysing Matrix tube and flash frozen in liquid nitrogen. The frozen samples were placed in a BeadBeater homogenizer and ground to a fine powder. The mRNA from each sample was enriched for using the Dynabeads mRNA DIRECT Kit, following the manufacturer's protocol with the additional steps of adding Ambion Plant Isolation Aid to the lysis buffer as well as a chloroform cleanup step after centrifuging the lysate.

Stranded RNA Seq library(s) were generated and quantified using qPCR. Sequencing was performed on an Illumina HiSeq 2500 (150mer paired end sequencing). Raw fastq file reads were filtered and trimmed using the JGI QC pipeline. Using BBDuk, raw reads were evaluated for sequence artifacts by kmer matching (kmer=25) allowing 1 mismatch, and detected artifacts were trimmed from the 3' end of the reads. RNA spike-in reads, PhiX reads and reads containing any Ns were removed. Quality trimming was performed using the phred trimming method set at Q6. Following trimming, reads under the length threshold were removed (minimum length 25 bases or ⅓ of the original read length; whichever was longer). Raw reads from each library were aligned to the reference genome using TopHat. Only reads that mapped uniquely to one locus were counted. FeatureCounts was used to generate raw gene counts. Raw gene counts were used to evaluate the level of correlation between biological replicates, using Pearson's correlation to identify which replicates would be used in the DGE analysis. DESeq2 (v1.2.10) (Cingolani P et al., *Fly* (*Austin*), 6: 80-92 (2012)) was subsequently used to determine which genes were differentially expressed between pairs of conditions. The parameters used to "call a gene" between conditions was determined at a p-value ≤0.05.

RNASeq differential expression analysis for *Sphaerulina* was performed using the Tuxedo suite pipeline. Illumina short paired reads were trimmed for quality, using Sickle (Trapnell et al., *Nat Protoc.* 7, 562-578 (2012)) set with a minimum quality score cutoff of 30 and a minimum read length of 100 bp. Using TopHat v2.1.0 and Bowtie2 v2.2.3, trimmed reads for each sample replicate were aligned to combined assembly contigs from *Sphaerulina musiva* strain SO2202 (GenBank accession: GCA_000320565.2) and *Populus trichocarpa* (GenBank accession: GCF_000002775.3). Reads were mapped with settings "-r 0 -i 36 -I 1000 -p 4" and "-G" with combined gene annotations from the *S. musiva* and *P. trichocarpa* reference genomes. *Sphaerulina musiva* contigs and mapped reads were extracted using Samtools v0.1.1.8. Transcript isoforms for each of the sample replicates were individually assembled and quantified using Cufflinks v2.2.1 (Cingolani P et al., *Fly* (*Austin*), 6: 80-92 (2012)) guided by the *S. musiva* reference genome and gene annotations. Transcripts assembled from each alignment were merged using Cuffmerge (Cingolani P et al., *Fly* (*Austin*), 6: 80-92 2012)).

Differential gene expression analysis was performed using Cuffdiff (Cingolani P et al., *Fly* (*Austin*), 6: 80-92 (2012)). Time-series comparisons were performed for resistant interaction between BESC-22 and *S. musiva* (24-h and 72-h post-inoculation) and the susceptible interaction with BESC-801 and *S. musiva* (24 h and 72 h), with three replicates per time point. These analyses excluded time point 0 due to low sequencing depth for *Sphaerulina*. Differential expression analyses were also performed comparing gene expression at time points 24 h and 72 h between the resistant and susceptible interactions.

Generation of Constructs for Protein Expression

The predicted lectin domains of G-type lecRLK and L-type lecRLK were cloned (23). Briefly, to create Gateway entry clones truncated coding regions of G-type lecRLK (Amino Acids 36-192) and L-type lecRLK (Amino Acids 30-281) were amplified from *P. trichocarpa* cDNA using the following gene specific primer pairs: G-RLK1-36F, 5'-AACTTGACTTI-CAAGGCCAGTCTCTCTCTGCAAGC-3' (SEQ ID NO:21)/G-RLK1-192R, 5'-ACAAGAAAGCTGGGTCCTAACCTGGTGCAG-GATCTT-3' (SEQ ID NO: 22) and L-RLK2-30F, 5'-AACTTGACITTCAAGGCCACTTCATCTATCATGG-3' (SEQ ID NO: 23)/L-RLK2-281, 5'-ACAAGAAAGCTGGGTCCTAAGGCAACTTTGACA-CATC-3' (SEQ ID NO: 24). The control protein was a non-catalytic peptide fragment of *Arabidopsis* ESK1 (Amino Acids 44-133), and was amplified from *Arabidopsis* cDNA using the following gene specific primer pairs: ESK1-44F, 5'-AACTTGACTTTCAAGGCGTGGAAT-TGCCGCCG-3' (SEQ ID NO: 25)/ESK1133R, 5'-ACAAGAAAGCTGGGTCCTACGAACGGGAAAT-GATAC-3' (SEQ ID NO: 26). Italicized sequences indicate the partial attB adapter sequences appended to the primers for the first round of PCR amplification, and the bold sequences denote the inserted STOP codon. A second set of universal primers, attB_Adapter-F, 5'-GGGGACAAGTTTGTACAAAAAAGCAGGCTCT-GAAAACTTGIACTTTCAAGGC-3' (SEQ ID NO: 27)/ attB_Adapter-R, 5'-GGGGACCACTTTGTA-CAAGAAAGCTCGGGTC-3' (SEQ ID NO: 28) was used to complete the attB recombination site and append a tobacco etch virus (TEV) protease cleavage site (Meng L, et al. (2013), *J. Biol. Chem.,* 288:34680-34698). The attB-PCR product was cloned into pDONR221 (Life technologies) using Gateway BP Clonase II Enzyme Mix (life technologies) to create entry clones. To generate expression clones of G-type lecRLK (pGEn2-EXP-G-type lecRLK36-192) and L-type lecRLK (pGEn2-EXP-L-type lecRLK30-281), the entry clones were recombined into a Gateway-adapted version of the pGEn2 mammalian expression vector (pGEn2-REST) (Gilbert H J. et al, (2013), *Curr. Opi.,* Struct. Biol. 23:669-677), using Gateway LR Clonase II Enzyme Mix (Life Technologies). The resulting expression constructs (His-GFP-G-type lecRLK$^{\Delta 36\text{-}192}$ and His-GFP-L-type lecRLK$^{\Delta 30\text{-}281}$) encode fusion proteins comprised of an amino-terminal signal sequence, an 8×His tag, an AviTag recognition site, the "superfolder" GFP (sfGFP) coding region, the recognition sequence of the tobacco etch virus (TEV) protease, and the indicated lectin domains. For transfection, plasmids were purified using the PureLink HiPure Plasmid Filter Maxiprep Kit (Life Technologies).

Expression and Purification of His-GFP-G-type lecRLK36-192 and His-GFP-L-type lecRLK30-281

Recombinant expression was performed by transient transfection of suspension culture HEK293-F cells (FreeStyle™ 293-F cells, Thermo Fisher Scientific, Waltham Mass.) in a humidified $CO_2$ platform shaker incubator at 37° C. with 80% humidity. The HEK293-F cells were maintained in Freestyle™ 293 expression medium (Thermo Fisher Scientific, Waltham, Mass.) and transfection with plasmid DNA using polyethyleneimine as transfection reagent (linear 25-kDa polyethyleneimine, Polysciences, Inc., Warrington, Pa.) was performed as previously described (Zhang Y, et al. (2010), *Plant Cell,* 22:3153-316, Urbanowicz B R et al., *Plant J.* 80:197-206). After 24 h, the cell cultures were diluted 1:1 with fresh media supplemented with valproic acid (2.2 mM final concentration) and protein production was continued for an additional 4-5 days at 37° C. The cell culture was harvested, clarified by sequential centrifugation at 1200 rpm for 10 min and 3500 rpm for 20 min, and passed through a 0.45 µM filter (Millipore, Billerica, Mass.).

All chromatography experiments were carried out on an ÄKTA FPLC System (GE Healthcare). The medium was adjusted to contain HEPES (50 mM, pH 7.2), sodium chloride (400 mM), and imidazole (20 mM) prior to column loading. Small scale purification of His8-GFP tagged enzymes secreted into the culture medium by HEK293 cells was performed using HisTrap HP columns (GE Healthcare). To eliminate the possibility of protein contamination, purification of each enzyme was carried out on individual 1 ml HisTrap HP column. Prior to use, a blank run was performed on each new column to remove any weakly bound $Ni^{2+}$ ions. Adjusted medium was loaded onto HisTrap HP columns (GE Healthcare) equilibrated with Buffer A (50 mM HEPES, pH 7.2, 0.4 M sodium chloride, and 20 mM imidazole). The columns were washed and eluted with a step gradient, consisting of five CV per condition of Buffer A to Buffer B (50 mM HEPES, pH 7.2, 0.4 M sodium chloride, and 500 mM imidazole). These consisted of three sequential wash steps of 0%, 10%, and 20% Buffer B, followed by two elution steps of 60% and 100% Buffer B. Fractions containing GFP fluorescence (60% Buffer B elution) were collected and pooled. Protein purity was assessed by SDS-Page. Purified His-GFP-G-type lecRLK36-192 and His-GFP-L-type lecRLK30-281 were concentrated to approximately 1.5 mg/ml using a 30-kDa molecular weight cut-off Amicon Ultra centrifugal filter device (Merck Millipore) and dialyzed (3500 MWCO) into binding buffer without divalent metals (75 mM HEPES-HCl, pH 6.8; 150 NaCl) in the presence of CI ELEX® 100 Molecular Biology Grade Resin (1 g L-1 Bio-Rad, USA) (CHELEX® 100 Resin chelates polyvalent metal ions, with a selectivity for divalent over monovalent ions of approximately 5,000 to 1. The resin avidly binds divalent cations such as $Mg^{2+}$, inactivating DNases and other enzymes, as well as binding other compounds that can interfere with enzyme-based applications such as PCR and ligation. Due to the high selectivity for divalent over monovalent ions, CHELEX® 100 Molecular Biology Grade Resin can be used for DNA purification from samples with high levels of salts) and used directly for binding experiments. Protein concentrations were determined with the Pierce BCA. Protein Assay Kit (Thermo Fisher Scientific, USA) and BSA standards.

Growth of *Sphaerulina musiva* in Liquid Culture

Sporulating 1-week old *S. musiva* cultures growing on solid K-V8 medium (V8 juice 180 ml/l, $CaCO_3$ 2 g/l, agar 2% v/v) were rinsed with 1 ml of sterile double distilled water, and the conidia were dislodged with an inoculating loop. For the inoculation of the liquid cultures, 200 µl aliquots of the spore suspensions were pipetted into 100 ml of liquid K-V8 medium in 250 ml Erlenmeyer flasks. The cultures were incubated at ambient temperature in darkness for five days. During the incubation, the cultures were constantly agitated at 150 rpm with an orbital platform shaker (Innova 2100, New Brunswick). To harvest the mycelium, the cultures were filtered with Miracloth. The harvested mycelium was rinsed with 50 ml of double distilled water and squeezed dry by pressing the mycelium inside the Miracloth between stacks of paper towels. Finally, 50 mg mycelium samples were collected and lyophilized for lectin binding assays.

Analysis of Lectin Binding to *Sphaerulina musiva* Cell Walls

In order to evaluate the ability of recombinant plant lectins to bind to *S. musiva*, cell walls from cultured fungi were sequentially extracted with cold-water, hot-water, and aqueous KOH (32), with minor modifications. Briefly, freeze dried fungal mycelium was resuspended in cold water (100 ml/g) containing sodium azide (0.02%) and extensively homogenized using a polytron homogenizer (Brinkmann Instruments, USA) in a cold room at 4° C. The homogenate was centrifuged (10,000 rpm, 15 min) and the pellet was washed extensively with cold water. The debris containing the cell walls was resuspended in hot water containing sodium azide (0.02%), homogenized again, and incubated at 60° C. overnight in a shaking incubator (250 rpm). The pellets were collected again by centrifugation and treated with hot water for 1 hr and centrifuged again. This was repeated another two times. The washed pellets were resuspended in 1 M KOH containing sodium borohydride (1%) and incubated overnight at 30° C. Next, residues were pelleted again and washed extensively with water. A portion of the hot water and KOH insoluble *S. musiva* cell walls were collected, washed extensively with acetone, and air dried under vacuum.

Lectin binding assays were carried out based on the methods of Lim et al. L et al, (1994), *Biochem. Biophys. Res. Com.* 202:1674-1680) with minor modifications. Microcrystalline cellulose (Avicel PH-101, SigmaAldrich, St. Louis, Mo.) was used as a control substrate for all binding assays. For lectin pull down assays, 2 mgs of each dry substrate were carefully weighed into tubes. Then 250 pi of protein (50 ug $ml^{-1}$) in lectin binding buffer (75 mM HEPES-HCl pH 6.8; 150 mM NaCl; 5 mM MnCl2, 5 mM CaCl2, 1 mg ml-1 BSA) was added, and samples were incubated for 2 h at room temperature with end over end rotation. Samples were centrifuged (12,000 rpm, 5 min), and 100 µl of the supernatants containing the unbound proteins were assayed for GFP fluorescence (Ex 415, Em 550). The percent of bound enzyme was calculated by the depletion method (Chundawat S P, et al. (2011), *J. Am. Chem. Soc.,* 133: 11163-11174).

In vivo Overexpression of L-Type lecRLK and G-Type lecRLK in *Populus* Protoplasts Protoplast transfection: Protoplasts from *P. tremula*x*P. alba* clone INRA 717-1-B4 were 409 isolated and subsequently transfected, as previously described (Guo J, et al. (2012), *PLoS One,* 7:e44908). For overexpression, 10 µg of L-type lecRLK constructs with a 35S promoter and vector control were transfected into 100 µl of protoplasts. After 12 h incubation, protoplasts were collected by a 2 min centrifugation at 2,000×g and frozen in liquid nitrogen for the qRT-PCR experiment.

Generation of Transgenic Populus Hairy Roots

To generate binary vectors of G-type lecRLK for hairy roots transformation, the cDNA sequence was first cloned into pENTR/D TOPO vectors and then into the pGWB402omega binary vector by LR recombination reaction. The binary vector was transformed into *A. rhizogenes* strain ARqua1 by electroporation, and hairy roots were generated by transforming *P. tremula*x*P. alba* clone INRA 717-1-B4 with *A. rhizogenes* (Yoshida K. et al., (2015), *Plant physiol.,* 167:693-710). Hairy root cultures were inoculated with *S. musiva* in a similar manner to that described above. Briefly, each plate was sprayed with a suspension of 1×106 spores ml-1 of *S. musiva* isolate MN-14. The mock-inoculated roots were sprayed with sterile distilled water. After a 24 h incubation period samples were flash frozen in liquid nitrogen for RNA extraction and the qRT-PCR experiment.

RNA Extract and qRT-PCR

RNA was extracted from protoplasts and hairy roots samples using Plant RNA extraction kit (Sigma, St Louis, Mo.). cDNA synthesis was performed using DNAse free total RNA (1.5 µg), oligo dT primers and RevertAid Reverse Transcriptase (Thermofisher). Quantitative reverse transcriptase PCR (qRT-PCR) was performed using 3 ng cDNA, 250 nM gene specific primers and iTaq Universal SYBR Green Supermix (Bio Rad). Gene expression was calculated by 2-ddCt method using UBQ10b as internal control.

```
Primers:
                                        (SEQ ID NO: 29)
UBQ10b_F:      5'GCCTTCGTGGTGGTTATTAAGC 3'

(SEQ ID NO: 30)
UBQ10b_R:      5'TCCAACAATGGCCAGTAAACAC 3'
```

-continued

```
BAK1a_F:     5'TGGCATCCTGATGAGAACAG 3'        (SEQ ID NO: 31)

BAK1a_R:     5'AAAGGTCCAAACCACTTACGC 3'       (SEQ ID NO: 32)

BAK1b_F:     5'GGAGATGGCATTTGTGAAGG 3'        (SEQ ID NO: 33)

BAK1b_R:     5'GCTCGAAAGATGACCAATCC 3'        (SEQ ID NO: 34)

WRKY40_F:    5'CATGGATGTCTTTCCCTCTTG 3'       (SEQ ID NO: 35)

WRKY40_R:    5'TTCTCTTTCTGCCTGTGTTCC 3'       (SEQ ID NO: 36)

WRKY70a_F:   5'ACTATCATCAAGCAGGGAAAGG 3'      (SEQ ID NO: 37)

WRKY70a_R:   5'TTCTGGAGGCGAATTTGAAG 3'        (SEQ ID NO: 38)

WRKY70b_F:   5'GAATCTGCTGATTTCGATGATG 3'      (SEQ ID NO: 39)

WRKY70b_R:   5'AGGCGGAAATTACAAAGAAGC 3'       (SEQ ID NO: 40)
```

Example 1: Discovering *S. musiva* Resistance and Susceptibility Loci in *P. trichocarpa*

In a replicated greenhouse experiment 3,404 plants, from a population of 1,081 unrelated trichocarpa genotypes, were characterized for post-inoculation phenotypic responses to *S. musiva*. Phenotypes were correlated to 8.2 million single nucleotide polymorphisms (SNPs) and insertion/deletions (indels). This process allowed identification of 82 candidate genes encompassing 113 polymorphisms within 5 months of planting the trees (Table 5). Notably, four of the most significant associations were to genes predicted to encode proteins with domains common to pattern recognition receptors (PRRs), including two paralogous leucine-rich receptor-like proteins (RLPs) [Potri.005G012100, p-value=1.56E-38; Potri.003G028200, p-value=2.78E-14], an L-type lectin receptor-like kinase (L-type lecRLK) [Potri.009G036300, p-value=2.115E-16] and a G-type lectin receptor-like kinase (G-type lecRLK) [Potri.005G018000, p-value=1.161E-13], See FIG. 1A-1E. Analyses of allelic effect direction suggested that the two RLPs and L-type lecRLK are associated with resistance whereas the G-type lecRLK is associated with susceptibility. Pairwise Linkage Disequilibrium (LD) for all four candidate loci decayed rapidly, falling below $R^2=0.10$ within 50 bp. A similar rate of LD decay has been reported for R-genes in other plant species (Xing Y. et al., (2007), *BMC Plant Biology*, 7:43).

The two RLPs are predicted to contain an extracellular leucine-rich repeat domain, a transmembrane domain, and a short cytoplasmic tail, but lack a kinase domain. The two RLKs contain predicted extracellular domains and intercellular kinase domains. RLPs have been shown to interact with RLKs to perceive a ligand signal and trigger protein phosphorylation cascades (Liebrand et al., *PNAS*, 110, 10010-10015 (2013)). A similar protein-protein interaction has been described for resistance to both *Cladosporium fulvum* and *Verticillium dahlia*, where two RLPs, (Cf-4 or Ve1) interact with an RLK, (SOBIR1/EVR) in tomato to mediate resistance to *C. fulvum* and *V. dahlia*, respectively (Duplessis et al., *Mol. Plant Microbe Interact*. 24, 808-818 (2011)). The absence of kinase domains from the candidate RLPs of *P. trichocarpa* is indicative of the proteins forming a complex with the L-type lecRLK in a similar manner. It is postulated that resistant *P. trichocarpa* genotypes perceive an *S. musiva* ligand, resulting in resistance.

Example 2: Transcriptome Analysis of Resistant and Susceptible Genotypes

Transcriptome changes of resistant (BESC-22) and susceptible (BESC-801) genotypes were compared at 0-, 24-, and 72-h post-inoculation (hpi) with *S. musiva*. Transcriptional changes within (different time points) and between genotypes (same time points) were analyzed. In total 4,872 genes were differentially expressed between the 0- and 72-hpi in the resistant compared to 79 in the susceptible genotype. PFAM domain-enrichment analysis revealed major protein families associated with innate immunity responses, with >2× up-regulation in the resistant genotype and no response in the susceptible genotype. Interestingly, these results are inconsistent with previous observations on co-evolved pathosystems, which suggested that resistant and susceptible responses share similar sets of differentially expressed genes that vary only in timing and amplitude of expression (Chen, W. et al., *Plant J.*, 46, 794-804 (2000)).

A specific examination of transcriptional responses of the candidate genes in the resistant genotype, the two RLPs and the L-type lecRLK, revealed a peak in expression at the 24-h time-point; a pairwise comparison indicated that these genes were significantly different in terms their expression (FIG. 2A-2C). In contrast, none of these three loci showed changes in expression in the susceptible interaction (FIG. 2A-2C), Furthermore, RLPs and L-type LecRLK expression between the 0- and 24-h time-points correlated with the expression of six genes commonly used as markers for defense responses (FIG. 4A-4F). In contrast, the G-type lecRLK was abundantly expressed at each of the time points in the susceptible genotype but was marginally detectable in the resistant genotype (FIG. 2D). The data presented herein demonstrate that the G-type lecRLK locus is necessary for susceptibility of *P. trichocarpa* to *S. musiva*.

Example 3: Population-Wide Mutation Analysis of the Susceptibility and Resistance Loci To correlate the predicted function of these loci within the *P. trichocarpa* population with susceptibility and resistance to the fungal pathogen the population-wide occurrence of mutations were examined using a SnpEff analysis (Cingolani P et al., *Fly (Austin)*, 6: 80-92 (2012)). This revealed extensive occurrences of high-impact (deleterious) mutations (early translation termination, frame-shift, and changes in splice-site acceptor, and/or splice-site donor sequences) in the putative resistance-associated RLP-encoding loci (FIG. 2E). In contrast, the putative susceptibility G-type lecRLK locus was highly conserved across the population (FIG. 2E). Only two high-impact mutations were found in 1.5% and 8.0% of the population, respectively. The first is a premature stop codon at position 1441171 bp (G>A) on chromosome 9, that is predicted to truncating the protein to 5% of its length. The second is a frame-shift at position 1443941 bp (AGGG>AGG) on chromosome 9, which is predicted to result in a premature stop codon truncating the protein to 75% of its length. As expected the minority of individuals with these rare alleles were more resistant to the pathogen.

Example 4: RNA Seq Identifies Differentially Expressed *S. musiva* Genes

The samples used in the RNAseq experiments contained both host and pathogen transcripts. To exploit this transcriptome changes of the pathogen were examined, a challenge because the biomass of the pathogen does not increase substantially during the initial 24 hours. As a consequence, the amount of RNA is low, resulting in low read counts and low statistical power. Nonetheless, 16 and 44 differentially expressed S. musiva genes 24 hpi were identified in the resistant and susceptible interactions, respectively. Further inspection of the gene annotations revealed that 7 and 19 of the genes in the resistant and susceptible interactions, respectively, encoded small proteins, with no conserved domains and had predicted secretion signals. These are hallmarks of fungal effectors (LeBoldus, J. M. et al., Plant Ms., 94, 1238-1242 (2010)) that are likely involved in mediating interactions with host plants and potentially influencing the host responses described above.

Putative pattern recognition receptors were identified that were significant in their associations with resistance and susceptibility to S. musiva consistent with contrasting expression responses between resistant and susceptible genotypes. Furthermore, the loss of function in genes encoding immunity receptors (RLPs and L-type lecRLK) in parallel with the conservation of a susceptibility locus (G-type lecRLK) resulted in population-wide susceptibility of P. trichocarpa to the allopathic pathogen S. musiva. Conservation of the G-type lecRLK within the sampled population suggests that this locus is under purifying selection and has been exapted by S. musiva. In addition, the observation that resistance loci in the sampled population harbor many predicted high-impact mutations is consistent with the absence of selection pressure maintaining the ability of the host to recognize S. musiva. The prevalence of the functional susceptibility locus and rarity of functional resistance loci implies that riparian ecosystems where P. trichocarpa serves as a keystone species are extremely vulnerable to the continued spread of this invasive pathogen.

Example 5: Transcriptome Changes of Resistant (BESC-22) and Susceptible (BESC-801) Genotypes Transcriptome changes of resistant (BESC-22) and susceptible (BESC-801) genotypes were determined at 0-, 24-, and 72-h post-inoculation (hpi) with S. musiva. The BESC-22 genotype was chosen for carrying functional alleles of the resistance-associated loci (RLP1, RLP2, and the L-type lecRLK) and a defective allele of the susceptibility-associated locus (G-type lecRLK). In contrast, BESC-801 was selected for carrying a functional allele of the susceptibility-associated locus (G-type lecRLK) and defective alleles of the resistance-associated loci (RLP1, RLP2, and the L-type lecRLK). Comparisons were made within (different time points) and between genotypes (same time points). In total 4,686 genes were differentially expressed between the 0- and 24-hpi in the resistant genotype compared to 76 in the susceptible genotype. Additionally, 16 of the 62 GWAS candidates exhibited differential expression. PFAM domain-enrichment analysis, comparing responses of resistant to susceptible genotypes, revealed major protein families associated with innate immunity responses with a ≥2× up-regulation in the resistant genotype.

The two RLPs and the L-type lecRLK, associated with resistance (FIGS. 1B, 1C and 1D), peaked in expression at 24-hpi (FIGS. 2A, 2B and 2C). In contrast, the three genes did not exhibit changes in expression in the susceptible genotype, regardless of the times compared. In the susceptible genotype, the G-type lecRLK, associated with susceptibility (FIG. 1E), was expressed at each examined time point. In the resistant genotype, expression of the G-type lecRLK was barely above the detectable threshold (FIG. 2D). The change in expression of six genes commonly used as markers for transcriptional reprogramming during host resistance were also compared between resistant and susceptible genotypes at 0-, 24-, and 72-hpi. All six of the marker genes peaked at 24-hpi in the resistant genotype. In the susceptible genotype, the six markers were expressed at statistically similar levels. The pattern of expression of all six marker genes is consistent with defense response signaling in plants described in the literature (Chinchilla D et al., (2009), Trends Plant Sci., 14:535-541; Xu X. et al., (2006), Plant Cell 18:1310-1326; Zhang Y. et al., (2003) Plant Cell, 15:2636-2646; Zhang Y. et al., (2010), Plant Cell, 22:3153-316).

Example 6: Overexpression Analyses

The N-terminal lectin domains of the L-type (AA 30-283) and G-type (AA 36-318) lecRLKs were expressed as a fusion to "superfolder" GFP in HEK293 cells (Urbanowicz Bret al., (2014), Plant 80:197-206; Meng L, et al. (2013), J. Biol. Chem., 288:34680-34698). The expressed proteins were purified and subsequently incubated with cell wall fractions of S. musiva. Microcrystalline cellulose was used as a binding substrate control and a non-catalytic fragment of Arabidopsis ERK1 was used as a protein control in all the experiments. The G-type and L-type lectin domains specifically bound to cell wall preparations of S. musiva, but not to the controls, indicating specificity for fungal cell wall carbohydrates or proteoglycans. The G-type lectin bound a larger proportion of the cell wall fractions than the L-type lectin regardless of treatment. Interestingly, binding of the L-type lectin to S. musiva significantly increased after treatment of the walls with indicating that recognition of the ligand is restricted by either alkaline-extractable cell wall components or esterification (Gilbert H J et al., (2013), Curr Opi. Struct, Biol., 23:669-677; Marcus S E, et al. (2008), BMC Plant Biology, 8:60). Very few LecRLKs have been functionally characterized. Ligand identification has been challenging, due to difficulties in expressing and purifying high-quality, functional preparations of these highly glycosylated eukaryotic proteins.

In summary, genes predicted to encode receptors that were significant in their association with resistance and susceptibility to S. musiva were identified. The population-wide allele analysis revealed that in the sampled population, the loci associated with resistance harbor many high-impact mutations, potentially impairing the ability of genotypes to recognize S. musiva and initiate an immune response. Furthermore, the loss of function in genes encoding putative immunity receptors (RLPs and L-type lecRLK) in parallel with the conservation of a locus implicated in susceptibility (G-type lecRLK) results in population-wide susceptibility of P. trichocarpa to the all allopatric pathogen S. musiva. The genes associated with host-pathogen interactions exhibited contrasting expression responses between resistant and susceptible genotypes. Biochemical analysis demonstrated that both the G-type and L-type lectin domains bind S. musiva cell walls. The associations and gene expression profiles are predictive of the resistance/susceptibility phenotype. As such, the use of high-resolution phenotyping and host resequencing across the species range enabled the identification of candidate loci associated with P. trichocarpa response to S. musiva. These loci can be incorporated into future breeding efforts that include marker-based selection of parents and progeny resistant to Septoria stem canker to potentially accelerate the mitigation of disease in native ecosystems.

TABLE 1

RLP1 Mutations

| | Chrom. | Genomic Position | Reference | Variant | Mutation type | Predicted impact |
|---|---|---|---|---|---|---|
| 1 | Chr05 | 935174 | C | T | STOP_GAINED | HIGH |
| 2 | Chr05 | 935184 | G | T | STOP_GAINED | HIGH |
| 3 | Chr05 | 935919 | G | T | STOP_GAINED | HIGH |
| 4 | Chr05 | 937059 | C | A | STOP_GAINED | HIGH |
| 5 | Chr05 | 937313 | C | T | STOP_GAINED | HIGH |
| 6 | Chr05 | 937316 | A | T | STOP_GAINED | HIGH |
| 7 | Chr05 | 937747 | A | C | STOP_GAINED | HIGH |
| 8 | Chr05 | 934892 | C | T | SPLICE_SITE_DONOR | HIGH |
| 9 | Chr05 | 934831 | C | G | SPLICE_SITE_ACCEPTOR | HIGH |
| 10 | Chr05 | 934206 | CAT | C | FRAME_SHIFT | HIGH |
| 11 | Chr05 | 936990 | CTTCAGCAGGT (SEQ ID NO: 41) | C | FRAME_SHIFT | HIGH |
| 12 | Chr05 | 937021 | TC | TCC | FRAME_SHIFT | HIGH |
| 13 | Chr05 | 937237 | TAAAAC | TC | FRAME_SHIFT | HIGH |
| 14 | Chr05 | 939353 | T | TA | FRAME_SHIFT | HIGH |
| 15 | Chr05 | 939360 | CA | C | FRAME_SHIFT | HIGH |
| 16 | Chr05 | 939608 | T | A | START_GAINED | LOW |
| 17 | Chr05 | 939658 | T | C | START_GAINED | LOW |
| 18 | Chr05 | 934166 | C | T | NON_SYNONYMOUS_CODING | MODERATE |
| 19 | Chr05 | 934176 | G | T | NON_SYNONYMOUS_CODING | MODERATE |
| 20 | Chr05 | 934177 | C | A | NON_SYNONYMOUS_CODING | MODERATE |
| 21 | Chr05 | 934183 | T | G | NON_SYNONYMOUS_CODING | MODERATE |
| 22 | Chr05 | 934192 | G | C | NON_SYNONYMOUS_CODING | MODERATE |
| 23 | Chr05 | 934202 | T | A | NON_SYNONYMOUS_CODING | MODERATE |
| 24 | Chr05 | 934203 | T | A | NON_SYNONYMOUS_CODING | MODERATE |
| 25 | Chr05 | 934225 | G | A | NON_SYNONYMOUS_CODING | MODERATE |
| 26 | Chr05 | 934254 | T | A | NON_SYNONYMOUS_CODING | MODERATE |
| 27 | Chr05 | 934255 | T | G | NON_SYNONYMOUS_CODING | MODERATE |
| 28 | Chr05 | 934274 | C | G | NON_SYNONYMOUS_CODING | MODERATE |
| 29 | Chr05 | 934294 | C | T | NON_SYNONYMOUS_CODING | MODERATE |
| 30 | Chr05 | 934336 | T | G | NON_SYNONYMOUS_CODING | MODERATE |
| 31 | Chr05 | 934408 | C | A | NON_SYNONYMOUS_CODING | MODERATE |
| 32 | Chr05 | 934429 | G | A | NON_SYNONYMOUS_CODING | MODERATE |
| 33 | Chr05 | 934430 | G | A | NON_SYNONYMOUS_CODING | MODERATE |
| 34 | Chr05 | 934441 | T | G | NON_SYNONYMOUS_CODING | MODERATE |
| 35 | Chr05 | 934460 | G | A | NON_SYNONYMOUS_CODING | MODERATE |
| 36 | Chr05 | 934469 | C | T | NON_SYNONYMOUS_CODING | MODERATE |
| 37 | Chr05 | 934471 | G | A | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 38 | Chr05 | 934477 | T | G | NON_SYNONYMOUS_CODING | MODERATE |
| 39 | Chr05 | 934496 | C | T | NON_SYNONYMOUS_CODING | MODERATE |
| 40 | Chr05 | 934510 | T | A | NON_SYNONYMOUS_CODING | MODERATE |
| 41 | Chr05 | 934522 | G | C | NON_SYNONYMOUS_CODING | MODERATE |
| 42 | Chr05 | 934550 | T | A | NON_SYNONYMOUS_CODING | MODERATE |
| 43 | Chr05 | 934556 | C | G | NON_SYNONYMOUS_CODING | MODERATE |
| 44 | Chr05 | 934564 | A | G | NON_SYNONYMOUS_CODING | MODERATE |
| 45 | Chr05 | 934565 | T | C | NON_SYNONYMOUS_CODING | MODERATE |
| 46 | Chr05 | 934566 | A | T | NON_SYNONYMOUS_CODING | MODERATE |
| 47 | Chr05 | 934568 | T | C | NON_SYNONYMOUS_CODING | MODERATE |
| 48 | Chr05 | 934570 | T | C | NON_SYNONYMOUS_CODING | MODERATE |
| 49 | Chr05 | 934573 | T | A | NON_SYNONYMOUS_CODING | MODERATE |
| 50 | Chr05 | 934576 | A | G | NON_SYNONYMOUS_CODING | MODERATE |
| 51 | Chr05 | 934577 | G | A | NON_SYNONYMOUS_CODING | MODERATE |
| 52 | Chr05 | 934580 | A | G | NON_SYNONYMOUS_CODING | MODERATE |
| 53 | Chr05 | 934585 | C | T | NON_SYNONYMOUS_CODING | MODERATE |
| 54 | Chr05 | 934597 | A | T | NON_SYNONYMOUS_CODING | MODERATE |
| 55 | Chr05 | 934598 | T | G | NON_SYNONYMOUS_CODING | MODERATE |
| 56 | Chr05 | 934604 | C | T | NON_SYNONYMOUS_CODING | MODERATE |
| 57 | Chr05 | 934618 | C | T | NON_SYNONYMOUS_CODING | MODERATE |
| 58 | Chr05 | 934619 | C | T | NON_SYNONYMOUS_CODING | MODERATE |
| 59 | Chr05 | 934630 | T | C | NON_SYNONYMOUS_CODING | MODERATE |
| 60 | Chr05 | 934633 | G | A | NON_SYNONYMOUS_CODING | MODERATE |
| 61 | Chr05 | 934639 | G | C | NON_SYNONYMOUS_CODING | MODERATE |
| 62 | Chr05 | 934640 | T | C | NON_SYNONYMOUS_CODING | MODERATE |
| 63 | Chr05 | 934652 | C | G | NON_SYNONYMOUS_CODING | MODERATE |
| 64 | Chr05 | 934672 | G | A | NON_SYNONYMOUS_CODING | MODERATE |
| 65 | Chr05 | 934689 | T | G | NON_SYNONYMOUS_CODING | MODERATE |
| 66 | Chr05 | 934708 | A | T | NON_SYNONYMOUS_CODING | MODERATE |
| 67 | Chr05 | 934716 | A | C | NON_SYNONYMOUS_CODING | MODERATE |
| 68 | Chr05 | 934721 | T | C | NON_SYNONYMOUS_CODING | MODERATE |
| 69 | Chr05 | 934733 | G | T | NON_SYNONYMOUS_CODING | MODERATE |
| 70 | Chr05 | 934743 | G | C | NON_SYNONYMOUS_CODING | MODERATE |
| 71 | Chr05 | 934753 | C | A | NON_SYNONYMOUS_CODING | MODERATE |
| 72 | Chr05 | 934759 | G | A | NON_SYNONYMOUS_CODING | MODERATE |
| 73 | Chr05 | 934768 | T | C | NON_SYNONYMOUS_CODING | MODERATE |
| 74 | Chr05 | 934780 | T | G | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 75 | Chr05 | 934818 | C | A | NON_SYNONYMOUS_CODING | MODERATE |
| 76 | Chr05 | 934829 | G | T | NON_SYNONYMOUS_CODING | MODERATE |
| 77 | Chr05 | 934896 | G | A | NON_SYNONYMOUS_CODING | MODERATE |
| 78 | Chr05 | 934905 | T | C | NON_SYNONYMOUS_CODING | MODERATE |
| 79 | Chr05 | 934906 | A | G | NON_SYNONYMOUS_CODING | MODERATE |
| 80 | Chr05 | 934911 | T | G | NON_SYNONYMOUS_CODING | MODERATE |
| 81 | Chr05 | 934914 | T | A | NON_SYNONYMOUS_CODING | MODERATE |
| 82 | Chr05 | 934959 | C | A | NON_SYNONYMOUS_CODING | MODERATE |
| 83 | Chr05 | 934966 | C | G | NON_SYNONYMOUS_CODING | MODERATE |
| 84 | Chr05 | 934975 | T | G | NON_SYNONYMOUS_CODING | MODERATE |
| 85 | Chr05 | 935029 | C | T | NON_SYNONYMOUS_CODING | MODERATE |
| 86 | Chr05 | 935035 | C | T | NON_SYNONYMOUS_CODING | MODERATE |
| 87 | Chr05 | 935041 | A | G | NON_SYNONYMOUS_CODING | MODERATE |
| 88 | Chr05 | 935075 | A | C | NON_SYNONYMOUS_CODING | MODERATE |
| 89 | Chr05 | 935082 | C | A | NON_SYNONYMOUS_CODING | MODERATE |
| 90 | Chr05 | 935097 | C | G | NON_SYNONYMOUS_CODING | MODERATE |
| 91 | Chr05 | 935099 | C | A | NON_SYNONYMOUS_CODING | MODERATE |
| 92 | Chr05 | 935100 | T | C | NON_SYNONYMOUS_CODING | MODERATE |
| 93 | Chr05 | 935101 | G | C | NON_SYNONYMOUS_CODING | MODERATE |
| 94 | Chr05 | 935102 | C | A | NON_SYNONYMOUS_CODING | MODERATE |
| 95 | Chr05 | 935106 | C | T | NON_SYNONYMOUS_CODING | MODERATE |
| 96 | Chr05 | 935110 | T | A | NON_SYNONYMOUS_CODING | MODERATE |
| 97 | Chr05 | 935112 | A | T | NON_SYNONYMOUS_CODING | MODERATE |
| 98 | Chr05 | 935113 | G | T | NON_SYNONYMOUS_CODING | MODERATE |
| 99 | Chr05 | 935118 | G | A | NON_SYNONYMOUS_CODING | MODERATE |
| 100 | Chr05 | 935155 | T | G | NON_SYNONYMOUS_CODING | MODERATE |
| 101 | Chr05 | 935178 | A | G | NON_SYNONYMOUS_CODING | MODERATE |
| 102 | Chr05 | 935179 | A | T | NON_SYNONYMOUS_CODING | MODERATE |
| 103 | Chr05 | 935187 | A | G | NON_SYNONYMOUS_CODING | MODERATE |
| 104 | Chr05 | 935190 | G | T | NON_SYNONYMOUS_CODING | MODERATE |
| 105 | Chr05 | 935191 | C | G | NON_SYNONYMOUS_CODING | MODERATE |
| 106 | Chr05 | 935205 | C | T | NON_SYNONYMOUS_CODING | MODERATE |
| 107 | Chr05 | 935221 | C | A | NON_SYNONYMOUS_CODING | MODERATE |
| 108 | Chr05 | 935225 | T | G | NON_SYNONYMOUS_CODING | MODERATE |
| 109 | Chr05 | 935240 | A | C | NON_SYNONYMOUS_CODING | MODERATE |
| 110 | Chr05 | 935250 | C | A | NON_SYNONYMOUS_CODING | MODERATE |
| 111 | Chr05 | 935256 | T | C | NON_SYNONYMOUS_CODING | MODERATE |
| 112 | Chr05 | 935257 | C | T | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 113 | Chr05 | 935267 | G | T | NON_SYNONYMOUS_CODING | MODERATE |
| 114 | Chr05 | 935269 | A | G | NON_SYNONYMOUS_CODING | MODERATE |
| 115 | Chr05 | 935272 | C | T | NON_SYNONYMOUS_CODING | MODERATE |
| 116 | Chr05 | 935292 | T | G | NON_SYNONYMOUS_CODING | MODERATE |
| 117 | Chr05 | 935319 | T | A | NON_SYNONYMOUS_CODING | MODERATE |
| 118 | Chr05 | 935340 | G | T | NON_SYNONYMOUS_CODING | MODERATE |
| 119 | Chr05 | 935341 | T | C | NON_SYNONYMOUS_CODING | MODERATE |
| 120 | Chr05 | 935345 | A | C | NON_SYNONYMOUS_CODING | MODERATE |
| 121 | Chr05 | 935354 | C | A | NON_SYNONYMOUS_CODING | MODERATE |
| 122 | Chr05 | 935377 | G | T | NON_SYNONYMOUS_CODING | MODERATE |
| 123 | Chr05 | 935400 | T | G | NON_SYNONYMOUS_CODING | MODERATE |
| 124 | Chr05 | 935401 | C | G | NON_SYNONYMOUS_CODING | MODERATE |
| 125 | Chr05 | 935403 | A | C | NON_SYNONYMOUS_CODING | MODERATE |
| 126 | Chr05 | 935448 | C | T | NON_SYNONYMOUS_CODING | MODERATE |
| 127 | Chr05 | 935464 | T | C | NON_SYNONYMOUS_CODING | MODERATE |
| 128 | Chr05 | 935479 | G | T | NON_SYNONYMOUS_CODING | MODERATE |
| 129 | Chr05 | 935501 | G | C, T | NON_SYNONYMOUS_CODING | MODERATE |
| 130 | Chr05 | 935506 | C | G | NON_SYNONYMOUS_CODING | MODERATE |
| 131 | Chr05 | 935509 | C | T | NON_SYNONYMOUS_CODING | MODERATE |
| 132 | Chr05 | 935518 | G | A | NON_SYNONYMOUS_CODING | MODERATE |
| 133 | Chr05 | 935523 | T | G | NON_SYNONYMOUS_CODING | MODERATE |
| 134 | Chr05 | 935536 | T | A | NON_SYNONYMOUS_CODING | MODERATE |
| 135 | Chr05 | 935541 | A | G | NON_SYNONYMOUS_CODING | MODERATE |
| 136 | Chr05 | 935542 | C | T | NON_SYNONYMOUS_CODING | MODERATE |
| 137 | Chr05 | 935553 | T | C | NON_SYNONYMOUS_CODING | MODERATE |
| 138 | Chr05 | 935554 | T | A | NON_SYNONYMOUS_CODING | MODERATE |
| 139 | Chr05 | 935559 | G | A | NON_SYNONYMOUS_CODING | MODERATE |
| 140 | Chr05 | 935562 | G | A | NON_SYNONYMOUS_CODING | MODERATE |
| 141 | Chr05 | 935576 | C | G | NON_SYNONYMOUS_CODING | MODERATE |
| 142 | Chr05 | 935580 | A | G | NON_SYNONYMOUS_CODING | MODERATE |
| 143 | Chr05 | 935589 | A | C | NON_SYNONYMOUS_CODING | MODERATE |
| 144 | Chr05 | 935592 | A | G | NON_SYNONYMOUS_CODING | MODERATE |
| 145 | Chr05 | 935593 | A | T | NON_SYNONYMOUS_CODING | MODERATE |
| 146 | Chr05 | 935602 | C | G | NON_SYNONYMOUS_CODING | MODERATE |
| 147 | Chr05 | 935611 | A | C | NON_SYNONYMOUS_CODING | MODERATE |
| 148 | Chr05 | 935620 | T | G | NON_SYNONYMOUS_CODING | MODERATE |
| 149 | Chr05 | 935628 | G | C | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 150 | Chr05 | 935653 | G | A | NON_SYNONYMOUS_CODING | MODERATE |
| 151 | Chr05 | 935662 | C | G | NON_SYNONYMOUS_CODING | MODERATE |
| 152 | Chr05 | 935667 | A | G | NON_SYNONYMOUS_CODING | MODERATE |
| 153 | Chr05 | 935668 | C | T | NON_SYNONYMOUS_CODING | MODERATE |
| 154 | Chr05 | 935680 | G | A | NON_SYNONYMOUS_CODING | MODERATE |
| 155 | Chr05 | 935689 | C | G | NON_SYNONYMOUS_CODING | MODERATE |
| 156 | Chr05 | 935695 | C | A | NON_SYNONYMOUS_CODING | MODERATE |
| 157 | Chr05 | 935697 | A | C | NON_SYNONYMOUS_CODING | MODERATE |
| 158 | Chr05 | 935698 | C | A | NON_SYNONYMOUS_CODING | MODERATE |
| 159 | Chr05 | 935701 | G | A | NON_SYNONYMOUS_CODING | MODERATE |
| 160 | Chr05 | 935707 | A | G | NON_SYNONYMOUS_CODING | MODERATE |
| 161 | Chr05 | 935714 | C | A | NON_SYNONYMOUS_CODING | MODERATE |
| 162 | Chr05 | 935742 | T | A | NON_SYNONYMOUS_CODING | MODERATE |
| 163 | Chr05 | 935745 | G | T | NON_SYNONYMOUS_CODING | MODERATE |
| 164 | Chr05 | 935746 | G | T | NON_SYNONYMOUS_CODING | MODERATE |
| 165 | Chr05 | 935775 | A | T | NON_SYNONYMOUS_CODING | MODERATE |
| 166 | Chr05 | 935776 | A | C | NON_SYNONYMOUS_CODING | MODERATE |
| 167 | Chr05 | 935778 | C | T | NON_SYNONYMOUS_CODING | MODERATE |
| 168 | Chr05 | 935788 | A | G | NON_SYNONYMOUS_CODING | MODERATE |
| 169 | Chr05 | 935793 | G | A | NON_SYNONYMOUS_CODING | MODERATE |
| 170 | Chr05 | 935796 | G | A | NON_SYNONYMOUS_CODING | MODERATE |
| 171 | Chr05 | 935799 | G | A | NON_SYNONYMOUS_CODING | MODERATE |
| 172 | Chr05 | 935802 | G | T | NON_SYNONYMOUS_CODING | MODERATE |
| 173 | Chr05 | 935815 | G | A | NON_SYNONYMOUS_CODING | MODERATE |
| 174 | Chr05 | 935818 | C | T | NON_SYNONYMOUS_CODING | MODERATE |
| 175 | Chr05 | 935820 | G | C | NON_SYNONYMOUS_CODING | MODERATE |
| 176 | Chr05 | 935821 | C | G | NON_SYNONYMOUS_CODING | MODERATE |
| 177 | Chr05 | 935824 | T | C | NON_SYNONYMOUS_CODING | MODERATE |
| 178 | Chr05 | 935844 | G | T | NON_SYNONYMOUS_CODING | MODERATE |
| 179 | Chr05 | 935845 | C | T | NON_SYNONYMOUS_CODING | MODERATE |
| 180 | Chr05 | 935848 | A | T | NON_SYNONYMOUS_CODING | MODERATE |
| 181 | Chr05 | 935851 | A | C | NON_SYNONYMOUS_CODING | MODERATE |
| 182 | Chr05 | 935863 | A | T | NON_SYNONYMOUS_CODING | MODERATE |
| 183 | Chr05 | 935890 | T | C | NON_SYNONYMOUS_CODING | MODERATE |
| 184 | Chr05 | 935896 | C | G | NON_SYNONYMOUS_CODING | MODERATE |
| 185 | Chr05 | 935905 | G | A | NON_SYNONYMOUS_CODING | MODERATE |
| 186 | Chr05 | 935920 | A | T | NON_SYNONYMOUS_CODING | MODERATE |
| 187 | Chr05 | 935925 | T | A | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 188 | Chr05 | 935928 | T | C | NON_SYNONYMOUS_CODING | MODERATE |
| 189 | Chr05 | 935929 | G | T | NON_SYNONYMOUS_CODING | MODERATE |
| 190 | Chr05 | 935934 | C | T | NON_SYNONYMOUS_CODING | MODERATE |
| 191 | Chr05 | 935938 | T | G | NON_SYNONYMOUS_CODING | MODERATE |
| 192 | Chr05 | 935950 | G | T | NON_SYNONYMOUS_CODING | MODERATE |
| 193 | Chr05 | 935951 | G | C | NON_SYNONYMOUS_CODING | MODERATE |
| 194 | Chr05 | 935958 | G | A | NON_SYNONYMOUS_CODING | MODERATE |
| 195 | Chr05 | 935959 | A | G | NON_SYNONYMOUS_CODING | MODERATE |
| 196 | Chr05 | 935985 | C | T | NON_SYNONYMOUS_CODING | MODERATE |
| 197 | Chr05 | 935986 | G | A | NON_SYNONYMOUS_CODING | MODERATE |
| 198 | Chr05 | 935992 | A | C | NON_SYNONYMOUS_CODING | MODERATE |
| 199 | Chr05 | 936000 | A | G | NON_SYNONYMOUS_CODING | MODERATE |
| 200 | Chr05 | 936001 | A | T | NON_SYNONYMOUS_CODING | MODERATE |
| 201 | Chr05 | 936009 | A | G | NON_SYNONYMOUS_CODING | MODERATE |
| 202 | Chr05 | 936023 | C | A | NON_SYNONYMOUS_CODING | MODERATE |
| 203 | Chr05 | 936025 | A | C | NON_SYNONYMOUS_CODING | MODERATE |
| 204 | Chr05 | 936028 | A | T | NON_SYNONYMOUS_CODING | MODERATE |
| 205 | Chr05 | 936040 | C | T | NON_SYNONYMOUS_CODING | MODERATE |
| 206 | Chr05 | 936049 | G | T | NON_SYNONYMOUS_CODING | MODERATE |
| 207 | Chr05 | 936058 | C | T | NON_SYNONYMOUS_CODING | MODERATE |
| 208 | Chr05 | 936066 | G | A | NON_SYNONYMOUS_CODING | MODERATE |
| 209 | Chr05 | 936067 | A | G | NON_SYNONYMOUS_CODING | MODERATE |
| 210 | Chr05 | 936071 | T | G | NON_SYNONYMOUS_CODING | MODERATE |
| 211 | Chr05 | 936072 | T | A | NON_SYNONYMOUS_CODING | MODERATE |
| 212 | Chr05 | 936083 | C | A | NON_SYNONYMOUS_CODING | MODERATE |
| 213 | Chr05 | 937007 | C | T | NON_SYNONYMOUS_CODING | MODERATE |
| 214 | Chr05 | 937011 | T | G | NON_SYNONYMOUS_CODING | MODERATE |
| 215 | Chr05 | 937019 | A | C | NON_SYNONYMOUS_CODING | MODERATE |
| 216 | Chr05 | 937023 | T | C | NON_SYNONYMOUS_CODING | MODERATE |
| 217 | Chr05 | 937024 | G | C | NON_SYNONYMOUS_CODING | MODERATE |
| 218 | Chr05 | 937025 | T | G | NON_SYNONYMOUS_CODING | MODERATE |
| 219 | Chr05 | 937026 | T | C | NON_SYNONYMOUS_CODING | MODERATE |
| 220 | Chr05 | 937038 | T | C | NON_SYNONYMOUS_CODING | MODERATE |
| 221 | Chr05 | 937055 | T | G | NON_SYNONYMOUS_CODING | MODERATE |
| 222 | Chr05 | 937061 | A | C | NON_SYNONYMOUS_CODING | MODERATE |
| 223 | Chr05 | 937068 | T | C | NON_SYNONYMOUS_CODING | MODERATE |
| 224 | Chr05 | 937079 | G | C | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 225 | Chr05 | 937080 | C | T | NON_SYNONYMOUS_CODING | MODERATE |
| 226 | Chr05 | 937086 | G | T | NON_SYNONYMOUS_CODING | MODERATE |
| 227 | Chr05 | 937094 | T | C | NON_SYNONYMOUS_CODING | MODERATE |
| 228 | Chr05 | 937095 | C | A | NON_SYNONYMOUS_CODING | MODERATE |
| 229 | Chr05 | 937104 | A | C | NON_SYNONYMOUS_CODING | MODERATE |
| 230 | Chr05 | 937110 | C | T | NON_SYNONYMOUS_CODING | MODERATE |
| 231 | Chr05 | 937118 | G | C | NON_SYNONYMOUS_CODING | MODERATE |
| 232 | Chr05 | 937122 | A | T | NON_SYNONYMOUS_CODING | MODERATE |
| 233 | Chr05 | 937129 | C | A | NON_SYNONYMOUS_CODING | MODERATE |
| 234 | Chr05 | 937130 | C | G | NON_SYNONYMOUS_CODING | MODERATE |
| 235 | Chr05 | 937131 | A | C | NON_SYNONYMOUS_CODING | MODERATE |
| 236 | Chr05 | 937222 | A | C | NON_SYNONYMOUS_CODING | MODERATE |
| 237 | Chr05 | 937227 | T | G | NON_SYNONYMOUS_CODING | MODERATE |
| 238 | Chr05 | 937232 | T | A | NON_SYNONYMOUS_CODING | MODERATE |
| 239 | Chr05 | 937233 | T | G | NON_SYNONYMOUS_CODING | MODERATE |
| 240 | Chr05 | 937243 | T | G | NON_SYNONYMOUS_CODING | MODERATE |
| 241 | Chr05 | 937247 | A | T | NON_SYNONYMOUS_CODING | MODERATE |
| 242 | Chr05 | 937249 | C | G | NON_SYNONYMOUS_CODING | MODERATE |
| 243 | Chr05 | 937254 | G | A | NON_SYNONYMOUS_CODING | MODERATE |
| 244 | Chr05 | 937255 | T | A | NON_SYNONYMOUS_CODING | MODERATE |
| 245 | Chr05 | 937286 | T | C | NON_SYNONYMOUS_CODING | MODERATE |
| 246 | Chr05 | 937294 | T | C | NON_SYNONYMOUS_CODING | MODERATE |
| 247 | Chr05 | 937311 | G | A | NON_SYNONYMOUS_CODING | MODERATE |
| 248 | Chr05 | 937314 | C | G | NON_SYNONYMOUS_CODING | MODERATE |
| 249 | Chr05 | 937315 | A | G | NON_SYNONYMOUS_CODING | MODERATE |
| 250 | Chr05 | 937317 | T | G | NON_SYNONYMOUS_CODING | MODERATE |
| 251 | Chr05 | 937320 | A | G | NON_SYNONYMOUS_CODING | MODERATE |
| 252 | Chr05 | 937324 | A | T | NON_SYNONYMOUS_CODING | MODERATE |
| 253 | Chr05 | 937329 | G | A | NON_SYNONYMOUS_CODING | MODERATE |
| 254 | Chr05 | 937330 | T | A | NON_SYNONYMOUS_CODING | MODERATE |
| 255 | Chr05 | 937337 | A | T | NON_SYNONYMOUS_CODING | MODERATE |
| 256 | Chr05 | 937710 | T | G | NON_SYNONYMOUS_CODING | MODERATE |
| 257 | Chr05 | 937713 | G | A | NON_SYNONYMOUS_CODING | MODERATE |
| 258 | Chr05 | 937716 | C | T | NON_SYNONYMOUS_CODING | MODERATE |
| 259 | Chr05 | 937725 | C | T | NON_SYNONYMOUS_CODING | MODERATE |
| 260 | Chr05 | 937731 | A | C | NON_SYNONYMOUS_CODING | MODERATE |
| 261 | Chr05 | 937733 | A | C | NON_SYNONYMOUS_CODING | MODERATE |
| 262 | Chr05 | 937739 | C | G | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 263 | Chr05 | 937740 | C | T | NON_SYNONYMOUS_CODING | MODERATE |
| 264 | Chr05 | 937749 | A | C | NON_SYNONYMOUS_CODING | MODERATE |
| 265 | Chr05 | 937764 | T | A | NON_SYNONYMOUS_CODING | MODERATE |
| 266 | Chr05 | 937851 | C | A | NON_SYNONYMOUS_CODING | MODERATE |
| 267 | Chr05 | 937853 | A | G | NON_SYNONYMOUS_CODING | MODERATE |
| 268 | Chr05 | 937857 | C | T | NON_SYNONYMOUS_CODING | MODERATE |
| 269 | Chr05 | 937862 | A | G | NON_SYNONYMOUS_CODING | MODERATE |
| 270 | Chr05 | 938958 | C | G | NON_SYNONYMOUS_CODING | MODERATE |
| 271 | Chr05 | 938964 | C | A | NON_SYNONYMOUS_CODING | MODERATE |
| 272 | Chr05 | 938966 | C | T | NON_SYNONYMOUS_CODING | MODERATE |
| 273 | Chr05 | 938967 | C | T | NON_SYNONYMOUS_CODING | MODERATE |
| 274 | Chr05 | 938972 | A | C | NON_SYNONYMOUS_CODING | MODERATE |
| 275 | Chr05 | 938973 | A | G | NON_SYNONYMOUS_CODING | MODERATE |
| 276 | Chr05 | 938987 | G | T | NON_SYNONYMOUS_CODING | MODERATE |
| 277 | Chr05 | 938990 | T | A | NON_SYNONYMOUS_CODING | MODERATE |
| 278 | Chr05 | 938997 | A | C | NON_SYNONYMOUS_CODING | MODERATE |
| 279 | Chr05 | 939020 | G | A | NON_SYNONYMOUS_CODING | MODERATE |
| 280 | Chr05 | 939027 | T | C | NON_SYNONYMOUS_CODING | MODERATE |
| 281 | Chr05 | 939036 | C | T | NON_SYNONYMOUS_CODING | MODERATE |
| 282 | Chr05 | 939050 | C | T | NON_SYNONYMOUS_CODING | MODERATE |
| 283 | Chr05 | 939060 | A | C | NON_SYNONYMOUS_CODING | MODERATE |
| 284 | Chr05 | 939065 | A | T | NON_SYNONYMOUS_CODING | MODERATE |
| 285 | Chr05 | 939069 | C | T | NON_SYNONYMOUS_CODING | MODERATE |
| 286 | Chr05 | 939076 | C | G | NON_SYNONYMOUS_CODING | MODERATE |
| 287 | Chr05 | 939090 | A | G | NON_SYNONYMOUS_CODING | MODERATE |
| 288 | Chr05 | 939275 | T | G | NON_SYNONYMOUS_CODING | MODERATE |
| 289 | Chr05 | 939279 | T | G | NON_SYNONYMOUS_CODING | MODERATE |
| 290 | Chr05 | 939284 | T | C | NON_SYNONYMOUS_CODING | MODERATE |
| 291 | Chr05 | 939285 | C | A | NON_SYNONYMOUS_CODING | MODERATE |
| 292 | Chr05 | 939343 | C | A | NON_SYNONYMOUS_CODING | MODERATE |
| 293 | Chr05 | 939347 | C | A | NON_SYNONYMOUS_CODING | MODERATE |
| 294 | Chr05 | 939354 | C | A | NON_SYNONYMOUS_CODING | MODERATE |
| 295 | Chr05 | 939363 | A | T | NON_SYNONYMOUS_CODING | MODERATE |
| 296 | Chr05 | 939365 | T | C | NON_SYNONYMOUS_CODING | MODERATE |
| 297 | Chr05 | 939366 | G | C | NON_SYNONYMOUS_CODING | MODERATE |
| 298 | Chr05 | 939369 | G | C | NON_SYNONYMOUS_CODING | MODERATE |
| 299 | Chr05 | 939375 | G | T | NON_SYNONYMOUS_CODING | MODERATE |

TABLE 1-continued

RLP1 Mutations

| | Chrom. | Genomic Position | Reference | Variant | Mutation type | Predicted impact |
|---|---|---|---|---|---|---|
| 300 | Chr05 | 939377 | T | C | NON_SYNONYMOUS_CODING | MODERATE |
| 301 | Chr05 | 939386 | C | T | NON_SYNONYMOUS_CODING | MODERATE |
| 302 | Chr05 | 939390 | T | C | NON_SYNONYMOUS_CODING | MODERATE |
| 303 | Chr05 | 939392 | G | T | NON_SYNONYMOUS_CODING | MODERATE |
| 304 | Chr05 | 939393 | T | C | NON_SYNONYMOUS_CODING | MODERATE |
| 305 | Chr05 | 939395 | G | A | NON_SYNONYMOUS_CODING | MODERATE |
| 306 | Chr05 | 939396 | T | A | NON_SYNONYMOUS_CODING | MODERATE |
| 307 | Chr05 | 939407 | T | A | NON_SYNONYMOUS_CODING | MODERATE |
| 308 | Chr05 | 939408 | C | T | NON_SYNONYMOUS_CODING | MODERATE |
| 309 | Chr05 | 939414 | C | A | NON_SYNONYMOUS_CODING | MODERATE |
| 310 | Chr05 | 939416 | G | T | NON_SYNONYMOUS_CODING | MODERATE |
| 311 | Chr05 | 939438 | T | C | NON_SYNONYMOUS_CODING | MODERATE |
| 312 | Chr05 | 939464 | A | T | NON_SYNONYMOUS_CODING | MODERATE |
| 313 | Chr05 | 939471 | C | A | NON_SYNONYMOUS_CODING | MODERATE |
| 314 | Chr05 | 939477 | G | T | NON_SYNONYMOUS_CODING | MODERATE |
| 315 | Chr05 | 939479 | A | G | NON_SYNONYMOUS_CODING | MODERATE |
| 316 | Chr05 | 939486 | C | G | NON_SYNONYMOUS_CODING | MODERATE |
| 317 | Chr05 | 939506 | A | G | NON_SYNONYMOUS_CODING | MODERATE |
| 318 | Chr05 | 939514 | T | A | NON_SYNONYMOUS_CODING | MODERATE |
| 319 | Chr05 | 939520 | C | A | NON_SYNONYMOUS_CODING | MODERATE |
| 320 | Chr05 | 939521 | A | G | NON_SYNONYMOUS_CODING | MODERATE |
| 321 | Chr05 | 939537 | G | A | NON_SYNONYMOUS_CODING | MODERATE |
| 322 | Chr05 | 939542 | C | T | NON_SYNONYMOUS_CODING | MODERATE |
| 323 | Chr05 | 939547 | A | T, G | NON_SYNONYMOUS_CODING | MODERATE |
| 324 | Chr05 | 939549 | C | T | NON_SYNONYMOUS_CODING | MODERATE |
| 325 | Chr05 | 939560 | G | A | NON_SYNONYMOUS_CODING | MODERATE |
| 326 | Chr05 | 939561 | T | C | NON_SYNONYMOUS_CODING | MODERATE |
| 327 | Chr05 | 939569 | G | A | NON_SYNONYMOUS_CODING | MODERATE |
| 328 | Chr05 | 939587 | C | T | NON_SYNONYMOUS_CODING | MODERATE |
| 329 | Chr05 | 939592 | T | A | NON_SYNONYMOUS_CODING | MODERATE |
| 330 | Chr05 | 939598 | C | A | NON_SYNONYMOUS_CODING | MODERATE |
| 331 | Chr05 | 939600 | T | C | NON_SYNONYMOUS_CODING | MODERATE |
| 332 | Chr05 | 937085 | A | ATAT | CODON_INSERTION | MODERATE |
| 333 | Chr05 | 939336 | AAT | AATTAT | CODON_INSERTION | MODERATE |
| 334 | Chr05 | 933925 | CAGTA | CA | CODON_DELETION | MODERATE |
| 335 | Chr05 | 935584 | GACC | GACCACC | CODON_CHANGE_PLUS_CODON_INSERTION | MODERATE |
| 336 | Chr05 | 939610 | G | GATA | UTR_5_PRIME | MODIFIER |
| 337 | Chr05 | 939618 | C | G | UTR_5_PRIME | MODIFIER |

TABLE 1-continued

RLP1 Mutations

| | Chrom. | Genomic Position | Reference | Variant | Mutation type | Predicted impact |
|---|---|---|---|---|---|---|
| 338 | Chr05 | 939619 | T | G | UTR_5_PRIME | MODIFIER |
| 339 | Chr05 | 939621 | T | G | UTR_5_PRIME | MODIFIER |
| 340 | Chr05 | 939626 | T | C | UTR_5_PRIME | MODIFIER |
| 341 | Chr05 | 939630 | A | G | UTR_5_PRIME | MODIFIER |
| 342 | Chr05 | 939640 | T | A | UTR_5_PRIME | MODIFIER |
| 343 | Chr05 | 939648 | T | C | UTR_5_PRIME | MODIFIER |
| 344 | Chr05 | 939657 | A | C | UTR_5_PRIME | MODIFIER |
| 345 | Chr05 | 939660 | T | C | UTR_5_PRIME | MODIFIER |
| 346 | Chr05 | 939681 | A | G | UTR_5_PRIME | MODIFIER |
| 347 | Chr05 | 939693 | T | C | UTR_5_PRIME | MODIFIER |
| 348 | Chr05 | 933705 | A | C | UTR_3_PRIME | MODIFIER |
| 349 | Chr05 | 933718 | T | C | UTR_3_PRIME | MODIFIER |
| 350 | Chr05 | 933746 | C | G | UTR_3_PRIME | MODIFIER |
| 351 | Chr05 | 933750 | G | T | UTR_3_PRIME | MODIFIER |
| 352 | Chr05 | 933752 | A | T | UTR_3_PRIME | MODIFIER |
| 353 | Chr05 | 933764 | G | T | UTR_3_PRIME | MODIFIER |
| 354 | Chr05 | 933808 | C | T | UTR_3_PRIME | MODIFIER |
| 355 | Chr05 | 933841 | C | T | UTR_3_PRIME | MODIFIER |
| 356 | Chr05 | 933849 | C | A | UTR_3_PRIME | MODIFIER |
| 357 | Chr05 | 933855 | C | T | UTR_3_PRIME | MODIFIER |
| 358 | Chr05 | 933857 | C | T | UTR_3_PRIME | MODIFIER |
| 359 | Chr05 | 933866 | T | C | UTR_3_PRIME | MODIFIER |
| 360 | Chr05 | 933869 | G | A | UTR_3_PRIME | MODIFIER |

TABLE 2

RLP2 Mutations

| | Chrom. | Gen. Pos. | Reference | Variant | Mutation type | Predicted impact |
|---|---|---|---|---|---|---|
| 1 | Chr03 | 3509298 | TGCC | TACGCC | FRAME_SHIFT | HIGH |
| 2 | Chr03 | 3509624 | CG | CAG | FRAME_SHIFT | HIGH |
| 3 | Chr03 | 3510653 | GA | G | FRAME_SHIFT | HIGH |
| 4 | Chr03 | 3510717 | TAAA | TAA | FRAME_SHIFT | HIGH |
| 5 | Chr03 | 3511960 | CT | CGTT | FRAME_SHIFT | HIGH |
| 6 | Chr03 | 3511976 | TGC | T | FRAME_SHIFT | HIGH |
| 7 | Chr03 | 3511983 | GTT | GATT | FRAME_SHIFT | HIGH |
| 8 | Chr03 | 3511986 | G | GC | FRAME_SHIFT | HIGH |
| 9 | Chr03 | 3513689 | TCC | TC | FRAME_SHIFT | HIGH |

TABLE 2-continued

RLP2 Mutations

| | Chrom. | Gen. Pos. | Reference | Variant | Mutation type | Predicted impact |
|---|---|---|---|---|---|---|
| 10 | Chr03 | 3513694 | T | TTG | FRAME_SHIFT | HIGH |
| 11 | Chr03 | 3513855 | TCCATTACCTTCC (SEQ ID NO: 42) | TC | FRAME_SHIFT | HIGH |
| 12 | Chr03 | 3514020 | ACTACCGTC | AC | FRAME_SHIFT | HIGH |
| 13 | Chr03 | 3514031 | CC | CTC | FRAME_SHIFT | HIGH |
| 14 | Chr03 | 3511277 | C | A | SPLICE_SITE_ACCEPTOR | HIGH |
| 15 | Chr03 | 3511627 | C | T | SPLICE_SITE_DONOR | HIGH |
| 16 | Chr03 | 3509109 | G | C | STOP_GAINED | HIGH |
| 17 | Chr03 | 3509714 | C | A | STOP_GAINED | HIGH |
| 18 | Chr03 | 3510880 | A | T | STOP_GAINED | HIGH |
| 19 | Chr03 | 3511157 | G | A | STOP_GAINED | HIGH |
| 20 | Chr03 | 3511958 | C | A | STOP_GAINED | HIGH |
| 21 | Chr03 | 3511969 | G | T | STOP_GAINED | HIGH |
| 22 | Chr03 | 3513616 | C | A | STOP_GAINED | HIGH |
| 23 | Chr03 | 3513695 | A | T | STOP_GAINED | HIGH |
| 24 | Chr03 | 3514010 | C | A | STOP_GAINED | HIGH |
| 25 | Chr03 | 3514161 | CAT | CATGAT | STOP_GAINED | HIGH |
| 26 | Chr03 | 3510241 | CAAAAA | CAAAAAAA | CODON_CHANGE_PLUS_CODON_INSERTION | MODERATE |
| 27 | Chr03 | 3510902 | G | GTAT | CODON_CHANGE_PLUS_CODON_INSERTION | MODERATE |
| 28 | Chr03 | 3511991 | TA | TACAA | CODON_CHANGE_PLUS_CODON_INSERTION | MODERATE |
| 29 | Chr03 | 3513680 | ATT | ATTTTT | CODON_CHANGE_PLUS_CODON_INSERTION | MODERATE |
| 30 | Chr03 | 3509303 | TCTC | T | CODON_DELETION | MODERATE |
| 31 | Chr03 | 3509997 | CAGAAGAAGAA (SEQ ID NO: 43) | CAGAAGAA | CODON_DELETION | MODERATE |
| 32 | Chr03 | 3513587 | ACCTCCT | ACCT | CODON_DELETION | MODERATE |
| 33 | Chr03 | 3509291 | ACACCAC | ACAGCACCAC | CODON_INSERTION | MODERATE |
| 34 | Chr03 | 3510462 | CA | CAGTA | CODON_INSERTION | MODERATE |
| 35 | Chr03 | 3511996 | T | TTAG | CODON_INSERTION | MODERATE |
| 36 | Chr03 | 3513344 | CT | CTTAT | CODON_INSERTION | MODERATE |
| 37 | Chr03 | 3513610 | CAT | CATAAT | CODON_INSERTION | MODERATE |
| 38 | Chr03 | 3514144 | G | GCCA | CODON_INSERTION | MODERATE |
| 39 | Chr03 | 3509086 | C | T | NON_SYNONYMOUS_CODING | MODERATE |
| 40 | Chr03 | 3509087 | G | A | NON_SYNONYMOUS_CODING | MODERATE |
| 41 | Chr03 | 3509102 | C | T | NON_SYNONYMOUS_CODING | MODERATE |
| 42 | Chr03 | 3509113 | C | T | NON_SYNONYMOUS_CODING | MODERATE |
| 43 | Chr03 | 3509126 | A | T | NON_SYNONYMOUS_CODING | MODERATE |
| 44 | Chr03 | 3509128 | T | C | NON_SYNONYMOUS_CODING | MODERATE |
| 45 | Chr03 | 3509152 | C | T | NON_SYNONYMOUS_CODING | MODERATE |
| 46 | Chr03 | 3509153 | G | A | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 47 | Chr03 | 3509162 | A | T | NON_SYNONYMOUS_CODING | MODERATE |
| 48 | Chr03 | 3509177 | G | A | NON_SYNONYMOUS_CODING | MODERATE |
| 49 | Chr03 | 3509182 | G | A | NON_SYNONYMOUS_CODING | MODERATE |
| 50 | Chr03 | 3509183 | C | T | NON_SYNONYMOUS_CODING | MODERATE |
| 51 | Chr03 | 3509185 | G | A | NON_SYNONYMOUS_CODING | MODERATE |
| 52 | Chr03 | 3509191 | G | A | NON_SYNONYMOUS_CODING | MODERATE |
| 53 | Chr03 | 3509204 | C | T | NON_SYNONYMOUS_CODING | MODERATE |
| 54 | Chr03 | 3509206 | G | A | NON_SYNONYMOUS_CODING | MODERATE |
| 55 | Chr03 | 3509238 | C | A | NON_SYNONYMOUS_CODING | MODERATE |
| 56 | Chr03 | 3509240 | C | T | NON_SYNONYMOUS_CODING | MODERATE |
| 57 | Chr03 | 3509246 | C | T | NON_SYNONYMOUS_CODING | MODERATE |
| 58 | Chr03 | 3509254 | C | T | NON_SYNONYMOUS_CODING | MODERATE |
| 59 | Chr03 | 3509261 | C | A | NON_SYNONYMOUS_CODING | MODERATE |
| 60 | Chr03 | 3509263 | C | G | NON_SYNONYMOUS_CODING | MODERATE |
| 61 | Chr03 | 3509265 | T | G | NON_SYNONYMOUS_CODING | MODERATE |
| 62 | Chr03 | 3509276 | T | C | NON_SYNONYMOUS_CODING | MODERATE |
| 63 | Chr03 | 3509282 | C | T | NON_SYNONYMOUS_CODING | MODERATE |
| 64 | Chr03 | 3509284 | G | A | NON_SYNONYMOUS_CODING | MODERATE |
| 65 | Chr03 | 3509285 | G | A | NON_SYNONYMOUS_CODING | MODERATE |
| 66 | Chr03 | 3509309 | T | C | NON_SYNONYMOUS_CODING | MODERATE |
| 67 | Chr03 | 3509320 | G | C | NON_SYNONYMOUS_CODING | MODERATE |
| 68 | Chr03 | 3509344 | G | T | NON_SYNONYMOUS_CODING | MODERATE |
| 69 | Chr03 | 3509354 | C | T | NON_SYNONYMOUS_CODING | MODERATE |
| 70 | Chr03 | 3509362 | C | T | NON_SYNONYMOUS_CODING | MODERATE |
| 71 | Chr03 | 3509369 | C | T | NON_SYNONYMOUS_CODING | MODERATE |
| 72 | Chr03 | 3509377 | C | G | NON_SYNONYMOUS_CODING | MODERATE |
| 73 | Chr03 | 3509378 | C | A | NON_SYNONYMOUS_CODING | MODERATE |
| 74 | Chr03 | 3509389 | A | T | NON_SYNONYMOUS_CODING | MODERATE |
| 75 | Chr03 | 3509395 | T | A | NON_SYNONYMOUS_CODING | MODERATE |
| 76 | Chr03 | 3509404 | T | C | NON_SYNONYMOUS_CODING | MODERATE |
| 77 | Chr03 | 3509423 | G | A | NON_SYNONYMOUS_CODING | MODERATE |
| 78 | Chr03 | 3509426 | C | T | NON_SYNONYMOUS_CODING | MODERATE |
| 79 | Chr03 | 3509453 | C | T | NON_SYNONYMOUS_CODING | MODERATE |
| 80 | Chr03 | 3509456 | C | T | NON_SYNONYMOUS_CODING | MODERATE |
| 81 | Chr03 | 3509458 | G | A | NON_SYNONYMOUS_CODING | MODERATE |
| 82 | Chr03 | 3509462 | A | G | NON_SYNONYMOUS_CODING | MODERATE |
| 83 | Chr03 | 3509474 | T | A | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 84 | Chr03 | 3509476 | G | A | NON_SYNONYMOUS_CODING | MODERATE |
| 85 | Chr03 | 3509494 | T | A | NON_SYNONYMOUS_CODING | MODERATE |
| 86 | Chr03 | 3509517 | A | C | NON_SYNONYMOUS_CODING | MODERATE |
| 87 | Chr03 | 3509520 | C | A | NON_SYNONYMOUS_CODING | MODERATE |
| 88 | Chr03 | 3509521 | A | T | NON_SYNONYMOUS_CODING | MODERATE |
| 89 | Chr03 | 3509540 | C | T | NON_SYNONYMOUS_CODING | MODERATE |
| 90 | Chr03 | 3509546 | T | C | NON_SYNONYMOUS_CODING | MODERATE |
| 91 | Chr03 | 3509548 | G | C | NON_SYNONYMOUS_CODING | MODERATE |
| 92 | Chr03 | 3509552 | C | T | NON_SYNONYMOUS_CODING | MODERATE |
| 93 | Chr03 | 3509554 | G | A | NON_SYNONYMOUS_CODING | MODERATE |
| 94 | Chr03 | 3509579 | C | A | NON_SYNONYMOUS_CODING | MODERATE |
| 95 | Chr03 | 3509591 | T | C | NON_SYNONYMOUS_CODING | MODERATE |
| 96 | Chr03 | 3509593 | C | G | NON_SYNONYMOUS_CODING | MODERATE |
| 97 | Chr03 | 3509620 | G | A | NON_SYNONYMOUS_CODING | MODERATE |
| 98 | Chr03 | 3509627 | T | C | NON_SYNONYMOUS_CODING | MODERATE |
| 99 | Chr03 | 3509632 | T | C | NON_SYNONYMOUS_CODING | MODERATE |
| 100 | Chr03 | 3509656 | A | G | NON_SYNONYMOUS_CODING | MODERATE |
| 101 | Chr03 | 3509657 | A | G | NON_SYNONYMOUS_CODING | MODERATE |
| 102 | Chr03 | 3509663 | A | T | NON_SYNONYMOUS_CODING | MODERATE |
| 103 | Chr03 | 3509665 | T | C | NON_SYNONYMOUS_CODING | MODERATE |
| 104 | Chr03 | 3509669 | G | C | NON_SYNONYMOUS_CODING | MODERATE |
| 105 | Chr03 | 3509674 | T | A | NON_SYNONYMOUS_CODING | MODERATE |
| 106 | Chr03 | 3509686 | C | T | NON_SYNONYMOUS_CODING | MODERATE |
| 107 | Chr03 | 3509687 | C | T | NON_SYNONYMOUS_CODING | MODERATE |
| 108 | Chr03 | 3509697 | A | C | NON_SYNONYMOUS_CODING | MODERATE |
| 109 | Chr03 | 3509716 | G | A | NON_SYNONYMOUS_CODING | MODERATE |
| 110 | Chr03 | 3509717 | T | C | NON_SYNONYMOUS_CODING | MODERATE |
| 111 | Chr03 | 3509726 | C | G | NON_SYNONYMOUS_CODING | MODERATE |
| 112 | Chr03 | 3509728 | G | A | NON_SYNONYMOUS_CODING | MODERATE |
| 113 | Chr03 | 3509738 | A | G | NON_SYNONYMOUS_CODING | MODERATE |
| 114 | Chr03 | 3509743 | A | G | NON_SYNONYMOUS_CODING | MODERATE |
| 115 | Chr03 | 3509744 | A | T | NON_SYNONYMOUS_CODING | MODERATE |
| 116 | Chr03 | 3509750 | T | G | NON_SYNONYMOUS_CODING | MODERATE |
| 117 | Chr03 | 3509758 | T | G | NON_SYNONYMOUS_CODING | MODERATE |
| 118 | Chr03 | 3509762 | C | A | NON_SYNONYMOUS_CODING | MODERATE |
| 119 | Chr03 | 3509788 | A | G | NON_SYNONYMOUS_CODING | MODERATE |
| 120 | Chr03 | 3509819 | C | T | NON_SYNONYMOUS_CODING | MODERATE |
| 121 | Chr03 | 3509825 | T | G | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 122 | Chr03 | 3509836 | G | T | NON_SYNONYMOUS_CODING | MODERATE |
| 123 | Chr03 | 3509837 | C | T | NON_SYNONYMOUS_CODING | MODERATE |
| 124 | Chr03 | 3509839 | A | C | NON_SYNONYMOUS_CODING | MODERATE |
| 125 | Chr03 | 3509860 | T | G | NON_SYNONYMOUS_CODING | MODERATE |
| 126 | Chr03 | 3509861 | C | A | NON_SYNONYMOUS_CODING | MODERATE |
| 127 | Chr03 | 3509867 | T | C | NON_SYNONYMOUS_CODING | MODERATE |
| 128 | Chr03 | 3509872 | A | G | NON_SYNONYMOUS_CODING | MODERATE |
| 129 | Chr03 | 3509875 | G | A | NON_SYNONYMOUS_CODING | MODERATE |
| 130 | Chr03 | 3509885 | C | T | NON_SYNONYMOUS_CODING | MODERATE |
| 131 | Chr03 | 3509897 | G | C | NON_SYNONYMOUS_CODING | MODERATE |
| 132 | Chr03 | 3509919 | G | T | NON_SYNONYMOUS_CODING | MODERATE |
| 133 | Chr03 | 3509937 | G | T | NON_SYNONYMOUS_CODING | MODERATE |
| 134 | Chr03 | 3509943 | T | G | NON_SYNONYMOUS_CODING | MODERATE |
| 135 | Chr03 | 3509945 | G | C | NON_SYNONYMOUS_CODING | MODERATE |
| 136 | Chr03 | 3509963 | G | T | NON_SYNONYMOUS_CODING | MODERATE |
| 137 | Chr03 | 3509965 | A | T | NON_SYNONYMOUS_CODING | MODERATE |
| 138 | Chr03 | 3509966 | T | C | NON_SYNONYMOUS_CODING | MODERATE |
| 139 | Chr03 | 3509968 | G | A | NON_SYNONYMOUS_CODING | MODERATE |
| 140 | Chr03 | 3509975 | C | T | NON_SYNONYMOUS_CODING | MODERATE |
| 141 | Chr03 | 3509986 | T | A | NON_SYNONYMOUS_CODING | MODERATE |
| 142 | Chr03 | 3509987 | G | T | NON_SYNONYMOUS_CODING | MODERATE |
| 143 | Chr03 | 3509992 | G | T | NON_SYNONYMOUS_CODING | MODERATE |
| 144 | Chr03 | 3509993 | C | A | NON_SYNONYMOUS_CODING | MODERATE |
| 145 | Chr03 | 3509996 | T | C | NON_SYNONYMOUS_CODING | MODERATE |
| 146 | Chr03 | 3510011 | T | C | NON_SYNONYMOUS_CODING | MODERATE |
| 147 | Chr03 | 3510016 | G | A | NON_SYNONYMOUS_CODING | MODERATE |
| 148 | Chr03 | 3510028 | C | T | NON_SYNONYMOUS_CODING | MODERATE |
| 149 | Chr03 | 3510029 | C | G | NON_SYNONYMOUS_CODING | MODERATE |
| 150 | Chr03 | 3510050 | C | T | NON_SYNONYMOUS_CODING | MODERATE |
| 151 | Chr03 | 3510052 | G | A | NON_SYNONYMOUS_CODING | MODERATE |
| 152 | Chr03 | 3510058 | C | T | NON_SYNONYMOUS_CODING | MODERATE |
| 153 | Chr03 | 3510063 | T | A | NON_SYNONYMOUS_CODING | MODERATE |
| 154 | Chr03 | 3510074 | C | T | NON_SYNONYMOUS_CODING | MODERATE |
| 155 | Chr03 | 3510088 | T | G | NON_SYNONYMOUS_CODING | MODERATE |
| 156 | Chr03 | 3510100 | A | T | NON_SYNONYMOUS_CODING | MODERATE |
| 157 | Chr03 | 3510106 | G | C | NON_SYNONYMOUS_CODING | MODERATE |
| 158 | Chr03 | 3510116 | A | C | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 159 | Chr03 | 3510122 | C | A | NON_SYNONYMOUS_CODING | MODERATE |
| 160 | Chr03 | 3510144 | A | T | NON_SYNONYMOUS_CODING | MODERATE |
| 161 | Chr03 | 3510146 | G | T | NON_SYNONYMOUS_CODING | MODERATE |
| 162 | Chr03 | 3510149 | C | T | NON_SYNONYMOUS_CODING | MODERATE |
| 163 | Chr03 | 3510159 | T | A | NON_SYNONYMOUS_CODING | MODERATE |
| 164 | Chr03 | 3510161 | G | T | NON_SYNONYMOUS_CODING | MODERATE |
| 165 | Chr03 | 3510169 | C | T | NON_SYNONYMOUS_CODING | MODERATE |
| 166 | Chr03 | 3510183 | T | C | NON_SYNONYMOUS_CODING | MODERATE |
| 167 | Chr03 | 3510188 | A | T | NON_SYNONYMOUS_CODING | MODERATE |
| 168 | Chr03 | 3510191 | C | T | NON_SYNONYMOUS_CODING | MODERATE |
| 169 | Chr03 | 3510205 | T | C | NON_SYNONYMOUS_CODING | MODERATE |
| 170 | Chr03 | 3510212 | G | A | NON_SYNONYMOUS_CODING | MODERATE |
| 171 | Chr03 | 3510229 | T | G | NON_SYNONYMOUS_CODING | MODERATE |
| 172 | Chr03 | 3510230 | G | C | NON_SYNONYMOUS_CODING | MODERATE |
| 173 | Chr03 | 3510233 | C | G | NON_SYNONYMOUS_CODING | MODERATE |
| 174 | Chr03 | 3510236 | A | G | NON_SYNONYMOUS_CODING | MODERATE |
| 175 | Chr03 | 3510250 | C | A | NON_SYNONYMOUS_CODING | MODERATE |
| 176 | Chr03 | 3510251 | T | C | NON_SYNONYMOUS_CODING | MODERATE |
| 177 | Chr03 | 3510260 | G | A | NON_SYNONYMOUS_CODING | MODERATE |
| 178 | Chr03 | 3510277 | C | T | NON_SYNONYMOUS_CODING | MODERATE |
| 179 | Chr03 | 3510278 | C | T | NON_SYNONYMOUS_CODING | MODERATE |
| 180 | Chr03 | 3510290 | T | G | NON_SYNONYMOUS_CODING | MODERATE |
| 181 | Chr03 | 3510292 | A | G | NON_SYNONYMOUS_CODING | MODERATE |
| 182 | Chr03 | 3510295 | C | T | NON_SYNONYMOUS_CODING | MODERATE |
| 183 | Chr03 | 3510301 | A | T | NON_SYNONYMOUS_CODING | MODERATE |
| 184 | Chr03 | 3510302 | T | A | NON_SYNONYMOUS_CODING | MODERATE |
| 185 | Chr03 | 3510305 | A | T | NON_SYNONYMOUS_CODING | MODERATE |
| 186 | Chr03 | 3510307 | A | C | NON_SYNONYMOUS_CODING | MODERATE |
| 187 | Chr03 | 3510318 | G | C | NON_SYNONYMOUS_CODING | MODERATE |
| 188 | Chr03 | 3510319 | C | A | NON_SYNONYMOUS_CODING | MODERATE |
| 189 | Chr03 | 3510320 | T | A | NON_SYNONYMOUS_CODING | MODERATE |
| 190 | Chr03 | 3510329 | G | A | NON_SYNONYMOUS_CODING | MODERATE |
| 191 | Chr03 | 3510332 | T | G | NON_SYNONYMOUS_CODING | MODERATE |
| 192 | Chr03 | 3510334 | C | A | NON_SYNONYMOUS_CODING | MODERATE |
| 193 | Chr03 | 3510335 | C | T | NON_SYNONYMOUS_CODING | MODERATE |
| 194 | Chr03 | 3510349 | T | G | NON_SYNONYMOUS_CODING | MODERATE |
| 195 | Chr03 | 3510350 | T | G | NON_SYNONYMOUS_CODING | MODERATE |
| 196 | Chr03 | 3510352 | C | T | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 197 | Chr03 | 3510365 | C | A | NON_SYNONYMOUS_CODING | MODERATE |
| 198 | Chr03 | 3510367 | T | C | NON_SYNONYMOUS_CODING | MODERATE |
| 199 | Chr03 | 3510368 | T | G | NON_SYNONYMOUS_CODING | MODERATE |
| 200 | Chr03 | 3510370 | C | A | NON_SYNONYMOUS_CODING | MODERATE |
| 201 | Chr03 | 3510373 | A | T | NON_SYNONYMOUS_CODING | MODERATE |
| 202 | Chr03 | 3510374 | C | T | NON_SYNONYMOUS_CODING | MODERATE |
| 203 | Chr03 | 3510375 | A | T | NON_SYNONYMOUS_CODING | MODERATE |
| 204 | Chr03 | 3510383 | T | C | NON_SYNONYMOUS_CODING | MODERATE |
| 205 | Chr03 | 3510386 | A | T | NON_SYNONYMOUS_CODING | MODERATE |
| 206 | Chr03 | 3510389 | A | C | NON_SYNONYMOUS_CODING | MODERATE |
| 207 | Chr03 | 3510391 | G | C | NON_SYNONYMOUS_CODING | MODERATE |
| 208 | Chr03 | 3510392 | G | A | NON_SYNONYMOUS_CODING | MODERATE |
| 209 | Chr03 | 3510395 | A | T | NON_SYNONYMOUS_CODING | MODERATE |
| 210 | Chr03 | 3510397 | T | C | NON_SYNONYMOUS_CODING | MODERATE |
| 211 | Chr03 | 3510404 | T | A | NON_SYNONYMOUS_CODING | MODERATE |
| 212 | Chr03 | 3510407 | G | T | NON_SYNONYMOUS_CODING | MODERATE |
| 213 | Chr03 | 3510425 | C | G | NON_SYNONYMOUS_CODING | MODERATE |
| 214 | Chr03 | 3510427 | T | C | NON_SYNONYMOUS_CODING | MODERATE |
| 215 | Chr03 | 3510428 | T | G | NON_SYNONYMOUS_CODING | MODERATE |
| 216 | Chr03 | 3510440 | A | T | NON_SYNONYMOUS_CODING | MODERATE |
| 217 | Chr03 | 3510441 | A | T | NON_SYNONYMOUS_CODING | MODERATE |
| 218 | Chr03 | 3510442 | T | G | NON_SYNONYMOUS_CODING | MODERATE |
| 219 | Chr03 | 3510443 | T | C | NON_SYNONYMOUS_CODING | MODERATE |
| 220 | Chr03 | 3510446 | G | T | NON_SYNONYMOUS_CODING | MODERATE |
| 221 | Chr03 | 3510449 | G | C | NON_SYNONYMOUS_CODING | MODERATE |
| 222 | Chr03 | 3510454 | G | T | NON_SYNONYMOUS_CODING | MODERATE |
| 223 | Chr03 | 3510458 | T | A | NON_SYNONYMOUS_CODING | MODERATE |
| 224 | Chr03 | 3510464 | C | T | NON_SYNONYMOUS_CODING | MODERATE |
| 225 | Chr03 | 3510466 | G | A | NON_SYNONYMOUS_CODING | MODERATE |
| 226 | Chr03 | 3510472 | G | A | NON_SYNONYMOUS_CODING | MODERATE |
| 227 | Chr03 | 3510476 | T | A | NON_SYNONYMOUS_CODING | MODERATE |
| 228 | Chr03 | 3510479 | T | G | NON_SYNONYMOUS_CODING | MODERATE |
| 229 | Chr03 | 3510484 | C | T | NON_SYNONYMOUS_CODING | MODERATE |
| 230 | Chr03 | 3510485 | C | T | NON_SYNONYMOUS_CODING | MODERATE |
| 231 | Chr03 | 3510504 | C | G | NON_SYNONYMOUS_CODING | MODERATE |
| 232 | Chr03 | 3510505 | T | C | NON_SYNONYMOUS_CODING | MODERATE |
| 233 | Chr03 | 3510509 | G | A | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 234 | Chr03 | 3510512 | C | A | NON_SYNONYMOUS_CODING | MODERATE |
| 235 | Chr03 | 3510514 | C | A | NON_SYNONYMOUS_CODING | MODERATE |
| 236 | Chr03 | 3510515 | A | T | NON_SYNONYMOUS_CODING | MODERATE |
| 237 | Chr03 | 3510520 | G | C | NON_SYNONYMOUS_CODING | MODERATE |
| 238 | Chr03 | 3510539 | T | G | NON_SYNONYMOUS_CODING | MODERATE |
| 239 | Chr03 | 3510542 | C | G | NON_SYNONYMOUS_CODING | MODERATE |
| 240 | Chr03 | 3510545 | T | C | NON_SYNONYMOUS_CODING | MODERATE |
| 241 | Chr03 | 3510549 | C | A | NON_SYNONYMOUS_CODING | MODERATE |
| 242 | Chr03 | 3510575 | A | C | NON_SYNONYMOUS_CODING | MODERATE |
| 243 | Chr03 | 3510577 | G | A | NON_SYNONYMOUS_CODING | MODERATE |
| 244 | Chr03 | 3510583 | G | T | NON_SYNONYMOUS_CODING | MODERATE |
| 245 | Chr03 | 3510584 | A | T | NON_SYNONYMOUS_CODING | MODERATE |
| 246 | Chr03 | 3510595 | C | T | NON_SYNONYMOUS_CODING | MODERATE |
| 247 | Chr03 | 3510596 | C | T | NON_SYNONYMOUS_CODING | MODERATE |
| 248 | Chr03 | 3510611 | T | C | NON_SYNONYMOUS_CODING | MODERATE |
| 249 | Chr03 | 3510614 | A | C | NON_SYNONYMOUS_CODING | MODERATE |
| 250 | Chr03 | 3510634 | G | T | NON_SYNONYMOUS_CODING | MODERATE |
| 251 | Chr03 | 3510635 | C | G | NON_SYNONYMOUS_CODING | MODERATE |
| 252 | Chr03 | 3510646 | G | T | NON_SYNONYMOUS_CODING | MODERATE |
| 253 | Chr03 | 3510648 | G | T | NON_SYNONYMOUS_CODING | MODERATE |
| 254 | Chr03 | 3510649 | T | C | NON_SYNONYMOUS_CODING | MODERATE |
| 255 | Chr03 | 3510650 | G | C | NON_SYNONYMOUS_CODING | MODERATE |
| 256 | Chr03 | 3510656 | T | G | NON_SYNONYMOUS_CODING | MODERATE |
| 257 | Chr03 | 3510673 | A | G | NON_SYNONYMOUS_CODING | MODERATE |
| 258 | Chr03 | 3510682 | G | A | NON_SYNONYMOUS_CODING | MODERATE |
| 259 | Chr03 | 3510683 | G | A | NON_SYNONYMOUS_CODING | MODERATE |
| 260 | Chr03 | 3510688 | T | G | NON_SYNONYMOUS_CODING | MODERATE |
| 261 | Chr03 | 3510691 | C | T | NON_SYNONYMOUS_CODING | MODERATE |
| 262 | Chr03 | 3510699 | G | C | NON_SYNONYMOUS_CODING | MODERATE |
| 263 | Chr03 | 3510700 | T | C | NON_SYNONYMOUS_CODING | MODERATE |
| 264 | Chr03 | 3510705 | G | C | NON_SYNONYMOUS_CODING | MODERATE |
| 265 | Chr03 | 3510706 | T | G | NON_SYNONYMOUS_CODING | MODERATE |
| 266 | Chr03 | 3510716 | C | A | NON_SYNONYMOUS_CODING | MODERATE |
| 267 | Chr03 | 3510722 | T | C | NON_SYNONYMOUS_CODING | MODERATE |
| 268 | Chr03 | 3510724 | G | A | NON_SYNONYMOUS_CODING | MODERATE |
| 269 | Chr03 | 3510725 | T | C | NON_SYNONYMOUS_CODING | MODERATE |
| 270 | Chr03 | 3510733 | G | A | NON_SYNONYMOUS_CODING | MODERATE |
| 271 | Chr03 | 3510737 | G | A | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 272 | Chr03 | 3510748 | T | G | NON_SYNONYMOUS_CODING | MODERATE |
| 273 | Chr03 | 3510761 | C | T | NON_SYNONYMOUS_CODING | MODERATE |
| 274 | Chr03 | 3510763 | C | T | NON_SYNONYMOUS_CODING | MODERATE |
| 275 | Chr03 | 3510767 | T | C | NON_SYNONYMOUS_CODING | MODERATE |
| 276 | Chr03 | 3510777 | G | C | NON_SYNONYMOUS_CODING | MODERATE |
| 277 | Chr03 | 3510788 | A | C | NON_SYNONYMOUS_CODING | MODERATE |
| 278 | Chr03 | 3510793 | T | C | NON_SYNONYMOUS_CODING | MODERATE |
| 279 | Chr03 | 3510797 | C | G | NON_SYNONYMOUS_CODING | MODERATE |
| 280 | Chr03 | 3510800 | A | T | NON_SYNONYMOUS_CODING | MODERATE |
| 281 | Chr03 | 3510845 | T | A | NON_SYNONYMOUS_CODING | MODERATE |
| 282 | Chr03 | 3510868 | G | A | NON_SYNONYMOUS_CODING | MODERATE |
| 283 | Chr03 | 3510869 | C | T | NON_SYNONYMOUS_CODING | MODERATE |
| 284 | Chr03 | 3510871 | C | T | NON_SYNONYMOUS_CODING | MODERATE |
| 285 | Chr03 | 3510878 | C | T | NON_SYNONYMOUS_CODING | MODERATE |
| 286 | Chr03 | 3510887 | A | T | NON_SYNONYMOUS_CODING | MODERATE |
| 287 | Chr03 | 3510899 | C | T | NON_SYNONYMOUS_CODING | MODERATE |
| 288 | Chr03 | 3510911 | T | A | NON_SYNONYMOUS_CODING | MODERATE |
| 289 | Chr03 | 3510928 | G | A | NON_SYNONYMOUS_CODING | MODERATE |
| 290 | Chr03 | 3510930 | A | C | NON_SYNONYMOUS_CODING | MODERATE |
| 291 | Chr03 | 3510943 | C | T | NON_SYNONYMOUS_CODING | MODERATE |
| 292 | Chr03 | 3510944 | G | T | NON_SYNONYMOUS_CODING | MODERATE |
| 293 | Chr03 | 3510945 | G | T | NON_SYNONYMOUS_CODING | MODERATE |
| 294 | Chr03 | 3510947 | A | G | NON_SYNONYMOUS_CODING | MODERATE |
| 295 | Chr03 | 3510950 | A | G | NON_SYNONYMOUS_CODING | MODERATE |
| 296 | Chr03 | 3510967 | G | A | NON_SYNONYMOUS_CODING | MODERATE |
| 297 | Chr03 | 3510968 | G | A | NON_SYNONYMOUS_CODING | MODERATE |
| 298 | Chr03 | 3510979 | T | A | NON_SYNONYMOUS_CODING | MODERATE |
| 299 | Chr03 | 3510980 | C | A | NON_SYNONYMOUS_CODING | MODERATE |
| 300 | Chr03 | 3510986 | C | T | NON_SYNONYMOUS_CODING | MODERATE |
| 301 | Chr03 | 3510988 | G | A | NON_SYNONYMOUS_CODING | MODERATE |
| 302 | Chr03 | 3510992 | G | A | NON_SYNONYMOUS_CODING | MODERATE |
| 303 | Chr03 | 3510995 | C | T | NON_SYNONYMOUS_CODING | MODERATE |
| 304 | Chr03 | 3510997 | G | T | NON_SYNONYMOUS_CODING | MODERATE |
| 305 | Chr03 | 3511049 | T | A | NON_SYNONYMOUS_CODING | MODERATE |
| 306 | Chr03 | 3511055 | G | C | NON_SYNONYMOUS_CODING | MODERATE |
| 307 | Chr03 | 3511059 | T | C | NON_SYNONYMOUS_CODING | MODERATE |
| 308 | Chr03 | 3511066 | A | G | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 309 | Chr03 | 3511081 | A | G | NON_SYNONYMOUS_CODING | MODERATE |
| 310 | Chr03 | 3511082 | G | A | NON_SYNONYMOUS_CODING | MODERATE |
| 311 | Chr03 | 3511106 | C | T | NON_SYNONYMOUS_CODING | MODERATE |
| 312 | Chr03 | 3511114 | A | T | NON_SYNONYMOUS_CODING | MODERATE |
| 313 | Chr03 | 3511124 | T | C | NON_SYNONYMOUS_CODING | MODERATE |
| 314 | Chr03 | 3511127 | G | A | NON_SYNONYMOUS_CODING | MODERATE |
| 315 | Chr03 | 3511135 | A | G | NON_SYNONYMOUS_CODING | MODERATE |
| 316 | Chr03 | 3511151 | T | A | NON_SYNONYMOUS_CODING | MODERATE |
| 317 | Chr03 | 3511161 | T | A | NON_SYNONYMOUS_CODING | MODERATE |
| 318 | Chr03 | 3511163 | C | T | NON_SYNONYMOUS_CODING | MODERATE |
| 319 | Chr03 | 3511170 | A | C | NON_SYNONYMOUS_CODING | MODERATE |
| 320 | Chr03 | 3511173 | T | G | NON_SYNONYMOUS_CODING | MODERATE |
| 321 | Chr03 | 3511193 | T | A | NON_SYNONYMOUS_CODING | MODERATE |
| 322 | Chr03 | 3511210 | G | A | NON_SYNONYMOUS_CODING | MODERATE |
| 323 | Chr03 | 3511214 | G | A | NON_SYNONYMOUS_CODING | MODERATE |
| 324 | Chr03 | 3511216 | G | A | NON_SYNONYMOUS_CODING | MODERATE |
| 325 | Chr03 | 3511222 | C | T | NON_SYNONYMOUS_CODING | MODERATE |
| 326 | Chr03 | 3511227 | A | C | NON_SYNONYMOUS_CODING | MODERATE |
| 327 | Chr03 | 3511235 | T | C | NON_SYNONYMOUS_CODING | MODERATE |
| 328 | Chr03 | 3511237 | G | A | NON_SYNONYMOUS_CODING | MODERATE |
| 329 | Chr03 | 3511241 | G | C | NON_SYNONYMOUS_CODING | MODERATE |
| 330 | Chr03 | 3511244 | G | C | NON_SYNONYMOUS_CODING | MODERATE |
| 331 | Chr03 | 3511256 | G | T | NON_SYNONYMOUS_CODING | MODERATE |
| 332 | Chr03 | 3511257 | A | C | NON_SYNONYMOUS_CODING | MODERATE |
| 333 | Chr03 | 3511372 | G | T | NON_SYNONYMOUS_CODING | MODERATE |
| 334 | Chr03 | 3511375 | C | T | NON_SYNONYMOUS_CODING | MODERATE |
| 335 | Chr03 | 3511378 | G | A | NON_SYNONYMOUS_CODING | MODERATE |
| 336 | Chr03 | 3511386 | C | T | NON_SYNONYMOUS_CODING | MODERATE |
| 337 | Chr03 | 3511390 | G | A | NON_SYNONYMOUS_CODING | MODERATE |
| 338 | Chr03 | 3511393 | G | A | NON_SYNONYMOUS_CODING | MODERATE |
| 339 | Chr03 | 3511400 | T | A | NON_SYNONYMOUS_CODING | MODERATE |
| 340 | Chr03 | 3511402 | C | T | NON_SYNONYMOUS_CODING | MODERATE |
| 341 | Chr03 | 3511404 | C | A | NON_SYNONYMOUS_CODING | MODERATE |
| 342 | Chr03 | 3511405 | C | G | NON_SYNONYMOUS_CODING | MODERATE |
| 343 | Chr03 | 3511410 | G | A | NON_SYNONYMOUS_CODING | MODERATE |
| 344 | Chr03 | 3511416 | A | G | NON_SYNONYMOUS_CODING | MODERATE |
| 345 | Chr03 | 3511423 | G | T | NON_SYNONYMOUS_CODING | MODERATE |
| 346 | Chr03 | 3511430 | C | G | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 347 | Chr03 | 3511438 | C | T | NON_SYNONYMOUS_CODING | MODERATE |
| 348 | Chr03 | 3511445 | C | A | NON_SYNONYMOUS_CODING | MODERATE |
| 349 | Chr03 | 3511471 | T | A | NON_SYNONYMOUS_CODING | MODERATE |
| 350 | Chr03 | 3511473 | T | C | NON_SYNONYMOUS_CODING | MODERATE |
| 351 | Chr03 | 3511474 | T | G | NON_SYNONYMOUS_CODING | MODERATE |
| 352 | Chr03 | 3511503 | G | A | NON_SYNONYMOUS_CODING | MODERATE |
| 353 | Chr03 | 3511506 | T | C | NON_SYNONYMOUS_CODING | MODERATE |
| 354 | Chr03 | 3511511 | C | G | NON_SYNONYMOUS_CODING | MODERATE |
| 355 | Chr03 | 3511518 | C | G | NON_SYNONYMOUS_CODING | MODERATE |
| 356 | Chr03 | 3511633 | C | T | NON_SYNONYMOUS_CODING | MODERATE |
| 357 | Chr03 | 3511675 | A | C | NON_SYNONYMOUS_CODING | MODERATE |
| 358 | Chr03 | 3511682 | A | G | NON_SYNONYMOUS_CODING | MODERATE |
| 359 | Chr03 | 3511702 | A | C | NON_SYNONYMOUS_CODING | MODERATE |
| 360 | Chr03 | 3511711 | G | A | NON_SYNONYMOUS_CODING | MODERATE |
| 361 | Chr03 | 3511901 | C | T | NON_SYNONYMOUS_CODING | MODERATE |
| 362 | Chr03 | 3511917 | C | T | NON_SYNONYMOUS_CODING | MODERATE |
| 363 | Chr03 | 3511918 | A | G | NON_SYNONYMOUS_CODING | MODERATE |
| 364 | Chr03 | 3511919 | T | C | NON_SYNONYMOUS_CODING | MODERATE |
| 365 | Chr03 | 3511925 | C | T | NON_SYNONYMOUS_CODING | MODERATE |
| 366 | Chr03 | 3511955 | G | A | NON_SYNONYMOUS_CODING | MODERATE |
| 367 | Chr03 | 3511963 | G | A | NON_SYNONYMOUS_CODING | MODERATE |
| 368 | Chr03 | 3511964 | G | A | NON_SYNONYMOUS_CODING | MODERATE |
| 369 | Chr03 | 3511971 | T | G | NON_SYNONYMOUS_CODING | MODERATE |
| 370 | Chr03 | 3511982 | C | T | NON_SYNONYMOUS_CODING | MODERATE |
| 371 | Chr03 | 3511997 | A | G | NON_SYNONYMOUS_CODING | MODERATE |
| 372 | Chr03 | 3511999 | C | G | NON_SYNONYMOUS_CODING | MODERATE |
| 373 | Chr03 | 3512000 | T | G | NON_SYNONYMOUS_CODING | MODERATE |
| 374 | Chr03 | 3512015 | C | T | NON_SYNONYMOUS_CODING | MODERATE |
| 375 | Chr03 | 3512021 | T | C | NON_SYNONYMOUS_CODING | MODERATE |
| 376 | Chr03 | 3512024 | C | T | NON_SYNONYMOUS_CODING | MODERATE |
| 377 | Chr03 | 3512025 | C | A | NON_SYNONYMOUS_CODING | MODERATE |
| 378 | Chr03 | 3512028 | A | T | NON_SYNONYMOUS_CODING | MODERATE |
| 379 | Chr03 | 3512029 | T | C | NON_SYNONYMOUS_CODING | MODERATE |
| 380 | Chr03 | 3512035 | G | A | NON_SYNONYMOUS_CODING | MODERATE |
| 381 | Chr03 | 3512036 | A | C | NON_SYNONYMOUS_CODING | MODERATE |
| 382 | Chr03 | 3512039 | T | A | NON_SYNONYMOUS_CODING | MODERATE |
| 383 | Chr03 | 3512043 | C | A | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 384 | Chr03 | 3512050 | C | G | NON_SYNONYMOUS_CODING | MODERATE |
| 385 | Chr03 | 3513333 | G | A | NON_SYNONYMOUS_CODING | MODERATE |
| 386 | Chr03 | 3513341 | C | A | NON_SYNONYMOUS_CODING | MODERATE |
| 387 | Chr03 | 3513346 | C | T, G | NON_SYNONYMOUS_CODING | MODERATE |
| 388 | Chr03 | 3513351 | T | A | NON_SYNONYMOUS_CODING | MODERATE |
| 389 | Chr03 | 3513384 | C | G | NON_SYNONYMOUS_CODING | MODERATE |
| 390 | Chr03 | 3513414 | C | T | NON_SYNONYMOUS_CODING | MODERATE |
| 391 | Chr03 | 3513416 | A | T | NON_SYNONYMOUS_CODING | MODERATE |
| 392 | Chr03 | 3513420 | T | A | NON_SYNONYMOUS_CODING | MODERATE |
| 393 | Chr03 | 3513423 | C | G | NON_SYNONYMOUS_CODING | MODERATE |
| 394 | Chr03 | 3513424 | A | C | NON_SYNONYMOUS_CODING | MODERATE |
| 395 | Chr03 | 3513426 | C | G | NON_SYNONYMOUS_CODING | MODERATE |
| 396 | Chr03 | 3513427 | T | C | NON_SYNONYMOUS_CODING | MODERATE |
| 397 | Chr03 | 3513432 | A | T | NON_SYNONYMOUS_CODING | MODERATE |
| 398 | Chr03 | 3513433 | G | C | NON_SYNONYMOUS_CODING | MODERATE |
| 399 | Chr03 | 3513446 | C | A | NON_SYNONYMOUS_CODING | MODERATE |
| 400 | Chr03 | 3513451 | T | G | NON_SYNONYMOUS_CODING | MODERATE |
| 401 | Chr03 | 3513463 | A | T | NON_SYNONYMOUS_CODING | MODERATE |
| 402 | Chr03 | 3513468 | A | T | NON_SYNONYMOUS_CODING | MODERATE |
| 403 | Chr03 | 3513475 | G | A | NON_SYNONYMOUS_CODING | MODERATE |
| 404 | Chr03 | 3513594 | G | A | NON_SYNONYMOUS_CODING | MODERATE |
| 405 | Chr03 | 3513600 | G | C | NON_SYNONYMOUS_CODING | MODERATE |
| 406 | Chr03 | 3513603 | G | A | NON_SYNONYMOUS_CODING | MODERATE |
| 407 | Chr03 | 3513609 | C | T | NON_SYNONYMOUS_CODING | MODERATE |
| 408 | Chr03 | 3513614 | C | G | NON_SYNONYMOUS_CODING | MODERATE |
| 409 | Chr03 | 3513615 | T | C | NON_SYNONYMOUS_CODING | MODERATE |
| 410 | Chr03 | 3513619 | A | T | NON_SYNONYMOUS_CODING | MODERATE |
| 411 | Chr03 | 3513630 | G | A | NON_SYNONYMOUS_CODING | MODERATE |
| 412 | Chr03 | 3513634 | T | C | NON_SYNONYMOUS_CODING | MODERATE |
| 413 | Chr03 | 3513639 | G | A | NON_SYNONYMOUS_CODING | MODERATE |
| 414 | Chr03 | 3513654 | T | C | NON_SYNONYMOUS_CODING | MODERATE |
| 415 | Chr03 | 3513666 | A | G | NON_SYNONYMOUS_CODING | MODERATE |
| 416 | Chr03 | 3513672 | C | T | NON_SYNONYMOUS_CODING | MODERATE |
| 417 | Chr03 | 3513675 | T | C | NON_SYNONYMOUS_CODING | MODERATE |
| 418 | Chr03 | 3513685 | T | C | NON_SYNONYMOUS_CODING | MODERATE |
| 419 | Chr03 | 3513696 | T | G | NON_SYNONYMOUS_CODING | MODERATE |
| 420 | Chr03 | 3513697 | A | C | NON_SYNONYMOUS_CODING | MODERATE |
| 421 | Chr03 | 3513698 | A | C | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 422 | Chr03 | 3513700 | T | G | NON_SYNONYMOUS_CODING | MODERATE |
| 423 | Chr03 | 3513705 | T | C | NON_SYNONYMOUS_CODING | MODERATE |
| 424 | Chr03 | 3513706 | C | A | NON_SYNONYMOUS_CODING | MODERATE |
| 425 | Chr03 | 3513710 | T | A | NON_SYNONYMOUS_CODING | MODERATE |
| 426 | Chr03 | 3513711 | T | A | NON_SYNONYMOUS_CODING | MODERATE |
| 427 | Chr03 | 3513712 | T | C | NON_SYNONYMOUS_CODING | MODERATE |
| 428 | Chr03 | 3513713 | C | G | NON_SYNONYMOUS_CODING | MODERATE |
| 429 | Chr03 | 3513736 | C | G | NON_SYNONYMOUS_CODING | MODERATE |
| 430 | Chr03 | 3513842 | A | T | NON_SYNONYMOUS_CODING | MODERATE |
| 431 | Chr03 | 3513850 | A | G | NON_SYNONYMOUS_CODING | MODERATE |
| 432 | Chr03 | 3513852 | C | G | NON_SYNONYMOUS_CODING | MODERATE |
| 433 | Chr03 | 3513870 | T | A | NON_SYNONYMOUS_CODING | MODERATE |
| 434 | Chr03 | 3513872 | C | T | NON_SYNONYMOUS_CODING | MODERATE |
| 435 | Chr03 | 3513883 | A | C | NON_SYNONYMOUS_CODING | MODERATE |
| 436 | Chr03 | 3513896 | G | A | NON_SYNONYMOUS_CODING | MODERATE |
| 437 | Chr03 | 3513898 | T | A | NON_SYNONYMOUS_CODING | MODERATE |
| 438 | Chr03 | 3513904 | A | G | NON_SYNONYMOUS_CODING | MODERATE |
| 439 | Chr03 | 3513912 | G | T | NON_SYNONYMOUS_CODING | MODERATE |
| 440 | Chr03 | 3513922 | C | A | NON_SYNONYMOUS_CODING | MODERATE |
| 441 | Chr03 | 3513940 | T | C | NON_SYNONYMOUS_CODING | MODERATE |
| 442 | Chr03 | 3513947 | A | C | NON_SYNONYMOUS_CODING | MODERATE |
| 443 | Chr03 | 3513964 | T | C | NON_SYNONYMOUS_CODING | MODERATE |
| 444 | Chr03 | 3513965 | G | C | NON_SYNONYMOUS_CODING | MODERATE |
| 445 | Chr03 | 3513968 | T | C | NON_SYNONYMOUS_CODING | MODERATE |
| 446 | Chr03 | 3513973 | C | T | NON_SYNONYMOUS_CODING | MODERATE |
| 447 | Chr03 | 3513988 | T | C | NON_SYNONYMOUS_CODING | MODERATE |
| 448 | Chr03 | 3513993 | C | G | NON_SYNONYMOUS_CODING | MODERATE |
| 449 | Chr03 | 3514000 | C | T | NON_SYNONYMOUS_CODING | MODERATE |
| 450 | Chr03 | 3514001 | T | C | NON_SYNONYMOUS_CODING | MODERATE |
| 451 | Chr03 | 3514003 | T | G | NON_SYNONYMOUS_CODING | MODERATE |
| 452 | Chr03 | 3514004 | G | C | NON_SYNONYMOUS_CODING | MODERATE |
| 453 | Chr03 | 3514008 | C | A | NON_SYNONYMOUS_CODING | MODERATE |
| 454 | Chr03 | 3514042 | A | C | NON_SYNONYMOUS_CODING | MODERATE |
| 455 | Chr03 | 3514045 | G | T | NON_SYNONYMOUS_CODING | MODERATE |
| 456 | Chr03 | 3514049 | C | G | NON_SYNONYMOUS_CODING | MODERATE |
| 457 | Chr03 | 3514052 | C | G | NON_SYNONYMOUS_CODING | MODERATE |
| 458 | Chr03 | 3514055 | C | G | NON_SYNONYMOUS_CODING | MODERATE |

TABLE 2-continued

RLP2 Mutations

| | Chrom. | Gen. Pos. | Reference | Variant | Mutation type | Predicted impact |
|---|---|---|---|---|---|---|
| 459 | Chr03 | 3514060 | T | A | NON_SYNONYMOUS_CODING | MODERATE |
| 460 | Chr03 | 3514061 | C | T | NON_SYNONYMOUS_CODING | MODERATE |
| 461 | Chr03 | 3514066 | G | A | NON_SYNONYMOUS_CODING | MODERATE |
| 462 | Chr03 | 3514071 | T | G | NON_SYNONYMOUS_CODING | MODERATE |
| 463 | Chr03 | 3514073 | G | T | NON_SYNONYMOUS_CODING | MODERATE |
| 464 | Chr03 | 3514088 | C | G | NON_SYNONYMOUS_CODING | MODERATE |
| 465 | Chr03 | 3514091 | T | C | NON_SYNONYMOUS_CODING | MODERATE |
| 466 | Chr03 | 3514101 | C | G | NON_SYNONYMOUS_CODING | MODERATE |
| 467 | Chr03 | 3514121 | G | T | NON_SYNONYMOUS_CODING | MODERATE |
| 468 | Chr03 | 3514126 | T | G | NON_SYNONYMOUS_CODING | MODERATE |
| 469 | Chr03 | 3514127 | A | G | NON_SYNONYMOUS_CODING | MODERATE |
| 470 | Chr03 | 3514146 | C | G | NON_SYNONYMOUS_CODING | MODERATE |
| 471 | Chr03 | 3514168 | C | G | NON_SYNONYMOUS_CODING | MODERATE |
| 472 | Chr03 | 3514169 | T | C | NON_SYNONYMOUS_CODING | MODERATE |
| 473 | Chr03 | 3508554 | C | T | UTR_3_PRIME | MODIFIER |
| 474 | Chr03 | 3508559 | G | A | UTR_3_PRIME | MODIFIER |
| 475 | Chr03 | 3508560 | A | C | UTR_3_PRIME | MODIFIER |
| 476 | Chr03 | 3508562 | G | A | UTR_3_PRIME | MODIFIER |
| 477 | Chr03 | 3508563 | T | G | UTR_3_PRIME | MODIFIER |
| 478 | Chr03 | 3508566 | TAAAAA | TAAAAAA | UTR_3_PRIME | MODIFIER |
| 479 | Chr03 | 3508574 | GGAGTT | G | UTR_3_PRIME | MODIFIER |
| 480 | Chr03 | 3508583 | GAATGGC | GATGGC | UTR_3_PRIME | MODIFIER |
| 481 | Chr03 | 3508594 | A | T | UTR_3_PRIME | MODIFIER |
| 482 | Chr03 | 3508601 | G | A | UTR_3_PRIME | MODIFIER |
| 483 | Chr03 | 3508606 | T | C | UTR_3_PRIME | MODIFIER |
| 484 | Chr03 | 3508610 | GTTAA | GTTAATTAA | UTR_3_PRIME | MODIFIER |
| 485 | Chr03 | 3508615 | A | G | UTR_3_PRIME | MODIFIER |
| 486 | Chr03 | 3508623 | C | T | UTR_3_PRIME | MODIFIER |
| 487 | Chr03 | 3508625 | G | A | UTR_3_PRIME | MODIFIER |
| 488 | Chr03 | 3508628 | G | A | UTR_3_PRIME | MODIFIER |
| 489 | Chr03 | 3508630 | GAA | G | UTR_3_PRIME | MODIFIER |
| 490 | Chr03 | 3508634 | G | A | UTR_3_PRIME | MODIFIER |
| 491 | Chr03 | 3508635 | C | T | UTR_3_PRIME | MODIFIER |
| 492 | Chr03 | 3508640 | A | T | UTR_3_PRIME | MODIFIER |
| 493 | Chr03 | 3508648 | GGTGAAGAAGCAGAG (SEQ ID NO: 44) | TATGA | UTR_3_PRIME | MODIFIER |
| 494 | Chr03 | 3508680 | G | A | UTR_3_PRIME | MODIFIER |
| 495 | Chr03 | 3508682 | A | G | UTR_3_PRIME | MODIFIER |

TABLE 2-continued

RLP2 Mutations

| | Chrom. | Gen. Pos. | Reference | Variant | Mutation type | Predicted impact |
|---|---|---|---|---|---|---|
| 496 | Chr03 | 3508683 | G | A | UTR_3_PRIME | MODIFIER |
| 497 | Chr03 | 3508684 | A | G | UTR_3_PRIME | MODIFIER |
| 498 | Chr03 | 3508685 | G | T | UTR_3_PRIME | MODIFIER |
| 499 | Chr03 | 3508689 | AAACGGCCAGGAAGG (SEQ ID NO: 45) | AG | UTR_3_PRIME | MODIFIER |
| 500 | Chr03 | 3508711 | G | A | UTR_3_PRIME | MODIFIER |
| 501 | Chr03 | 3508713 | A | G | UTR_3_PRIME | MODIFIER |
| 502 | Chr03 | 3508714 | G | T | UTR_3_PRIME | MODIFIER |
| 503 | Chr03 | 3508716 | A | T | UTR_3_PRIME | MODIFIER |
| 504 | Chr03 | 3508720 | G | A | UTR_3_PRIME | MODIFIER |
| 505 | Chr03 | 3508724 | C | T | UTR_3_PRIME | MODIFIER |
| 506 | Chr03 | 3508727 | C | T | UTR_3_PRIME | MODIFIER |
| 507 | Chr03 | 3508728 | T | C | UTR_3_PRIME | MODIFIER |
| 508 | Chr03 | 3508730 | GC | G | UTR_3_PRIME | MODIFIER |
| 509 | Chr03 | 3508733 | C | T | UTR_3_PRIME | MODIFIER |
| 510 | Chr03 | 3508734 | C | T | UTR_3_PRIME | MODIFIER |
| 511 | Chr03 | 3508735 | G | A | UTR_3_PRIME | MODIFIER |
| 512 | Chr03 | 3508740 | C | T | UTR_3_PRIME | MODIFIER |
| 513 | Chr03 | 3508744 | G | A | UTR_3_PRIME | MODIFIER |
| 514 | Chr03 | 3508745 | C | G | UTR_3_PRIME | MODIFIER |
| 515 | Chr03 | 3508749 | G | C | UTR_3_PRIME | MODIFIER |
| 516 | Chr03 | 3508751 | TT | ATGAGGCAATTTATTTTCA (SEQ ID NO: 46) | UTR_3_PRIME | MODIFIER |
| 517 | Chr03 | 3508758 | A | C | UTR_3_PRIME | MODIFIER |
| 518 | Chr03 | 3508764 | GGTCGCCCTTGAAACGA (SEQ ID NO: 47) | | UTR_3_PRIME | MODIFIER |
| 519 | Chr03 | 3508792 | G | A | UTR_3_PRIME | MODIFIER |
| 520 | Chr03 | 3508795 | C | T | UTR_3_PRIME | MODIFIER |
| 521 | Chr03 | 3508797 | T | A | UTR_3_PRIME | MODIFIER |
| 522 | Chr03 | 3508801 | G | A | UTR_3_PRIME | MODIFIER |
| 523 | Chr03 | 3508809 | T | A | UTR_3_PRIME | MODIFIER |
| 524 | Chr03 | 3508812 | A | T | UTR_3_PRIME | MODIFIER |
| 525 | Chr03 | 3508814 | T | C | UTR_3_PRIME | MODIFIER |
| 526 | Chr03 | 3508822 | G | T | UTR_3_PRIME | MODIFIER |
| 527 | Chr03 | 3508826 | C | A | UTR_3_PRIME | MODIFIER |
| 528 | Chr03 | 3508835 | T | C | UTR_3_PRIME | MODIFIER |
| 529 | Chr03 | 3508837 | C | T | UTR_3_PRIME | MODIFIER |

TABLE 2-continued

RLP2 Mutations

| | Chrom. | Gen. Pos. | Reference | Variant | Mutation type | Predicted impact |
|---|---|---|---|---|---|---|
| 530 | Chr03 | 3508838 | G | A | UTR_3_PRIME | MODIFIER |
| 531 | Chr03 | 3508839 | G | A | UTR_3_PRIME | MODIFIER |
| 532 | Chr03 | 3508856 | G | A | UTR_3_PRIME | MODIFIER |
| 533 | Chr03 | 3508860 | G | T | UTR_3_PRIME | MODIFIER |
| 534 | Chr03 | 3508862 | G | A | UTR_3_PRIME | MODIFIER |
| 535 | Chr03 | 3508867 | C | T | UTR_3_PRIME | MODIFIER |
| 536 | Chr03 | 3508869 | C | T | UTR_3_PRIME | MODIFIER |
| 537 | Chr03 | 3508871 | C | T | UTR_3_PRIME | MODIFIER |
| 538 | Chr03 | 3508872 | C | T | UTR_3_PRIME | MODIFIER |
| 539 | Chr03 | 3508874 | G | A | UTR_3_PRIME | MODIFIER |
| 540 | Chr03 | 3508875 | A | T | UTR_3_PRIME | MODIFIER |
| 541 | Chr03 | 3508877 | T | A | UTR_3_PRIME | MODIFIER |
| 542 | Chr03 | 3508882 | G | A | UTR_3_PRIME | MODIFIER |
| 543 | Chr03 | 3508884 | C | A | UTR_3_PRIME | MODIFIER |
| 544 | Chr03 | 3508885 | C | A | UTR_3_PRIME | MODIFIER |
| 545 | Chr03 | 3508886 | A | G | UTR_3_PRIME | MODIFIER |
| 546 | Chr03 | 3508887 | A | G | UTR_3_PRIME | MODIFIER |
| 547 | Chr03 | 3508890 | CAAA | CAA | UTR_3_PRIME | MODIFIER |
| 548 | Chr03 | 3508894 | T | C | UTR_3_PRIME | MODIFIER |
| 549 | Chr03 | 3508895 | C | A | UTR_3_PRIME | MODIFIER |
| 550 | Chr03 | 3508896 | A | T | UTR_3_PRIME | MODIFIER |
| 551 | Chr03 | 3508897 | GUT | GTT | UTR_3_PRIME | MODIFIER |
| 552 | Chr03 | 3508907 | T | A | UTR_3_PRIME | MODIFIER |
| 553 | Chr03 | 3508910 | T | G | UTR_3_PRIME | MODIFIER |
| 554 | Chr03 | 3508912 | A | G | UTR_3_PRIME | MODIFIER |
| 555 | Chr03 | 3508915 | C | T | UTR_3_PRIME | MODIFIER |
| 556 | Chr03 | 3508917 | G | A | UTR_3_PRIME | MODIFIER |
| 557 | Chr03 | 3508928 | TCC | TC | UTR_3_PRIME | MODIFIER |
| 558 | Chr03 | 3508933 | CTT | CTTT | UTR_3_PRIME | MODIFIER |
| 559 | Chr03 | 3508937 | T | C | UTR_3_PRIME | MODIFIER |
| 560 | Chr03 | 3508940 | A | G | UTR_3_PRIME | MODIFIER |
| 561 | Chr03 | 3508945 | A | G | UTR_3_PRIME | MODIFIER |
| 562 | Chr03 | 3508946 | C | A | UTR_3_PRIME | MODIFIER |
| 563 | Chr03 | 3508948 | C | T | UTR_3_PRIME | MODIFIER |
| 564 | Chr03 | 3508954 | A | G | UTR_3_PRIME | MODIFIER |
| 565 | Chr03 | 3508955 | C | T | UTR_3_PRIME | MODIFIER |
| 566 | Chr03 | 3508957 | A | T | UTR_3_PRIME | MODIFIER |
| 567 | Chr03 | 3508960 | C | T | UTR_3_PRIME | MODIFIER |

TABLE 2-continued

RLP2 Mutations

| | Chrom. | Gen. Pos. | Reference | Variant | Mutation type | Predicted impact |
|---|---|---|---|---|---|---|
| 568 | Chr03 | 3508971 | G | A | UTR_3_PRIME | MODIFIER |
| 569 | Chr03 | 3508972 | C | T | UTR_3_PRIME | MODIFIER |
| 570 | Chr03 | 3508973 | T | C | UTR_3_PRIME | MODIFIER |
| 571 | Chr03 | 3508974 | G | A | UTR_3_PRIME | MODIFIER |
| 572 | Chr03 | 3508976 | G | A | UTR_3_PRIME | MODIFIER |
| 573 | Chr03 | 3508979 | TAGAGA | TAGA | UTR_3_PRIME | MODIFIER |
| 574 | Chr03 | 3508985 | T | C | UTR_3_PRIME | MODIFIER |
| 575 | Chr03 | 3508992 | C | T | UTR_3_PRIME | MODIFIER |
| 576 | Chr03 | 3508995 | C | T | UTR_3_PRIME | MODIFIER |
| 577 | Chr03 | 3509001 | G | A | UTR_3_PRIME | MODIFIER |
| 578 | Chr03 | 3509003 | C | A | UTR_3_PRIME | MODIFIER |
| 579 | Chr03 | 3509008 | A | G | UTR_3_PRIME | MODIFIER |
| 580 | Chr03 | 3509010 | T | A | UTR_3_PRIME | MODIFIER |
| 581 | Chr03 | 3509018 | C | T | UTR_3_PRIME | MODIFIER |
| 582 | Chr03 | 3509020 | A | T | UTR_3_PRIME | MODIFIER |
| 583 | Chr03 | 3509025 | C | G | UTR_3_PRIME | MODIFIER |
| 584 | Chr03 | 3509037 | A | G | UTR_3_PRIME | MODIFIER |
| 585 | Chr03 | 3509038 | C | T | UTR_3_PRIME | MODIFIER |
| 586 | Chr03 | 3509039 | G | A | UTR_3_PRIME | MODIFIER |
| 587 | Chr03 | 3509040 | A | G | UTR_3_PRIME | MODIFIER |
| 588 | Chr03 | 3509042 | C | T | UTR_3_PRIME | MODIFIER |
| 589 | Chr03 | 3509047 | C | T | UTR_3_PRIME | MODIFIER |
| 590 | Chr03 | 3509050 | C | T | UTR_3_PRIME | MODIFIER |
| 591 | Chr03 | 3509052 | AT | AGT | UTR_3_PRIME | MODIFIER |
| 592 | Chr03 | 3514189 | ATCT | TTAGATAATTCTATGAACT (SEQ ID NO: 48) | UTR_5_PRIME | MODIFIER |

TABLE 3

L-Type lecRLK Mutations

| | Chrom. | Genomic Position | Reference | Variant | Mutation type | Predicted impact |
|---|---|---|---|---|---|---|
| 1 | Chr09 | 4552716 | A | T | STOPGAINED | HIGH |
| 2 | Chr09 | 4553229 | G | T | STOPGAINED | HIGH |
| 3 | Chr09 | 4551319 | T | G | NON_SYNONYMOUS_CODING | MODERATE |
| 4 | Chr09 | 4551325 | T | A | NON_SYNONYMOUS_CODING | MODERATE |
| 5 | Chr09 | 4551330 | C | A | NON_SYNONYMOUS_CODING | MODERATE |
| 6 | Chr09 | 4551349 | T | C | NON_SYNONYMOUS_CODING | MODERATE |
| 7 | Chr09 | 4551353 | G | C | NON_SYNONYMOUS_CODING | MODERATE |

TABLE 3-continued

L-Type lecRLK Mutations

| | Chrom. | Genomic Position | Reference | Variant | Mutation type | Predicted impact |
|---|---|---|---|---|---|---|
| 8 | Chr09 | 4551366 | G | A | NON_SYNONYMOUS_CODING | MODERATE |
| 9 | Chr09 | 4551375 | G | C | NON_SYNONYMOUS_CODING | MODERATE |
| 10 | Chr09 | 4551383 | C | G | NON_SYNONYMOUS_CODING | MODERATE |
| 11 | Chr09 | 4551430 | T | A | NON_SYNONYMOUS_CODING | MODERATE |
| 12 | Chr09 | 4551478 | C | A | NON_SYNONYMOUS_CODING | MODERATE |
| 13 | Chr09 | 4551499 | T | G | NON_SYNONYMOUS_CODING | MODERATE |
| 14 | Chr09 | 4551583 | T | C | NON_SYNONYMOUS_CODING | MODERATE |
| 15 | Chr09 | 4551645 | A | G | NON_SYNONYMOUS_CODING | MODERATE |
| 16 | Chr09 | 4551664 | C | T | NON_SYNONYMOUS_CODING | MODERATE |
| 17 | Chr09 | 4551670 | A | C | NON_SYNONYMOUS_CODING | MODERATE |
| 18 | Chr09 | 4551702 | G | A | NON_SYNONYMOUS_CODING | MODERATE |
| 19 | Chr09 | 4551744 | A | G | NON_SYNONYMOUS_CODING | MODERATE |
| 20 | Chr09 | 4551748 | G | A | NON_SYNONYMOUS_CODING | MODERATE |
| 21 | Chr09 | 4551844 | G | A | NON_SYNONYMOUS_CODING | MODERATE |
| 22 | Chr09 | 4551870 | G | A | NON_SYNONYMOUS_CODING | MODERATE |
| 23 | Chr09 | 4551886 | T | A | NON_SYNONYMOUS_CODING | MODERATE |
| 24 | Chr09 | 4551919 | T | G | NON_SYNONYMOUS_CODING | MODERATE |
| 25 | Chr09 | 4552020 | T | C | NON_SYNONYMOUS_CODING | MODERATE |
| 26 | Chr09 | 4552063 | G | C | NON_SYNONYMOUS_CODING | MODERATE |
| 27 | Chr09 | 4552173 | C | T | NON_SYNONYMOUS_CODING | MODERATE |
| 28 | Chr09 | 4552237 | C | T | NON_SYNONYMOUS_CODING | MODERATE |
| 29 | Chr09 | 4552260 | T | A | NON_SYNONYMOUS_CODING | MODERATE |
| 30 | Chr09 | 4552312 | C | G | NON_SYNONYMOUS_CODING | MODERATE |
| 31 | Chr09 | 4552342 | G | A | NON_SYNONYMOUS_CODING | MODERATE |
| 32 | Chr09 | 4552362 | G | C | NON_SYNONYMOUS_CODING | MODERATE |
| 33 | Chr09 | 4552415 | A | T | NON_SYNONYMOUS_CODING | MODERATE |
| 34 | Chr09 | 4552431 | A | C | NON_SYNONYMOUS_CODING | MODERATE |
| 35 | Chr09 | 4552453 | T | A | NON_SYNONYMOUS_CODING | MODERATE |
| 36 | Chr09 | 4552486 | T | C | NON_SYNONYMOUS_CODING | MODERATE |
| 37 | Chr09 | 4552609 | G | A | NON_SYNONYMOUS_CODING | MODERATE |
| 38 | Chr09 | 4552666 | C | T | NON_SYNONYMOUS_CODING | MODERATE |
| 39 | Chr09 | 4552677 | A | C | NON_SYNONYMOUS_CODING | MODERATE |
| 40 | Chr09 | 4552694 | G | C | NON_SYNONYMOUS_CODING | MODERATE |
| 41 | Chr09 | 4552793 | C | A | NON_SYNONYMOUS_CODING | MODERATE |
| 42 | Chr09 | 4552878 | G | A | NON_SYNONYMOUS_CODING | MODERATE |
| 43 | Chr09 | 4552945 | C | T | NON_SYNONYMOUS_CODING | MODERATE |
| 44 | Chr09 | 4552947 | G | T | NON_SYNONYMOUS_CODING | MODERATE |
| 45 | Chr09 | 4552952 | G | T | NON_SYNONYMOUS_CODING | MODERATE |

TABLE 3-continued

L-Type lecRLK Mutations

| | Chrom. | Genomic Position | Reference | Variant | Mutation type | Predicted impact |
|---|---|---|---|---|---|---|
| 46 | Chr09 | 4553016 | G | A | NON_SYNONYMOUS_CODING | MODERATE |
| 47 | Chr09 | 4553029 | C | G | NON_SYNONYMOUS_CODING | MODERATE |
| 48 | Chr09 | 4553059 | T | A | NON_SYNONYMOUS_CODING | MODERATE |
| 49 | Chr09 | 4553061 | G | A | NON_SYNONYMOUS_CODING | MODERATE |
| 50 | Chr09 | 4553071 | T | C | NON_SYNONYMOUS_CODING | MODERATE |
| 51 | Chr09 | 4553086 | G | A | NON_SYNONYMOUS_CODING | MODERATE |
| 52 | Chr09 | 4553097 | C | T | NON_SYNONYMOUS_CODING | MODERATE |
| 53 | Chr09 | 4553139 | C | A | NON_SYNONYMOUS_CODING | MODERATE |
| 54 | Chr09 | 4553145 | T | G | NON_SYNONYMOUS_CODING | MODERATE |
| 55 | Chr09 | 4553146 | C | T | NON_SYNONYMOUS_CODING | MODERATE |
| 56 | Chr09 | 4553178 | G | A | NON_SYNONYMOUS_CODING | MODERATE |
| 57 | Chr09 | 4553183 | G | A | NON_SYNONYMOUS_CODING | MODERATE |
| 58 | Chr09 | 4553200 | G | C | NON_SYNONYMOUS_CODING | MODERATE |
| 59 | Chr09 | 4553224 | A | G | NON_SYNONYMOUS_CODING | MODERATE |
| 60 | Chr09 | 4553251 | C | G | NON_SYNONYMOUS_CODING | MODERATE |
| 61 | Chr09 | 4553253 | T | C | NON_SYNONYMOUS_CODING | MODERATE |
| 62 | Chr09 | 4553257 | A | G | NON_SYNONYMOUS_CODING | MODERATE |
| 63 | Chr09 | 4553278 | C | T | NON_SYNONYMOUS_CODING | MODERATE |
| 64 | Chr09 | 4553287 | T | G | NON_SYNONYMOUS_CODING | MODERATE |
| 65 | Chr09 | 4553305 | T | G | NON_SYNONYMOUS_CODING | MODERATE |
| 66 | Chr09 | 4553335 | A | G | UTR_3_PRIME | MODIFIER |
| 67 | Chr09 | 4553350 | C | A | UTR_3_PRIME | MODIFIER |
| 68 | Chr09 | 4553355 | A | C | UTR_3_PRIME | MODIFIER |
| 69 | Chr09 | 4553356 | C | T | UTR_3_PRIME | MODIFIER |
| 70 | Chr09 | 4553359 | A | C | UTR_3_PRIME | MODIFIER |
| 71 | Chr09 | 4553360 | A | T | UTR_3_PRIME | MODIFIER |
| 72 | Chr09 | 4553389 | G | T | UTR_3_PRIME | MODIFIER |
| 73 | Chr09 | 4553402 | A | C | UTR_3_PRIME | MODIFIER |
| 74 | Chr09 | 4553417 | T | G | UTR_3_PRIME | MODIFIER |
| 75 | Chr09 | 4553443 | T | C | UTR_3_PRIME | MODIFIER |
| 76 | Chr09 | 4553447 | C | T | UTR_3_PRIME | MODIFIER |
| 77 | Chr09 | 4553448 | A | T | UTR_3_PRIME | MODIFIER |
| 78 | Chr09 | 4553458 | A | G | UTR_3_PRIME | MODIFIER |
| 79 | Chr09 | 4553466 | A | G | UTR_3_PRIME | MODIFIER |
| 80 | Chr09 | 4553468 | A | G | UTR_3_PRIME | MODIFIER |
| 81 | Chr09 | 4553469 | C | A | UTR_3_PRIME | MODIFIER |
| 82 | Chr09 | 4553472 | A | C | UTR_3_PRIME | MODIFIER |
| 83 | Chr09 | 4553488 | T | A | UTR_3_PRIME | MODIFIER |

TABLE 3-continued

L-Type lecRLK Mutations

| | Chrom. | Genomic Position | Reference | Variant | Mutation type | Predicted impact |
|---|---|---|---|---|---|---|
| 84 | Chr09 | 4553505 | A | T | UTR_3_PRIME | MODIFIER |
| 85 | Chr09 | 4553507 | C | T | UTR_3_PRIME | MODIFIER |
| 86 | Chr09 | 4553508 | A | T | UTR_3_PRIME | MODIFIER |
| 87 | Chr09 | 4553511 | C | G | UTR_3_PRIME | MODIFIER |
| 88 | Chr09 | 4553513 | A | C | UTR_3_PRIME | MODIFIER |
| 89 | Chr09 | 4553515 | C | A | UTR_3_PRIME | MODIFIER |
| 90 | Chr09 | 4553519 | G | A | UTR_3_PRIME | MODIFIER |
| 91 | Chr09 | 4553573 | GAAA | GAAAA | UTR_3_PRIME | MODIFIER |
| 92 | Chr09 | 4553597 | C | T | UTR_3_PRIME | MODIFIER |
| 93 | Chr09 | 4553600 | T | G | UTR_3_PRIME | MODIFIER |
| 94 | Chr09 | 4553638 | C | T | UTR_3_PRIME | MODIFIER |
| 95 | Chr09 | 4553654 | C | T | UTR_3_PRIME | MODIFIER |
| 96 | Chr09 | 4553696 | C | T | UTR_3_PRIME | MODIFIER |
| 97 | Chr09 | 4553701 | T | G | UTR_3_PRIME | MODIFIER |
| 98 | Chr09 | 4553717 | T | C | UTR_3_PRIME | MODIFIER |
| 99 | Chr09 | 4553766 | C | A | UTR_3_PRIME | MODIFIER |
| 100 | Chr09 | 4553770 | A | C, T | UTR_3_PRIME | MODIFIER |
| 101 | Chr09 | 4553781 | T | C | UTR_3_PRIME | MODIFIER |
| 102 | Chr09 | 4553806 | A | G | UTR_3_PRIME | MODIFIER |
| 103 | Chr09 | 4553816 | A | G | UTR_3_PRIME | MODIFIER |
| 104 | Chr09 | 4553817 | C | G | UTR_3_PRIME | MODIFIER |
| 105 | Chr09 | 4553826 | C | A | UTR_3_PRIME | MODIFIER |
| 106 | Chr09 | 4553843 | A | G | UTR_3_PRIME | MODIFIER |
| 107 | Chr09 | 4553852 | T | A | UTR_3_PRIME | MODIFIER |
| 108 | Chr09 | 4553861 | C | A | UTR_3_PRIME | MODIFIER |
| 109 | Chr09 | 4553864 | A | G | UTR_3_PRIME | MODIFIER |
| 110 | Chr09 | 4553881 | T | C | UTR_3_PRIME | MODIFIER |
| 111 | Chr09 | 4553914 | C | T | UTR_3_PRIME | MODIFIER |
| 112 | Chr09 | 4553927 | T | A | UTR_3_PRIME | MODIFIER |
| 113 | Chr09 | 4553950 | G | A | UTR_3_PRIME | MODIFIER |
| 114 | Chr09 | 4553952 | C | G | UTR_3_PRIME | MODIFIER |
| 115 | Chr09 | 4553953 | T | A | UTR_3_PRIME | MODIFIER |
| 116 | Chr09 | 4553959 | C | T | UTR_3_PRIME | MODIFIER |
| 117 | Chr09 | 4553960 | C | T | UTR_3_PRIME | MODIFIER |
| 118 | Chr09 | 4553961 | G | C | UTR_3_PRIME | MODIFIER |
| 119 | Chr09 | 4553981 | A | G | UTR_3_PRIME | MODIFIER |
| 120 | Chr09 | 4554000 | A | T | UTR_3_PRIME | MODIFIER |
| 121 | Chr09 | 4554001 | T | G | UTR_3_PRIME | MODIFIER |

TABLE 3-continued

L-Type lecRLK Mutations

| | Chrom. | Genomic Position | Reference | Variant | Mutation type | Predicted impact |
|---|---|---|---|---|---|---|
| 122 | Chr09 | 4554003 | G | C | UTR_3_PRIME | MODIFIER |
| 123 | Chr09 | 4554010 | T | G | UTR_3_PRIME | MODIFIER |
| 124 | Chr09 | 4554033 | C | T | UTR_3_PRIME | MODIFIER |
| 125 | Chr09 | 4554035 | C | G | UTR_3_PRIME | MODIFIER |
| 126 | Chr09 | 4554037 | CATATA | CATA | UTR_3_PRIME | MODIFIER |
| 127 | Chr09 | 4554046 | GTTTT | GTT | UTR_3_PRIME | MODIFIER |
| 128 | Chr09 | 4554071 | A | C | UTR_3_PRIME | MODIFIER |
| 129 | Chr09 | 4554079 | A | G | UTR_3_PRIME | MODIFIER |
| 130 | Chr09 | 4554101 | G | C | UTR_3_PRIME | MODIFIER |
| 131 | Chr09 | 4554104 | GATATA | GATATATA | UTR_3_PRIME | MODIFIER |
| 132 | Chr09 | 4554112 | C | T | UTR_3_PRIME | MODIFIER |
| 133 | Chr09 | 4554123 | T | G | UTR_3_PRIME | MODIFIER |
| 134 | Chr09 | 4554127 | C | T | UTR_3_PRIME | MODIFIER |
| 135 | Chr09 | 4554133 | A | T | UTR_3_PRIME | MODIFIER |
| 136 | Chr09 | 4554137 | T | A | UTR_3_PRIME | MODIFIER |
| 137 | Chr09 | 4554154 | GAAAAA | GAAAA | UTR_3_PRIME | MODIFIER |
| 138 | Chr09 | 4554201 | C | T | UTR_3_PRIME | MODIFIER |
| 139 | Chr09 | 4554213 | T | C | UTR_3_PRIME | MODIFIER |
| 140 | Chr09 | 4554239 | T | G | UTR_3_PRIME | MODIFIER |
| 141 | Chr09 | 4554265 | G | T | UTR_3_PRIME | MODIFIER |
| 142 | Chr09 | 4554268 | G | C | UTR_3_PRIME | MODIFIER |
| 143 | Chr09 | 4554269 | T | C | UTR_3_PRIME | MODIFIER |
| 144 | Chr09 | 4554277 | A | T | UTR_3_PRIME | MODIFIER |
| 145 | Chr09 | 4554310 | C | A | UTR_3_PRIME | MODIFIER |
| 146 | Chr09 | 4554322 | C | T | UTR_3_PRIME | MODIFIER |
| 147 | Chr09 | 4554323 | G | A | UTR_3_PRIME | MODIFIER |
| 148 | Chr09 | 4554346 | G | C | UTR_3_PRIME | MODIFIER |
| 149 | Chr09 | 4554352 | G | A | UTR_3_PRIME | MODIFIER |
| 150 | Chr09 | 4554366 | T | C | UTR_3_PRIME | MODIFIER |
| 151 | Chr09 | 4554377 | T | C | UTR_3_PRIME | MODIFIER |
| 152 | Chr09 | 4554383 | C | A | UTR_3_PRIME | MODIFIER |
| 153 | Chr09 | 4554390 | G | C | UTR_3_PRIME | MODIFIER |
| 154 | Chr09 | 4554397 | A | T | UTR_3_PRIME | MODIFIER |
| 155 | Chr09 | 4554417 | A | C | UTR_3_PRIME | MODIFIER |
| 156 | Chr09 | 4554423 | T | C | UTR_3_PRIME | MODIFIER |
| 157 | Chr09 | 4554431 | G | A | UTR_3_PRIME | MODIFIER |
| 158 | Chr09 | 4554469 | G | T | UTR_3_PRIME | MODIFIER |
| 159 | Chr09 | 4554471 | TCCC | TCC | UTR_3_PRIME | MODIFIER |

TABLE 3-continued

L-Type lecRLK Mutations

| | Chrom. | Genomic Position | Reference | Variant | Mutation type | Predicted impact |
|---|---|---|---|---|---|---|
| 160 | Chr09 | 4554489 | C | A | UTR_3_PRIME | MODIFIER |
| 161 | Chr09 | 4554498 | T | G | UTR_3_PRIME | MODIFIER |
| 162 | Chr09 | 4554514 | T | G | UTR_3_PRIME | MODIFIER |
| 163 | Chr09 | 4554525 | T | C | UTR_3_PRIME | MODIFIER |
| 164 | Chr09 | 4554538 | G | A | UTR_3_PRIME | MODIFIER |
| 165 | Chr09 | 4554542 | G | A | UTR_3_PRIME | MODIFIER |
| 166 | Chr09 | 4554555 | T | G | UTR_3_PRIME | MODIFIER |
| 167 | Chr09 | 4554561 | G | A | UTR_3_PRIME | MODIFIER |
| 168 | Chr09 | 4554568 | G | A | UTR_3_PRIME | MODIFIER |
| 169 | Chr09 | 4554571 | T | C | UTR_3_PRIME | MODIFIER |
| 170 | Chr09 | 4551139 | C | A | UTR_5_PRIME | MODIFIER |
| 171 | Chr09 | 4551174 | G | T | UTR_5_PRIME | MODIFIER |
| 172 | Chr09 | 4551180 | G | C | UTR_5_PRIME | MODIFIER |
| 173 | Chr09 | 4551225 | G | A | UTR_5_PRIME | MODIFIER |
| 174 | Chr09 | 4551234 | G | T | UTR_5_PRIME | MODIFIER |
| 175 | Chr09 | 4551262 | G | A | UTR_5_PRIME | MODIFIER |
| 176 | Chr09 | 4551268 | G | C | UTR_5_PRIME | MODIFIER |
| 177 | Chr09 | 4551274 | A | G | UTR_5_PRIME | MODIFIER |
| 178 | Chr09 | 4551293 | T | A | UTR_5_PRIME | MODIFIER |

TABLE 4

G-type lecRLK Mutations

| | Chromosome | Genomic Position | Reference | Variant | Mutation type | Predicted impact |
|---|---|---|---|---|---|---|
| 1 | Chr05 | 1443941 | AGGG | AGG | FRAME_SHIFT | HIGH |
| 2 | Chr05 | 1441171 | G | A | STOP_GAINED | HIGH |
| 3 | Chr05 | 1440955 | G | C | NON_SYNONYMOUS_CODING | MODERATE |
| 4 | Chr05 | 1441257 | A | C | NON_SYNONYMOUS_CODING | MODERATE |
| 5 | Chr05 | 1441285 | C | A | NON_SYNONYMOUS_CODING | MODERATE |
| 6 | Chr05 | 1441299 | G | A | NON_SYNONYMOUS_CODING | MODERATE |
| 7 | Chr05 | 1441335 | G | T | NON_SYNONYMOUS_CODING | MODERATE |
| 8 | Chr05 | 1441342 | G | C | NON_SYNONYMOUS_CODING | MODERATE |
| 9 | Chr05 | 1441521 | A | G | NON_SYNONYMOUS_CODING | MODERATE |
| 10 | Chr05 | 1441527 | G | T | NON_SYNONYMOUS_CODING | MODERATE |
| 11 | Chr05 | 1441714 | A | G | NON_SYNONYMOUS_CODING | MODERATE |
| 12 | Chr05 | 1441774 | G | A | NON_SYNONYMOUS_CODING | MODERATE |
| 13 | Chr05 | 1441801 | G | T | NON_SYNONYMOUS_CODING | MODERATE |
| 14 | Chr05 | 1442114 | G | A | NON_SYNONYMOUS_CODING | MODERATE |

TABLE 4-continued

G-type lecRLK Mutations

| | Chromosome | Genomic Position | Reference | Variant | Mutation type | Predicted impact |
|---|---|---|---|---|---|---|
| 15 | Chr05 | 1442155 | A | G | NON_SYNONYMOUS_CODING | MODERATE |
| 16 | Chr05 | 1442216 | C | G | NON_SYNONYMOUS_CODING | MODERATE |
| 17 | Chr05 | 1442248 | A | T | NON_SYNONYMOUS_CODING | MODERATE |
| 18 | Chr05 | 1443622 | C | T | NON_SYNONYMOUS_CODING | MODERATE |
| 19 | Chr05 | 1443631 | C | A | NON_SYNONYMOUS_CODING | MODERATE |
| 20 | Chr05 | 1443654 | G | T | NON_SYNONYMOUS_CODING | MODERATE |
| 21 | Chr05 | 1443681 | T | C | NON_SYNONYMOUS_CODING | MODERATE |
| 22 | Chr05 | 1443723 | A | G | NON_SYNONYMOUS_CODING | MODERATE |
| 23 | Chr05 | 1443742 | A | T | NON_SYNONYMOUS_CODING | MODERATE |
| 24 | Chr05 | 1443863 | G | A | NON_SYNONYMOUS_CODING | MODERATE |
| 25 | Chr05 | 1443876 | T | A | NON_SYNONYMOUS_CODING | MODERATE |
| 26 | Chr05 | 1443890 | G | A | NON_SYNONYMOUS_CODING | MODERATE |
| 27 | Chr05 | 1444399 | A | G | NON_SYNONYMOUS_CODING | MODERATE |
| 28 | Chr05 | 1444407 | G | T | NON_SYNONYMOUS_CODING | MODERATE |
| 29 | Chr05 | 1444417 | T | C | NON_SYNONYMOUS_CODING | MODERATE |
| 30 | Chr05 | 1444418 | C | A | NON_SYNONYMOUS_CODING | MODERATE |
| 31 | Chr05 | 1444420 | A | G | NON_SYNONYMOUS_CODING | MODERATE |
| 32 | Chr05 | 1444421 | A | T | NON_SYNONYMOUS_CODING | MODERATE |
| 33 | Chr05 | 1444422 | T | A | NON_SYNONYMOUS_CODING | MODERATE |
| 34 | Chr05 | 1444438 | A | T | NON_SYNONYMOUS_CODING | MODERATE |
| 35 | Chr05 | 1444448 | T | C | NON_SYNONYMOUS_CODING | MODERATE |
| 36 | Chr05 | 1444451 | T | C | NON_SYNONYMOUS_CODING | MODERATE |
| 37 | Chr05 | 1444520 | G | T | NON_SYNONYMOUS_CODING | MODERATE |
| 38 | Chr05 | 1444525 | G | T | NON_SYNONYMOUS_CODING | MODERATE |
| 39 | Chr05 | 1444541 | T | C | NON_SYNONYMOUS_CODING | MODERATE |
| 40 | Chr05 | 1444554 | A | G | NON_SYNONYMOUS_CODING | MODERATE |
| 41 | Chr05 | 1444565 | C | T | NON_SYNONYMOUS_CODING | MODERATE |
| 42 | Chr05 | 1444579 | G | T | NON_SYNONYMOUS_CODING | MODERATE |
| 43 | Chr05 | 1444635 | A | C | NON_SYNONYMOUS_CODING | MODERATE |
| 44 | Chr05 | 1444636 | G | A | NON_SYNONYMOUS_CODING | MODERATE |
| 45 | Chr05 | 1444664 | C | A | NON_SYNONYMOUS_CODING | MODERATE |
| 46 | Chr05 | 1444670 | C | T | NON_SYNONYMOUS_CODING | MODERATE |
| 47 | Chr05 | 1444678 | G | A | NON_SYNONYMOUS_CODING | MODERATE |
| 48 | Chr05 | 1444694 | T | C | NON_SYNONYMOUS_CODING | MODERATE |
| 49 | Chr05 | 1444735 | T | A | UTR_3_PRIME | MODIFIER |
| 50 | Chr05 | 1444736 | G | T | UTR_3_PRIME | MODIFIER |
| 51 | Chr05 | 1444746 | CAATA | CA | UTR_3_PRIME | MODIFIER |
| 52 | Chr05 | 1444751 | T | C | UTR_3_PRIME | MODIFIER |

TABLE 4-continued

G-type lecRLK Mutations

| | Chromosome | Genomic Position | Reference | Variant | Mutation type | Predicted impact |
|---|---|---|---|---|---|---|
| 53 | Chr05 | 1444768 | T | C | UTR_3_PRIME | MODIFIER |
| 54 | Chr05 | 1444769 | G | A | UTR_3_PRIME | MODIFIER |
| 55 | Chr05 | 1444772 | T | C | UTR_3_PRIME | MODIFIER |
| 56 | Chr05 | 1444778 | G | C | UTR_3_PRIME | MODIFIER |
| 57 | Chr05 | 1444780 | T | G | UTR_3_PRIME | MODIFIER |
| 58 | Chr05 | 1444855 | C | A | UTR_3_PRIME | MODIFIER |
| 59 | Chr05 | 1444864 | G | T | UTR_3_PRIME | MODIFIER |
| 60 | Chr05 | 1444877 | A | C | UTR_3_PRIME | MODIFIER |
| 61 | Chr05 | 1444897 | A | T | UTR_3_PRIME | MODIFIER |
| 62 | Chr05 | 1444911 | C | A | UTR_3_PRIME | MODIFIER |
| 63 | Chr05 | 1444915 | T | C | UTR_3_PRIME | MODIFIER |
| 64 | Chr05 | 1444940 | T | G | UTR_3_PRIME | MODIFIER |
| 65 | Chr05 | 1444946 | T | C | UTR_3_PRIME | MODIFIER |

TABLE 5

Significant GWAS associations after correcting for multiple testing.

| | Gene Model | Chrom. | SNP_Position | P-value | Annotation |
|---|---|---|---|---|---|
| 1 | Potri.005G012100 | Chr05 | 942546 | 1.56E-38 | Receptor like protein 9 |
| 2 | Potri.005G012100 | Chr05 | 942550 | 1.56E-38 | Receptor like protein 9 |
| 3 | Potri.005G012100 | Chr05 | 942545 | 1.56E-38 | Receptor like protein 9 |
| 4 | Potri.008G109900 | Chr08 | 6995698 | 1.64E-32 | Aminoalcoholphosphotransferase 1 |
| 5 | Potri.008G109900 | Chr08 | 6995698 | 1.64E-32 | Aminoalcoholphosphotransferase 1 |
| 6 | Potri.008G109900 | Chr08 | 6995698 | 1.64E-32 | Aminoalcoholphosphotransferase 1 |
| 7 | Potri.008G109900 | Chr08 | 6995698 | 1.64E-32 | Aminoalcoholphosphotransferase 1 |
| 8 | Potri.009G038300 | Chr09 | 4667416 | 1.57E-16 | Hypothetical protein |
| 9 | Potri.009G038300 | Chr09 | 4667416 | 1.57E-16 | Hypothetical protein |
| 10 | Potri.009G036300 | Chr09 | 4548711 | 2.15E-16 | Concanavalin A-like lectin protein kinase fam. Prot. |
| 11 | Potri.003G028200 | Chr03 | 3517268 | 2.78E-14 | Receptor like protein 9 |
| 12 | Potri.005G017800 | Chr05 | 1440266 | 1.61E-13 | Hypothetical protein |
| 13 | Potri.005G017900 | Chr05 | 1440266 | 1.61E-13 | Photosystem II reaction center protein A |
| 14 | Potri.005G018000 | Chr05 | 1440266 | 1.61E-13 | Receptor kinase 3 |
| 15 | Potri.017G112200 | Chr17 | 12775856 | 1.86E-12 | DNAJ heat shock N-terminal domain-containing protein |
| 16 | Potri.017G112200 | Chr17 | 12775856 | 1.86E-12 | DNAJ heat shock N-terminal domain-containing protein |
| 17 | Potri.017G112100 | Chr17 | 12775856 | 1.86E-12 | ROTUNDIFOLIA like 21 |
| 18 | Potri.001G343800 | Chr01 | 34910409 | 1.93E-12 | NAC (No Apical Meristern) dom. transcr. Reg. superfamily prot. |

TABLE 5-continued

Significant GWAS associations after correcting for multiple testing.

|    | Gene Model       | Chrom.    | SNP_Position | P-value  | Annotation                                         |
|----|------------------|-----------|--------------|----------|----------------------------------------------------|
| 19 | Potri.001G343800 | Chr01     | 34910409     | 1.93E-12 | NAC domain containing protein 44                   |
| 20 | Potri.013G134000 | Chr13     | 14483703     | 3.68E-12 | Acyl-CoA N-acyltransferases (NAT) superfamily protein |
| 21 | Potri.013G134100 | Chr13     | 14483703     | 3.68E-12 | Acyl-CoA N-acyltransferases (NAT) superfamily protein |
| 22 | Potri.T171100    | scaf_1090 | 11811        | 4.19E-12 | Alpha/beta-Hydrolases superfamily protein          |
| 23 | Potri.005G006100 | Chr05     | 347660       | 4.50E-12 | Glucose-6-phosphate dehydrogenase 4                |
| 24 | Potri.001G405800 | Chr01     | 4282396      | 6.70E-12 | Hypothetical protein                               |
| 25 | Potri.001G356900 | Chr01     | 36549964     | 2.47E-11 | Aspartic proteinase A1                             |
| 26 | Potri.001G356900 | Chr01     | 36549964     | 2.47E-11 | Saposin-like aspartyl protease family protein      |
| 27 | Potri.011G157900 | Chr11     | 17521421     | 2.81E-11 | FAD-binding Berberine family protein               |
| 28 | Potri.011G158000 | Chr11     | 17521421     | 2.81E-11 | FAD-binding Berberine family protein               |
| 29 | Potri.012G015200 | Chr12     | 1482730      | 4.63E-11 | Hypothetical protein                               |
| 30 | Potri.004G081000 | Chr04     | 6679501      | 6.06E-11 | NAC domain containing protein 28                   |
| 31 | Potri.012G017400 | Chr12     | 1637110      | 9.51E-11 | Hypothetical protein                               |
| 32 | Potri.014G175200 | Chr14     | 14251122     | 1.29E-10 | FRIGIDA-like protein                               |
| 33 | Potri.014G175300 | Chr14     | 14251122     | 1.29E-10 | Tetratricopeptide repeat (TPR)-like superfamily protein |
| 34 | Potri.014G175400 | Chr14     | 14255734     | 1.51E-10 | Autophagocytosis-associated family protein         |
| 35 | Potri.001G230100 | Chr01     | 24216639     | 1.67E-10 | Hypothetical protein                               |
| 36 | Potri.001G230000 | Chr01     | 24216639     | 1.67E-10 | Callose synthase 1                                 |
| 37 | Potri.T124400    | scaf_219  | 20246        | 2.48E-10 | Protein of unknown function (DUF784)               |
| 38 | Potri.014G175400 | Chr14     | 14254718     | 2.63E-10 | Autophagocytosis-associated family protein         |
| 39 | Potri.014G175400 | Chr14     | 14254989     | 2.88E-10 | Autophagocytosis-associated family protein         |
| 40 | Potri.019G103000 | Chr19     | 13185553     | 3.13E-10 | Protein of unknown function (DUF789)               |
| 41 | Potri.015G070600 | Chr15     | 9510893      | 3.35E-10 | Aldehyde dehydrogenase 10A8                        |
| 42 | Potri.001G123800 | Chr01     | 10058355     | 3.58E-10 | K+ uptake permease 11                              |
| 43 | Potri.008G072200 | Chr08     | 4466268      | 4.13E-10 | Glutaredoxin family protein                        |
| 44 | Potri.014G175400 | Chr14     | 14256095     | 4.17E-10 | Autophagocytosis-associated family protein         |
| 45 | Potri.005G124200 | Chr05     | 9704811      | 4.35E-10 | Sulfite exporter TauE/SafE family protein          |
| 46 | Potri.014G175200 | Chr14     | 14244625     | 4.93E-10 | FRIGIDA-like protein                               |
| 47 | Potri.002G227300 | Chr02     | 21695916     | 5.70E-10 | Cellulose synthase-like B4                         |
| 48 | Potri.014G175400 | Chr14     | 14255234     | 5.99E-10 | Autophagocytosis-associated family protein         |
| 49 | Potri.002G094200 | Chr02     | 6755705      | 6.83E-10 | Related to AP2 4                                   |
| 50 | Potri.002G094000 | Chr02     | 6730841      | 6.99E-10 | Glycosyl hydrolase family protein                  |
| 51 | Potri.014G175200 | Chr14     | 14245369     | 7.46E-10 | FRIGIDA-like protein                               |

TABLE 5-continued

Significant GWAS associations after correcting for multiple testing.

| | Gene Model | Chrom. | SNP_Position | P-value | Annotation |
|---|---|---|---|---|---|
| 52 | Potri.001G255200 | Chr01 | 26481859 | 7.49E-10 | Hypothetical protein |
| 53 | Potri.014G175100 | Chr14 | 14241230 | 7.71E-10 | Hypothetical protein |
| 54 | Potri.014G175200 | Chr14 | 14241230 | 7.71E-10 | FRIGIDA-like protein |
| 55 | Potri.014G175400 | Chr14 | 14256035 | 7.96E-10 | Autophagocytosis-associated family protein |
| 56 | Potri.014G135900 | Chr14 | 10379855 | 9.17E-10 | Alpha/beta-Hydrolases superfamily protein |
| 57 | Potri.011G116600 | Chr11 | 14184154 | 9.28E-10 | Hypothetical protein |
| 58 | Potri.011G116700 | Chr11 | 14184154 | 9.28E-10 | Protein phosphatase 2C family protein |
| 59 | Potri.014G175200 | Chr14 | 14244219 | 1.21E-09 | FRIGIDA-like protein |
| 60 | Potri.014G175400 | Chr14 | 14254916 | 1.23E-09 | Autophagocytosis-associated family protein |
| 61 | Potri.014G175400 | Chr14 | 14254848 | 1.23E-09 | Autophagocytosis-associated family protein |
| 62 | Potri.014G175400 | Chr14 | 14253905 | 1.27E-09 | Autophagocytosis-associated family protein |
| 63 | Potri.014G175400 | Chr14 | 14254273 | 1.32E-09 | Autophagocytosis-associated family protein |
| 64 | Potri.014G175400 | Chr14 | 14254137 | 1.32E-09 | Autophagocytosis-associated family protein |
| 65 | Potri.014G175400 | Chr14 | 14256452 | 0.34E-09 | Autophagocytosis-associated family protein |
| 66 | Potri.001G376000 | Chr01 | 39141278 | 1.38E-09 | Hypothetical protein |
| 67 | Potri.018G120400 | Chr18 | 14437558 | 1.43E-09 | Serine-rich protein-related |
| 68 | Potri.T142000 | scaf_376 | 17926 | 1.45E-09 | Hypothetical protein |
| 69 | Potri.T142000 | scaf_376 | 17932 | 1.45E-09 | Hypothetical protein |
| 70 | Potri.001G360600 | Chr01 | 37130691 | 1.45E-09 | Beta-1,2-xylosyltransferase |
| 71 | Potri.001G084500 | Chr01 | 671473 | 1.56E-09 | Hypothetical protein |
| 72 | Potri.005G229700 | Chr05 | 23858336 | 1.90E-09 | ADPGLC-PPase large subunit |
| 73 | Potri.014G175400 | Chr14 | 14253643 | 1.95E-09 | Autophagocytosis-associated family protein |
| 74 | Potri.004G080800 | Chr04 | 6654075 | 2.10E-09 | Protein prenyltransferase superfamily protein |
| 75 | Potri.017G096300 | Chr17 | 11367197 | 2.13E-09 | Ralf-like 27 |
| 76 | Potri.010G225100 | Chr10 | 20868986 | 2.16E-09 | P-loop containing nucleoside triphosphate hydrolases sup.fam. Prot. |
| 77 | Potri.010G225000 | Chr10 | 20868986 | 2.16E-09 | SERINETIEIREONINE-PROTEIN KINASE WNK WITH NO LYSINE -RELATED |
| 78 | Potri.014G062900 | Chr14 | 4950047 | 2.19E-09 | Receptor-like protein kinase-related family protein |
| 79 | Potri.002G094200 | Chr02 | 6754052 | 2.30E-09 | Related to AP2 4 |
| 80 | Potri.011G153600 | Chr11 | 17210797 | 2.44E-09 | Hypothetical protein |
| 81 | Potri.011G153500 | Chr11 | 17210797 | 2.44E-09 | HXXXD-type acyl-transferase family protein |

TABLE 5-continued

Significant GWAS associations after correcting for multiple testing.

| | Gene Model | Chrom. | SNP_Position | P-value | Annotation |
|---|---|---|---|---|---|
| 82 | Potri.009G083400 | Chr09 | 7856879 | 2.45E-09 | Basic pathogenesis-related protein 1 |
| 83 | Potri.009G083500 | Chr09 | 7856879 | 2.45E-09 | Cell wall/vacuolar inhibitor of fructosidase 1 |
| 84 | Potri.017G054800 | Chr17 | 4860231 | 3.02E-09 | Homeodomain-like superfamily protein |
| 85 | Potri.014G175400 | Chr14 | 14255253 | 3.11E-09 | Autophagocytosis-associated family protein |
| 86 | Potri.001G294000 | Chr01 | 29906043 | 3.17E-09 | Voltage dependent anion channel 2 |
| 87 | Potri.014G175700 | Chr14 | 14279419 | 3.22E-09 | Alpha/beta-Hydrolases superfamily protein |
| 88 | Potri.014G175400 | Chr14 | 14253400 | 3.23E-09 | Autophagocytosis-associated family protein |
| 89 | Potri.008G220900 | Chr08 | 18637008 | 3.45E-09 | Stigma-specific Stig1 family protein |
| 90 | Potri.012G138700 | Chr12 | 15331436 | 3.59E-09 | Hypothetical protein |
| 91 | Potri.013G116500 | Chr13 | 12995989 | 4.09E-09 | Gerrnin-like protein 5 |
| 92 | Potri.018G051500 | Chr18 | 5361852 | 4.11E-09 | Hypothetical protein |
| 93 | Potri.018G051600 | Chr18 | 5361852 | 4.11E-09 | Mitochondrial transcription termination factor family protein |
| 94 | Potri.003G058000 | Chr03 | 8608000 | 4.21E-09 | Pyridoxal phosphate PLP)-dependent transferases superfamily protein |
| 95 | Potri.003G058100 | Chr03 | 8608000 | 4.21E-09 | Zinc ion binding;nucleic acid binding |
| 96 | Potri.001G462200 | Chr01 | 49633144 | 4.22E-09 | FAD-binding Berberine family protein |
| 97 | Potri.012G103600 | Chr12 | 12790529 | 4.24E-09 | Hypothetical protein |
| 98 | Potri.012G103500 | Chr12 | 12790529 | 4.24E-09 | NAC domain containing protein 83 |
| 99 | Potri.012G103400 | Chr12 | 12790529 | 4.24E-09 | Translocase inner membrane subunit 8 |
| 100 | Potri.007G138100 | Chr07 | 14981038 | 4.32E-09 | Erf domain protein 9 |
| 101 | Potri.007G138000 | Chr07 | 14981038 | 4.32E-09 | Tyrosine transaminase family protein |
| 102 | Potri.001G059500 | Chr01 | 4572079 | 4.35E-09 | Hypothetical protein |
| 103 | Potri.001G059600 | Chr01 | 4572079 | 4.35E-09 | Hypothetical protein |
| 104 | Potri.001G059700 | Chr01 | 4572079 | 4.35E-09 | Hypothetical protein |
| 105 | Potri.001G392500 | Chr01 | 41105156 | 4.77E-09 | Ubiquitin-conjugating enzyme 35 |
| 106 | Potri.001G392500 | Chr01 | 41105156 | 4.77E-09 | Ubiquitin-conjugating enzyme 36 |
| 107 | Potri.001G392500 | Chr01 | 41105156 | 4.77E-09 | Ubiquitin-conjugating enzyme 36 |
| 108 | Potri.014G174800 | Chr14 | 14190922 | 5.01E-09 | Thioesterase/thiol ester dehydrase-isomerase superfamily protein |
| 109 | Potri.014G1.68000 | Chr14 | 13423394 | 5.24E-09 | ATPase, F0 complex, subunit A protein |
| 110 | Potri.010G065200 | Chr10 | 9291084 | 5.28E-09 | Auxin-induced protein 13 |
| 111 | Potri.011G116600 | Chr11 | 14183823 | 5.38E-09 | Hypothetical protein |
| 112 | Potri.002G074700 | Chr02 | 5162812 | 5.75E-09 | F-box/RNI-like superfamily protein |
| 113 | Potri.010G138500 | Chr10 | 15105784 | 5.77E-09 | P-loop containing nucleoside triphosphate hydrolases superfamily protein |

What is claimed is:

1. A method of selecting a *Populus* plant resistant to a necrotrophic fungus comprising sequencing the Potri.003G028200, Potri.005G012100, and Potri.009G036300 genes of said plant, and;

determining the functionality of the Potri.003G028200, Potri.005G012100, and Potri.009G036300 genes in said plant, thereby identifying that said plant is resistant to a necrotrophic fungus when each of the Potri.003G028200, Potri.005G012100, and Potri.009G036300 genes in said plant is substantially functional, wherein the Potri.003G028200 gene is substantially functional when the amino acid sequences of the Leucine-rich Repeat (LRR) domain, the plant specific Leucine-rich Repeat (LRR) domain and the signal peptide encoded by the RLP1 gene are identical to the respective domains of the protein encoded by the wild type Potri.003G028200 gene as defined by SEQ ID NO: 2;

wherein Potri.005G012100 gene is substantially functional when the amino acid sequences of the Leucine-rich Repeat (LRR) domain, the plant specific Leucine-rich Repeat (LRR) domain and the signal peptide of the Potri.005G012100 gene are identical to the respective domains of the protein encoded by the wild type Potri.005G012100 gene as defined by SEQ ID NO: 4;

and wherein L-type lecRLK gene is substantially functional when the amino acid sequences of the Protein Kinase domain, transmembrane domain, Legume lectin domain and the signal peptide of the L-type lecRLK gene are identical to the respective domains of the protein encoded by the wild type L-type lecRLK gene as defined by SEQ ID NO: 6.

2. The method of claim 1, wherein said necrotropic fungus is from the *Sphaerulina* genus.

3. The method of claim 2, wherein said necrotropic fungus is selected from the group consisting of *Sphaerulina abeliceae, Sphaerulina aceris, Sphaerulina acetabulum, Sphaerulina acori, Sphaerulina aechmeae, Sphaerulina affinis, Sphaerulina albispiculata, Sphaerulina alni, Sphaerulina amelanchier, Sphaerulina amicta, Sphaerulina amphilomatis, Sphaerulina amygdali, Sphaerulina anemones, Sphaerulina annae, Sphaerulina antarctica, Sphaerulina arctica, Sphaerulina arthoniae, Sphaerulina assurgens, Sphaerulina aucubae, Sphaerulina azaleae, Sphaerulina baccarum, Sphaerulina bambusicola, Sphaerulina berberidis, Sphaerulina betulae, Sphaerulina blyttii, Sphaerulina bonariana, Sphaerulina boudieriana, Sphaerulina bryophila, Sphaerulina callista, Sphaerulina camelliae, Sphaerulina camelliae, Sphaerulina carestiae, Sphaerulina caricae, Sphaerulina caricis, Sphaerulina ceanothi, Sphaerulina centellae, Sphaerulina cercidis, Sphaerulina cetraricola, Sphaerulina cetrariicola, Sphaerulina chlorococca, Sphaerulina cibotii, Sphaerulina citri, Sphaerulina codiicola, Sphaerulina coffaeicola, Sphaerulina coffeicola, Sphaerulina concinna, Sphaerulina conflicta, Sphaerulina coriariae, Sphaerulina cornicola, Sphaerulina corniculata, Sphaerulina coronillaejunceae, Sphaerulina corynephora, Sphaerulina cucumeris, Sphaerulina cucurbitae, Sphaerulina datiscae, Sphaerulina diapensiae, Sphaerulina dioscoreae, Sphaerulina divergens, Sphaerulina dolichotera, Sphaerulina dryadis, Sphaerulina dryophila, Sphaerulina dubiella, Sphaerulina empetri, Sphaerulina endococcoidea, Sphaerulina epigaea, Sphaerulina eucalypti, Sphaerulina ferruginosa, Sphaerulina frondicola, Sphaerulina fuegiana, Sphaerulina gei, Sphaerulina gentianae, Sphaerulina gigantea, Sphaerulina giliae, Sphaerulina hainensis, Sphaerulina halophila, Sphaerulina hamadryadum, Sphaerulina hederae, Sphaerulina helicicola, Sphaerulina hyperici, Sphaerulina inaequalis, Sphaerulina inquinans, Sphaerulina intermedia, Sphaerulina intermixta, Sphaerulina Ipomoeae, Sphaerulina islandica, Sphaerulina iwatensis, Sphaerulina juglandis, Sphaerulina leightonii, Sphaerulina lepidiotae, Sphaerulina limnanthemi, Sphaerulina lini, Sphaerulina linicola, Sphaerulina ludwigiae, Sphaerulina mappiae, Sphaerulina marattiae, Sphaerulina marginata, Sphaerulina maroccana, Sphaerulina marsileae, Sphaerulina maydis, Sphaerulina menispermi, Sphaerulina microthyrioides, Sphaerulina mimosaepigrae, Sphaerulina miyakei, Sphaerulina musae, Sphaerulina muscicola, Sphaerulina muscorum, Sphaerulina musicola, Sphaerulina musiva, Sphaerulina myriadea, Sphaerulina myriadea subsp. myriadea, Sphaerulina myrtillina, Sphaerulina naumovii, Sphaerulina nephromiaria, Sphaerulina oleifolia, Sphaerulina orae-maris, Sphaerulina oryzae, Sphaerulina oryzina, Sphaerulina oxalidis, Sphaerulina oxyacanthae, Sphaerulina pallens, Sphaerulina parvipuncta, Sphaerulina patriniae, Sphaerulina paulistana, Sphaerulina peckii, Sphaerulina pedicellata, Sphaerulina pelargonii, Sphaerulina phalaenopsidis, Sphaerulina phellogena, Sphaerulina phoenicis, Sphaerulina phyllostachydis, Sphaerulina pini, Sphaerulina plantaginea, Sphaerulina pleuropogonis, Sphaerulina polygonorum, Sphaerulina polypodii, Sphaerulina polypodii, Sphaerulina polyspora, Sphaerulina populi, Sphaerulina populicola, Sphaerulina porothelia, Sphaerulina potebniae, Sphaerulina potentillae, Sphaerulina poterii, Sphaerulina primuli-* cola, *Sphaerulina pruni, Sphaerulina pseudovirgaureae, Sphaerulina pterocarpi, Sphaerulina pulii, Sphaerulina quercicola, Sphaerulina quercifolia, Sphaerulina quitensis, Sphaerulina rehmiana, Sphaerulina rhabdoclinis, Sphaerulina rhodeae, Sphaerulina rhododendri, Sphaerulina rhododendricola, Sphaerulina rubi, Sphaerulina saccardiana, Sphaerulina saccardoana, Sphaerulina sacchari, Sphaerulina salicina, Sphaerulina sambucina, Sphaerulina sasae, Sphaerulina schaereri, Sphaerulina scirpi, Sphaerulina sepincola, Sphaerulina serograpta, Sphaerulina silacincola, Sphaerulina smilacincola, Sphaerulina socia, Sphaerulina spartii, Sphaerulina staphyleae, Sphaerulina staurochili, Sphaerulina steganostroma, Sphaerulina subgen, Pharcidiella, Sphaerulina subgen, Sphaerulina, Sphaerulina subglacialis, Sphaerulina subtropica, Sphaerulina suchumica, Sphaerulina tabacinae, Sphaerulina tanaceti, Sphaerulina tarda, Sphaerulina taxi, Sphaerulina taxicola, Sphaerulina thujopsidis, Sphaerulina tiliaris, Sphaerulina tirolensis, Sphaerulina todeae, Sphaerulina trapae-bispinosae, Sphaerulina trifolii, Sphaerulina tritici, Sphaerulina umbilicata, Sphaerulina valerianae, Sphaerulina viciae, Sphaerulina vincae, Sphaerulina violae, Sphaerulina vismiae, Sphaerulina vulpina, Sphaerulina westendorpii, Sphaerulina worsdellii, Sphaerulina xerophylli, Sphaerulina yerbae, Sphaerulina ziziphi, Sphaerulina zizyphae,* and *Sphaerulina zizyphi.*

4. A method of determining necrotropic fungi resistance in a *Populus* plant comprising
infecting said plant with a necrotropic fungus; and
detecting the expression level of at least one gene selected from the group consisting of Potri.003G028200, Potri.005G012100, and Potri.009G036300 genes before and after the infection, wherein a transient increase in the expression level of the at least one gene 24 hours after the infection indicates that the plant is resistant to said necrotropic fungus.

5. The method of claim 4, wherein said necrotropic fungus is from genus *Sphaerulina.*

6. The method of claim 5, wherein said necrotropic fungus is selected from the group consisting of *Sphaerulina abeliceae, Sphaerulina aceris, Sphaerulina acetabulum, Sphaerulina acori, Sphaerulina aechmeae, Sphaerulina affinis, Sphaerulina albispiculata, Sphaerulina alni, Sphaerulina amelanchier, Sphaerulina amicta, Sphaerulina amphilomatis, Sphaerulina amygdali, Sphaerulina anemones, Sphaerulina annae, Sphaerulina antarctica, Sphaerulina arctica, Sphaerulina arthoniae, Sphaerulina assurgens, Sphaerulina aucubae, Sphaerulina azaleae, Sphaerulina baccarum, Sphaerulina bambusicola, Sphaerulina berberidis, Sphaerulina betulae, Sphaerulina blyttii, Sphaerulina bonariana, Sphaerulina boudieriana, Sphaerulina bryophila, Sphaerulina callista, Sphaerulina camelliae, Sphaerulina camelliae, Sphaerulina carestiae, Sphaerulina caricae, Sphaerulina caricis, Sphaerulina ceanothi, Sphaerulina centellae, Sphaerulina cercidis, Sphaerulina cetraricola, Sphaerulina cetrariicola, Sphaerulina chlorococca, Sphaerulina cibotii, Sphaerulina citri, Sphaerulina codiicola, Sphaerulina coffaeicola, Sphaerulina coffeicola, Sphaerulina concinna, Sphaerulina conflicta, Sphaerulina coriariae, Sphaerulina cornicola, Sphaerulina corniculata, Sphaerulina coronillaejunceae, Sphaerulina corynephora, Sphaerulina cucumeris, Sphaerulina cucurbitae, Sphaerulina datiscae, Sphaerulina diapensiae, Sphaerulina dioscoreae, Sphaerulina divergens, Sphaerulina dolichotera, Sphaerulina dryadis, Sphaerulina dryophila, Sphaerulina dubiella, Sphaerulina empetri, Sphaerulina endococcoidea, Sphaerulina epigaea, Sphaerulina eucalypti, Sphaerulina ferruginosa, Sphaerulina frondicola, Sphaerulina fuegiana, Sphaerulina gei, Sphaerulina gentianae, Sphaerulina gigantea, Sphaerulina giliae, Sphaerulina hainensis, Sphaerulina halophila, Sphaerulina hamadryadum, Sphaerulina hederae, Sphaerulina helicicola, Sphaerulina hyperici, Sphaerulina inaequalis, Sphaerulina inquinans, Sphaerulina intermedia, Sphaerulina intermixta, Sphaerulina Ipomoeae, Sphaerulina islandica, Sphaerulina iwatensis, Sphaerulina juglandis, Sphaerulina leightonii, Sphaerulina lepidiotae, Sphaerulina limnanthemi, Sphaerulina lini, Sphaerulina linicola, Sphaerulina ludwigiae, Sphaerulina mappiae, Sphaerulina marattiae, Sphaerulina marginata, Sphaerulina maroccana, Sphaerulina marsileae, Sphaerulina maydis, Sphaerulina menispermi, Sphaerulina microthyrioides, Sphaerulina mimosaepigrae, Sphaerulina miyakei, Sphaerulina musae, Sphaerulina muscicola, Sphaerulina muscorum, Sphaerulina musicola, Sphaerulina musiva, Sphaerulina myriadea, Sphaerulina myriadea* subsp. *myriadea, Sphaerulina myrtillina, Sphaerulina naumovii, Sphaerulina nephromiaria, Sphaerulina oleifolia, Sphaerulina orae-maris, Sphaerulina oryzae, Sphaerulina oryzina, Sphaerulina oxalidis, Sphaerulina oxyacanthae, Sphaerulina pallens, Sphaerulina parvipuncta, Sphaerulina patriniae, Sphaerulina paulistana, Sphaerulina peckii, Sphaerulina pedicellata, Sphaerulina pelargonii, Sphaerulina phalaenopsidis, Sphaerulina phellogena, Sphaerulina phoenicis, Sphaerulina phyllostachydis, Sphaerulina pini, Sphaerulina plantaginea, Sphaerulina pleuropogonis, Sphaerulina polygonorum, Sphaerulina polypodii, Sphaerulina polypodii, Sphaerulina polyspora, Sphaerulina populi, Sphaerulina populicola, Sphaerulina porothelia, Sphaerulina potebniae, Sphaerulina potentillae, Sphaerulina poterii, Sphaerulina primulicola, Sphaerulina pruni, Sphaerulina pseudovirgaureae, Sphaerulina pterocarpi, Sphaerulina pulii, Sphaerulina quercicola, Sphaerulina quercifolia, Sphaerulina quitensis, Sphaerulina rehmiana, Sphaerulina rhabdoclinis, Sphaerulina rhodeae, Sphaerulina rhododendri, Sphaerulina rhododendricola, Sphaerulina rubi, Sphaerulina saccardiana, Sphaerulina saccardoana, Sphaerulina sacchari, Sphaerulina salicina, Sphaerulina sambucina, Sphaerulina sasae, Sphaerulina schaereri, Sphaerulina scirpi, Sphaerulina sepincola, Sphaerulina serograpta, Sphaerulina silacincola, Sphaerulina smilacincola, Sphaerulina socia, Sphaerulina spartii, Sphaerulina staphyleae, Sphaerulina staurochili, Sphaerulina steganostroma, Sphaerulina subgen, Pharcidiella, Sphaerulina subgen, Sphaerulina, Sphaerulina subglacialis, Sphaerulina subtropica, Sphaerulina suchumica, Sphaerulina tabacinae, Sphaerulina tanaceti, Sphaerulina tarda, Sphaerulina taxi, Sphaerulina taxicola, Sphaerulina thujopsidis, Sphaerulina tiliaris, Sphaerulina tirolensis, Sphaerulina todeae, Sphaerulina trapae-bispinosae, Sphaerulina trifolii, Sphaerulina tritici, Sphaerulina umbilicata, Sphaerulina valerianae, Sphaerulina viciae, Sphaerulina vincae, Sphaerulina violae, Sphaerulina vismiae, Sphaerulina vulpina, Sphaerulina westendorpii, Sphaerulina worsdellii, Sphaerulina xerophylli, Sphaerulina yerbae, Sphaerulina ziziphi, Sphaerulina zizyphae,* and *Sphaerulina zizyphi.*

7. A method of converting a necrotropic fungi-susceptible *Populus* plant into a necrotropic fungi-resistant *Populus* plant comprising
sequencing the Potri.003G028200, Potri.005G012100, and Potri.009G036300 genes in said plant;
determining the presence of a deleterious mutation in at least one of the Potri.003G028200, Potri.005G012100, and Potri.009G036300; and restoring the function of said at least one of the Potri.003G028200, Potri.005G012100, Potri.009G036300 genes comprising said deleterious mutation.

8. The method of claim 7, wherein said restoring of the function of said at least one of said Potri.003G028200, Potri.005G012100, Potri.009G036300 genes is achieved by CRISPR-mediated genome editing.

9. The method of claim 8, wherein said CRISPR-mediated genome editing comprises introducing said plant a first nucleic acid encoding a Cas9 nuclease, a second nucleic acid comprising a guide RNA (gRNA) and a third nucleic acid comprising a homologous repair template of said at least one of the Potri.003G028200, Potri.005G012100, and Potri.009G036300 genes comprising said deleterious mutation.

10. The method of claim 7, wherein said restoring of the function of said at least one of said Potri.003G028200, Potri.005G012100, Potri.009G036300 genes comprising said deleterious mutation is achieved by introducing into said plant at least one plasmid comprising a substantially functional Potri.003G028200, Potri.005G012100, or Potri.009G036300 gene corresponding to the at least one mutated Potri.003G028200, Potri.005G012100, or Potri.009G036300 gene.

11. The method of claim 7, wherein the deleterious mutation in the Potri.003G028200 gene is selected from the group consisting of the genomic mutations described Table 1.

12. The method of claim 7, wherein the deleterious mutation in the Potri.005G012100 gene is selected from the group consisting of the genomic mutations described Table 2.

13. The method of claim 7, wherein the deleterious mutation in the Potri.009G036300 gene is selected from the group consisting of the genomic mutations described Table 3.

14. The method of claim 7, further comprising inactivating the Potri.005G018000 gene in said plant.

15. The method of claim 7, wherein said necrotropic fungus is from genus *Sphaerulina*.

16. The method of claim 7, wherein said necrotropic fungus is selected from the group consisting of *Sphaerulina musiva*, *Sphaerulina oryzina*, *Sphaerulina rehmiana* and *Sphaerulina rubi*.

17. A method of converting a necrotropic fungi-susceptible plant into a necrotropic fungi-resistant plant comprising inactivating a Potri.005G018000 gene in said plant.

18. The method of claim 17, wherein said necrotropic fungus is from genus *Sphaerulina*.

19. The method of claim 17, wherein said necrotropic fungus is selected from the group consisting of *Sphaerulina musiva*, *Sphaerulina oryzina*, *Sphaerulina rehmiana* and *Sphaerulina rubi*.

20. A method of determining necrotropic fungi resistance in a *Populus* plant comprising
  infecting said plant with a necrotropic fungus; and
  determining the expression levels of one or more genes selected from the group consisting of Potri.003G028200, Potri.005G012100, Potri.009G036300, Potri.017G003600, Potri.T075000, Potri.017G035500, Potri.018G019700, Potri.013G090300 and Potri.013G090300 genes before and after the infection, wherein a transient increase in the expression level of said one or more genes around 24 hours after the infection indicates that the plant is resistant to said necrotropic fungus.

21. The method of claim 20, wherein said necrotropic fungus is from genus *Sphaerulina*.

22. The method of claim 20, wherein said necrotropic fungus is selected from the group consisting of *Sphaerulina abeliceae, Sphaerulina aceris, Sphaerulina acetabulum, Sphaerulina acori, Sphaerulina aechmeae, Sphaerulina affinis, Sphaerulina albispiculata, Sphaerulina alni, Sphaerulina amelanchier, Sphaerulina amicta, Sphaerulina amphilomatis, Sphaerulina amygdali, Sphaerulina anemones, Sphaerulina annae, Sphaerulina antarctica, Sphaerulina arctica, Sphaerulina arthoniae, Sphaerulina assurgens, Sphaerulina aucubae, Sphaerulina azaleae, Sphaerulina baccarum, Sphaerulina bambusicola, Sphaerulina berberidis, Sphaerulina betulae, Sphaerulina blyttii, Sphaerulina bonariana, Sphaerulina boudieriana, Sphaerulina bryophila, Sphaerulina callista, Sphaerulina camelliae, Sphaerulina camelliae, Sphaerulina carestiae, Sphaerulina caricae, Sphaerulina caricis, Sphaerulina ceanothi, Sphaerulina centellae, Sphaerulina cercidis, Sphaerulina cetraricola, Sphaerulina cetrariicola, Sphaerulina chlorococca, Sphaerulina cibotii, Sphaerulina citri, Sphaerulina codiicola, Sphaerulina coffaeicola, Sphaerulina coffeicola, Sphaerulina concinna, Sphaerulina conflicta, Sphaerulina coriariae, Sphaerulina cornicola, Sphaerulina corniculata, Sphaerulina coronillae-junceae, Sphaerulina corynephora, Sphaerulina cucumeris, Sphaerulina cucurbitae, Sphaerulina datiscae, Sphaerulina diapensiae, Sphaerulina dioscoreae, Sphaerulina divergens, Sphaerulina dolichotera, Sphaerulina dryadis, Sphaerulina dryophila, Sphaerulina dubiella, Sphaerulina empetri, Sphaerulina endococcoidea, Sphaerulina epigaea, Sphaerulina eucalypti, Sphaerulina ferruginosa, Sphaerulina frondicola, Sphaerulina fuegiana, Sphaerulina gei, Sphaerulina gentianae, Sphaerulina gigantea, Sphaerulina giliae, Sphaerulina hainensis, Sphaerulina halophila, Sphaerulina hamadryadum, Sphaerulina hederae, Sphaerulina helicicola, Sphaerulina hyperici, Sphaerulina inaequalis, Sphaerulina inquinans, Sphaerulina intermedia, Sphaerulina intermixta, Sphaerulina Ipomoeae, Sphaerulina islandica, Sphaerulina iwatensis, Sphaerulina juglandis, Sphaerulina leightonii, Sphaerulina lepidiotae, Sphaerulina limnanthemi, Sphaerulina lini, Sphaerulina linicola, Sphaerulina ludwigiae, Sphaerulina mappiae, Sphaerulina marattiae, Sphaerulina marginata, Sphaerulina maroccana, Sphaerulina marsileae, Sphaerulina maydis, Sphaerulina menispermi, Sphaerulina microthyrioides, Sphaerulina mimosae-pigrae, Sphaerulina miyakei, Sphaerulina musae, Sphaerulina muscicola, Sphaerulina muscorum, Sphaerulina musicola, Sphaerulina musiva, Sphaerulina myriadea, Sphaerulina myriadea* subsp. *myriadea, Sphaerulina myrtillina, Sphaerulina naumovii, Sphaerulina nephromiaria, Sphaerulina oleifolia, Sphaerulina orae-maxis, Sphaerulina oryzae, Sphaerulina oryzina, Sphaerulina oxalidis, Sphaerulina oxyacanthae, Sphaerulina pallens, Sphaerulina parvipuncta, Sphaerulina patriniae, Sphaerulina paulistana, Sphaerulina peckii, Sphaerulina pedicellata, Sphaerulina pelargonii, Sphaerulina phalaenopsidis, Sphaerulina phellogena, Sphaerulina phoenicis, Sphaerulina phyllostachydis, Sphaerulina pini, Sphaerulina plantaginea, Sphaerulina pleuropogonis, Sphaerulina polygonorum, Sphaerulina polypodii, Sphaerulina polypodii, Sphaerulina polyspora, Sphaerulina populi, Sphaerulina populicola, Sphaerulina porothelia, Sphaerulina potebniae, Sphaerulina potentillae, Sphaerulina poterii, Sphaerulina primulicola, Sphaerulina pruni, Sphaerulina pseudovirgaureae, Sphaerulina pterocarpi, Sphaerulina pulii, Sphaerulina quercicola, Sphaerulina quercifolia, Sphaerulina quitensis, Sphaerulina rehmiana,*

*Sphaerulina rhabdoclinis, Sphaerulina rhodeae, Sphaerulina rhododendri, Sphaerulina rhododendricola, Sphaerulina rubi, Sphaerulina saccardiana, Sphaerulina saccardoana, Sphaerulina sacchari, Sphaerulina salicina, Sphaerulina sambucina, Sphaerulina sasae, Sphaerulina schaereri, Sphaerulina scirpi, Sphaerulina sepincola, Sphaerulina serograpta, Sphaerulina silacincola, Sphaerulina smilacincola, Sphaerulina socia, Sphaerulina spartii, Sphaerulina staphyleae, Sphaerulina staurochili, Sphaerulina steganostroma, Sphaerulina subgen, Pharcidiella, Sphaerulina subgen, Sphaerulina, Sphaerulina sub glacialis, Sphaerulina subtropica, Sphaerulina suchumica, Sphaerulina tabacinae, Sphaerulina tanaceti, Sphaerulina tarda, Sphaerulina taxi, Sphaerulina taxicola, Sphaerulina thujopsidis, Sphaerulina tiliaris, Sphaerulina tirolensis, Sphaerulina todeae, Sphaerulina trapae-bispinosae, Sphaerulina trifolii, Sphaerulina tritici, Sphaerulina umbilicata, Sphaerulina valerianae, Sphaerulina viciae, Sphaerulina vincae, Sphaerulina violae, Sphaerulina vismiae, Sphaerulina vulpina, Sphaerulina westendorpii, Sphaerulina worsdellii, Sphaerulina xerophylli, Sphaerulina yerbae, Sphaerulina ziziphi, Sphaerulina zizyphae,* and *Sphaerulina zizyphi.*

\* \* \* \* \*

UNITED STATES PATENT AND TRADEMARK OFFICE
CERTIFICATE OF CORRECTION

PATENT NO. : 10,900,094 B2
APPLICATION NO. : 16/148319
DATED : January 26, 2021
INVENTOR(S) : Muchero et al.

Page 1 of 1

It is certified that error appears in the above-identified patent and that said Letters Patent is hereby corrected as shown below:

In the Specification

Column 1, Lines 16-19 under the heading STATEMENT REGARDING FEDERALLY SPONSORED RESEARCH OR DEVELOPMENT, should read as follows:
This invention was made with government support under a research project supported by Prime Contract No. DE-AC05-00OR22725 and DE-SC0018196 awarded by the U.S. Department of Energy. The government has certain rights in this invention.

Signed and Sealed this
Second Day of August, 2022

Katherine Kelly Vidal
*Director of the United States Patent and Trademark Office*